US012778930B2

(12) United States Patent
Yates et al.

(10) Patent No.: US 12,778,930 B2
(45) Date of Patent: Nov. 3, 2026

(54) PHARMACEUTICAL COMPOSITIONS COMPRISING CANNABINOID AGONIST

(71) Applicant: ARTELO BIOSCIENCES LIMITED, Cheshire (GB)

(72) Inventors: Andrew Yates, Cheshire (GB); Paul Dickinson, Cheshire (GB); Robert Ward, Flintshire (GB)

(73) Assignee: ARTELO BIOSCIENCES LIMITED, Cheshire (GB)

( * ) Notice: Subject to any disclaimer, the term of this patent is extended or adjusted under 35 U.S.C. 154(b) by 562 days.

(21) Appl. No.: 18/256,198

(22) PCT Filed: Jul. 12, 2021

(86) PCT No.: PCT/GB2021/053200
§ 371 (c)(1),
(2) Date: Jun. 6, 2023

(87) PCT Pub. No.: WO2022/123233
PCT Pub. Date: Jun. 16, 2022

(65) Prior Publication Data

US 2024/0024290 A1 Jan. 25, 2024

(30) Foreign Application Priority Data

Dec. 8, 2020 (GB) ...................................... 2019335

(51) Int. Cl.
*A61K 31/4184* (2006.01)
*A61K 9/48* (2006.01)
*A61P 1/14* (2006.01)

(52) U.S. Cl.
CPC ........ *A61K 31/4184* (2013.01); *A61K 9/4858* (2013.01); *A61K 9/4866* (2013.01); *A61P 1/14* (2018.01)

(58) Field of Classification Search
CPC .............. A61K 31/4184; A61K 9/4858; A61K 9/4866; A61P 1/00; A61P 1/14
See application file for complete search history.

(56) References Cited

U.S. PATENT DOCUMENTS 8,895,553 B2 11/2014 Riggs-Sauthier
2006/0264490 A1* 11/2006 Page ...................... A61P 25/28 514/394

(Continued)

FOREIGN PATENT DOCUMENTS

JP 2008514593 5/2008
JP 2010537989 12/2010

(Continued)

OTHER PUBLICATIONS

D'Souza et al. (Expert Opinion On Drug Delivery, 2016 vol. 13, No. 9, 1257-127 (Year: 2016).*

(Continued)

*Primary Examiner* — Savitha M Rao
(74) *Attorney, Agent, or Firm* — Prince IP; Robert Prince

(57) ABSTRACT

The present disclosure relates to pharmaceutical compositions comprising Compound I, or a pharmaceutically acceptable salt thereof, as the active substance. The pharmaceutical compositions are suitable for use in immediate release pharmaceutical formulations. The pharmaceutical formulations are suitable for use in the treatment of medical conditions in which treatment with agonists of CB1/CB2 receptors are beneficial.

21 Claims, 29 Drawing Sheets

TPGS

Dissolution profiles in 0.1M HCl for 50 μg active capsules (50 mg fill) manufactured with Vitamin TPGS

(56) References Cited

U.S. PATENT DOCUMENTS

| | | | | |
|---|---|---|---|---|
| 2007/0104741 | A1 | 5/2007 | Murty | |
| 2007/0225346 | A1 | 9/2007 | Bohlin | |
| 2016/0228405 | A1 * | 8/2016 | Goskonda ............ | A61K 9/0095 |

FOREIGN PATENT DOCUMENTS

| | | | |
|---|---|---|---|
| JP | 2017521448 | | 8/2017 |
| WO | 2005030732 | | 4/2005 |
| WO | 2006033631 | A1 | 3/2006 |

OTHER PUBLICATIONS

Magnus Schou et al; "Radiolabeling of the cannabinoid receptor agonist AZD1940 with carbon-11 and PET microdosing in non-human primate"; Nuclear Medicine and Biology; vol. 40, Issue 3, Apr. 2013, pp. 410-414; 5 pages.
Aaron Gazendam et al; "Cannabinoids in the Management of Acute Pain: A Systematic Review and Meta-analysis"; Cannabis and Cannabinoid Research vol. 5, No. 4,2020; pp. 290-297.
Astra Zeneca; Study to Investigate the Safety, Tolerability and Pharmacokinetics of AZD1940 for subjects with ; Chronic Low Back Pain; Clinical Trials.gov ID NCT00689780; date posted Dec. 10, 2010; https://clinicaltrials.gov/search?intr=azd1940.
Astra Zeneca; Study to investigate the analgesic efficacy of a single dose of AZD1940; https://www.astrazenecaclinicaltrials.com/study/D3120C00006/.
Barry Laird, et al; "Cancer Appetite Recovery Study (CARES): Study Protocol for a Dose-Ascending, Multicenter, Randomized Controlled Phase 1/2 Trial of ART27.13 in Patients With Cancer Anorexia and Weight Loss"; 1Institute of Genetics and Molecular Medicine, University of Edinburgh, Edinburgh; 1 page.
Saoirse Elizabeth O'Sullivan, et al; "The Peripheral Cannabinoid Receptor Type 1 (CB1) as a Molecular Target for Modulating Body Weight in Man"; Molecules 2021, 26, 6178. https://doi.org/10.3390/molecules26206178; 15 pages.
International Search Report and Written Opinion dated Mar. 11, 2022 issued in PCT/GB2021/053200.
Clinical and experimental pharmacology and physiology, vol. 40, 2013, Jarkko Kalliomaki et al., "Evaluation of the analgesic efficacy and psychoactive effects of AZD 1940, a novel peripherally acting cannabinoid agonist, in human capsaicin-induced pain and hyperalgesia", 212-218.
Scandinavian journal of pain, vol. 4, 2013, Jarkko Kalliomaki et al., "Evaluation of the analgesic efficacy of AZD1940, a novel cannabinoid agonist, on post-operative pain after lower third molar surgical removal", 17-22.
Letters in drug design & discovery, vol. 7, 2010, Daniel Page et al., "5-sulfonamide benzimidazoles: a class of cannabinoid receptors agonists with potent in vivo antinociception activity", 208-213.

* cited by examiner

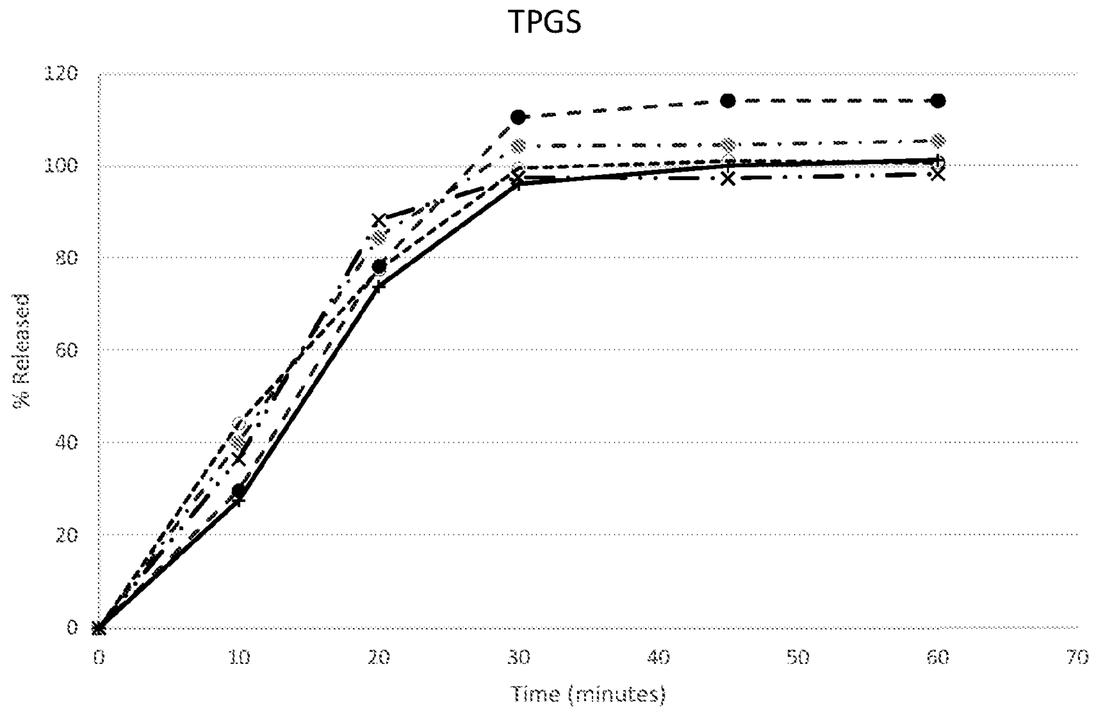
Figure 1: Dissolution profiles in 0.1M HCl for 50 µg active capsules (50 mg fill) manufactured with Vitamin TPGS

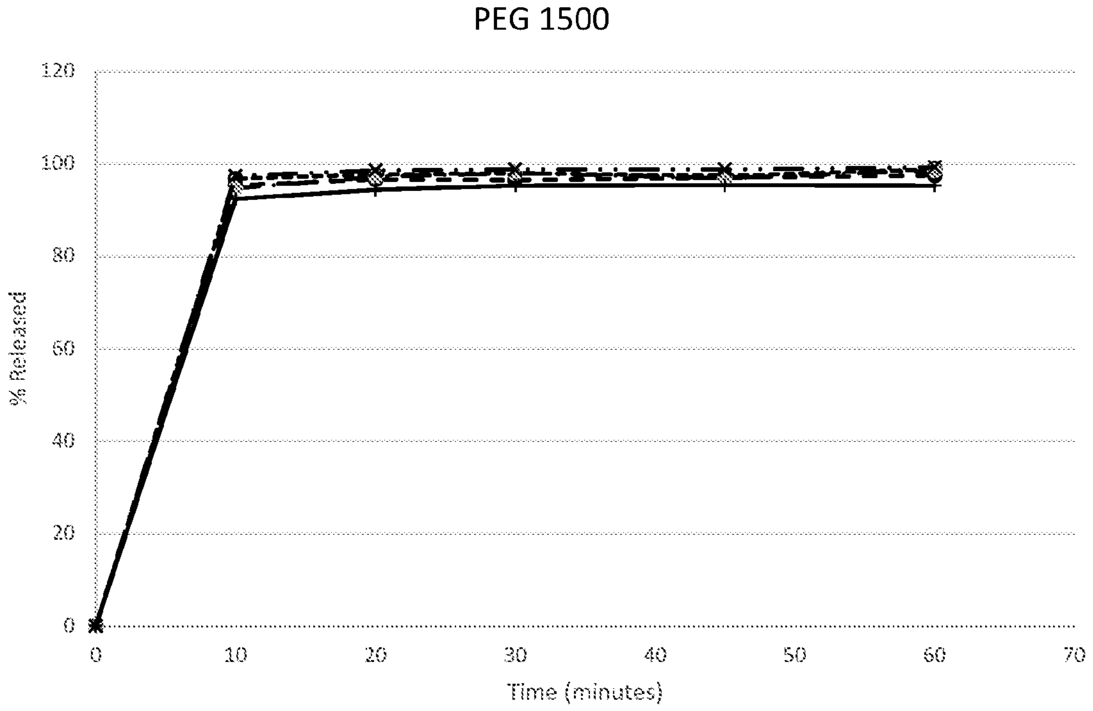
Figure 2: Dissolution profiles in 0.1M HCl for 50 µg active substance capsules (50 mg fill) manufactured with PEG 1500

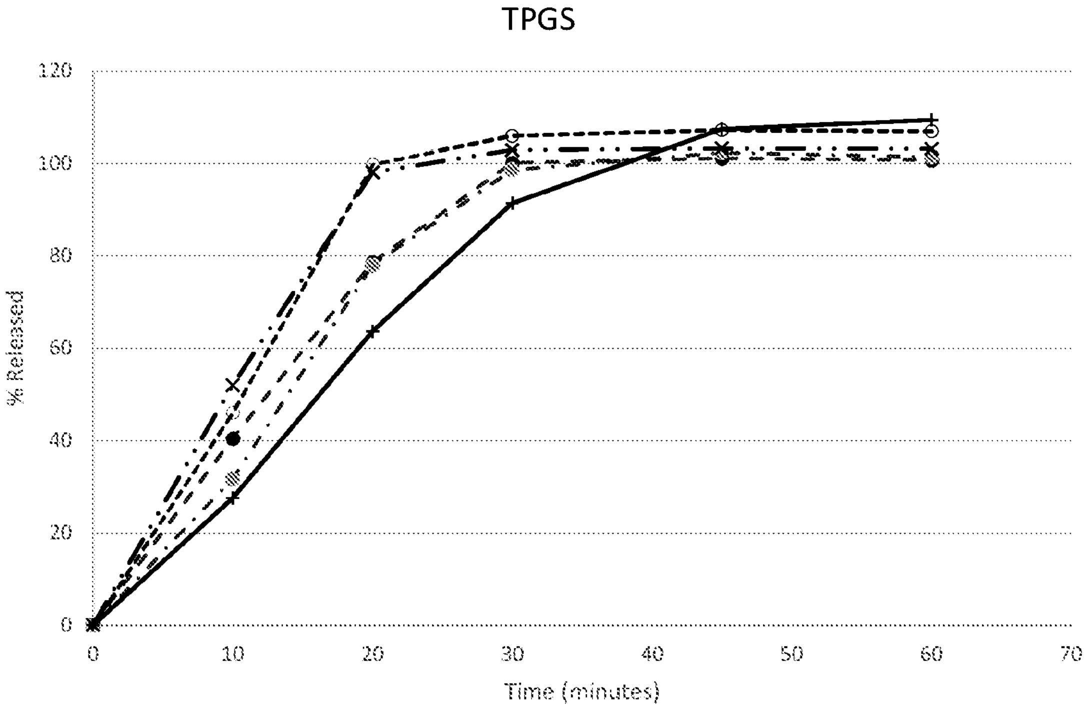
Figure 3: Dissolution profiles in 0.1M HCl for 200 µg active substance capsules (50 mg fill) manufactured with Vitamin E TPGS

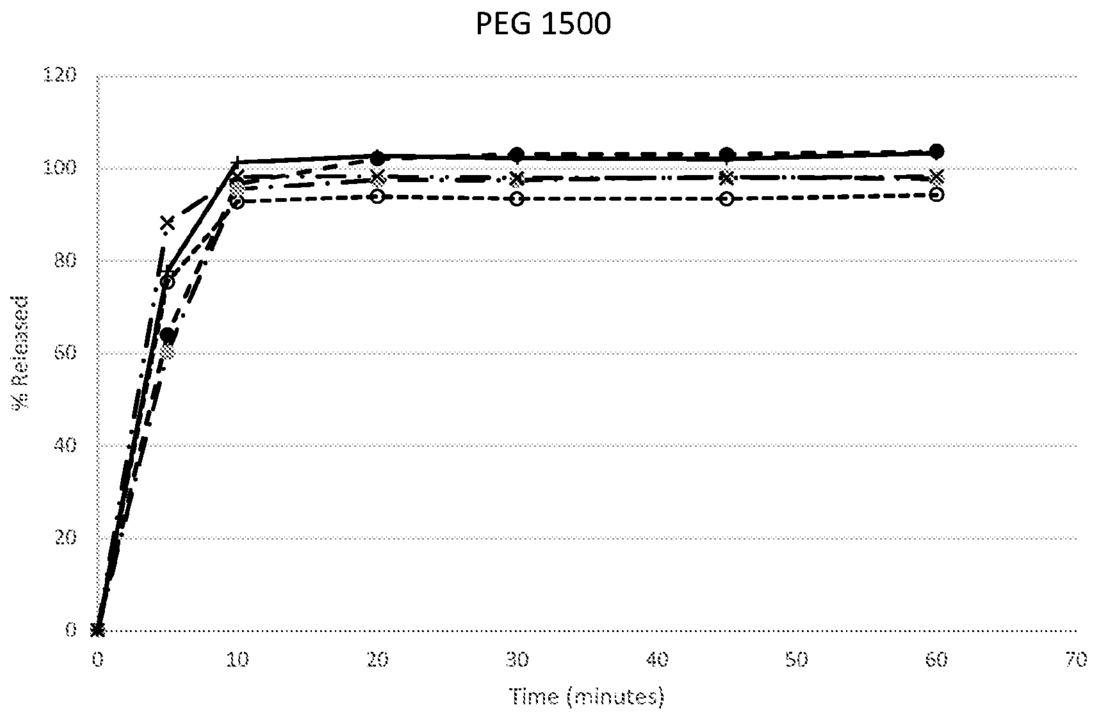
Figure 4: Dissolution profiles in 0.1M HCl for 200 µg active substance capsules (50 mg fill) manufactured with PEG 1500

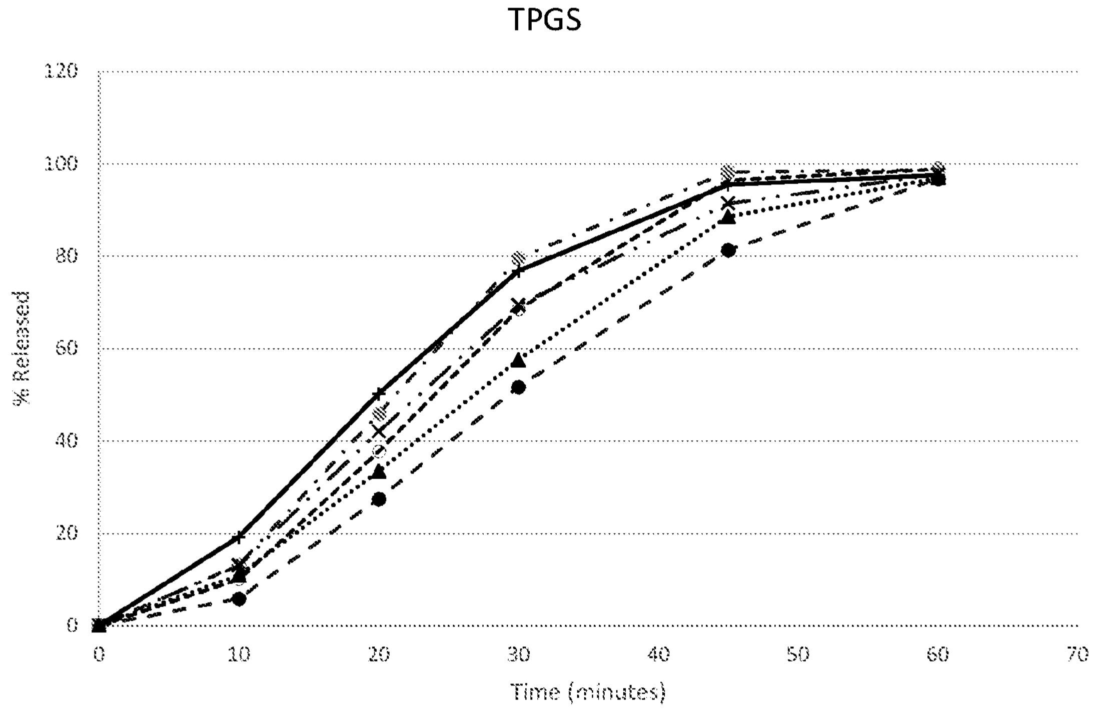
Figure 5: Dissolution profiles in 0.1M HCl for 200 µg active substance capsules (200 mg fill) manufactured with Vitamin E TPGS

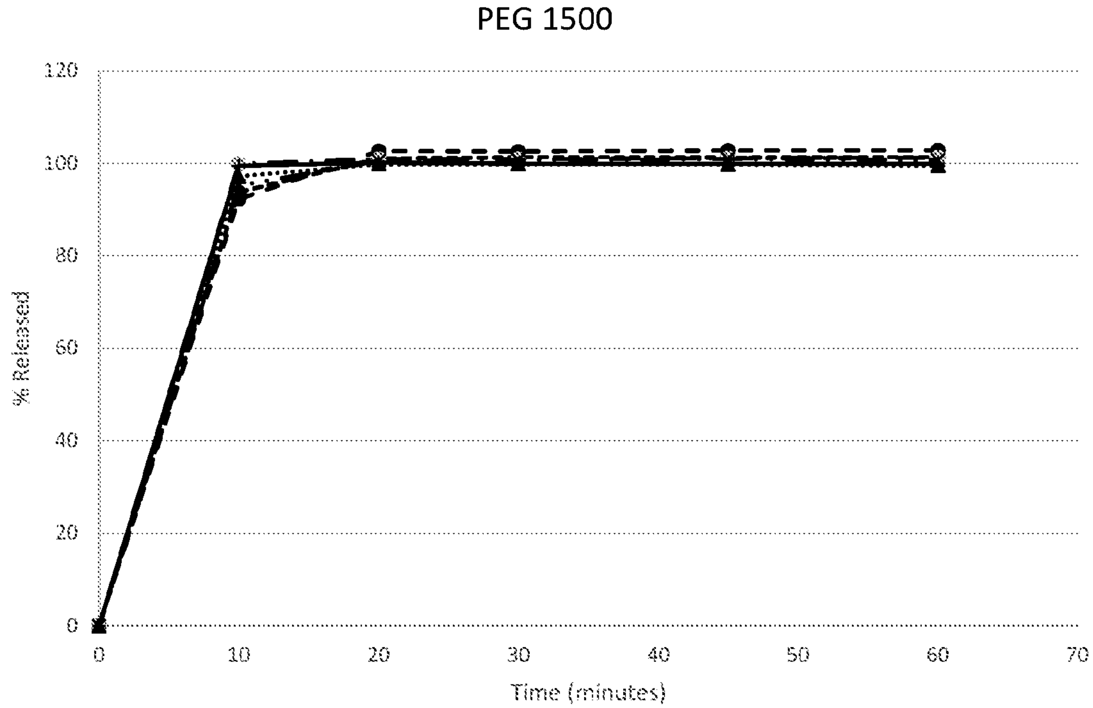
Figure 6: Dissolution profiles in 0.1M HCl for 200 µg active substance capsules (200 mg fill) manufactured with PEG 1500

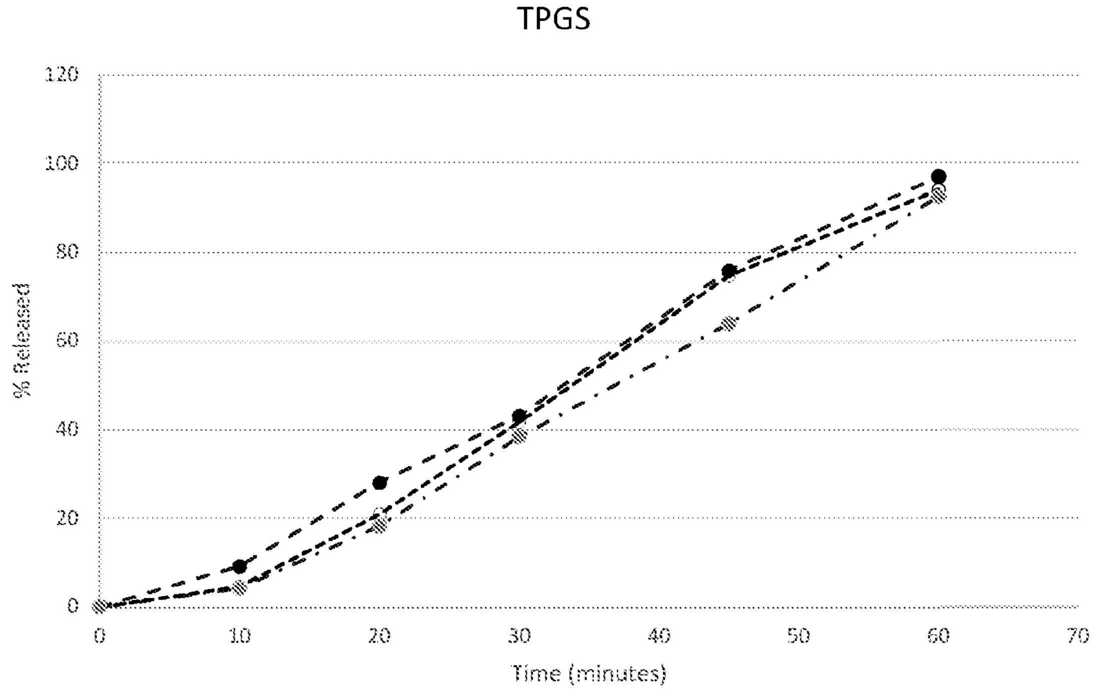
Figure 7: Dissolution profiles in pH 6.8 phosphate buffer for 50 µg active substance capsules (50 mg fill) manufactured with Vitamin E TPGS

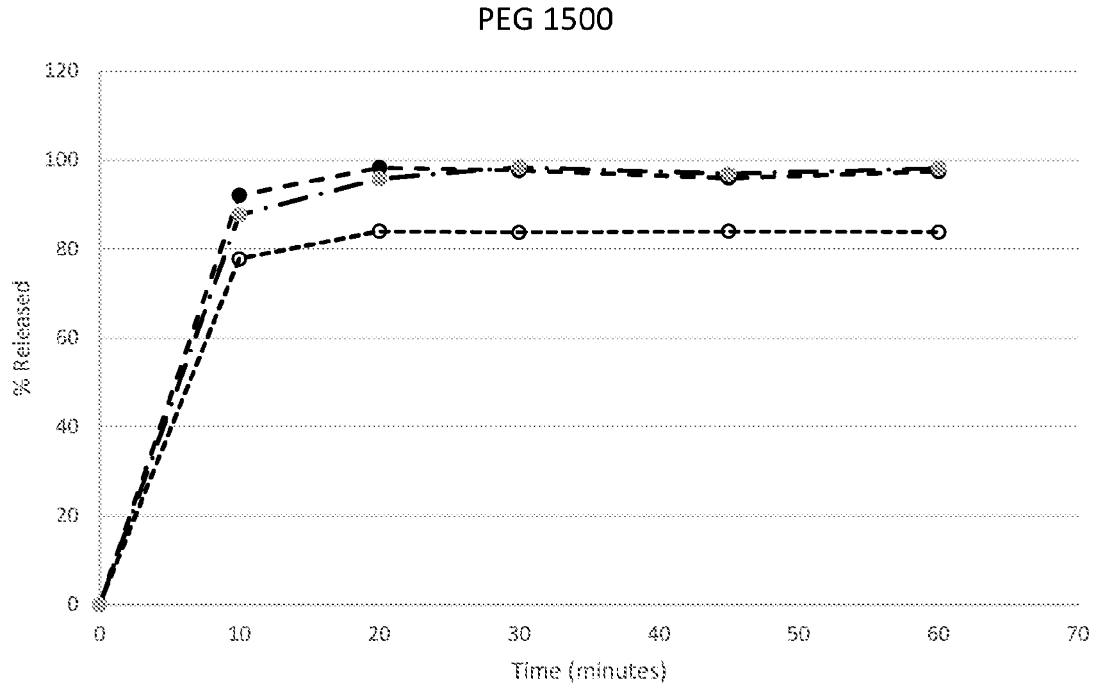
Figure 8: Dissolution profiles in pH 6.8 phosphate buffer for 50 µg active substance capsules (50 mg fill) manufactured with PEG 1500

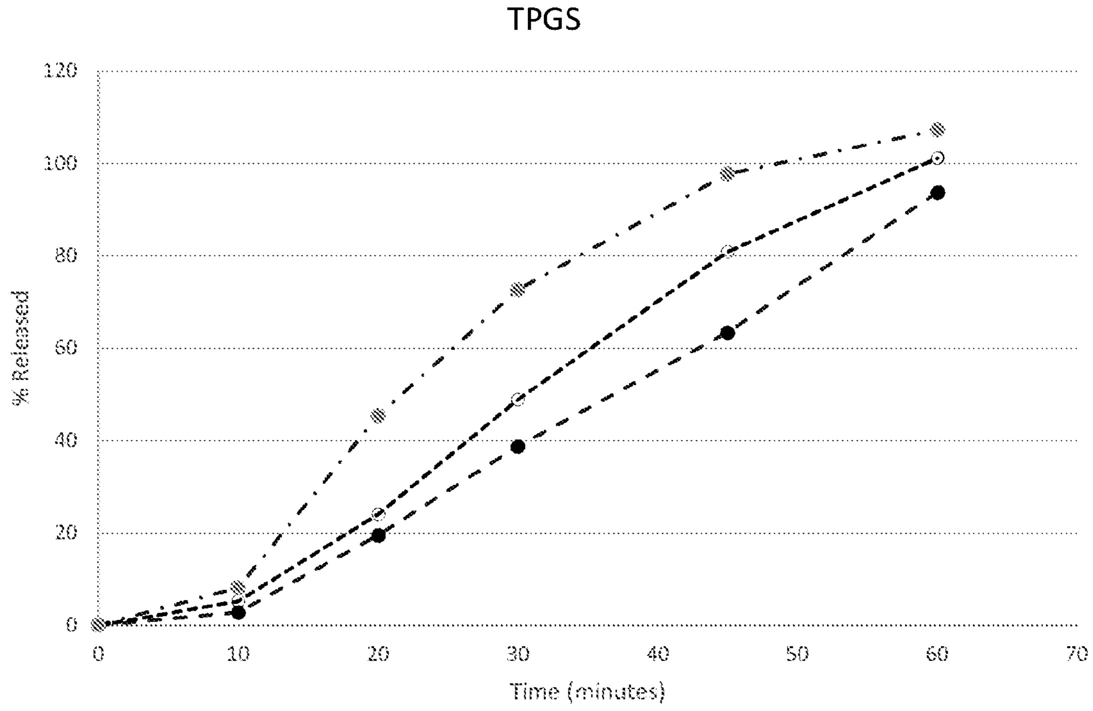
Figure 9: Dissolution profiles in pH 6.8 phosphate buffer for 200 µg active substance IR capsules (50 mg fill) manufactured with Vitamin E TPGS

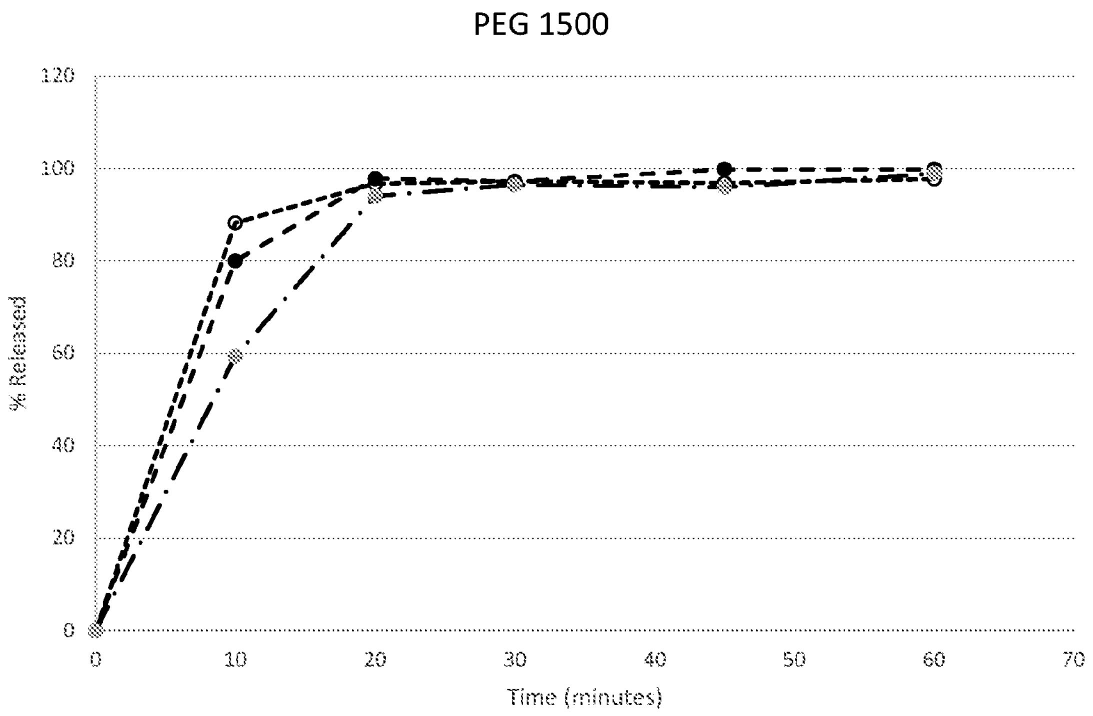
Figure 10: Dissolution profiles in pH 6.8 phosphate buffer for 200 µg active substance capsules (50 mg fill) manufactured with PEG 1500

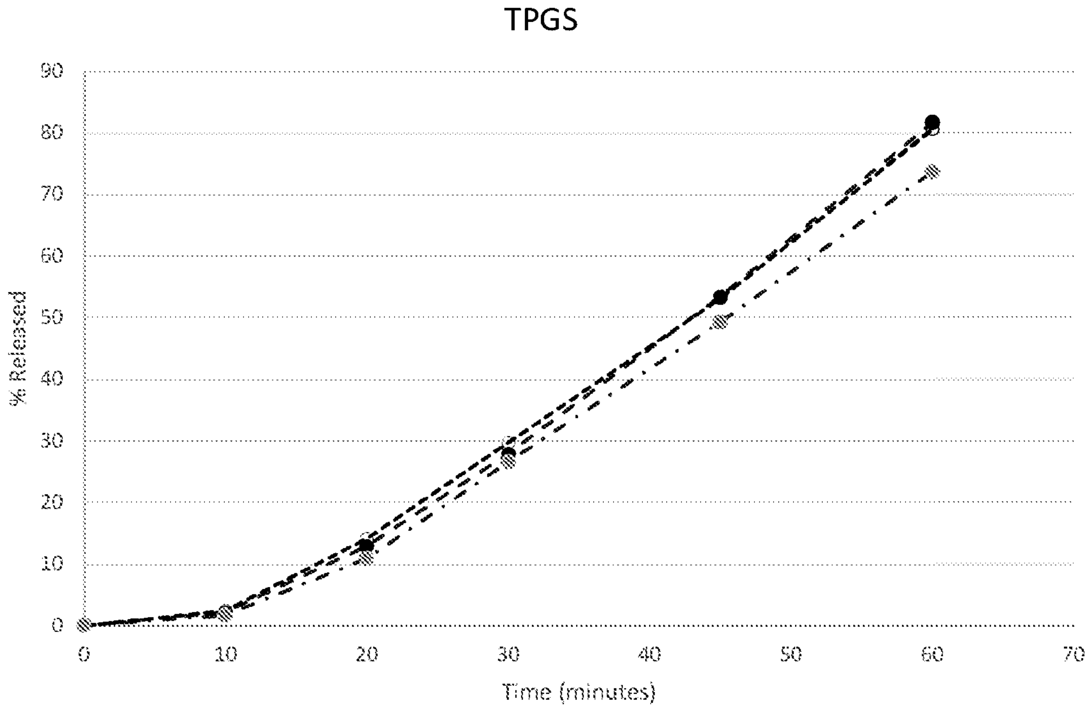
Figure 11: Dissolution profiles in pH 6.8 phosphate buffer for 200 µg active substance capsules (200 mg fill) manufactured with Vitamin E TPGS

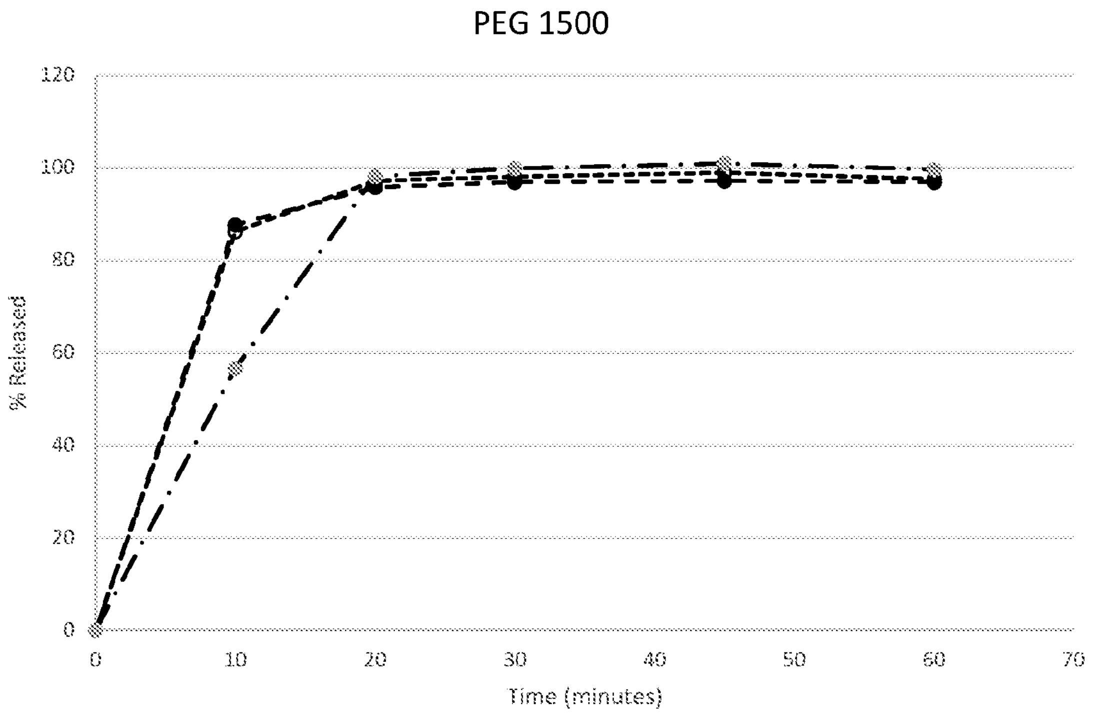
Figure 12: Dissolution profiles in pH 6.8 phosphate buffer for 200 µg active substance capsules (200 mg fill) manufactured with PEG 1500

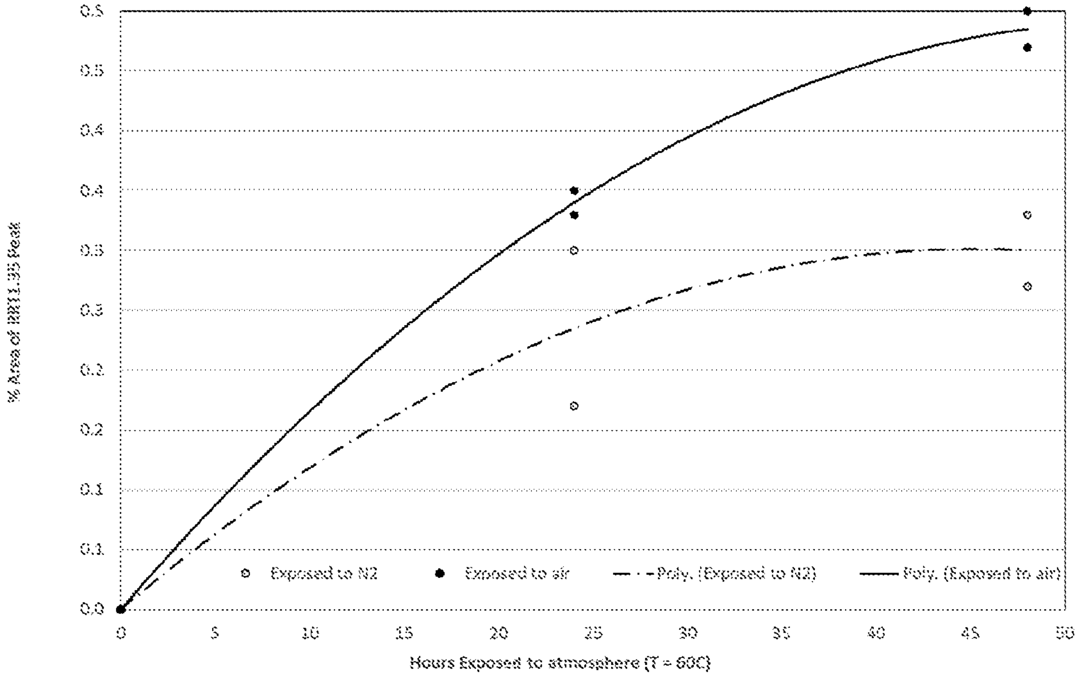
Figure 13: % Area of RRT 1.35 peak in vial aliquots of the 50 µg filling fluid as a function of incubation time at 60 °C

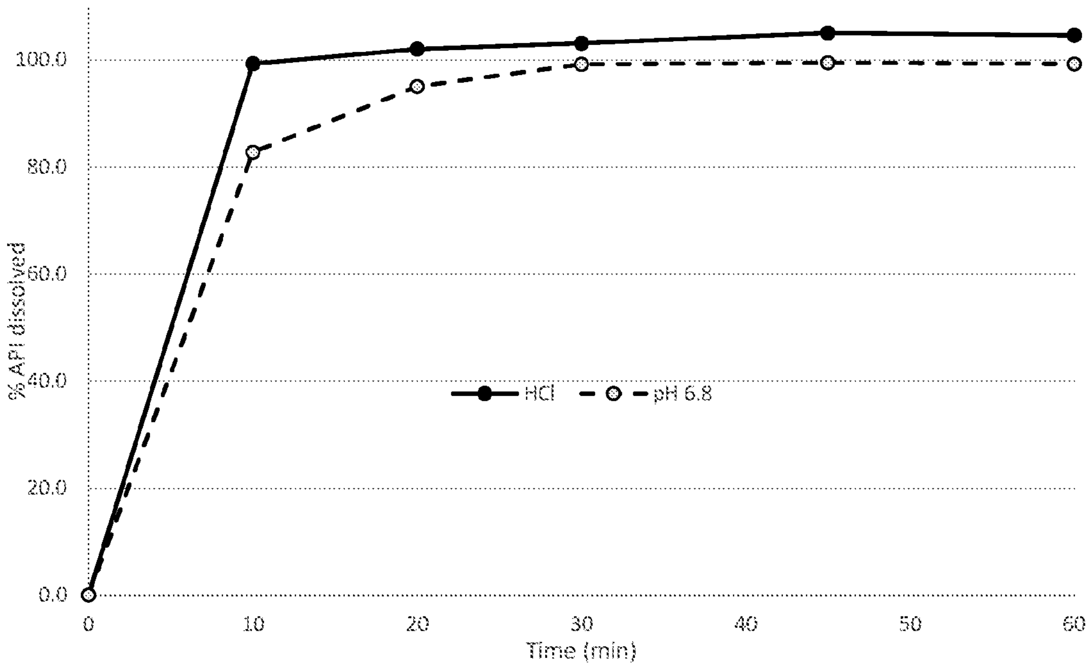
Figure 14: Mean release of active substance (%label claim) from 50 µg capsules versus time in 0.1M HCl and pH 6.8 media

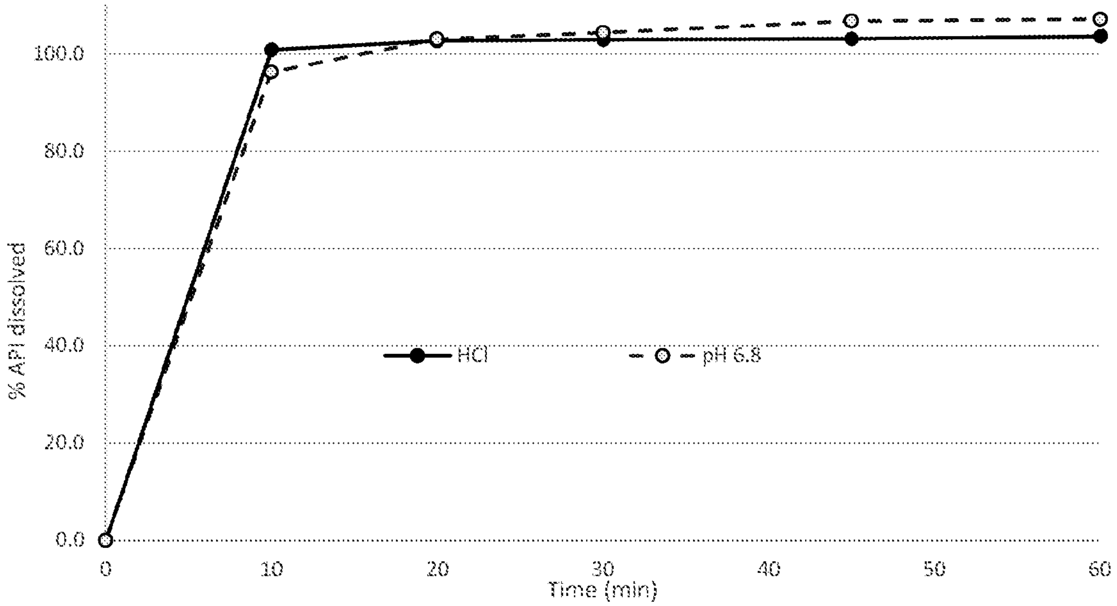
Figure 15: Mean release of active substance (%label claim) from 200 μg capsules versus time in 0.1M HCl and pH 6.8 media

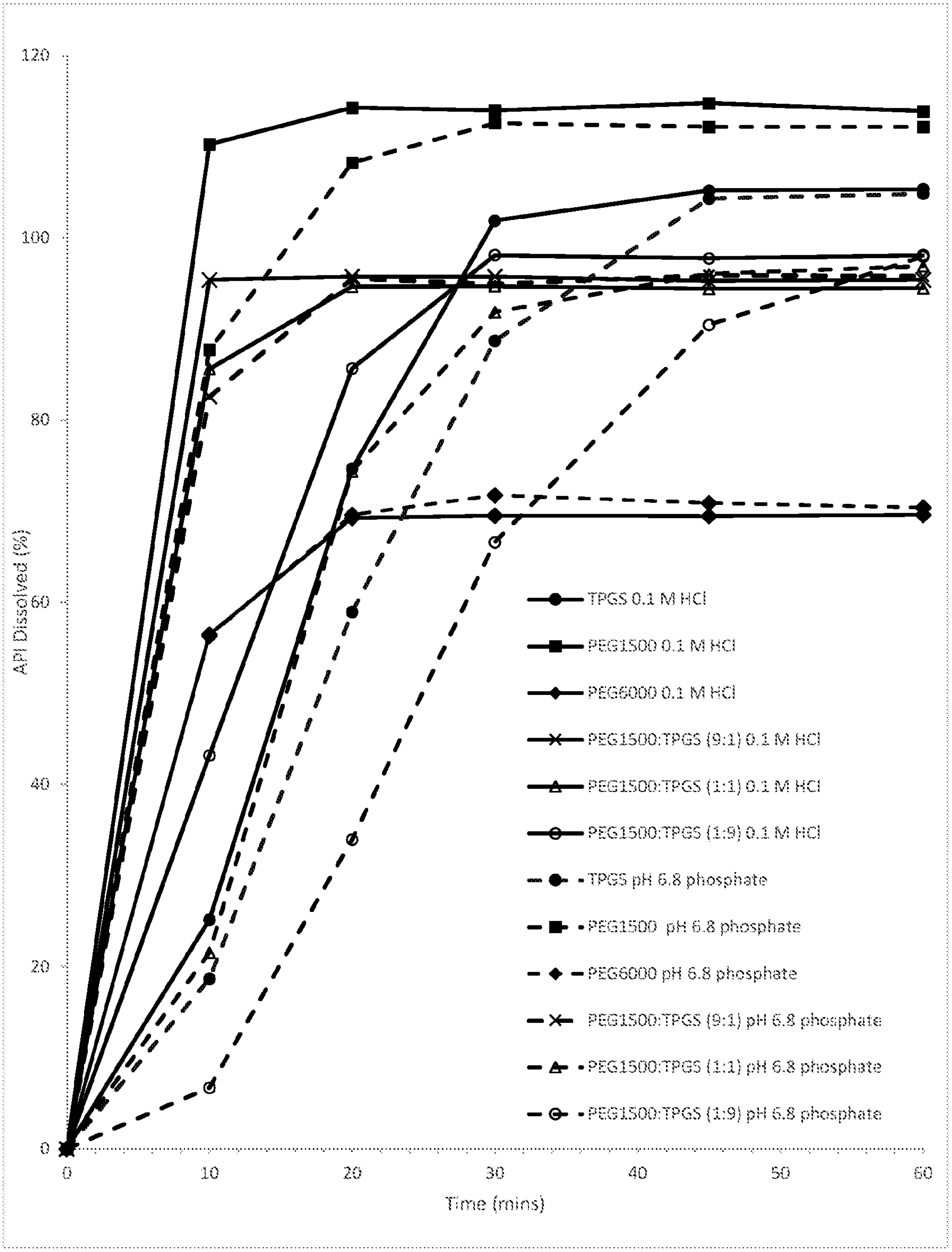
Figure 16: Mean release of active substance (% of nominal dose) for 0.4% w/w API and solvent capsules (solvent = TPGS, PEG1500, PEG6000, PEG1500:TPGS (1:1), PEG1500:TPGS (9:1), and PEG1500:TPGS (1:9))

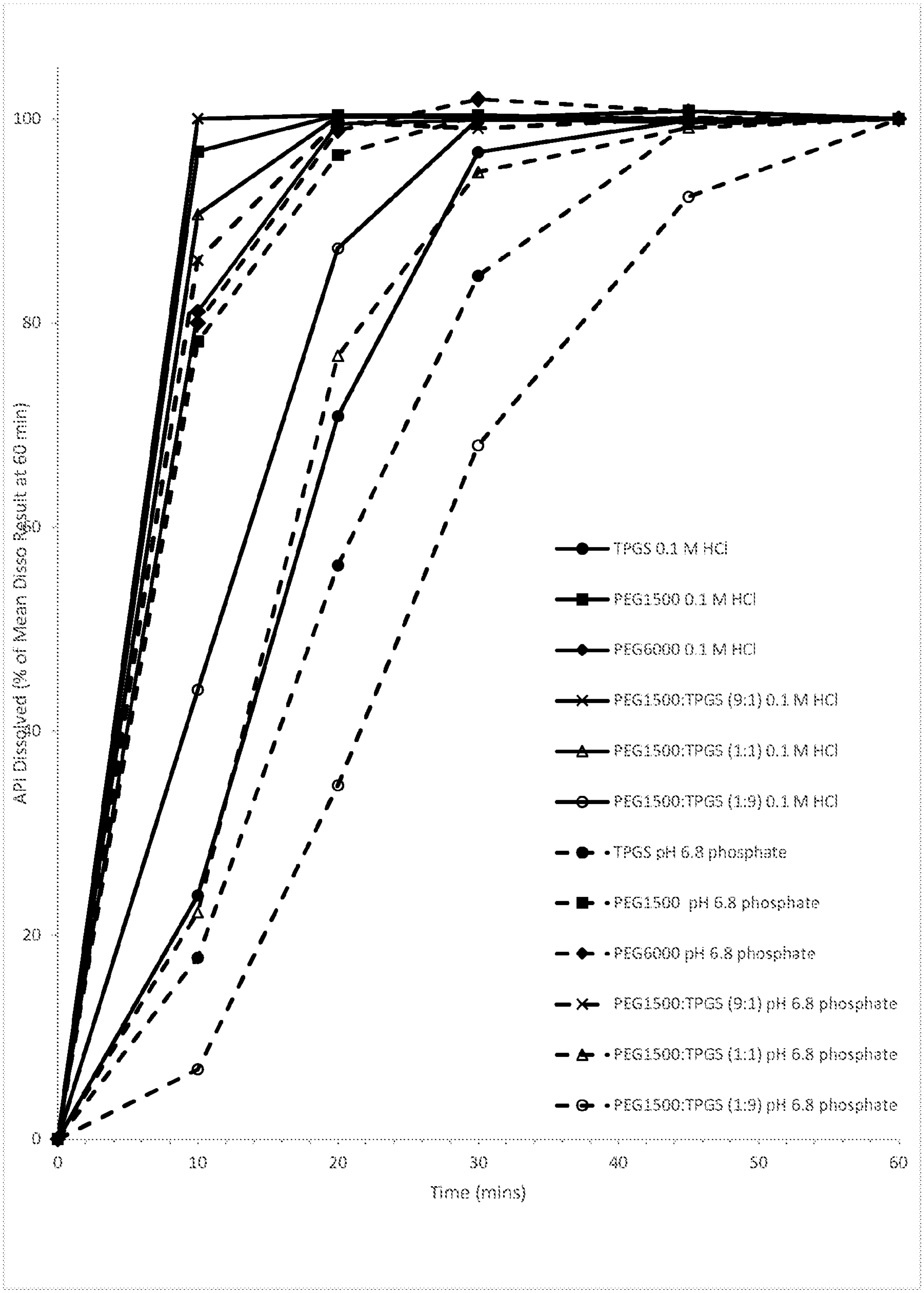
Figure 17: Mean release of active substance (normalised data) for 0.4% w/w API and solvent capsules (solvent = TPGS, PEG1500, PEG6000, PEG1500:TPGS (1:1), PEG1500:TPGS (9:1), and PEG1500:TPGS (1:9))

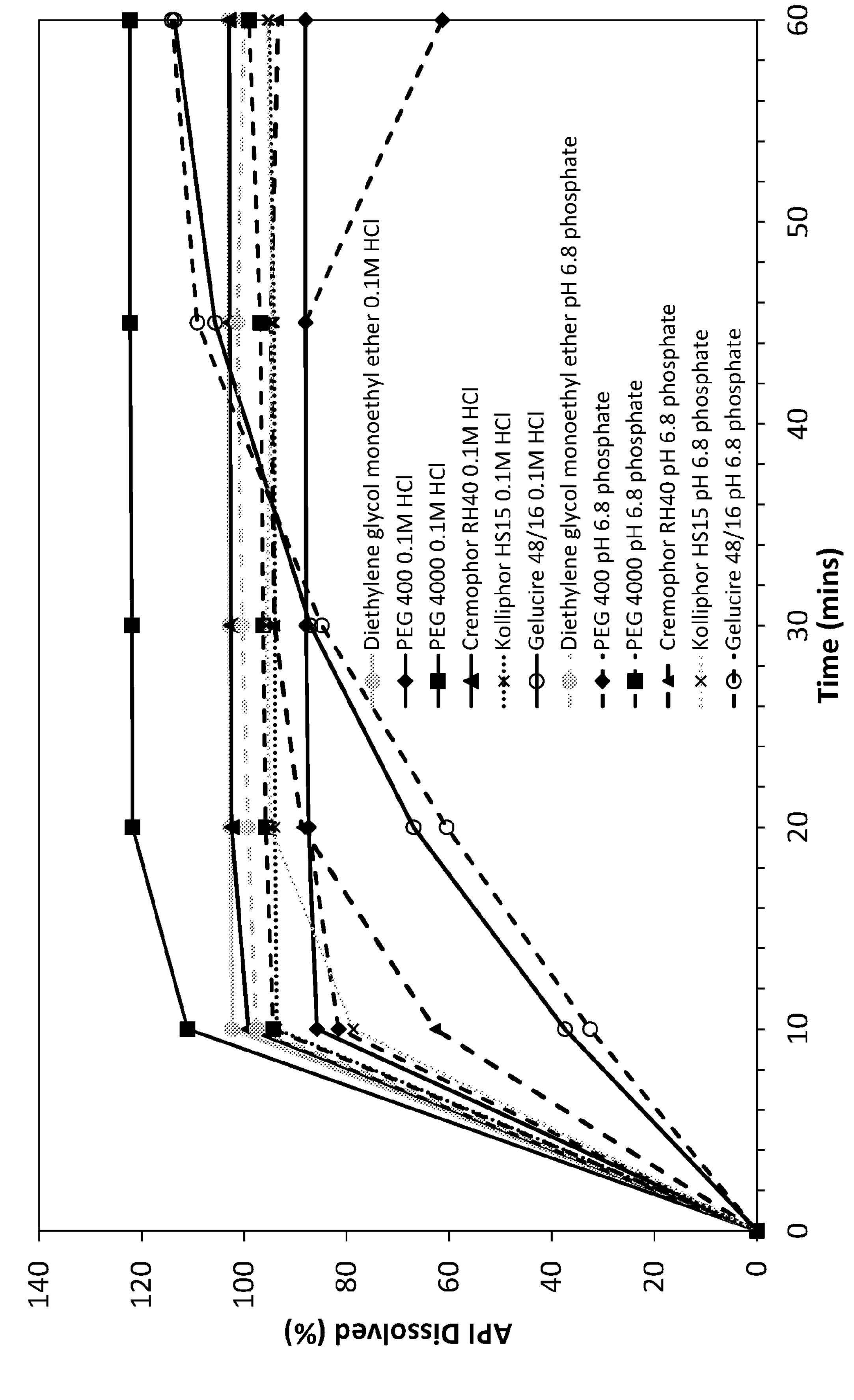
Figure 18: Mean release of active substance (% of nominal dose) for single solvent and API capsules

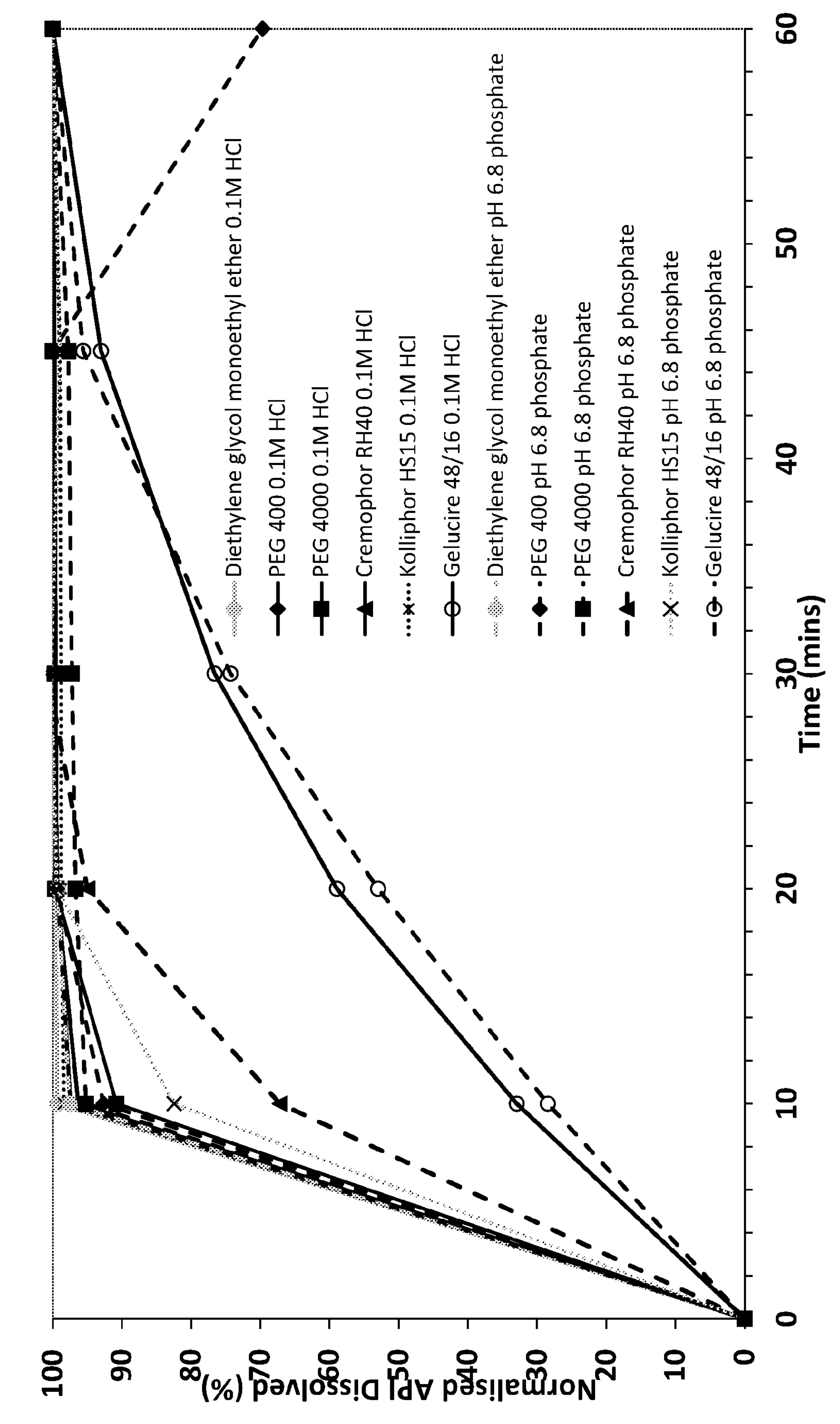
Figure 19: Mean release of active substance (normalised data) for single solvent and API capsules

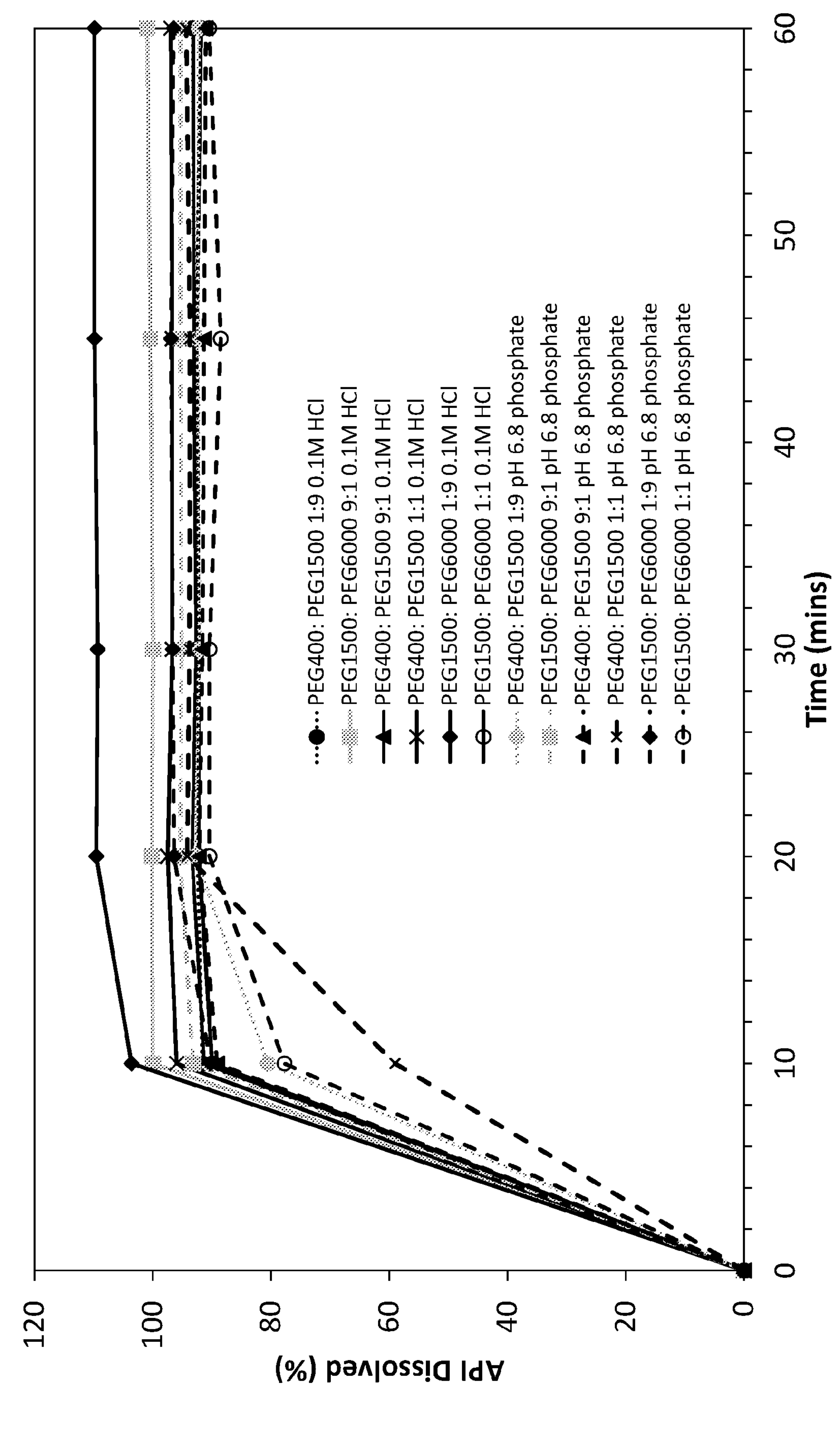
Figure 20: Mean release of active substance (% of nominal dose) for binary solvent and API capsules

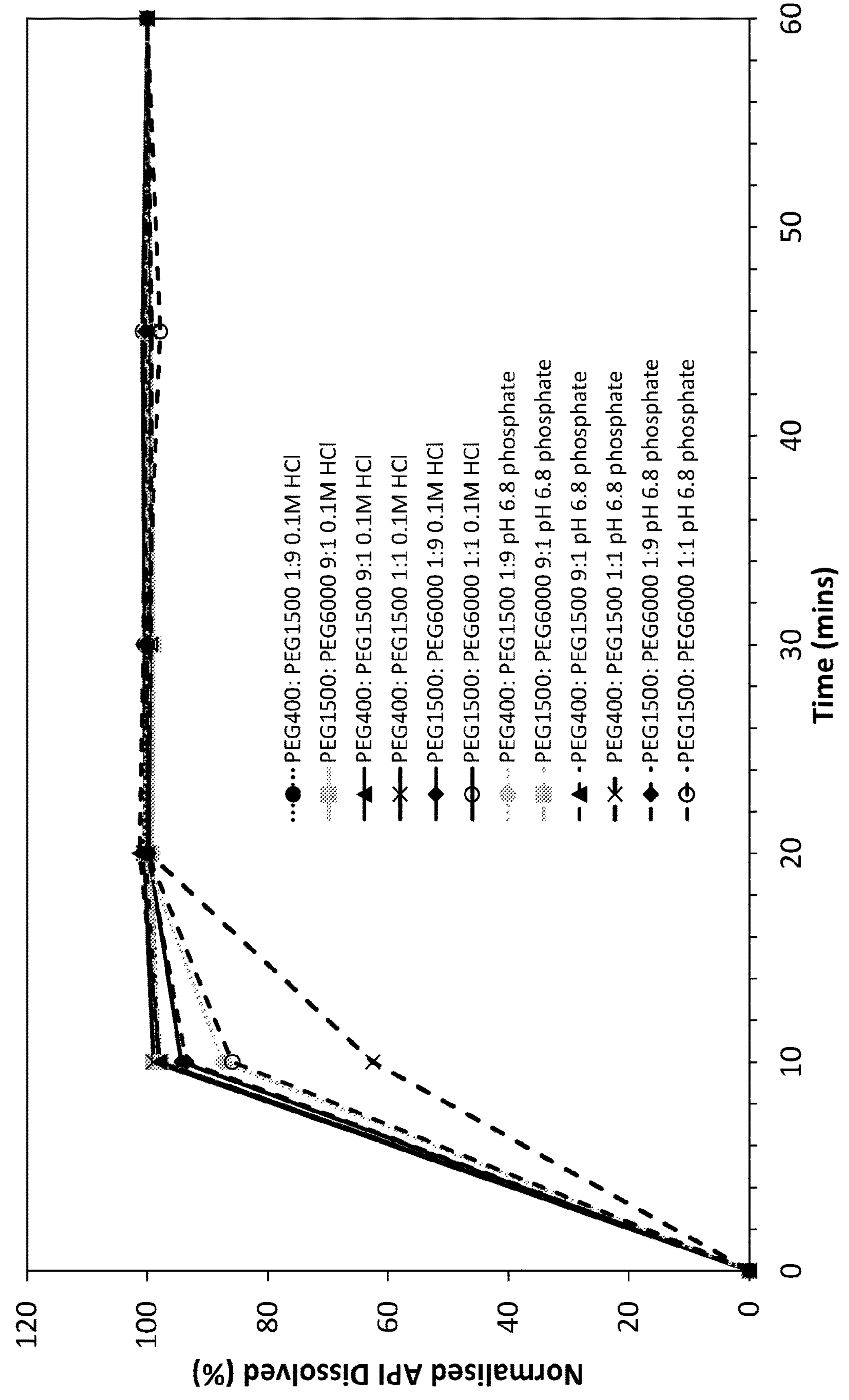
Figure 21: Mean release of active substance (normalised data) for binary solvent and API capsules

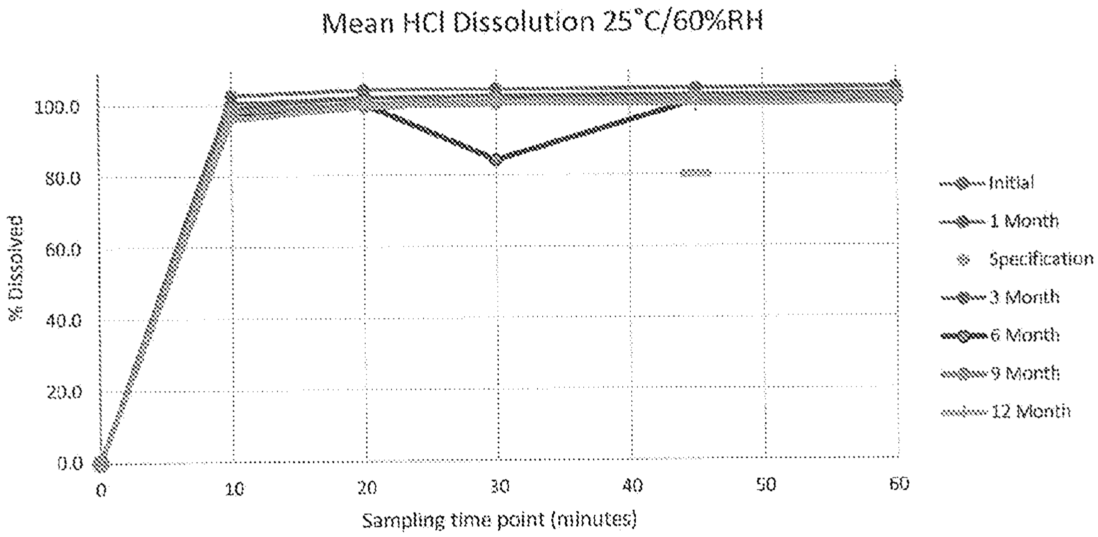
Figure 22: Mean release of active substance (%dissolved) from 50 µg capsules stored at 25°C/60%RH in 0.1M HCl

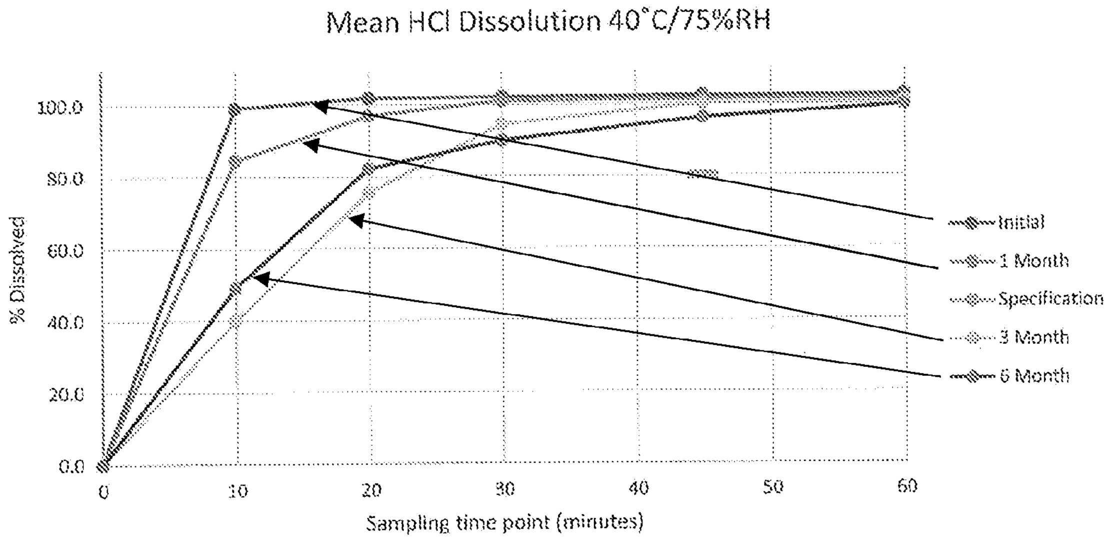
Figure 23: Mean release of active substance (%dissolved) from 50 μg capsules stored at 40°C/75%RH in 0.1M HCl

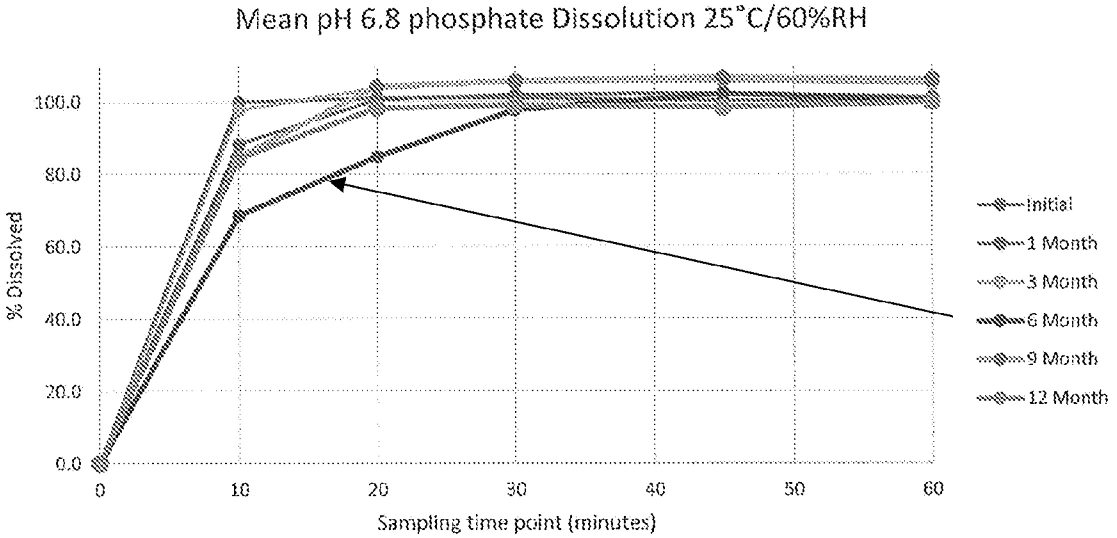
Figure 24: Mean release of active substance (%dissolved) from 50 µg capsules stored at 25°C/60%RH in pH 6.8 phosphate buffer

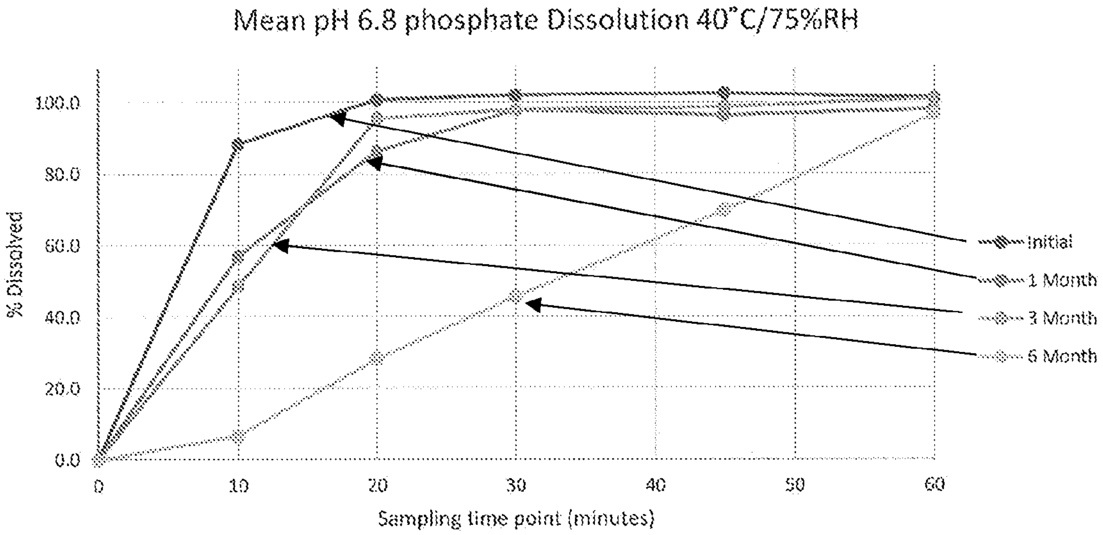
Figure 25: Mean release of active substance (%dissolved) from 50 μg capsules stored at 40°C/75%RH in pH 6.8 phosphate buffer

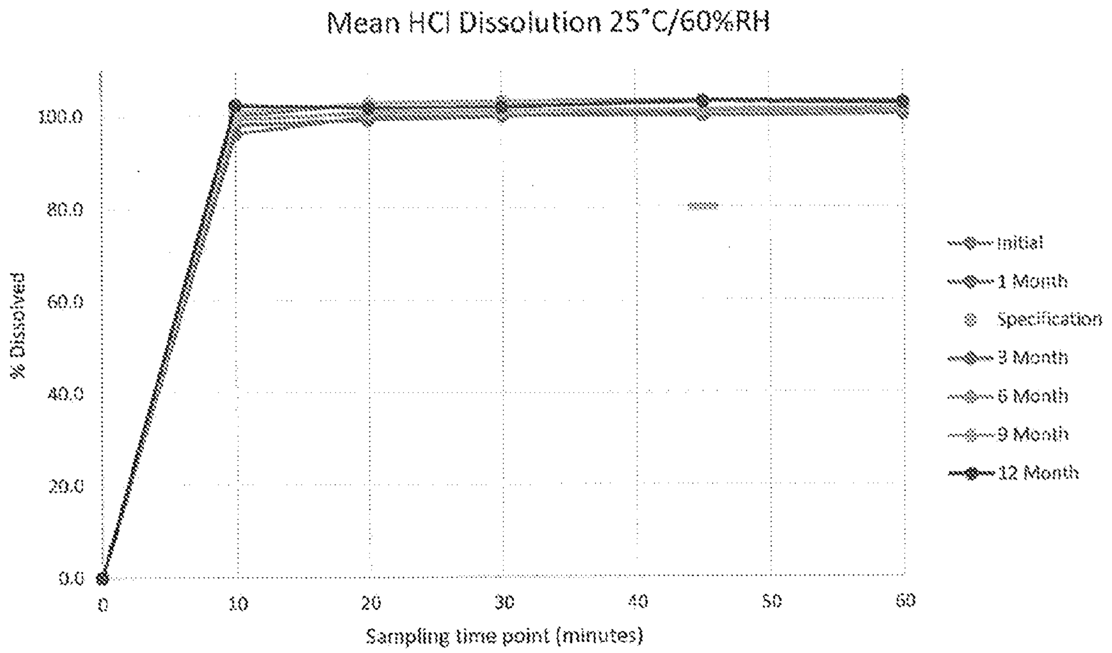
Figure 26: Mean release of active substance (%dissolved) from 200 µg capsules stored at 25°C/60%RH in 0.1M HCl

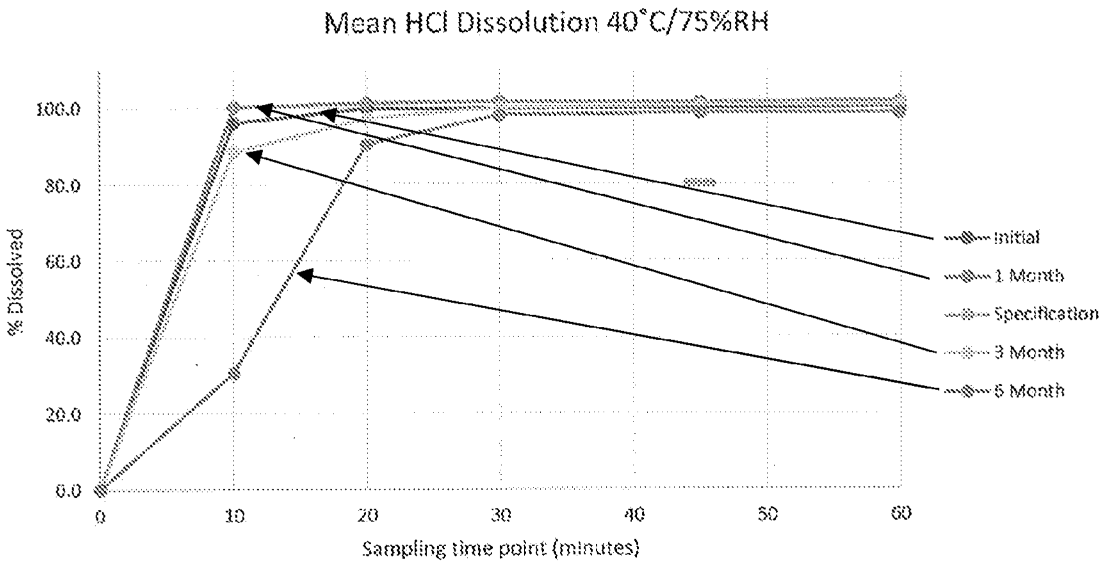
Figure 27: Mean release of active substance (%dissolved) from 200 μg capsules stored at 40°C/75%RH in 0.1M HCl

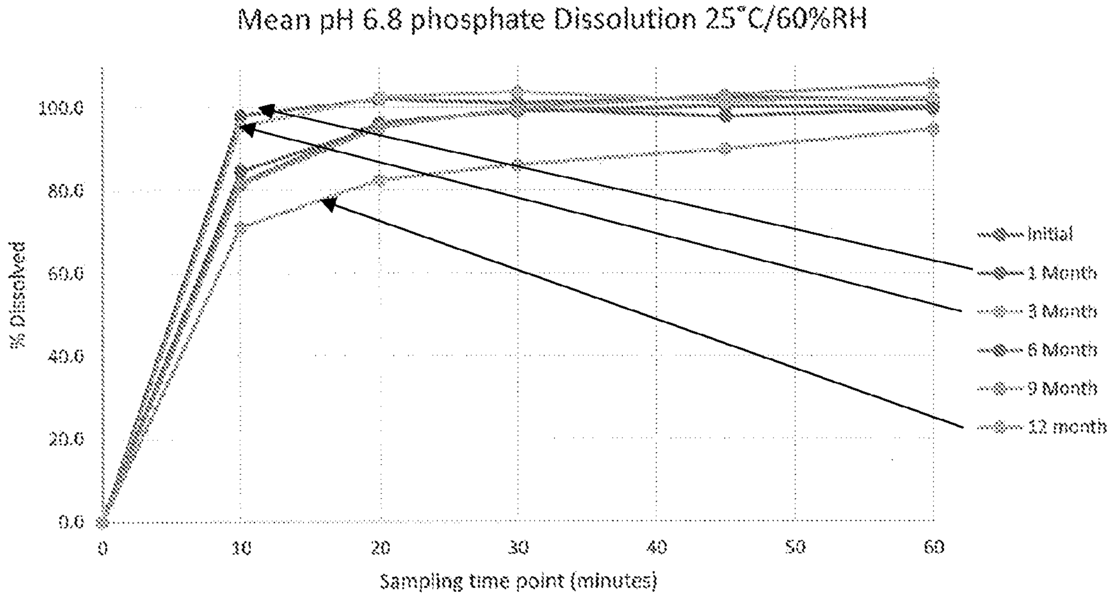
Figure 28: Mean release of active substance (%dissolved) from 200 µg capsules stored at 25°C/60%RH in pH 6.8 phosphate buffer

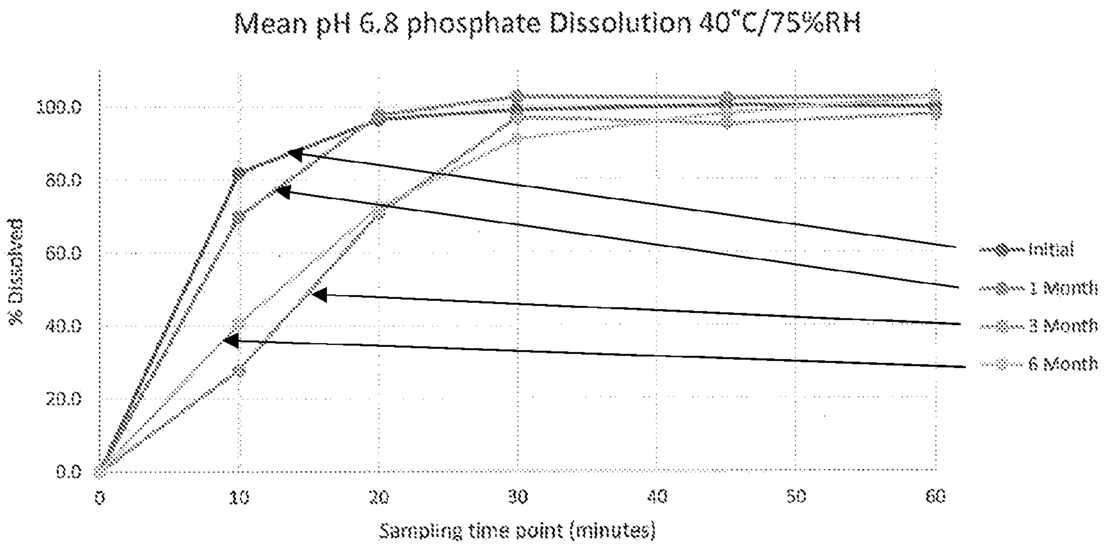
Figure 29: Mean release of active substance (%dissolved) from 200 μg capsules stored at 40°C/75%RH in pH 6.8 phosphate buffer

PHARMACEUTICAL COMPOSITIONS COMPRISING CANNABINOID AGONIST

This patent application is a U.S. National Phase filing of International Application No. PCT/GB2021/053200, filed on Dec. 7, 2021, which claims the benefit of priority to GB2019335.5, filed on Dec. 8, 2020, all of which are incorporated by reference herein in their entireties, including the drawings.

FIELD OF THE DISCLOSURE

The present disclosure relates to pharmaceutical compositions comprising N-(2-(tert-butyl)-1-((4,4-difluorocyclohexyl)methyl)-1H-benzimidazol-5-yl)ethanesulfonamide, or a pharmaceutically acceptable salt thereof, as an active substance. The pharmaceutical compositions are suitable for use in immediate release pharmaceutical formulations. The pharmaceutical formulations are suitable for use in the treatment of medical conditions in which treatment with agonists of $CB_1/CB_2$ receptors are beneficial.

BACKGROUND OF THE DISCLOSURE

N-(2-(tert-butyl)-1-((4,4-difluorocyclohexyl)methyl)-1H-benzimidazol-5-yl)ethanesulfonamide is a highly potent, peripherally restricted synthetic, dual cannabinoid agonist which targets the peripheral $CB_1/CB_2$ receptors (Groblewski T, Yu X H, Lessard E. Pre-clinical pharmacological properties of novel peripherally acting CB1-CB2 agonists. 20th Annual Symposium of the International Cannabinoid Research Society; 2010; Abstract #37). The structure of N-(2-(tert-butyl)-1-((4,4-difluorocyclohexyl)methyl)-1H-benzimidazol-5-yl)ethanesulfonamide (Compound I) is shown below.

Compound I

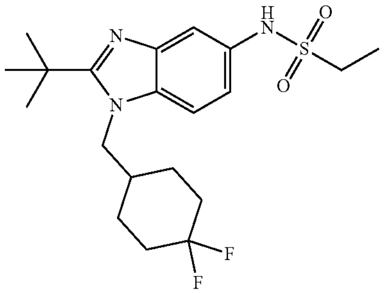

Compound I and a synthetic route to prepare it were first disclosed in WO2006/033631 A1. Compound I has been evaluated in a number of phase 1 clinical trials as a potential treatment for pain.

Cannabinoid agonists have potential uses in a number of clinical settings, which include pain relief and cancer therapy (Cancer Prev Res (Phila). 2011 January; 4(1): 65-75).

Furthermore, multiple cannabinoid agonists have been approved in the US and other major markets for the treatment of nausea and vomiting related to cancer, and clinical studies have been conducted which evaluate the potential for cannabinoids to be used for anorexia and cachexia associated with cancer.

Compound I has been shown to stimulate appetite in a dose-dependent manner. Compound I acts peripherally on the part of the endocannabinoid system that stimulates hunger and does not cause CNS-psychoactive effects.

Due to the high potency of Compound I, very low therapeutic doses of the active substance (in the microgram range) are required. Pharmaceutical formulations requiring very low amounts of an active substance are difficult to manufacture as it can be difficult to achieve an acceptable level of content uniformity. It is imperative that pharmaceutical formulations have an acceptable content uniformity as it ensures that the patient receiving the pharmaceutical formulation receives the intended dose. This is critical from a safety and an efficacy perspective. In the present case it is anticipated the lowest dose could be as low as 50 µg.

Because of the very low amounts of active substance needed, problems can arise during mixing and formulation of the active substance, for example due to segregation, content uniformity and physical stability. The small quantity of the active substance required must be evenly distributed throughout a powder blend. This is especially difficult if the active substance is poor flowing and/or cohesive.

Furthermore, Compound I is prone to degradation when present in a solution and on exposure to light, see Example 1 herein. This is problematic when considering viable formulations for this active substance. The active substance needs to be stable during manufacturing process of the pharmaceutical formulation and the resultant formulation must also be stable over an extended period of time.

The combination of requiring a low dose of Compound I and its instability in solution present difficulties when it comes to developing a suitable pharmaceutical formulation.

In the present case, an immediate release pharmaceutical formulation comprising Compound I is also required to provide optimal absorption. Thus, there is a need for an immediate release oral dosage form of Compound I with good uniformity of content and good physical and chemical stability over prolonged period of times.

The present disclosure was devised with the foregoing in mind.

SUMMARY OF THE DISCLOSURE

Disclosed herein are pharmaceutical compositions for oral use comprising as an active substance Compound I, or a pharmaceutically acceptable salt thereof, and immediate release pharmaceutical formulations comprising the pharmaceutical composition.

According to a first aspect of the disclosure, there is provided a pharmaceutical composition for oral use comprising as an active substance Compound I, or a pharmaceutically acceptable salt thereof, and a non-aqueous solvent for the active substance.

According to a second aspect of the disclosure, there is provided a pharmaceutical composition for oral use comprising as an active substance Compound I, or a pharmaceutically acceptable salt thereof, wherein the pharmaceutical composition is a semi-solid at room temperature.

According to a further aspect of the disclosure, there is provided a pharmaceutical composition for oral use comprising as an active substance Compound I, or a pharmaceutically acceptable salt thereof, wherein the active substance is stable in the pharmaceutical composition for at least about 2 weeks, about 1 month, about 2 months, about 3 months, about 6 months, about 12 months, or about 24 months.

According to a further aspect of the disclosure, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and b. the pharmaceutical composition is a semi-solid at room temperature.

According to a further aspect of the disclosure, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent.

In a further aspect, there is a method of manufacturing the pharmaceutical composition described herein comprising the step of mixing as an active substance Compound I, or a pharmaceutically acceptable salt thereof, into a non-aqueous solvent.

In a further aspect, there is provided an immediate release pharmaceutical formulation for oral use comprising the pharmaceutical composition as defined herein.

In a further aspect, there is provided a pharmaceutical composition as defined herein or an immediate release pharmaceutical formulation as defined herein for use as a medicament.

Preferred, suitable, and optional features of any one particular aspect of the present disclosure are also preferred, suitable, and optional features of any other aspect.

BRIEF DESCRIPTION OF THE DRAWINGS

For a better understanding of the disclosure, and to show how embodiments of the same are put into effect, reference is now made, by way of example, to the following figures, in which:

FIG. 1: Dissolution profiles in 0.1M HCl for 50 μg active substance capsules (50 mg fill) manufactured with D-α-Tocopherol polyethylene glycol 1000 succinate (Vitamin E TPGS).

FIG. 2: Dissolution profiles in 0.1M HCl for 50 μg active substance capsules (50 mg fill) manufactured with polyethylene glycol (PEG) 1500.

FIG. 3: Dissolution profiles in 0.1M HCl for 200 μg active substance capsules (50 mg fill) manufactured with Vitamin E TPGS.

FIG. 4: Dissolution profiles in 0.1M HCl for 200 μg active substance capsules (50 mg fill) manufactured with PEG 1500.

FIG. 5: Dissolution profiles in 0.1M HCl for 200 μg active substance capsules (200 mg fill) manufactured with Vitamin E TPGS.

FIG. 6: Dissolution profiles in 0.1M HCl for 200 μg active substance capsules (200 mg fill) manufactured with PEG 1500.

FIG. 7: Dissolution profiles in pH 6.8 phosphate buffer for 50 μg active substance capsules (50 mg fill) manufactured with Vitamin E TPGS.

FIG. 8: Dissolution profiles in pH 6.8 phosphate buffer for 50 μg active substance capsules (50 mg fill) manufactured with PEG 1500.

FIG. 9: Dissolution profiles in pH 6.8 phosphate buffer for 200 μg active substance immediate release (IR) capsules (50 mg fill) manufactured with Vitamin E TPGS.

FIG. 10: Dissolution profiles in pH 6.8 phosphate buffer for 200 μg active substance capsules (50 mg fill) manufactured with PEG 1500.

FIG. 11: Dissolution profiles in pH 6.8 phosphate buffer for 200 μg active substance capsules (200 mg fill) manufactured with Vitamin E TPGS FIG. 12: Dissolution profiles in pH 6.8 phosphate buffer for 200 μg active substance capsules (200 mg fill) manufactured with PEG 1500

FIG. 13: % Area of RRT 1.35 peak in vial aliquots of the 50 μg filling fluid as a function of incubation time at 60° C.

FIG. 14: Mean release of active substance (% label claim) from 50 μg capsules versus time in 0.1M HCl and pH 6.8 media.

FIG. 15: Mean release of active substance (% label claim) from 200 μg capsules versus time in 0.1M HCl and pH 6.8 media.

FIG. 16: Mean release of active substance (% of nominal dose) for 0.4% w/w API and solvent capsules (solvent=Vitamin E TPGS, PEG1500, PEG6000, PEG1500:TPGS (1:1), PEG1500:TPGS (9:1), and PEG1500:TPGS (1:9))

FIG. 17: Mean release of active substance (normalised data) for 0.4% w/w API and solvent capsules (solvent=Vitamin E TPGS, PEG1500, PEG6000, PEG1500:TPGS (1:1), PEG1500:TPGS (9:1), and PEG1500:TPGS (1:9))

FIG. 18: Mean release of active substance (% of nominal dose) for single solvent and API capsules FIG. 19: Mean release of active substance (normalised data) for single solvent and API capsules FIG. 20: Mean release of active substance (% of nominal dose) for binary solvent and API capsules FIG. 21: Mean release of active substance (normalised data) for binary solvent and API capsules FIG. 22: Mean release of active substance (% dissolved) from 50 μg capsules stored at 25° C./60% RH in 0.1M HCl FIG. 23: Mean release of active substance (% dissolved) from 50 μg capsules stored at 40° C./75% RH in 0.1M HCl FIG. 24: Mean release of active substance (% dissolved) from 50 μg capsules stored at 25° C./60% RH in pH 6.8 phosphate buffer FIG. 25: Mean release of active substance (% dissolved) from 50 μg capsules stored at 40° C./75% RH in pH 6.8 phosphate buffer FIG. 26: Mean release of active substance (% dissolved) from 200 μg capsules stored at 25° C./60% RH in 0.1M HCl FIG. 27: Mean release of active substance (% dissolved) from 200 μg capsules stored at 40° C./75% RH in 0.1M HCl FIG. 28: Mean release of active substance (% dissolved) from 200 μg capsules stored at 25° C./60% RH in pH 6.8 phosphate buffer FIG. 29: Mean release of active substance (% dissolved) from 200 μg capsules stored at 40° C./75% RH in pH 6.8 phosphate buffer

DETAILED DESCRIPTION OF THE DISCLOSURE

Unless otherwise stated, the following terms used in the specification and claims have the following meanings set out below.

The disclosed compositions, formulations, processes of manufacture and methods may be understood more readily by reference to the following detailed description taken in connection with the accompanying figures, which form a part of this disclosure. It is to be understood that the disclosed compositions, formulations, processes of manufacture and methods are not limited to the specific compositions, formulations, processes of manufacture and methods described and/or shown herein, and that the terminology used herein is for the purpose of describing particular embodiments by way of example only and is not intended to be limiting of the claimed compositions, formulations, processes of manufacture and methods Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

The term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

It is to be appreciated that certain features of the disclosed compositions, formulations, processes of manufacture and methods which are, for clarity, described herein in the context of separate embodiments, may also be provided in combination in a single embodiment. Conversely, various features of the disclosed compositions, formulations processes of manufacture and methods that are, for brevity, described in the context of a single embodiment, may also be provided separately or in any sub-combination.

As used herein, the singular forms "a," "an," and "the" include the plural.

Where a composition is said to comprise a stipulated ingredient, it is to include the composition comprising one type of the stipulated ingredient, or a mixture of types of the stipulated ingredients. For example, said composition may comprise at least one type of the stipulated ingredient, such as at least two types, at least three types, or at least four types. Suitably, the composition comprises one type of the stipulated ingredient, two types of the stipulated ingredients, three types of the stipulated ingredients or four types of the stipulated ingredients.

Where a composition is said to comprise a stipulated ingredient (optionally in a stipulated amount or concentration), said composition may optionally include additional ingredients other than that stipulated. However, in certain embodiments, a composition said to comprise a stipulated ingredient may in fact consist essentially of or consist of all the stipulated ingredient.

Herein, where a composition is said to "consists essentially of" a particular component, said composition suitably comprises at least 70 wt % of said component, suitably at least 80 wt % thereof, suitably at least 90 wt % thereof, suitably at least 95 wt % thereof, most suitably at least 99 wt % thereof. Suitably, a composition said to "consist essentially of" a particular component consists of said component save for one or more trace impurities.

Herein, the term semi-solid is used to indicate a material which is a solid at room temperature and is a liquid at a temperature above room temperature, for example, the material has a melting point of at least about 30° C., such as at least about 35° C., at least about 40° C. Suitably, the material has a melting point between about 35° C. and about 80° C., such as between about 35° C. and about 70° C., about 35° C. and about 60° C., about 35° C. and about 50° C., or about 40° C. and about 50° C. Suitably, the material has a melting point of at least 30° C., such as at least 35° C., at least 40° C. Suitably, the material has a melting point between 35° C. and 80° C., such as between 35° C. and 70° C., 35° C. and 60° C., 35° C. and 50° C., or 40° C. and 50° C.

Room temperature is herein defined as a temperature of about 15° C. to about 25° C., such as about 20° C. to about 25° C. Suitably, room temperature is about 20° C. Suitably, room temperature is 15° C. to 25° C., such as 20° C. to 25° C. Suitably, room temperature is 20° C.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

As used herein, the phrase "therapeutically effective dose" refers to an amount of the pharmaceutical composition or immediate release pharmaceutical formulation comprising the active substance, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of the benign or malignant disease or prevention of the development of the benign or malignant disease, as determined by any means suitable in the art.

As used herein, "subject" includes a vertebrate; mammal, such as primates, humans, dogs, cattle, and horses; or a domestic animal.

Pharmaceutical Compositions

According to a first aspect of the disclosure, there is provided a pharmaceutical composition for oral use comprising as an active substance Compound I, or a pharmaceutically acceptable salt thereof, and a non-aqueous solvent for the active substance.

Suitably, there is provided a pharmaceutical composition for oral use consisting of:

a. as an active substance Compound I, or a pharmaceutically acceptable salt thereof; and
b. a non-aqueous solvent for the active substance.

Suitably, there is provided a pharmaceutical composition for oral use comprising as an active substance Compound I, or a pharmaceutically acceptable salt thereof, and a non-aqueous solvent for the active substance, wherein the pharmaceutical composition is a semi-solid at room temperature.

Suitably, there is provided a pharmaceutical composition for oral use comprising as an active substance Compound I, or a pharmaceutically acceptable salt thereof, and a non-aqueous solvent for the active substance, and wherein the non-aqueous solvent is a semi-solid at room temperature.

Suitably, there is provided a pharmaceutical composition for oral use comprising as an active substance Compound I, or a pharmaceutically acceptable salt thereof, and a non-aqueous solvent for the active substance, wherein the active substance has a solubility in the non-aqueous solvent of at least about 0.1% w/w at room temperature.

Suitably, the non-aqueous solvent comprises polyethylene glycol, ethanol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, oleoyl polyoxylglyceride, propylene glycol mono fatty ester, propylene glycol di fatty acid ester, diethylene glycol monoethyl ether, poloxamer, or vitamin E TPGS or combinations thereof.

Suitably, the non-aqueous solvent comprises polyethylene glycol, stearoyl polyoxylglyceride, polyoxyethylene stearate, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, or poloxamer or combinations thereof.

Suitably, there is provided a pharmaceutical composition for oral use comprising as an active substance Compound I, or a pharmaceutically acceptable salt thereof, and a non-aqueous solvent for the active substance, wherein the active substance has a solubility in the non-aqueous solvent of at least about 0.1% w/w at room temperature, and the pharmaceutical composition is a semi-solid at room temperature.

Suitably, there is provided a pharmaceutical composition for oral use comprising as an active substance Compound I, or a pharmaceutically acceptable salt thereof, and a non-aqueous solvent for the active substance, wherein the active substance is dissolved in the non-aqueous solvent.

Suitably, there is provided a pharmaceutical composition for oral use comprising as an active substance Compound I, or a pharmaceutically acceptable salt thereof, and a non-aqueous solvent for the active substance, wherein the non-aqueous solvent is water soluble.

Suitably, there is provided a pharmaceutical composition for oral use comprising as an active substance Compound I, or a pharmaceutically acceptable salt thereof, and a non-aqueous solvent for the active substance, wherein the pharmaceutical composition comprises at least about 20% w/w of the non-aqueous solvent by weight of the total pharmaceutical composition, such as at least about 30% w/w, at least about 40% w/w, at least about 50% w/w, at least about 60% w/w, at least about 70% w/w, at least about 80% w/w, at least about 90% w/w, at least about 95% w/w, at least about 96% w/w, at least about 97% w/w, at least about 98% w/w, at least about 99% w/w, at least about 99.2% w/w, or at least about 99.5% w/w.

Suitably, there is provided a pharmaceutical composition for oral use comprising as an active substance Compound I, or a pharmaceutically acceptable salt thereof, and a non-aqueous solvent for the active substance, wherein the pharmaceutical composition comprises between about 20 and about 99.99% w/w of the non-aqueous solvent by weight of the total pharmaceutical composition, such as between about 30 and about 99.99% w/w, about 40 and about 99.99% w/w, about 50 and about 99.99% w/w, about 60 and about 99.99% w/w, about 70 and about 99.99% w/w, about 80 and about 99.99% w/w, about 90 and about 99.99% w/w, about 95 and about 99.99% w/w, about 96 and about 99.99% w/w, about 97 and about 99.99% w/w, about 98 and about 99.99% w/w, about 99 and about 99.99% w/w, about 99.2 and about 99.99% w/w, or about 99.5 and about 99.99% w/w.

Suitably, there is provided a pharmaceutical composition for oral use comprising as an active substance Compound I, or a pharmaceutically acceptable salt thereof, and a non-aqueous solvent for the active substance, wherein the pharmaceutical composition comprises at least about 20% w/w of the non-aqueous solvent by weight of the total pharmaceutical composition, and between about 0.001 and about 0.8% w/w of the active substance by weight of the total pharmaceutical composition.

Suitably, there is provided a pharmaceutical composition for oral use comprising as an active substance Compound I, or a pharmaceutically acceptable salt thereof, and a non-aqueous solvent for the active substance, wherein the pharmaceutical composition comprises between about 20 and about 99.99% w/w of the non-aqueous solvent by weight of the total pharmaceutical composition, and between about 0.001 and about 0.8% w/w of the active substance by weight of the total pharmaceutical composition.

Suitably, there is provided a pharmaceutical composition for oral use comprising as an active substance Compound I, or a pharmaceutically acceptable salt thereof, and a non-aqueous solvent for the active substance, wherein the non-aqueous solvent comprises polyethylene glycol.

Suitably, there is provided a pharmaceutical composition for oral use comprising as an active substance Compound I, or a pharmaceutically acceptable salt thereof, and a non-aqueous solvent for the active substance, wherein the non-aqueous solvent comprises polyethylene glycol wherein the polyethylene glycol has an average molecular weight between about 200 and about 25000 g/mol, such as between about 400 and about 6000 g/mol, such as between about 1000 and about 6000 g/mol, such as between about 1200 and about 1800 g/mol, such as between about 1400 and about 1600 g/mol. Suitably, the polyethylene glycol has an average molecular weight of about 400 g/mol, about 1500 g/mol, about 4000 g/mol, or about 6000 g/mol.

Suitably, there is provided a pharmaceutical composition for oral use comprising as an active substance Compound I, or a pharmaceutically acceptable salt thereof, and a non-aqueous solvent for the active substance, wherein:

a. the non-aqueous solvent is polyethylene glycol;
b. the pharmaceutical composition comprises between about 20 and about 99.99% w/w of the non-aqueous solvent by weight of the total pharmaceutical composition; and
c. the pharmaceutical composition comprises between about 0.001 and about 0.8% w/w of the active substance by weight of the total pharmaceutical composition.

Suitably, there is provided a pharmaceutical composition for oral use comprising as an active substance Compound I, or a pharmaceutically acceptable salt thereof, and a non-aqueous solvent for the active substance, wherein:

a. the non-aqueous solvent is polyethylene glycol wherein the polyethylene glycol has an average molecular weight between about 200 and about 25000 g/mol;
b. the pharmaceutical composition comprises between about 50 and about 99.99% w/w of the non-aqueous solvent by weight of the total pharmaceutical composition; and
c. the pharmaceutical composition comprises between about 0.01 and about 0.8% w/w of the active substance by weight of the total pharmaceutical composition.

Suitably, there is provided a pharmaceutical composition for oral use comprising as an active substance Compound I, or a pharmaceutically acceptable salt thereof, and a non-aqueous solvent for the active substance, wherein:

a. the non-aqueous solvent is polyethylene glycol wherein the polyethylene glycol has an average molecular weight between about 1000 and about 6000 g/mol;
b. the pharmaceutical composition comprises between about 50 and about 99.99% w/w of the non-aqueous solvent by weight of the total pharmaceutical composition; and
c. the pharmaceutical composition comprises between about 0.01 and about 0.8% w/w of the active substance by weight of the total pharmaceutical composition.

Suitably, there is provided a pharmaceutical composition for oral use comprising as an active substance Compound I, or a pharmaceutically acceptable salt thereof, a non-aqueous solvent for the active substance and vitamin E TPGS; wherein the non-aqueous solvent comprises polyethylene glycol.

Suitably, there is provided a pharmaceutical composition for oral use comprising as an active substance Compound I, or a pharmaceutically acceptable salt thereof, and a non-aqueous solvent for the active substance, wherein the active substance is stable in the pharmaceutical composition for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, and a non-aqueous solvent for the active substance, wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or
b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, and a non-aqueous solvent for the active substance, wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, there is provided a pharmaceutical composition for oral use comprising as an active substance Compound I, or a pharmaceutically acceptable salt thereof, and a non-aqueous solvent for the active substance, wherein the active substance is homogeneously distributed throughout the non-aqueous solvent.

According to a second aspect of the disclosure, there is provided a pharmaceutical composition for oral use comprising as an active substance Compound I, or a pharmaceutically acceptable salt thereof, wherein the pharmaceutical composition is a semi-solid at room temperature.

A semi-solid is any material which at room temperature is a solid and at a temperature above room temperature is a liquid. Suitably, room temperature is about 15° C. to about 25° C., such as about 20° C. to about 25° C. Suitably, room temperature is about 20° C. Suitably, room temperature is 15° C. to 25° C., such as 20° C. to 25° C. Suitably, room temperature is 20° C.

Advantageously, the semi-solid nature of the pharmaceutical composition facilitates the continued uniform distribution of the active substance within the non-aqueous solvent upon storage, and/or an acceptable stability profile of the pharmaceutical composition as the active substance is dispersed/dissolved in a semi-solid within the pharmaceutical composition at typical storage conditions, i.e., room temperature. Furthermore, during manufacture the pharmaceutical composition is a liquid which facilitates the uniform distribution of the active substance throughout the pharmaceutical composition.

Suitably, there is provided a pharmaceutical composition for oral use comprising as an active substance Compound I, or a pharmaceutically acceptable salt thereof, wherein the pharmaceutical composition is a semi-solid at room temperature and has a melting point of at least about 30° C., such as at least about 35° C., or at least about 40° C.

Suitably, there is provided a pharmaceutical composition for oral use comprising as an active substance Compound I, or a pharmaceutically acceptable salt thereof, wherein the pharmaceutical composition is a semi-solid at room temperature and has a melting point between about 35° C. and about 80° C., such as between about 35° C. and about 70° C., about 35° C. and about 60° C., about 35° C. and about 50° C., or about 40° C. and about 50° C.

Suitably, there is provided a pharmaceutical composition for oral use comprising as an active substance Compound I, or a pharmaceutically acceptable salt thereof, wherein the pharmaceutical composition is a semi-solid at room temperature and the pharmaceutical composition comprises a non-aqueous solvent for the active substance.

Suitably, there is provided a pharmaceutical composition for oral use comprising as an active substance Compound I, or a pharmaceutically acceptable salt thereof, wherein the pharmaceutical composition is a semi-solid at room temperature and wherein the active substance is stable in the pharmaceutical for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein the pharmaceutical composition is a semi-solid at room temperature and wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein the pharmaceutical composition is a semi-solid at room temperature and wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, there is provided a pharmaceutical composition for oral use comprising as an active substance Compound I, or a pharmaceutically acceptable salt thereof, and a non-aqueous solvent for the active substance wherein the pharmaceutical composition is a semi-solid at room temperature and the active substance is homogeneously distributed throughout the non-aqueous solvent.

According to a further aspect of the disclosure, there is provided a pharmaceutical composition for oral use comprising as an active substance Compound I, or a pharmaceutically acceptable salt thereof, wherein the active substance is stable in the pharmaceutical composition for at least about 2 weeks, about 1 month, about 2 months, about 3 months, about 6 months, about 12 months, or about 24 months.

Advantageously, the active substance is stable in the pharmaceutical composition. Stability of a pharmaceutical composition is required to ensure the end user, i.e., the patient, receives the intended dose of the active substance and is not exposed to degradants of the active substance. This is critical from a patient safety and efficacy perspective. Furthermore, a stable pharmaceutical composition which does not require special storage conditions, for example, refrigerated storage, is advantageous as means supply chains are simpler and/or cheaper.

Suitably, there is provided a pharmaceutical composition for oral use comprising as an active substance Compound I, or a pharmaceutically acceptable salt thereof, wherein the active substance is stable in the pharmaceutical composition for at least 2 weeks, 1, 2, 3, 6, 12, or 24 months.

Suitably, there is provided a pharmaceutical composition for oral use comprising as an active substance Compound I, or a pharmaceutically acceptable salt thereof, wherein the active substance is stable in the pharmaceutical composition when the pharmaceutical composition is stored at 25° C./60% RH and/or 40° C./75% RH for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein the active substance is stable in the pharmaceutical composition when the pharmaceutical composition is stored at 25° C./60% RH and/or 40° C./75% RH for 2 weeks, 1, 2, 3, 6, 12, or 24 months.

Suitably, there is provided a pharmaceutical composition for oral use comprising as an active substance Compound I, or a pharmaceutically acceptable salt thereof, wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein:

a. the total amount of degradation products of the active substance is less than or equal to about 3 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 95 to about 105% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein:

a. the total amount of degradation products of the active substance is less than or equal to about 2 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 95 to about 105% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

There is provided a pharmaceutical composition for oral use comprising as an active substance Compound I, or a pharmaceutically acceptable salt thereof, wherein the active substance is stable in the pharmaceutical composition for at least about 2 weeks, about 1 month, about 2 months, about 3 months, about 6 months, about 12 months, or about 24 months, and wherein the pharmaceutical composition is a semi-solid at room temperature.

Suitably, the non-aqueous solvent comprises polyethylene glycol, stearoyl polyoxylglyceride, medium chain fatty acid, medium chain monoglyceride, medium chain diglyceride, polyoxyethylene castor oil derivative, polyoxyethylene sorbitan fatty acid ester, polyoxyethylated 12-hydroxystearic acid, propylene glycol di fatty acid ester, diethylene glycol monoethyl ether, or poloxamer or combinations thereof. Suitably, the polyoxyethylene castor oil derivative comprises polyoxyl 40 hydrogenated castor oil. Suitably, the polyoxyethylene castor oil derivative is polyoxyl 40 hydrogenated castor oil.

Suitably, the non-aqueous solvent comprises polyethylene glycol, stearoyl polyoxylglyceride, polyoxyethylene stearate, medium chain monoglyceride, medium chain diglyceride, polyoxyethylene sorbitan fatty acid ester, propylene glycol di fatty acid ester, or combinations thereof.

Suitably, there is provided a pharmaceutical composition for oral use comprising as an active substance Compound I, or a pharmaceutically acceptable salt thereof, wherein the active substance is stable in the pharmaceutical composition for at least about 2 weeks, about 1 month, about 2 months, about 3 months, about 6 months, about 12 months, or about 24 months, and wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

There is provided a pharmaceutical composition for oral use comprising as an active substance Compound I, or a pharmaceutically acceptable salt thereof, and a non-aqueous solvent for the active substance wherein the active substance is stable in the pharmaceutical composition for at least about 2 weeks, about 1 month, about 2 months, about 3 months, about 6 months, about 12 months, or about 24 months.

There is provided a pharmaceutical composition for oral use comprising as an active substance Compound I, or a pharmaceutically acceptable salt thereof, and a non-aqueous solvent for the active substance wherein the active substance is stable in the pharmaceutical composition for at least about 2 weeks, about 1 month, about 2 months, about 3 months, about 6 months, about 12 months, or about 24 months, and wherein active substance is homogeneously dispersed throughout the non-aqueous solvent.

According to a further aspect of the disclosure, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and
b. the pharmaceutical composition is a semi-solid at room temperature.

Advantageously, the release rate of the active substance from the pharmaceutical composition provides optimal absorption of the pharmaceutical composition upon oral administration to a patient.

Suitably, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm;
b. the pharmaceutical composition is a semi-solid at room temperature; and
c. the pharmaceutical composition comprises a non-aqueous solvent.

Suitably, the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, poloxamer, vitamin E TPGS or combinations thereof.

Suitably, the non-aqueous solvent comprises polyethylene glycol, polyoxyethylene stearate, polyoxyethylene castor oil derivative, polyoxyethylated 12-hydroxystearic acid, diethylene glycol monoethyl ether, or poloxamer, vitamin E TPGS, or combinations thereof.

Suitably, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 30 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and
b. the pharmaceutical composition is a semi-solid at room temperature.

Suitably, there is provided a pharmaceutical composition for oral use comprising as an active substance Compound I, or a pharmaceutically acceptable salt thereof, wherein:

a. at least about 85% of the total amount of the active substance contained in the pharmaceutical composition is released within about the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and
b. the pharmaceutical composition is a semi-solid at room temperature.

Suitably, there is provided a pharmaceutical composition for oral use comprising as an active substance Compound I, or a pharmaceutically acceptable salt thereof, wherein:

a. at least about 85% of the total amount of the active substance contained in the pharmaceutical composition is released within about the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm;
b. the pharmaceutical composition is a semi-solid at room temperature; and
c. the pharmaceutical comprises a non-aqueous solvent.

Suitably, the non-aqueous solvent comprises polyethylene glycol, stearoyl polyoxylglyceride, medium chain fatty acid, long chain monoglyceride, long chain diglyceride, medium chain monoglyceride, medium chain diglyceride, polyoxyethylene sorbitan fatty acid ester, caprylocaproyl polyoxylglyceride, propylene glycol mono fatty ester, propylene glycol di fatty acid ester, diethylene glycol monoethyl ether, poloxamer, or combinations thereof.

Suitably, the non-aqueous solvent comprises polyethylene glycol, polyoxyethylene castor oil derivative, polyoxyethylated 12-hydroxystearic acid, diethylene glycol monoethyl ether, or poloxamer, or combinations thereof.

Suitably, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm;
b. the pharmaceutical composition is a semi-solid at room temperature; and
c. the active substance is stable in the pharmaceutical composition for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm;
b. the pharmaceutical composition is a semi-solid at room temperature; and
c. the pharmaceutical composition has a melting point between about 35° C. and about 80° C.

Suitably, there is provided a pharmaceutical composition for oral use comprising as an active substance Compound I, or a pharmaceutically acceptable salt thereof, and a non-aqueous solvent for the active substance wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and
b. the pharmaceutical composition is a semi-solid at room temperature.

Suitably, there is provided a pharmaceutical composition for oral use comprising as an active substance Compound I, or a pharmaceutically acceptable salt thereof, and a non-aqueous solvent for the active substance wherein:

a. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm;
b. the pharmaceutical composition is a semi-solid at room temperature; and
c. the active substance is homogenously distributed throughout the non-aqueous solvent.

According to a further aspect of the disclosure, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent.

Advantageously, the active substance is uniformly dispersed within the pharmaceutical composition. This ensures the required amount of the active substance is present in the portion of the pharmaceutical composition, for example, upon dosing of the pharmaceutical composition to a patient, or the use of the pharmaceutical composition in the preparation of an immediate release pharmaceutical formulation. This is important from a patient safety and efficacy perspective.

Suitably, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent for at least about 2 weeks, about 1 month, about 2 months, about 3 months, about 6 months, about 12 months, or about 24 months.

Suitably, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent for at least about 2 weeks, about 1 month, about 2 months, about 3 months, about 6 months, about 12 months, or about 24 months upon storage of the pharmaceutical composition at room temperature.

Suitably, there is provided a pharmaceutical composition for oral use comprising as an active substance Compound I, or a pharmaceutically acceptable salt thereof, and a non-aqueous solvent for the active substance wherein:

a. the active substance is homogenously distributed throughout the non-aqueous solvent; and
b. the homogeneous distribution of the active substance in the non-aqueous solvent is determined by determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

Suitably, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent and the pharmaceutical composition is a semi-solid at room temperature.

Suitably, there is provided a pharmaceutical composition for oral use comprising as an active substance Compound I, or a pharmaceutically acceptable salt thereof, and a non-aqueous solvent for the active substance wherein the active substance is homogenously distributed throughout the non-aqueous solvent and the active substance is stable in the pharmaceutical composition for at least about 2 weeks, about 1 month, about 2 months, about 3 months, about 6 months, about 12 months, or about 24 months.

Suitably, there is provided a pharmaceutical composition for oral use comprising as an active substance N-(2-(tert-butyl)-1-((4,4-difluorocyclohexyl)methyl)-1H-benzimidazol-5-yl)ethanesulfonamide, or a pharmaceutically acceptable salt thereof, and a non-aqueous solvent for the active substance wherein the active substance is homogenously distributed throughout the non-aqueous solvent and wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Pharmaceutical Formulations

In one aspect, there is provided a pharmaceutical formulation comprising the pharmaceutical composition as defined herein.

In a further aspect, there is provided an immediate release pharmaceutical formulation for oral use comprising the pharmaceutical composition as defined herein.

Suitably, the immediate release pharmaceutical formulation comprises a capsule shell and the pharmaceutical composition as defined herein.

Suitably, the immediate release pharmaceutical formulation consists of the pharmaceutical composition.

Suitably, there is provided an immediate release pharmaceutical formulation for oral use comprising the pharmaceutical composition as defined herein wherein when the immediate release pharmaceutical formulation is subjected to a content uniformity test as described in the European Pharmacopeia the acceptance value is less than 15.

Advantageously, having a good content uniformity ensures each dosage form of the immediate release pharmaceutical formulation contains the intended quantity of the active substance. This is critical from a patient safety and efficacy perspective.

Suitably, there is provided an immediate release pharmaceutical formulation for oral use comprising the pharmaceutical composition as defined herein wherein the immediate release pharmaceutical formulation is an immediate release capsule formulation. Suitably, the immediate release capsule formulation comprises a capsule shell.

Suitably, there is provided an immediate release pharmaceutical formulation for oral use comprising the pharmaceutical composition as defined herein wherein the immediate release pharmaceutical formulation is an immediate release spray formulation.

Suitably, there is provided an immediate release pharmaceutical formulation for oral use comprising the pharmaceutical composition as defined herein wherein the immediate release formulation comprises between about 10 μg and about 1000 μg of the active substance, such as between about 10 μg and about 500 μg, about 20 μg and about 500 μg, about 30 μg and about 300 μg, or about 40 μg and about 250 μg.

Suitably, there is provided an immediate release pharmaceutical formulation for oral use comprising the pharmaceutical composition as defined herein wherein the immediate release formulation comprises about 50 μg or about 200 μg of the active substance Suitably, there is provided an immediate release pharmaceutical formulation for oral use comprising a pharmaceutical composition wherein the pharmaceutical composition comprises as an active substance Compound I, or a pharmaceutically acceptable salt thereof, and a non-aqueous solvent for the active substance.

Suitably, there is provided an immediate release pharmaceutical formulation for oral use comprising a pharmaceutical composition wherein the pharmaceutical composition comprises as an active substance Compound I, or a pharmaceutically acceptable salt thereof, and a non-aqueous solvent for the active substance, and wherein the immediate release pharmaceutical formulation is an immediate release capsule formulation.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof and a non-aqueous solvent for the active substance; and
b. the non-aqueous solvent comprises polyethylene glycol.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof and a non-aqueous solvent for the active substance;
b. the non-aqueous solvent is polyethylene glycol wherein the polyethylene glycol has an average molecular weight between about 1000 and about 6000 g/mol;
c. the pharmaceutical composition comprises between about 50 and about 99.99% w/w of the non-aqueous solvent by weight of the total pharmaceutical composition; and
d. the pharmaceutical composition comprises between about 0.01 and about 0.8% w/w of the active substance by weight of the total pharmaceutical composition.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof and a non-aqueous solvent for the active substance;
b. the non-aqueous solvent is polyethylene glycol wherein the polyethylene glycol has an average molecular weight between 1000 and 6000 g/mol;
c. the pharmaceutical composition comprises between 50 and 99.99% w/w of the non-aqueous solvent by weight of the total pharmaceutical composition; and
d. the pharmaceutical composition comprises between 0.01 and 0.8% w/w of the active substance by weight of the total pharmaceutical composition.

Suitably, there is provided an immediate release pharmaceutical formulation for oral use comprising a pharmaceutical composition wherein the pharmaceutical composition comprises as an active substance Compound I, or a pharmaceutically acceptable salt thereof, and wherein the pharmaceutical composition is a semi-solid at room temperature.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof; and b. the active substance is stable in the pharmaceutical composition for at least about 2 weeks, about 1 month, about 2 months, about 3 months, about 6 months, about 12 months, or about 24 months.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof; and b. at least about 75% of the total amount of the active substance contained in the immediate release pharmaceutical formulation is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof; and b. at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, there is provided an immediate release pharmaceutical formulation for oral use comprising a pharmaceutical composition wherein:

a. the pharmaceutical composition comprises as an active substance Compound I, or a pharmaceutically acceptable salt thereof and a non-aqueous solvent for the active substance; and b. the active substance is homogenously distributed throughout the non-aqueous solvent.

Active Substance

The active substance is N-(2-(tert-butyl)-1-((4,4-difluorocyclohexyl)methyl)-1H-benzimidazol-5-yl)ethanesulfonamide (Compound I) or a pharmaceutically acceptable salt thereof.

Suitably, the pharmaceutical composition comprises between about 0.001 and about 0.8% w/w of the active substance by weight of the total pharmaceutical composition, such as between about 0.01 and about 0.8% w/w, about 0.05 and about 0.6% w/w, about 0.08 and about 0.5% w/w, or about 0.1 and about 0.4% w/w. Suitably, the pharmaceutical composition comprises between 0.001 and 0.8% w/w of the active substance by weight of the total pharmaceutical composition, such as between 0.01 and 0.8% w/w, 0.05 and 0.6% w/w, 0.08 and 0.5% w/w, or 0.1 and 0.4% w/w.

Suitably, the pharmaceutical composition comprises about 0.1% w/w of the active substance by weight of the total pharmaceutical composition. Suitably, the pharmaceutical composition comprises about 0.4% w/w of the active substance by weight of the total pharmaceutical composition. Suitably, the pharmaceutical composition comprises 0.1% w/w of the active substance by weight of the total pharmaceutical composition. Suitably, the pharmaceutical composition comprises 0.4% w/w of the active substance by weight of the total pharmaceutical composition.

Suitably, the pharmaceutical composition comprises between about 0.001 and about 0.8% w/w of the active substance by weight of the total pharmaceutical composition and at least about 20% w/w of the non-aqueous solvent by weight of the total pharmaceutical composition. Suitably, the pharmaceutical composition comprises between 0.001 and 0.8% w/w of the active substance by weight of the total pharmaceutical composition and at least 20% w/w of the non-aqueous solvent by weight of the total pharmaceutical composition.

Suitably, the pharmaceutical composition comprises between about 0.001 and about 0.8% w/w of the active substance by weight of the total pharmaceutical composition and at least about 50% w/w of the non-aqueous solvent by weight of the total pharmaceutical composition. Suitably, the pharmaceutical composition comprises between 0.001 and 0.8% w/w of the active substance by weight of the total pharmaceutical composition and at least 50% w/w of the non-aqueous solvent by weight of the total pharmaceutical composition.

Suitably, the pharmaceutical composition comprises between about 0.01 and about 0.8% w/w of the active substance by weight of the total pharmaceutical composition and at least about 50% w/w of the non-aqueous solvent by weight of the total pharmaceutical composition. Suitably, the pharmaceutical composition comprises between 0.01 and 0.8% w/w of the active substance by weight of the total pharmaceutical composition and at least 50% w/w of the non-aqueous solvent by weight of the total pharmaceutical composition.

Suitably, the pharmaceutical composition comprises between about 0.001 and about 0.8% w/w of the active substance by weight of the total pharmaceutical composition and at least about 90% w/w of the non-aqueous solvent by weight of the total pharmaceutical composition. Suitably, the pharmaceutical composition comprises between 0.001 and 0.8% w/w of the active substance by weight of the total pharmaceutical composition and at least 90% w/w of the non-aqueous solvent by weight of the total pharmaceutical composition.

Suitably, the pharmaceutical composition comprises between about 0.1 and about 0.4% w/w of the active substance by weight of the total pharmaceutical composition and at least about 90% w/w of the non-aqueous solvent by weight of the total pharmaceutical composition. Suitably, the pharmaceutical composition comprises between 0.1 and 0.4% w/w of the active substance by weight of the total pharmaceutical composition and at least 90% w/w of the non-aqueous solvent by weight of the total pharmaceutical composition.

Non-Aqueous Solvent for the Active Substance

Suitably, there is provided a pharmaceutical composition for oral use comprising as an active substance N-(2-(tert-butyl)-1-((4,4-difluorocyclohexyl)methyl)-1H-benzimidazol-5-yl)ethanesulfonamide, or a pharmaceutically acceptable salt thereof, and a non-aqueous solvent for the active substance.

Suitably, the pharmaceutical composition comprises at least one non-aqueous solvent, such as at least two, at least three, or at least four. Suitably, the pharmaceutical composition comprises one non-aqueous solvent, two non-aqueous solvents, three non-aqueous solvents or four non-aqueous solvents. Suitably, the pharmaceutical composition comprises a mixture of non-aqueous solvents.

Suitably, the active substance has a solubility in the non-aqueous solvent of at least about 0.1% w/w at room temperature, such as at least about 0.2% w/w, at least about 0.5% w/w, or at least about 1.0% w/w. Suitably, the active substance has a solubility in the non-aqueous solvent of about 0.1% w/w to about 50% w/w, such as about 0.1% w/w to about 25% w/w, or about 0.1% w/w to about 10% w/w. Suitably, the active substance has a solubility in the non-aqueous solvent of at least 0.1% w/w at room temperature, such as at least 0.2% w/w, at least 0.5% w/w, or at least 1.0% w/w. Suitably, the active substance has a solubility in the non-aqueous solvent of 0.1% w/w to 50% w/w, such as 0.1% w/w to 25% w/w, or 0.1% w/w to 10% w/w.

Suitably, the active substance is dispersed in the non-aqueous solvent at room temperature.

Suitably, the active substance is dissolved in the non-aqueous solvent at room temperature.

Suitably, at least about 85% by weight of the active substance is dissolved in the non-aqueous solvent at room temperature, such as at least about 90% by weight, at least about 95% by weight, at least about 99% by weight, or at least about 99.9% by weight. Suitably, at least 85% by weight of the active substance is dissolved in the non-aqueous solvent at room temperature, such as at least 90% by weight, at least 95% by weight, at least 99% by weight, or at least 99.9% by weight Suitably, all of the active substance is dissolved in the non-aqueous solvent at room temperature. The skilled person would know how to assess whether the active substance is dissolved in the non-aqueous solvent, for example, this may be assessed by eye or microscopy.

Suitably, the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, poloxamer, vitamin E TPGS or combinations thereof.

Suitably, the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, poloxamer, or combinations thereof.

Suitably, the non-aqueous solvent comprises polyethylene glycol, ethanol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, oleoyl polyoxylglyceride, propylene glycol mono fatty ester, propylene glycol di fatty acid ester, diethylene glycol monoethyl ether, poloxamer, or vitamin E TPGS or combinations thereof. Suitably, the polyoxyethylene castor oil derivative comprises polyoxyl 40 hydrogenated castor oil. Suitably, the polyoxyethylene castor oil derivative is polyoxyl 40 hydrogenated castor oil.

Suitably, the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, poloxamer, vitamin E TPGS or combinations thereof. Suitably, the polyoxyethylene castor oil derivative comprises polyoxyl 40 hydrogenated castor oil. Suitably, the polyoxyethylene castor oil derivative is polyoxyl 40 hydrogenated castor oil.

Suitably, the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, or poloxamer or combinations thereof, wherein the polyethylene glycol has an average molecular weight of about 400 g/mol or about 1500 g/mol and is super-refined as defined herein.

Suitably, the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, or poloxamer or combinations thereof, wherein the polyethylene glycol is has an average molecular weight between about 1000 and about 25000 g/mol, such as between about 1000 and about 6000 g/mol, about 1200 and about 1800 g/mol, about 1400 and about 1600 g/mol.

Suitably, the non-aqueous solvent comprises polyethylene glycol, stearoyl polyoxylglyceride, medium chain fatty acid, medium chain monoglyceride, medium chain diglyceride, polyoxyethylene castor oil derivative, polyoxyethylene sorbitan fatty acid ester, polyoxyethylated 12-hydroxystearic acid, propylene glycol di fatty acid ester, diethylene glycol monoethyl ether, or poloxamer or combinations thereof. Suitably, the polyoxyethylene castor oil derivative comprises polyoxyl 40 hydrogenated castor oil. Suitably, the polyoxyethylene castor oil derivative is polyoxyl 40 hydrogenated castor oil Suitably, the non-aqueous solvent comprises polyethylene glycol, stearoyl polyoxylglyceride, polyoxyethylene stearate, medium chain monoglyceride, medium chain diglyceride, polyoxyethylene sorbitan fatty acid ester, propylene glycol di fatty acid ester, or combinations thereof.

Suitably, the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, or poloxamer or combinations thereof.

Suitably, the non-aqueous solvent comprises polyethylene glycol, stearoyl polyoxylglyceride, medium chain fatty acid, long chain monoglyceride, long chain diglyceride, medium chain monoglyceride, medium chain diglyceride, polyoxyethylene sorbitan fatty acid ester, caprylocaproyl polyoxylglyceride, propylene glycol mono fatty ester, propylene glycol di fatty acid ester, diethylene glycol monoethyl ether, or poloxamer or combinations thereof.

Suitably, the non-aqueous solvent comprises polyethylene glycol, polyoxyethylene stearate, polyoxyethylene castor oil derivative, polyoxyethylated 12-hydroxystearic acid, diethylene glycol monoethyl ether, or poloxamer, vitamin E TPGS, or combinations thereof.

Suitably, the non-aqueous solvent comprises polyethylene glycol, polyoxyethylene castor oil derivative, polyoxyethylated 12-hydroxystearic acid, diethylene glycol monoethyl ether, or poloxamer, or combinations thereof.

Suitably, the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

Suitably, the non-aqueous solvent comprises polyethylene glycol, stearoyl polyoxylglyceride, or polyoxyethylene stearate or combinations thereof.

Suitably, the non-aqueous solvent is water soluble. Solubility is determined at room temperature. Water solubility in this context is defined as at least 1 part of the non-aqueous solvent is soluble in 10 to 30 parts of water, for example at least 1 part of the non-aqueous solvent is soluble in 1 to 10 parts of water, or at least 1 part of the non-aqueous solvent is soluble in less than 1 part of water. Sparingly soluble is defined as 1 part of the non-aqueous solvent is soluble in 30 to 100 parts of water. Slightly soluble is defined as 1 part of the non-aqueous solvent is soluble in 100 to 1000 parts of water. Very slightly soluble is defined as 1 part of the non-aqueous solvent is soluble in 1000 to 10000 parts of water. Practically insoluble or insoluble is defined as 1 part of the non-aqueous solvent is soluble in more than 10000 parts of water.

Suitably, the non-aqueous solvent is miscible with water. Miscibility is herein defined as when the non-aqueous solvent forms a homogeneous mixture when added to water at room temperature.

Suitably, the non-aqueous solvent comprises polyethylene glycol, propylene glycol, ethanol, glycerol, polyoxyethylene castor oil derivative, polyoxyethylene sorbitan fatty acid ester, polyoxyethylated 12-hydroxystearic acid, or poloxamer or combinations thereof.

Suitably, the non-aqueous solvent comprises polyethylene glycol.

Suitably, the non-aqueous solvent consists essentially of polyethylene glycol.

Suitably, the non-aqueous solvent consists of polyethylene glycol.

Suitably, the polyethylene glycol has an average molecular weight between about 200 and about 25000 g/mol, such as between about 300 and about 10000 g/mol, about 400 and about 6000 g/mol, about 1000 and about 6000 g/mol, about 1200 and about 1800 g/mol, about 1400 and about 1600 g/mol. Suitably, the polyethylene glycol has an average molecular weight between 200 and 25000 g/mol, such as between 300 and 10000 g/mol, 400 and 6000 g/mol, 1000 and 6000 g/mol, 1200 and 1800 g/mol, or 1400 and 1600 g/mol.

The skilled person would be able to determine the average molecular weight of polyethylene glycol. For example, molecular weight assay analytical tests are disclosed in US Pharmacopeia Monograph for polyethylene glycol.

Suitably, the average molecular weight of polyethylene glycol can be determined using the following assay:

Phthalic anhydride solution: Place 49.0 g of phthalic anhydride into an amber bottle, and dissolve in 300 mL of pyridine from a freshly opened bottle or pyridine that has been freshly distilled over phthalic anhydride. Shake vigorously until completely dissolved. Add 7 g of imidazole, swirl carefully to dissolve, and allow to stand for 16 h before using.

Sample solution for liquid Polyethylene Glycols: Carefully introduce 25.0 mL of the Phthalic anhydride solution into a dry, heat-resistant pressure bottle. Add an amount of the specimen equivalent to its expected average molecular weight divided by 160. Insert the stopper in the bottle, and wrap it securely in a cloth bag.

Sample solution for solid Polyethylene Glycols: Carefully introduce 25.0 mL of Phthalic anhydride solution into a dry, heat-resistant pressure bottle. Add an amount of the specimen equivalent to its expected molecular weight divided by 160; however, because of limited solubility, do not use more than 25 g. Add 25 mL of pyridine, from a freshly opened bottle or pyridine that has been freshly distilled over phthalic anhydride. Swirl to dissolve, insert the stopper in the bottle, and wrap it securely in a cloth bag.

Blank: 25.0 mL of Phthalic anhydride solution plus any additional pyridine added to the bottle Analysis: Immerse the bottle in a water bath maintained at a temperature between 96° and 100°, to the same depth as that of the mixture in the bottle. Remove the bottles the bath after 5 min and, without unwrapping, swirl for 30 s to homogenize. Heat in the water bath for 30 min (60 min for Polyethylene Glycols having molecular weights of 3000 or more), then remove from the bath, and allow it to cool to room temperature. Uncap the bottle carefully to release any pressure, remove from the bag, add 10 mL of water and swirl thoroughly. Wait 2 min, add 0.5 mL of a solution of phenolphthalein in pyridine (1 in 100), and titrate with 0.5 N sodium hydroxide VS to the first pink colour that persists for 15 s. Perform a blank determination.

Calculate the average molecular weight taken:

$$Result = (2000 \times W)/[(V_B - V_S) \times N]$$

W=weight of the Polyethylene Glycol taken for the Sample solution (g)

$V_B$=volume of 0.5 N sodium hydroxide consumed by the Blank (mL)

$V_S$=volume of 0.5 N sodium hydroxide consumed by the specimen (mL)

N=normality of the sodium hydroxide solution

Suitably, the polyethylene glycol has an average molecular weight of about 400, about 1000, about 1500, about 1540, about 2000, about 3000, about 4000, about 6000, about 8000, or about 20000 g/mol. Suitably, the polyethylene glycol has an average molecular weight of 400, 1000, 1500, 1540, 2000, 3000, 4000, 6000, 8000, or 20000 g/mol.

Suitably, the polyethylene glycol has an average molecular weight of about 400, about 1500, about 4000, or about 6000 g/mol. Suitably, the polyethylene glycol has an average molecular weight of 400, 1500, 4000, or 6000 g/mol.

Suitably, the polyethylene glycol has an average molecular weight of about 400 g/mol. Suitably, the polyethylene glycol has an average molecular weight of about 1500 g/mol. Suitably, the polyethylene glycol has an average molecular weight of about 4000 g/mol. Suitably, the polyethylene glycol has an average molecular weight of about 6000 g/mol. Suitably, the polyethylene glycol has an average molecular weight of 400 g/mol. Suitably, the polyethylene glycol has an average molecular weight of 1500 g/mol. Suitably, the polyethylene glycol has an average molecular weight of 4000 g/mol. Suitably, the polyethylene glycol has an average molecular weight of 6000 g/mol.

Suitably, the non-aqueous solvent comprises polyethylene glycol having an average weight of about 1500 g/mol. Suitably, the non-aqueous solvent comprises polyethylene glycol having an average weight of 1500 g/mol.

Suitably, the non-aqueous solvent consists essentially of polyethylene glycol having an average weight of about 1500 g/mol. Suitably, the non-aqueous solvent consists essentially of polyethylene glycol having an average weight of 1500 g/mol.

Suitably, the non-aqueous solvent consists of polyethylene glycol having an average weight of about 1500 g/mol. Suitably, the non-aqueous solvent consists of polyethylene glycol having an average weight of 1500 g/mol.

Suitably, the non-aqueous solvent comprises polyethylene glycol having an average weight of about 4000 g/mol. Suitably, the non-aqueous solvent comprises polyethylene glycol having an average weight of 4000 g/mol.

Suitably, the non-aqueous solvent consists essentially of polyethylene glycol having an average weight of about 4000 g/mol. Suitably, the non-aqueous solvent consists essentially of polyethylene glycol having an average weight of 4000 g/mol.

Suitably, the non-aqueous solvent consists of polyethylene glycol having an average weight of about 4000 g/mol. Suitably, the non-aqueous solvent consists of polyethylene glycol having an average weight of 4000 g/mol.

Suitably, the non-aqueous solvent comprises polyethylene glycol having an average weight of about 6000 g/mol. Suitably, the non-aqueous solvent comprises polyethylene glycol having an average weight of 6000 g/mol.

Suitably, the non-aqueous solvent consists essentially of polyethylene glycol having an average weight of about 6000 g/mol. Suitably, the non-aqueous solvent consists essentially of polyethylene glycol having an average weight of 6000 g/mol.

Suitably, the non-aqueous solvent consists of polyethylene glycol having an average weight of about 6000 g/mol. Suitably, the non-aqueous solvent consists of polyethylene glycol having an average weight of 6000 g/mol.

Suitably, the non-aqueous solvent comprises polyethylene glycol having an average weight of about 400 g/mol. Suitably, the non-aqueous solvent comprises polyethylene glycol having an average weight of 400 g/mol.

Suitably, the non-aqueous solvent consists essentially of polyethylene glycol having an average weight of about 400 g/mol. Suitably, the non-aqueous solvent consists essentially of polyethylene glycol having an average weight of 400 g/mol.

Suitably, the non-aqueous solvent consists of polyethylene glycol having an average weight of about 400 g/mol. Suitably, the non-aqueous solvent consists of polyethylene glycol having an average weight of 400 g/mol.

Suitably, the polyethylene glycol is a super refined polyethylene glycol. Suitably, the super refined polyethylene glycol has an average molecular weight between about 200 and about 25000 g/mol, such as between about 300 and about 10000 g/mol, between about 400 and about 6000 g/mol, between about 1000 and about 6000 g/mol, between about 1200 and about 1800 g/mol, between about 1400 and about 1600 g/mol, between about 350 and about 450 g/mol, or between about 380 and about 420 g/mol. Suitably, the super refined polyethylene glycol has an average molecular weight of about 400 g/mol.

Suitably, the super refined polyethylene glycol:

(a) has a pH of between 4.5 and 7.5, such as between 4.0 and 7.0;
(b) contains between 0 and 10 ppm ethylene oxide, such as between 0 and 1 ppm;
(c) contains between 0 and 10 ppm dioxane;
(d) contains between 0.0 and 0.4% ethylene glycol, such as between 0.00 and
(e) contains between 0.0 and 0.4% diethylene glycol, such as between 0.00 and 0.25%, such as no more than 0.062%;
(f) contains no more than 0.25% of ethylene glycol and diethylene glycol combined;
(g) contains no more than 30 ppm formaldehyde, such as no more than 15 ppm;
(h) contains between 0.0 and 2.0% water, such as no more than 1.0%;
(i) contains no more than 0.5% acetic acid; and/or
(j) has a peroxide value of between 0.0 and 5.0 meqO2/kg.

Suitably, the non-aqueous solvent comprises two different polyethylene glycols, wherein the first polyethylene glycol has an average weight of less than about 1000 g/mol, such as less than about 800 g/mol, or such as less than about 600 g/mol, and wherein the second polyethylene glycol has an average weight of at least about 1000 g/mol, such as at least about 1200 g/mol, or such as at least about 1400 g/mol.

Suitably, the non-aqueous solvent comprises two different polyethylene glycols, wherein the first polyethylene glycol has an average weight of between 200 and 999 g/mol, such as between 400 and 800 g/mol, and wherein the second polyethylene glycol has an average weight of between 1000 and 25000 g/mol, such as between 1200 and 10000 g/mol, such as between 1200 and 6000 g/mol.

Suitably, the non-aqueous solvent comprises two different polyethylene glycols, wherein the first polyethylene glycol has an average weight about 400 g/mol, and wherein the second polyethylene glycol has an average weight of about 1500, 4000 or 6000 g/mol.

Suitably, the weight ratio of the first polyethylene glycol to the second polyethylene glycol is between 1:20 and 20:1, such as between 1:10 and 10:1, such as between 1:9 and 9:1.

Suitably, the first polyethylene glycol is a super refined polyethylene glycol.

Suitably, the pharmaceutical composition comprises two non-aqueous solvents, wherein the first non-aqueous solvent comprises vitamin E TPGS and the second non-aqueous solvent is polyethylene glycol. Suitably, the polyethylene glycol has an average weight of at least about 1000 g/mol, such as at least about 1200 g/mol, or such as at least about 1400 g/mol. Suitably, the polyethylene glycol has an average weight of between 1000 and 25000 g/mol, such as between 1200 and 10000 g/mol, such as between 1200 and 6000 g/mol. Suitably, the polyethylene glycol has an average weight of about 1500, 4000 or 6000 g/mol. Suitably, the weight ratio of the polyethylene glycol to vitamin E TPGS is between 1:20 and 20:1, such as between 1:10 and 10:1, such as between 1:9 and 9:1.

Suitably, the polyoxyethylene stearate is PEG-32 stearate or polyethylene glycol monostearate or a mixture thereof.

Glycerol has three hydroxyl functional groups, which can be esterified with one, two, or three fatty acids to form mono-, di-, or triglycerides respectively. Mono-, di-, and triglycerides comprise fatty acids in a bound state.

A long chain triglyceride is a triglyceride with three fatty acids having aliphatic tails of 13 to 21 carbons. Suitably, the long chain triglyceride comprises a fatty acid with an aliphatic tail of 13 to 21 carbons. Suitably, the long chain triglyceride comprises a fatty acid with an aliphatic tail of 16 to 20 carbons. Suitably, the long chain triglyceride comprises oleic acid. Suitably, the long chain triglyceride is selected from corn oil and soy bean oil A medium chain triglyceride is a triglyceride with three fatty acids having aliphatic tails of 6 to 12 carbons. Suitably, the medium chain triglyceride comprises a fatty acid with an aliphatic tail of 6 to 12 carbons. Suitably, the medium chain triglyceride comprises caprylic acid or capric acid or a mixture thereof.

A long chain monoglyceride is a monoglyceride with one fatty acid having an aliphatic tail of 13 to 21 carbons. Suitably, the long chain monoglyceride comprises a fatty acid with an aliphatic tail of 13 to 21 carbons. Suitably, the long chain monoglyceride comprises a fatty acid with an aliphatic tail of 16 to 20 carbons. Suitably, the long chain monoglyceride is glyceryl monooleate.

A medium chain monoglyceride is a monoglyceride with one fatty acid having an aliphatic tail of 6 to 12 carbons. Suitably, the medium chain monoglyceride comprises a fatty acid with an aliphatic tail of 6 to 12 carbons. Suitably, the medium chain monoglyceride comprises a fatty acid with an aliphatic tail of 8 to 12 carbons. Suitably, the medium chain monoglyceride is glyceryl monocaprylate.

A long chain fatty acid is a free fatty acid (i.e., not bound to another molecule, for example, a glycerol molecule in a mono-, di-, or tri-glyceride) with an aliphatic tail of at least 13 carbon atoms, suitably 13 to 21 carbons. Suitably, the long chain fatty acid has an aliphatic chain comprising 13 to 21 carbons. Suitably, the long chain fatty acid has an aliphatic chain comprising 16 to 20 carbons. Suitably, the long chain fatty acid is a very long chain fatty acid. Suitably, the long chain fatty acid is a free fatty acid with an aliphatic tail at least 22 carbons. Suitably, the long chain fatty acid is a saturated long chain fatty acid. Suitably, the long chain fatty acid is an unsaturated long chain fatty acid. Suitably, the long chain fatty acid is oleic acid, palmitic acid, stearic acid, arachidic acid, palmitoleic acid, nervonic acid, linoleic acid, alpha-linolenic acid, arachidonic acid, or eicosapentaenoic acid.

A medium chain fatty acid is a free fatty acid (i.e., not bound to another molecule, for example, a glycerol molecule in a mono-, di-, or tri-glyceride) with an aliphatic tail of 6 to 12 carbons. Suitably, the medium chain fatty acid has an aliphatic chain comprising 6 to 12 carbons. Suitably, the medium chain fatty acid has an aliphatic chain comprising 6 to 10 carbons. Suitably, the medium chain fatty acid is a saturated medium chain fatty acid. Suitably, the medium chain fatty acid is an unsaturated medium chain fatty acid. Suitably, the medium chain fatty acid is caprylic acid, capric acid or lauric acid.

Polyoxyethylene castor oil derivatives are obtained by reacting varying amounts of ethylene oxide with either castor oil or hydrogenated castor oil. Suitably, the polyoxyethylene castor oil derivative comprises polyoxyl 40 hydrogenated castor oil, polyoxyl-35 castor oil, or a mixture thereof. Suitably, the polyoxyethylene castor oil derivative is polyoxyl 40 hydrogenated castor oil, polyoxyl-35 castor oil, or a mixture thereof. Suitably, the polyoxyethylene castor oil derivative comprises polyoxyl 40 hydrogenated castor oil. Suitably, the polyoxyethylene castor oil derivative is polyoxyl 40 hydrogenated castor oil.

Suitably, the polyoxyethylene sorbitan fatty acid ester is polysorbate 20, polysorbate 80, or a mixture thereof. Suitably, the polyoxyethylene sorbitan fatty acid is polysorbate 20.

Suitably, the propylene glycol mono fatty ester is propylene glycol monocaprylate.

Suitably, the propylene glycol di fatty acid ester is propylene glycol dilaurate.

A poloxamer is non-ionic triblock copolymers composed of a central hydrophobic chain of polyoxypropylene (poly (propylene oxide)) flanked by two hydrophilic chains of polyoxyethylene (poly(ethylene oxide)). Suitably, the poloxamer is poloxamer 124, poloxamer 188, poloxamer 237, poloxamer 338, or poloxamer 407.

Suitably, the non-aqueous solvent comprises more than one non-aqueous solvent, for example two, three or four non-aqueous solvents.

Suitably, the pharmaceutical composition comprises at least about 20% w/w of the non-aqueous solvent by weight of the total pharmaceutical composition, such as at least about 30% w/w, at least about 40% w/w, at least about 50% w/w, at least about 60% w/w, at least about 70% w/w, at least about 80% w/w, at least about 90% w/w, at least about 95% w/w, at least about 96% w/w, at least about 97% w/w, at least about 98% w/w, at least about 99% w/w, at least about 99.2% w/w, or at least about 99.5% w/w. Suitably, the pharmaceutical composition comprises at least 20% w/w of the non-aqueous solvent by weight of the total pharmaceutical composition, such as at least 30% w/w, at least 40% w/w, at least 50% w/w, at least 60% w/w, at least 70% w/w, at least 80% w/w, at least 90% w/w, at least 95% w/w, at least 96% w/w, at least 97% w/w, at least 98% w/w, at least 99% w/w, at least 99.2% w/w, or at least 99.5% w/w.

Suitably, the pharmaceutical composition comprises between about 20 and about 99.99% w/w of the non-aqueous solvent by weight of the total pharmaceutical composition, such as between about 30 and about 99.99% w/w, about 40 and about 99.99% w/w, about 50 and about 99.99% w/w, about 60 and about 99.99% w/w, about 70 and about 99.99% w/w, about 80 and about 99.99% w/w, about 90 and about 99.99% w/w, about 95 and about 99.99% w/w, about 96 and about 99.99% w/w, about 97 and about 99.99% w/w, about 98 and about 99.99% w/w, about 99 and about 99.99% w/w, about 99.2 and about 99.99% w/w, or about 99.5 and about 99.99% w/w. Suitably, the pharmaceutical composition comprises between 20 and 99.99% w/w of the non-aqueous solvent by weight of the total pharmaceutical composition, such as between 30 and 99.99% w/w, 40 and 99.99% w/w, 50 and 99.99% w/w, 60 and 99.99% w/w, 70 and 99.99% w/w, 80 and 99.99% w/w, 90 and 99.99% w/w, 95 and 99.99% w/w, 96 and 99.99% w/w, 97 and 99.99% w/w, 98 and 99.99% w/w, 99 and 99.99% w/w, 99.2 and 99.99% w/w, or 99.5 and 99.99% w/w.

Suitably, the pharmaceutical composition comprises about 99.6% w/w of the non-aqueous solvent by weight of the total pharmaceutical composition. Suitably, the pharmaceutical composition comprises about 99.9% w/w of the non-aqueous solvent by weight of the total pharmaceutical composition.

Suitably, the non-aqueous solvent is a semi-solid at room temperature. A semi-solid is any material which at room temperature is a solid and at a temperature above room temperature is a liquid.

Suitably, the non-aqueous solvent has a melting point of at least 30° C., such as at least 35° C., at least 40° C. Suitably, the non-aqueous solvent has a melting point of at least about 30° C., such as at least about 35° C., at least about 40° C.

Suitably, the non-aqueous solvent has a melting point between about 35° C. and about 80° C., such as between about 35° C. and about 70° C., about 35° C. and about 60° C., about 35° C. and about 50° C., or about 40° C. and about 50° C. Suitably, the non-aqueous solvent has a melting point between 35° C. and 80° C., such as between 35° C. and 70° C., 35° C. and 60° C., 35° C. and 50° C., or 40° C. and 50° C.

Additional Excipients in the Pharmaceutical Composition

Optionally, additional excipients may be included in the pharmaceutical composition according to the present disclosure.

Suitably, the pharmaceutical composition further comprises vitamin E TPGS or lauroyl polyoxylglyceride. Suitably, the pharmaceutical composition comprises vitamin E TPGS.

Suitably, the weight ratio of the non-aqueous solvent to vitamin E TPGS is between 1:20 and 20:1, such as between 1:10 and 10:1, such as between 1:9 and 9:1.

Suitably, the pharmaceutical composition comprises a non-aqueous solvent and vitamin E TPGS, wherein the non-aqueous solvent comprises polyethylene glycol. Suitably, the polyethylene glycol has an average weight of at least about 1000 g/mol, such as at least about 1200 g/mol, or such as at least about 1400 g/mol. Suitably, the polyethylene glycol has an average weight of between 1000 and 25000 g/mol, such as between 1200 and 10000 g/mol, such as between 1200 and 6000 g/mol. Suitably, the polyethylene glycol has an average weight of about 1500, 4000 or 6000 g/mol. Suitably, the weight ratio of the polyethylene glycol to vitamin E TPGS is between 1:20 and 20:1, such as between 1:10 and 10:1, such as between 1:9 and 9:1.

Suitably, the pharmaceutical composition further comprises a viscosity modifier, opacifier, colouring, sweetening flavouring, and/or a preservatives agent such as an antioxidant.

The viscosity modifier is an excipient which gives the pharmaceutical composition suitable viscosity properties to allow consistent manufacturing, for example, to modify the viscosity of the pharmaceutical composition so that the pharmaceutical composition has the desired flow properties during manufacture to ensure the desired volumes of the pharmaceutical composition is dispensed. Suitably, the viscosity modifier is a liquid at room temperature. Suitably, the viscosity modifier is vitamin E TPGS and/or polyethylene glycol having an average weight of less than 1000 g/mol, such as less than 600 g/mol. Suitably, the polyethylene glycol has an average weight between about 200 and about 1000 g/mol, such as between about 300 and 500 g/mol. Suitably, the polyethylene glycol has an average weight of about 400 g/mol.

An opacifier is an excipient which makes the pharmaceutical composition opaque.

Suitably, the antioxidant comprises butylated hydroxyanisole, butylated hydroxytoluene, ascorbic acid, or alpha tocopherol.

Semi-Solid Pharmaceutical Composition

Suitably, the pharmaceutical composition is a semi-solid at room temperature. A semi-solid is any material which at room temperature is a solid and at a temperature above room temperature is a liquid.

Suitably, the pharmaceutical composition has a melting point of at least about 30° C., such as at least about 35° C., at least about 40° C. Suitably, the pharmaceutical composition has a melting point of at least 30° C., such as at least 35° C., at least 40° C.

Suitably, the pharmaceutical composition has a melting point between about 35° C. and about 80° C., such as between about 35° C. and about 70° C., about 35° C. and about 60° C., about 35° C. and about 50° C., or about 40° C. and about 50° C. Suitably, the pharmaceutical composition has a melting point between 35° C. and 80° C., such as between 35° C. and 70° C., 35° C. and 60° C., 35° C. and 50° C., or 40° C. and 50° C.

Advantageously, having a pharmaceutical composition which is a semi-solid at room temperature whose melting point is between 35° C. and 80° C. means that the active substance is not exposed to elevated temperatures during manufacture and thereby minimising degradation of the active substance during manufacture. Furthermore, a pharmaceutical composition which can be melted facilitates the transfer of the desired quantity of the pharmaceutical composition, for example into a capsule shell.

Stability of the Pharmaceutical Composition

Suitably, the active substance is stable in the pharmaceutical composition. Suitably, the active substance is stable in the pharmaceutical composition for at least about 2 weeks, about 1 month, about 2 months, about 3 months, about 6 months, about 12 months, or about 24 months. Suitably, the active substance is stable in the pharmaceutical composition for at least 2 weeks, 1, 2, 3, 6, 12, or 24 months.

Suitably, the active substance is chemically stable in the pharmaceutical composition for at least about 2 weeks, about 1 month, about 2 months, about 3 months, about 6 months, about 12 months, or about 24 months. Suitably, the active substance is chemically stable in the pharmaceutical composition for at least 2 weeks, 1, 2, 3, 6, 12, or 24 months.

Advantageously, the active substance is stable within the pharmaceutical composition during the lifetime of the pharmaceutical composition, for example during the manufacture of the pharmaceutical composition and at least until the pharmaceutical composition is administered to a patient. Stability is an important safety aspect of a pharmaceutical composition as a stable pharmaceutical composition results in the assay of the active substance being consistent over time which inturn allows for consistent dosing of the active substance to a patient. Therefore, resulting in the desired dose being administered to the patient. Furthermore, the degradation products of the active substance in a stable pharmaceutical composition are at minimal levels which ensures the end user, for example the patient, is not administered degradation products of the active substance. Stability of the active substance within the pharmaceutical composition is critical from a patient safety and efficacy perspective.

Suitably, the active substance is stable in the pharmaceutical composition for at least about 2 weeks, about 1 month, about 2 months, about 3 months, about 6 months, about 12 months, or about 24 months when the pharmaceutical composition is stored at 25° C./60% RH and/or 40° C./75% RH. Suitably, the active substance is stable in the pharmaceutical composition for at least 2 weeks, 1, 2, 3, 6, 12, or 24 months when the pharmaceutical composition is stored at 25° C./60% RH and/or 40° C./75% RH.

Suitably, the active substance is stable in the pharmaceutical composition for at least about 2 weeks, about 1 month, about 2 months, about 3 months, about 6 months, about 12 months, or about 24 months when the pharmaceutical composition is stored at 25° C./60% RH and/or 40° C./75% RH. Suitably, the active substance is stable in the pharmaceutical composition for 2 weeks, 1, 2, 3, 6, 12, or 24 months when the pharmaceutical composition is stored at 25° C./60% RH and/or 40° C./75% RH.

Suitably, the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the total amount of degradation products of the active substance is less than or equal to 4 area % as determined by a chromatographic method when the pharmaceutical composition is stored at 25° C./60% RH and/or 40° C./75% RH for 2 weeks, 1, 2, 3, 6, 12, or 24 months.

Suitably, the total amount of degradation products of the active substance is less than or equal to about 3 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the total amount of degradation products of the active substance is less than or equal to 3 area % as determined by a chromatographic method when the pharmaceutical composition is stored at 25° C./60% RH and/or 40° C./75% RH for 2 weeks, 1, 2, 3, 6, 12, or 24 months.

Suitably, the total amount of degradation products of the active substance is less than or equal to about 2 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the total amount of degradation products of the active substance is less than or equal to 2 area % as determined by a chromatographic method when the pharmaceutical composition is stored at 25° C./60% RH and/or 40° C./75% RH for 2 weeks, 1, 2, 3, 6, 12, or 24 months.

Suitably, the pharmaceutical composition does not contain more than about 1 area % of a single degradation product of the active substance as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the pharmaceutical composition does not contain more than 1 area % of a single degradation product of the active substance as determined by a chromatographic method when the pharmaceutical composition is stored at 25° C./60% RH and/or 40° C./75% RH for 2 weeks, 1, 2, 3, 6, 12, or 24 months.

A degradation product of the active substance is an impurity which forms upon storage of the active substance (or during manufacture of the pharmaceutical composition). The degradation product may be formed from exposure of the active substance to water, oxygen, peroxides, or UV light.

Suitably, the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the assay of the active substance is 90 to 110% of nominal as determined by a chromatographic method when the pharmaceutical composition is stored at 25° C./60% RH and/or 40° C./75% RH for 2 weeks, 1, 2, 3, 6, 12, or 24 months.

Suitably, the assay of the active substance is about 95 to about 105% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the assay of the active substance is 95 to 105% of nominal as determined by a chromatographic method when the pharmaceutical composition is stored at 25° C./60% RH and/or 40° C./75% RH for 2 weeks, 1, 2, 3, 6, 12, or 24 months.

Suitably, the assay of the active substance is about 98 to about 102% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the assay of the active substance is 98 to 102% of nominal as determined by a chromatographic method when the pharmaceutical composition is stored at 25° C./60% RH and/or 40° C./75% RH for 2 weeks, 1, 2, 3, 6, 12, or 24 months.

Suitably, the total amount of degradation products of the active substance is less than or equal to about 4 area % as determined by a chromatographic method and the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months. Suitably, the total amount of degradation products of the active substance is less than or equal to 4 area % and the assay of the active substance is 90 to 110% of nominal as determined by a chromatographic method when the pharmaceutical composition is stored at 25° C./60% RH and/or 40° C./75% RH for 2 weeks, 1, 2, 3, 6, 12, or 24 months.

Suitably, the active substance is stable in the pharmaceutical composition for at least about 2 weeks, about 1 month, about 2 months, about 3 months, about 6 months, about 12 months, or about 24 months when the pharmaceutical composition is protected from light, suitably UV radiation. Suitably, the active substance is stable in the pharmaceutical composition for at least 2 weeks, 1, 2, 3, 6, 12, or 24 months when the pharmaceutical composition is protected from light, suitably UV radiation.

Suitably, the chromatographic method is a HPLC method. HPLC in this context includes UPLC.

Suitably the HPLC method comprises a UV detector. Suitably, the UV detector measures the assay and/or degradation products of the active substance at about 256 nm.

Suitably, the HPLC method is a reverse phase HPLC method. Suitably, the reverse phase HPLC method comprises two eluents wherein the ratio of the two eluents changes during the course of the HPLC analysis. Suitably, the first eluent comprises water and the second eluent comprises acetonitrile. Suitably, the first eluent comprises water and ammonium acetate and the second eluent comprises acetonitrile. Suitably, the first eluent comprises water and 10 mM ammonium acetate and the second eluent comprises acetonitrile.

Suitably, the reverse phase HPLC method comprises a HPLC column. Suitably, the HPLC column comprises a C18 stationary phase. Suitably, the HPLC column temperature is at about 40° C.

Suitably, the eluents flow through the HPLC column at about 0.3 mL/min.

Suitably, the chromatographic method is a reverse phase HPLC method wherein the reverse phase HPLC method comprises:

a. a UV detector;

b. a HPLC column; and c. two eluents wherein the ratio of the two eluents changes during the course of the HPLC analysis.

Release Rate of the Active Substance from the Pharmaceutical Composition

Suitably, at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined at about 37° C. using a rotation speed of about 50 rpm. Suitably, at least 75% of the total amount of the active substance contained in the pharmaceutical composition is released within the first 45 minutes when the pharmaceutical composition is subjected to an in vitro dissolution test employing 0.1 M HCl or pH 6.8 phosphate buffer as the dissolution medium and the dissolution profile is determined at 37° C. using a rotation speed of 50 rpm.

Advantageously, such a release profile provides optimal absorption of the active substance when administered to a patient.

Suitably, at least about 75% of the total amount of the active substance contained in the pharmaceutical composition is released within about the first 30 minutes when the pharmaceutical composition is subjected to an in vitro dissolution test employing 0.1 M HCl or pH 6.8 phosphate buffer as the dissolution medium and the dissolution profile is determined at about 37° C. using a rotation speed of about 50 rpm. Suitably, at least 75% of the total amount of the active substance contained in the pharmaceutical composition is released within the first 30 minutes when the pharmaceutical composition is subjected to an in vitro dissolution test employing 0.1 M HCl or pH 6.8 phosphate buffer as the dissolution medium and the dissolution profile is determined at 37° C. using a rotation speed of 50 rpm.

Suitably, at least about 85% of the total amount of the active substance contained in the pharmaceutical composition is released within about the first 15 minutes when the pharmaceutical composition is subjected to an in vitro dissolution test employing 0.1 M HCl or pH 6.8 phosphate buffer as the dissolution medium and the dissolution profile is determined at about 37° C. using a rotation speed of about 50 rpm. Suitably, at least 85% of the total amount of the active substance contained in the pharmaceutical composition is released within the first 15 minutes when the pharmaceutical composition is subjected to an in vitro dissolution test employing 0.1 M HCl or pH 6.8 phosphate buffer as the dissolution medium and the dissolution profile is determined at 37° C. using a rotation speed of 50 rpm.

Suitably, at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at about 37° C. using a rotation speed of about 50 rpm. Suitably, at least 75% of the total amount of the active substance contained in the pharmaceutical composition is released within the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, at least about 75% of the total amount of the active substance contained in the pharmaceutical composition is released within about the first 30 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at about 37° C. using a rotation speed of about 50 rpm. Suitably, at least 75% of the total amount of the active substance contained in the pharmaceutical composition is released within the first 30 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, at least about 75% of the total amount of the active substance contained in the pharmaceutical composition is released within about the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at about 37° C. using a rotation speed of about 50 rpm. Suitably, at least 75% of the total amount of the active substance contained in the pharmaceutical composition is released within the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, at least about 85% of the total amount of the active substance contained in the pharmaceutical composition is released within about the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at about 37° C. using a rotation speed of about 50 rpm. Suitably, at least 85% of the total amount of the active substance contained in the pharmaceutical composition is released within the first 15 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

Suitably, the in vitro dissolution tests comprises a vessel filled with about 500 mL of dissolution medium wherein the dissolution medium is 0.1 M HCl or pH 6.8 phosphate buffer. Suitably, the in vitro dissolution tests comprises a vessel filled with 500 mL of dissolution medium wherein the dissolution medium is 0.1 M HCl or pH 6.8 phosphate buffer.

Suitably, the dissolution medium has a temperature of about 37° C. Suitably, the dissolution medium has a temperature of 37° C.

Suitably, the in vitro dissolution tests comprises a vessel filled with about 500 mL of dissolution medium wherein the dissolution medium is 0.1 M HCl or pH 6.8 phosphate buffer and the dissolution profile is determined as described in the United States Pharmacopoeia at about 37° C. using a rotation speed of about 50 rpm. Suitably, the in vitro dissolution tests comprises a vessel filled with 500 mL of dissolution medium wherein the dissolution medium is 0.1 M HCl or pH 6.8 phosphate buffer and the dissolution profile is determined as described in the United States Pharmacopoeia at 37° C. using a rotation speed of 50 rpm.

Suitably, the in vitro dissolution test comprises a vessel filled with about 500 mL of dissolution medium wherein the dissolution medium is 0.1 M HCl or pH 6.8 phosphate buffer and the dissolution profile is determined as described in the United States Pharmacopoeia wherein a paddle rotates at about 50 rpm in the vessel, and wherein the dissolution medium has a temperature of about 37° C. Suitably, the in vitro dissolution test comprises a vessel filled with 500 mL of dissolution medium wherein the dissolution medium is 0.1 M HCl or pH 6.8 phosphate buffer and the dissolution profile is determined as described in the United States Pharmacopoeia wherein a paddle rotates at 50 rpm in the vessel, and wherein the dissolution medium has a temperature of 37° C.

Suitably, the in vitro dissolution test comprises a vessel filled with about 500 mL of dissolution medium wherein the dissolution medium is 0.1 M HCl or pH 6.8 phosphate buffer and the dissolution profile is determined as described in the United States Pharmacopoeia wherein a paddle rotates at about 50 rpm in the vessel for about the first 45 minutes of the test and then about 200 rpm after about 45 minutes, and wherein the dissolution medium has a temperature of about 37° C. Suitably, the in vitro dissolution test comprises a vessel filled with 500 mL of dissolution medium wherein the dissolution medium is 0.1 M HCl or pH 6.8 phosphate buffer and the dissolution profile is determined as described in the United States Pharmacopoeia wherein a paddle rotates at 50 rpm in the vessel for the first 45 minutes of the test and then 200 rpm after 45 minutes, and wherein the dissolution medium has a temperature of 37° C.

Suitably, the in vitro dissolution test comprises a paddle wherein the paddle rotates. Suitably, the in vitro dissolution test comprises a paddle wherein the paddle rotates at about 50 rpm. Suitably, the in vitro dissolution test comprises a paddle wherein the paddle rotates at about 50 rpm for about the first 45 minutes of the test and then about 200 rpm after about 45 minutes. Suitably, the in vitro dissolution test comprises a paddle wherein the paddle rotates at 50 rpm. Suitably, the in vitro dissolution test comprises a paddle wherein the paddle rotates at 50 rpm for the first 45 minutes of the test and then 200 rpm after 45 minutes.

Suitably, the in vitro dissolution test comprises a basket wherein the basket rotates. Suitably, the in vitro dissolution test comprises a basket wherein the basket rotates at about 50 rpm. Suitably, the in vitro dissolution test comprises a basket wherein the basket rotates at about 50 rpm for about the first 45 minutes of the test and then about 200 rpm after about 45 minutes. Suitably, the in vitro dissolution test comprises a basket wherein the basket rotates at 50 rpm. Suitably, the in vitro dissolution test comprises a basket wherein the basket rotates at 50 rpm for the first 45 minutes of the test and then 200 rpm after 45 minutes.

Suitably, the in vitro dissolution test further comprises sinkers for the pharmaceutical composition. Suitably, the sinkers are O-ring sinkers.

Suitably, the in vitro dissolution test comprises a detector. Suitably the detector comprises a UV detector.

Suitably, the total amount of the active substance released from the pharmaceutical composition when the pharmaceutical composition is subjected to an in vitro dissolution profile is determined by a chromatographic method or UV spectroscopy. Suitably, the chromatographic method is a HPLC method. Suitably the HPLC method comprises a UV detector. Suitably, the UV detector measures the assay of the active substance at about 217 nm.

Suitably, the HPLC method is a reverse phase HPLC method. Suitably, the reverse phase HPLC method comprises two eluents wherein the ratio of the two eluents changes during the course of the HPLC analysis. Suitably, the first eluent comprises water and the second eluent comprises acetonitrile. Suitably, the first eluent comprises water and phosphoric acid and the second eluent comprises acetonitrile. Suitably, the first eluent comprises water and 0.1% phosphoric acid and the second eluent comprises acetonitrile.

Suitably, the reverse phase HPLC method comprises a HPLC column. Suitably, the HPLC column comprises a C18 stationary phase. Suitably, the HPLC column temperature is at about 40° C. Suitably, the eluents flow through the HPLC column at about 0.5 mL/min.

Suitably, the chromatographic method is a reverse phase HPLC method wherein the reverse phase HPLC method comprises:

a. a UV detector;
b. a HPLC column; and
c. two eluents wherein the ratio of the two eluents changes during the course of the HPLC analysis.

Uniformity of the Active Substance in the Pharmaceutical Composition

Suitably, the active substance is homogeneously distributed throughout the non-aqueous solvent. Suitably, the active substance is homogeneously distributed throughout the non-aqueous solvent at room temperature.

Advantageously, the active substance is homogeneously dispersed within the pharmaceutical composition. This ensures that the required amount of the active substance is present in the portion of pharmaceutical composition, for example, upon dosing of the pharmaceutical composition to a patient, or the use of the pharmaceutical composition in the preparation of an immediate release pharmaceutical formulation. This is critical from a patient safety and efficacy perspective.

In this context, homogeneously dispersed is defined as the uniform distribution of the active substance throughout the non-aqueous solvent. For example, if separate portions of the pharmaceutical composition were analysed to determine the active substance content within that portion, there would be minimal variability (i.e., less than about 10%, such as less than about 8%, less than about 6%, less than about 5%, less than about 4%, less than about 3%, less than about 2%, less than about 1%, or less than about 0.5% variability) in the active substance content determined for each portion).

Suitably, the active substance is homogeneously distributed throughout the non-aqueous solvent for at least about 2 weeks, about 1 month, about 2 months, about 3 months, about 6 months, about 12 months, or about 24 months. Suitably, the active substance is homogeneously distributed throughout the non-aqueous solvent for at least 2 weeks, 1, 2, 3, 6, 12, or 24 months.

Suitably, the active substance is homogeneously distributed throughout the non-aqueous solvent for at least about 2 weeks, about 1 month, about 2 months, about 3 months, about 6 months, about 12 months, or about 24 months upon storage of the pharmaceutical composition at room temperature. Suitably, the active substance is homogeneously distributed throughout the non-aqueous solvent for at least 2 weeks, 1, 2, 3, 6, 12, or 24 months upon storage of the pharmaceutical composition at room temperature.

Suitably, the active substance is homogeneously distributed throughout the non-aqueous solvent for at least about 2 weeks, about 1 month, about 2 months, about 3 months, about 6 months, about 12 months, or about 24 months upon storage of the pharmaceutical composition at 25° C./60% RH and/or 40° C./75% RH. Suitably, the active substance is homogeneously distributed throughout the non-aqueous solvent for at least 2 weeks, 1, 2, 3, 6, 12, or 24 months upon storage of the pharmaceutical composition at 25° C./60% RH and/or 40° C./75% RH.

Suitably, the homogeneous distribution of the active substance in the non-aqueous solvent is determined by an analytical method.

Suitably, the analytical method comprises determining the weight percentage of the active substance within a portion of the pharmaceutical composition.

Suitably, the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

Suitably, the analytical method comprises determining the weight percentage of the active substance within a portion of the pharmaceutical composition and wherein the weight percentage of the active substance within the portion of the pharmaceutical composition is ±2% of the expected value based on the total amount of the active substance added to the total amount of the pharmaceutical composition.

Suitably, the analytical method comprises determining the weight percentage of the active substance within a portion of the pharmaceutical composition and wherein the weight percentage of the active substance within the portion of the pharmaceutical composition is ±1% of the expected value based on the total amount of the active substance added to the total amount of the pharmaceutical composition.

Suitably, the analytical method comprises determining the weight percentage of the active substance within a portion of the pharmaceutical composition and wherein the weight percentage of the active substance within the portion of the pharmaceutical composition is ±0.5% of the expected value based on the total amount of the active substance added to the total amount of the pharmaceutical composition.

Suitably, the portion of the pharmaceutical composition is less than about 10% by the total weight of the pharmaceutical composition, such as less than about 5% by weight, about 4% by weight, about 3% by weight or about 2% by weight. Suitably, the portion of the pharmaceutical composition is less than 10% by the total weight of the pharmaceutical composition, such as less than 5% by weight, 4% by weight, 3% by weight or 2% by weight.

Suitably, the analytical method comprises a chromatographic method or a spectroscopic method.

Suitably, the spectroscopic method is NMR.

Suitably, the chromatographic method is HPLC or UPLC. Suitably the HPLC or UPLC method comprises a UV detector. Suitably, the UV detector measures the assay of the active substance at about 217 nm.

Suitably, the HPLC method is a reverse phase HPLC method. Suitably, the reverse phase HPLC method comprises two eluents wherein the ratio of the two eluents changes during the course of the HPLC analysis. Suitably, the first eluent comprises water and the second eluent comprises acetonitrile. Suitably, the first eluent comprises water and phosphoric acid and the second eluent comprises acetonitrile. Suitably, the first eluent comprises water and 0.1% phosphoric acid and the second eluent comprises acetonitrile.

Suitably, the reverse phase HPLC method comprises a HPLC column. Suitably, the HPLC column comprises a C18 stationary phase. Suitably, the HPLC column temperature is at about 40° C. Suitably, the eluents flow through the HPLC column at about 0.5 mL/min.

Suitably, the chromatographic method is a reverse phase HPLC method wherein the reverse phase HPLC method comprises:

a. a UV detector;
b. a HPLC column; and
c. two eluents wherein the ratio of the two eluents changes during the course of the HPLC analysis.

Pharmaceutical Formulation

Suitably, there is provided an immediate release pharmaceutical formulation for oral use comprising the pharmaceutical composition as defined herein.

Suitably, the immediate release pharmaceutical formulation may be in a form suitable for oral use (for example, hard or soft capsules, suspensions, emulsions, syrups or elixirs, sprays).

Suitably, the immediate release pharmaceutical formulation, when subjected to a content uniformity test as described in the European Pharmacopeia, the acceptance value is less than 15. Suitably, the immediate release pharmaceutical formulation, when subjected to a content uniformity test as described in the European Pharmacopeia, the acceptance value is less than 10. Suitably, the content uniformity test comprises a chromatographic assay of the immediate release pharmaceutical formulation. Suitably, the chromatographic assay comprises HPLC. HPLC in this context includes UPLC.

Advantageously, the active substance in the pharmaceutical composition is uniformly distributed and meets the regulatory requirements. Thereby ensuring the correct dose of the active substance is present in each pharmaceutical formulation dosage unit. This is critical from a patient safety and efficacy perspective.

Suitably, the European Pharmacopeia content uniformity test is 2.9.40.

Suitably, the content uniformity test comprises determining the amount of active substance in the immediate release pharmaceutical formulation. Suitably, the amount of active substance in the immediate release pharmaceutical formulation is determined using a chromatographic method. Suitably, the chromatographic method is a HPLC method.

Suitably the HPLC method comprises a UV detector. Suitably, the UV detector measures the assay of the active substance at about 217 nm.

Suitably, the HPLC method is a reverse phase HPLC method. Suitably, the reverse phase HPLC method comprises two eluents wherein the ratio of the two eluents changes during the course of the HPLC analysis. Suitably, the first eluent comprises water and the second eluent comprises acetonitrile. Suitably, the first eluent comprises water and phosphoric acid and the second eluent comprises acetonitrile. Suitably, the first eluent comprises water and 0.1% phosphoric acid and the second eluent comprises acetonitrile.

Suitably, the reverse phase HPLC method comprises a HPLC column. Suitably, the HPLC column comprises a C18 stationary phase. Suitably, the HPLC column is at about 40° C. Suitably, the eluents flow through the HPLC column at about 0.5 mL/min.

Suitably, the chromatographic method is a reverse phase HPLC method wherein the reverse phase HPLC method comprises:

a. a UV detector;

b. a HPLC column; and c. two eluents wherein the ratio of the two eluents changes during the course of the HPLC analysis.

Suitably, the immediate release pharmaceutical formulation is added to a diluent and the active substance is dissolved in the diluent. Suitably, the diluent is 90:10 v/v 0.1M HCl:acetonitrile.

Suitably, the acceptance value is determined using the following formula:

$$AV = |M - X| + ks$$

wherein:

X=Mean of individual contents ($x_1$, $x_2$ . . . $x_3$) expressed as a percentage of the label claim;

k=acceptability constant. If n=10 then k=2.4, if n=30 then 2.0 where n=sample size;

s=Sample standard deviation;

M=Reference Value wherein:

for case 1 when T≤101.5:

If 98.5%≤X≤101.5% then M=X (therefore AV=ks)

If X<98.5% then M=98.5% (therefore AV=98.5−X+ks)

If X>101.5%, then M=101.5% (therefore AV=X−101.5+ks)

for case 2 when T>101.5:

If 98.5%≤X≤T then M=X (therefore AV=ks)

If X<98.5% then M=98.5% (therefore AV=98.5−X+ks)

If X>T, then M=T % (therefore AV=X−T+ks); and

T=target test sample amount at time of manufacture.

Suitably, the immediate release pharmaceutical formulation is an immediate release capsule formulation comprising a capsule shell.

Suitably, the capsule shell comprises gelatin or HPMC.

Suitably, the capsule shell comprises gelatin, such as hard gelatin.

Suitably, the capsules shell is a size 2, 3 or 4 size capsule shell.

Suitably, the immediate release pharmaceutical formulation is a spray.

Suitably, the immediate release formulation comprises between about 10 and about 1000 μg of the active substance. Suitably, the immediate release formulation comprises between 10 and 1000 μg of the active substance. Suitably, the immediate release pharmaceutical formulation comprises between about 10 and about 650 μg of the active substance. Suitably, the immediate release pharmaceutical formulation comprises between 10 and 650 μg of the active substance. Suitably, the immediate release pharmaceutical formulation comprises between about 50 and about 200 μg of the active substance. Suitably, the immediate release pharmaceutical formulation comprises between 50 and 200 μg of the active substance. Suitably, the immediate release pharmaceutical formulation comprises between about 100 and about 650 μg of the active substance. Suitably, the immediate release pharmaceutical formulation comprises between 100 and 650 μg of the active substance. release pharmaceutical formulation comprises between 25 and 75 μg of the active substance. Suitably, the immediate release pharmaceutical formulation comprises between about 150 and about 250 μg of the active substance.

Suitably, the immediate release pharmaceutical formulation comprises about 50 μg of the active substance.

Suitably, the immediate release pharmaceutical formulation comprises about 200 μg of the active substance.

Suitably, the immediate release pharmaceutical formulation comprises about 650 μg of the active substance.

Process of Manufacture

In a further aspect, there is a method of manufacturing the pharmaceutical composition described herein comprising the step of mixing as an active substance Compound I, or a pharmaceutically acceptable salt thereof, into a non-aqueous solvent.

Suitably, the non-aqueous solvent is a liquid in the mixing step.

Suitably, the step of mixing the active substance into the non-aqueous solvent is performed at a temperature greater than room temperature, such as between about 35° C. and about 80° C., about 40° C. and about 80° C., about 50° C. and about 80° C., or about 60° C. and about 80° C. Suitably, the step of mixing the active substance into the non-aqueous solvent is performed at a temperature greater than room temperature, such as between 35° C. and 80° C., 40° C. and 80° C., 50° C. and 80° C., or 60° C. and 80° C.

Suitably, the step of mixing the active substance into the non-aqueous solvent is performed at a temperature greater than the melting point of the non-aqueous solvent.

Suitably, the step of mixing the active substance into the non-aqueous solvent is performed under an inert atmosphere. Suitably, the inert atmosphere is a nitrogen atmosphere.

Suitably, the step of mixing the active substance into the non-aqueous solvent comprises protecting the active substance from light. Suitably, the step of mixing the active substance into the non-aqueous solvent is performed in a dark room. Suitably, the step of mixing the active substance into the non-aqueous solvent comprises using vessels for the active substance and non-aqueous solvent mixture wherein the vessels protect the contents of the vessel from light.

Advantageously, performing the mixing step in low light and/or under an inert atmosphere minimises the number of degradation products formed during manufacture and/or upon storage of the pharmaceutical composition.

Therapeutic Uses and Applications

The present disclosure provides a pharmaceutical composition as defined herein or an immediate release pharmaceutical formulation as defined herein for use as a medicament.

The present disclosure provides a pharmaceutical composition as defined herein or an immediate release pharmaceutical formulation as defined herein for use in therapy.

The present disclosure provides a pharmaceutical composition as defined herein or an immediate release pharmaceutical formulation as defined herein for use in a disease state or disorder in which dysfunction of $CB_1$ and/or $CB_2$ receptors are present or implicated.

The present disclosure provides a pharmaceutical composition or an immediate release pharmaceutical formulation as defined herein for use in the treatment of an anorexia associated condition; a cachexia associated condition; or anorexia nervosa.

Suitably, the anorexia associated condition is anorexia associated with cancer, anorexia associated with HIV (Human Immunodeficiency Virus), anorexia associated with Chronic Kidney Disease, anorexia associated with dementia, or anorexia associated with chronic congestive heart failure.

Suitably, the anorexia associated condition is anorexia associated with cancer.

Suitably, the cachexia associated condition is cachexia associated with cancer, cachexia associated with HIV, cachexia associated with Chronic Kidney Disease, cachexia associated with dementia, or cachexia associated with chronic congestive heart failure.

The present disclosure provides a pharmaceutical composition or an immediate release pharmaceutical formulation as defined herein for use in the treatment of a pain condition. Suitably, the pain condition is a pain condition in cancer, acute pain, chronic pain, neuropathic pain, back pain, cancer pain, visceral pain, pain caused by rheumatoid arthritis, migraine. Suitably, the pain condition in cancer is a pain condition in cancer associated with the reduction of opiate use, associated with the reduction in nausea and/or vomiting in cancer patients.

The present disclosure provides a pharmaceutical composition as defined herein or an immediate release pharmaceutical formulation as defined herein for use in the treatment of anxiety disorders, cancer, multiple sclerosis, Parkinson's disease, Huntington's chorea, Alzheimer's disease, AIDS (Acquired Immune Deficiency Syndrome), amyotrophic lateral sclerosis, gastrointestinal disorders, cardiovascular disorders, or insomnia.

The present disclosure provides a pharmaceutical composition as defined herein or an immediate release pharmaceutical formulation as defined herein for use as an immunomodulator. Suitably, the pharmaceutical composition as defined herein or the immediate release pharmaceutical formulation is for use in the treatment of autoimmune diseases such as arthritis, collagen diseases, or allergies. Suitably, the pharmaceutical composition as defined herein or the immediate release pharmaceutical formulation is for use in skin graft therapy, organ transplant therapy and other surgical needs. Suitably, the pharmaceutical composition as defined herein or the immediate release pharmaceutical formulation is for use as an anti-tumor agent or an anti-viral agent.

The present disclosure provides a pharmaceutical composition as defined herein or an immediate release pharmaceutical formulation as defined herein for use in the treatment of diarrhoea; depression; anxiety and stress-related disorders such as post-traumatic stress disorders, panic disorder, generalized anxiety disorder, social phobia, and obsessive compulsive disorder; urinary incontinence; premature ejaculation; various mental illnesses; cough; lung oedema; various gastro-intestinal disorders, e.g. constipation, functional gastrointestinal disorders such as Irritable Bowel Syndrome and Functional Dyspepsia; Parkinson's disease and other motor disorders; traumatic brain injury; stroke; cardioprotection following miocardial infarction; spinal injury and drug addiction including the treatment of alcohol, nicotine, opioid and other drug abuse; and for disorders of the sympathetic nervous system, such as hypertension.

The present disclosure provides a pharmaceutical composition as defined herein or an immediate release pharmaceutical formulation as defined herein for use as an analgesic agent, for example for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

The present disclosure therefore provides a method of activating the $CB_1$ and/or $CB_2$ receptor in vitro or in vivo, said method comprising contacting a cell with an effective amount of a pharmaceutical composition as defined herein or an immediate release pharmaceutical formulation as defined herein.

The present disclosure also provides a method of treating a disease or disorder in which dysfunction of $CB_1$ and/or $CB_2$ receptors are implicated in a patient in need of such treatment, said method comprising administering to said patient a therapeutically effective amount of a pharmaceutical composition as defined herein or an immediate release pharmaceutical formulation as defined herein.

A therapeutically effective amount of a pharmaceutical composition or immediate release pharmaceutical formulation comprising the active substance of the present disclosure for use in therapy is an amount to achieve a particular biological or therapeutic result such as, but not limited to, biological or therapeutic results disclosed, described, or exemplified herein. For example, to treat or prevent a disease or condition referred to herein, slow its progression and/or reduce the symptoms associated with the condition and/or disease.

The amount of the active substance that is combined with one or more excipients to produce the pharmaceutical composition or the immediate release pharmaceutical formulation will necessarily vary depending upon the individual treated and the particular route of administration. An immediate release formulation intended for oral administration to humans will generally contain, for example, from about 10 μg to about 1000 μg of the active substance (for example about 10 μg to about 650 μg) compounded with an appropriate and convenient amount of excipients which may vary from about 0.01 to about 99.99 percent by weight of the total pharmaceutical composition or the immediate release pharmaceutical formulation.

The size of the dose for therapeutic or prophylactic purposes of the active substance will naturally vary according to the nature and severity of the conditions, the age and sex of the animal or patient and the route of administration, according to well known principles of medicine.

The present disclosure provides a method of treating an anorexia associated condition, a cachexia associated condition or anorexia nervosa, said method comprising administering to said patient a therapeutically effective amount of a pharmaceutical composition as defined herein or the immediate release pharmaceutical formulation as defined herein.

Suitably, the anorexia associated condition is anorexia associated with cancer, anorexia associated with HIV, anorexia associated with Chronic Kidney Disease, anorexia associated with cancer dementia, or anorexia associated with chronic congestive heart failure.

Suitably, the anorexia associated condition is anorexia associated with cancer.

Suitably, the cachexia associated condition is cachexia associated with cancer, cachexia associated with HIV, cachexia associated with Chronic Kidney Disease, cachexia associated with dementia, or cachexia associated with chronic congestive heart failure.

The present disclosure provides a method of treating a pain condition in a patient in need of such treatment, said method comprising administering to said patient a therapeutically effective amount of a pharmaceutical composition as defined herein or the immediate release pharmaceutical formulation as defined herein. Suitably, the pain condition is a pain condition in cancer, acute pain, chronic pain, neuropathic pain, back pain, cancer pain, visceral pain, pain caused by rheumatoid arthritis, migraine. Suitably, the pain condition in cancer is a pain condition in cancer associated with the reduction of opiate use, associated with the reduction in nausea and/or vomiting in cancer patients.

The present disclosure provides a method of treating anxiety disorders, cancer, multiple sclerosis, Parkinson's disease, Huntington's chorea, Alzheimer's disease, AIDS, amyotrophic lateral sclerosis, gastrointestinal disorders, cardiovascular disorders, or insomnia, said method comprising administering to said patient a therapeutically effective amount of a pharmaceutical composition as defined herein or the immediate release pharmaceutical formulation as defined herein.

The present disclosure provides a method of treating autoimmune diseases such as arthritis, collagen diseases, or allergies, said method comprising administering to said patient a therapeutically effective amount of a pharmaceutical composition or the immediate release pharmaceutical formulation as defined herein. The present disclosure provides a method of treatment in skin graft therapy, organ transplant therapy and other surgical needs, said method comprising administering to said patient a therapeutically effective amount of a pharmaceutical composition as defined herein or the immediate release pharmaceutical formulation as defined herein.

The present disclosure provides a method of treating diarrhoea; depression; anxiety and stress-related disorders such as post-traumatic stress disorders, panic disorder, generalized anxiety disorder, social phobia, and obsessive compulsive disorder; urinary incontinence; premature ejaculation; various mental illnesses; cough; lung oedema; various gastro-intestinal disorders, e.g. constipation, functional gastrointestinal disorders such as Irritable Bowel Syndrome and Functional Dyspepsia; Parkinson's disease and other motor disorders; traumatic brain injury; stroke; cardioprotection following miocardial infarction; spinal injury and drug addiction including the treatment of alcohol, nicotine, opioid and other drug abuse; and for disorders of the sympathetic nervous system, such as hypertension, said method comprising administering to said patient a therapeutically effective amount of a pharmaceutical composition as defined herein or the immediate release pharmaceutical formulation as defined herein.

The present disclosure provides a method of providing an analgesic effect, for example for use during general anaesthesia and monitored anaesthesia care, said method comprising administering to said patient a therapeutically effective amount of a pharmaceutical composition as defined herein or the immediate release pharmaceutical formulation as defined herein. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

The present disclosure provides use of a pharmaceutical composition as defined herein or an immediate release pharmaceutical formulation as defined herein for use in the manufacture of a medicament.

The present disclosure provides use of a pharmaceutical composition as defined herein or an immediate release pharmaceutical formulation as defined herein for use in the manufacture of a medicament for use in a disease state or disorder in which dysfunction of $CB_1$ and/or $CB_2$ receptors are present or implicated.

The present disclosure provides use of a pharmaceutical composition as defined herein or an immediate release pharmaceutical formulation as defined herein for use in the manufacture of a medicament for the treatment of an anorexia associated condition; a cachexia associated conditions; or anorexia nervosa.

Suitably, the anorexia associated condition is anorexia associated with cancer, anorexia associated with HIV, anorexia associated with Chronic Kidney Disease, anorexia associated with dementia, or anorexia associated with chronic congestive heart failure.

Suitably, the anorexia associated condition is anorexia associated with cancer.

Suitably, the cachexia associated condition is cachexia associated with cancer, cachexia associated with HIV, cachexia associated with Chronic Kidney Disease, cachexia associated with dementia, or cachexia associated with chronic congestive heart failure.

The present disclosure provides use of a pharmaceutical composition as defined herein or an immediate release pharmaceutical formulation as defined herein for use in the manufacture of a medicament for the treatment of a pain condition. Suitably, the pain condition is a pain condition in cancer, acute pain, chronic pain, neuropathic pain, back pain, cancer pain, visceral pain, pain caused by rheumatoid arthritis, migraine. Suitably, the pain condition in cancer is a pain condition in cancer associated with the reduction of opiate use, associated with the reduction in nausea and/or vomiting in cancer patients.

The present disclosure provides use of a pharmaceutical composition as defined herein or an immediate release pharmaceutical formulation as defined herein for use in the manufacture of a medicament for the treatment of anxiety disorders, cancer, multiple sclerosis, Parkinson's disease, Huntington's chorea, Alzheimer's disease, AIDS, amyotrophic lateral sclerosis, gastrointestinal disorders, cardiovascular disorders, or insomnia.

The present disclosure provides use of a pharmaceutical composition as defined herein or an immediate release pharmaceutical formulation as defined herein for use in the manufacture of a medicament for use as an immunomodulator. The present disclosure provides use of a pharmaceutical composition as defined herein or an immediate release pharmaceutical formulation as defined herein for use in the manufacture of a medicament for the treatment of autoimmune diseases such as arthritis, collagen diseases, or allergies. The present disclosure provides use of a pharmaceutical composition as defined herein or an immediate release pharmaceutical formulation as defined herein for use in the manufacture of a medicament for use in skin graft therapy, organ transplant therapy and other surgical needs. The present disclosure provides use of a pharmaceutical composition as defined herein or an immediate release pharmaceutical formulation as defined herein for use in the manufacture of a medicament for use an anti-tumour agent or an anti-viral agent.

The present disclosure provides use of a pharmaceutical composition as defined herein or an immediate release pharmaceutical formulation as defined herein for use in the manufacture of a medicament for use in the treatment of diarrhoea; depression; anxiety and stress-related disorders such as post-traumatic stress disorders, panic disorder, generalized anxiety disorder, social phobia, and obsessive compulsive disorder; urinary incontinence; premature ejaculation; various mental illnesses; cough; lung oedema; various gastro-intestinal disorders, e.g. constipation, functional gastrointestinal disorders such as Irritable Bowel Syndrome and Functional Dyspepsia; Parkinson's disease and other motor disorders; traumatic brain injury; stroke; cardioprotection following miocardial infarction; spinal injury and drug addiction including the treatment of alcohol, nicotine, opioid and other drug abuse; and for disorders of the sympathetic nervous system, such as hypertension.

The present disclosure provides use of a pharmaceutical composition as defined herein or an immediate release pharmaceutical formulation as defined herein for use in the manufacture of a medicament for use as an analgesic agent, for example for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

In one embodiment, between about 25 and about 700 μg/dose/day of Compound I is administered to the patient, such as between about 50 and about 650 μg/dose/day. Suitably, about 50, 150, 250, 400 or 650 μg/dose/day of Compound I is administered to the patient, Routes of Administration The pharmaceutical compositions or the immediate release pharmaceutical formulations of the disclosure may be administered to a subject by any convenient oral route of administration (e.g. by ingestion).

Combination Therapies

The pharmaceutical compositions and/or pharmaceutical formulations of the present disclosure are useful for the treatment of conditions in which therapy with an agonist of CB1 and/or CB2 is beneficial. Examples of such conditions are outlined above in the therapeutic use section of the present disclosure.

The pharmaceutical compositions and pharmaceutical formulations of the present disclosure may be used in combination with one or more additional therapeutic agents for the treatment of the condition concerned.

An additional therapeutic agent may be included in the pharmaceutical composition or pharmaceutical formulation of the present disclosure with the Compound I, or a pharmaceutically acceptable salt thereof, as defined herein, or, alternatively, it may be administered separately, either at the same time as the pharmaceutical composition or pharmaceutical formulation of the present disclosure or at an earlier or later time.

Therefore, in a further aspect of the disclosure, there is provided a combination product comprising a pharmaceutical composition and/or pharmaceutical formulation of the present disclosure and a pharmaceutical composition comprising an additional therapeutic agent useful in the treatment or prevention of any one of the therapeutic conditions referred to herein, wherein the pharmaceutical composition and/or pharmaceutical formulation of the present disclosure and the pharmaceutical composition comprising the additional therapeutic agent are administered simultaneously, sequentially or separately.

According to this aspect of the disclosure there is provided a combination for use in the treatment of disease or condition in which therapy with a CB1 and/or CB2 agonist is beneficial (e.g. cancer anorexia), comprising a pharmaceutical composition or pharmaceutical formulation of the present disclosure as defined hereinbefore, and one or more additional therapeutic agents.

The present disclosure also provides a pharmaceutical composition and/or pharmaceutical formulation of the present disclosure and one or more additional therapeutic agents for use in the treatment of anorexia, especially cancer anorexia, wherein the pharmaceutical composition and/or formulation of the present disclosure and the additional therapeutic agent are administered simultaneously, sequentially or separately.

In certain embodiments, the pharmaceutical composition and/or pharmaceutical formulation of the present disclosure may be used for the treatment of cancer anorexia in patients undergoing cancer therapy. The cancer therapy may in the form of radiotherapy, surgical therapy, chemotherapy, immunotherapy or a combination thereof.

Herein, where the term "combination" is used it is to be understood that this refers to simultaneous, separate, or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

As indicated above, the combination therapy of the present disclosure may be achieved by way of the simultaneous, sequential, or separate dosing of the individual components of the treatment. Such combination products employ the compositions and formulations of the present disclosure within the dosage range described hereinbefore and one or more further pharmaceutically-active agents, wherein each additional agent is used within its approved dosage range.

PARTICULAR ASPECTS AND EMBODIMENTS OF THE PRESENT DISCLOSURE

The following numbered paragraphs further define particular aspects and embodiments of the present disclosure.

(1) A pharmaceutical composition for oral use comprising as an active substance Compound I, or a pharmaceutically acceptable salt thereof, and a non-aqueous solvent for the active substance.

(2) The pharmaceutical composition according to paragraph (1) wherein the active substance has a solubility in the non-aqueous solvent of at least about 0.1% w/w at room temperature.

(3) The pharmaceutical composition according to paragraphs (1) or (2) wherein the active substance is dissolved in the non-aqueous solvent.

(4) The pharmaceutical composition according to paragraphs (1) to (3) wherein the non-aqueous solvent is water soluble.

(5) The pharmaceutical composition according to any preceding paragraph wherein the pharmaceutical composition comprises at least about 20% w/w of the non-aqueous solvent by weight of the total pharmaceutical composition.

(6) The pharmaceutical composition according to paragraphs (1) to (5) wherein the pharmaceutical composition comprises at least two non-aqueous solvents for the active substance.

(7) The pharmaceutical composition according to paragraphs (1) to (6) wherein the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, a poloxamer, or vitamin E TPGS or combinations thereof.

(8) The pharmaceutical composition according to paragraphs (1) to (7) wherein the non-aqueous solvent comprises polyethylene glycol, ethanol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, oleoyl polyoxylglyceride, propylene glycol mono fatty ester, propylene glycol di fatty acid ester, diethylene glycol monoethyl ether, poloxamer, or vitamin E TPGS or combinations thereof.

(9) The pharmaceutical composition according to paragraphs (1) to (8) the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, poloxamer, vitamin E TPGS or combinations thereof.

(10) The pharmaceutical composition according to paragraphs (1) to (9) wherein the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

(11) The pharmaceutical composition according to paragraphs (1) to (10) wherein the non-aqueous solvent comprises polyethylene glycol, stearoyl polyoxylglyceride, or polyoxyethylene stearate or combinations thereof.

(12) The pharmaceutical composition according to paragraphs (1) to (11) wherein the non-aqueous solvent comprises polyethylene glycol.

(13) The pharmaceutical composition according to paragraphs (1) to (12) wherein the non-aqueous solvent consists essentially of polyethylene glycol.

(14) The pharmaceutical composition according to paragraphs (1) to (13) wherein the non-aqueous solvent consists of polyethylene glycol.

(15) The pharmaceutical composition according to paragraphs (7) to (14) wherein the polyethylene glycol has an average molecular weight between about 200 and about 25000 g/mol, between about 300 and about 10000 g/mol, between about 400 and about 6000 g/mol, or between about 1000 and about 6000 g/mol.

(16) The pharmaceutical composition according to paragraphs (7) to (15) wherein the polyethylene glycol has an average molecular weight of about 400, about 1000, about 1500, about 1540, about 2000, about 3000, about 4000, about 6000, about 8000, or about 20000 g/mol.

(17) The pharmaceutical composition according to paragraphs (7) to (16) wherein the polyethylene glycol has an average molecular weight of about 400, about 1500, about 4000, or about 6000 g/mol.

(18) The pharmaceutical composition according to paragraphs (7) to (17) wherein the polyethylene glycol has an average molecular weight of about 1500 g/mol.

(19) The pharmaceutical composition according to paragraphs (7) to (11) wherein the polyoxyethylene stearate is PEG-32 stearate or polyethylene glycol monostearate or a mixture thereof.

(20) The pharmaceutical composition according to paragraph (7) wherein the long chain triglyceride is selected from corn oil and soy bean oil.

(21) The pharmaceutical composition according to paragraph (7) wherein the medium chain triglyceride comprises caprylic acid or capric acid or a mixture thereof.

(22) The pharmaceutical composition according to paragraph (7) wherein the long chain fatty acid is oleic acid, palmitic acid, stearic acid, arachidic acid, palmitoleic acid, nervonic acid, linoleic acid, alpha-linolenic acid, arachidonic acid, or eicosapentaenoic acid.

(23) The pharmaceutical composition according to paragraphs (7)-(9) wherein the medium chain fatty acid is caprylic acid, capric acid or lauric acid.

(24) The pharmaceutical composition according to paragraphs (7)-(9) wherein the long chain monoglyceride is glyceryl monooleate.

(25) The pharmaceutical composition according to paragraphs (7)-(9) wherein the medium chain monoglyceride is glyceryl monocaprylate.

(26) The pharmaceutical composition according to paragraphs (7) to (10) wherein the polyoxyethylene castor oil derivative is polyoxyl 40 hydrogenated castor oil, polyoxyl-35 castor oil, or a mixture thereof.

(27) The pharmaceutical composition according to paragraph (26) wherein the polyoxyethylene castor oil derivative is polyoxyl 40 hydrogenated castor oil.

(28) The pharmaceutical composition according to paragraphs (7) to (10) wherein the polyoxyethylene sorbitan fatty acid ester is polysorbate 20, polysorbate 80, or a mixture thereof.

(29) The pharmaceutical composition according to paragraph (28) wherein the polyoxyethylene sorbitan fatty acid ester is polysorbate 20.

(30) The pharmaceutical composition according to paragraphs (7) to (9) wherein the propylene glycol mono fatty ester is propylene glycol monocaprylate.

(31) The pharmaceutical composition according to paragraphs (7) to (9) wherein the propylene glycol di fatty acid ester is propylene glycol dilaurate.

(32) The pharmaceutical composition according to any preceding paragraph further comprising vitamin E TPGS or lauroyl polyoxylglyceride.

(33) The pharmaceutical composition according to paragraphs (1) to (32) wherein the non-aqueous solvent is a semi-solid at room temperature.

(34) The pharmaceutical composition according to paragraph (33) wherein the non-aqueous solvent has a melting point between about 35° C. and about 80° C.

(35) The pharmaceutical composition according to the preceding paragraphs wherein the pharmaceutical composition comprises about 0.001 to about 0.8% w/w of the active substance by weight of the total pharmaceutical composition, or about 0.1 to about 0.4% w/w of the active substance by weight of the total pharmaceutical composition.

(36) The pharmaceutical composition according to any preceding paragraph wherein the pharmaceutical composition further comprises a viscosity modifier, colouring, opacifier, sweetening flavouring, and/or preservatives agents such as an antioxidant.

(37) The pharmaceutical composition according to paragraph (36) wherein the antioxidant comprises butylated hydroxyanisole, butylated hydroxytoluene, ascorbic acid, or alpha tocopherol.

(38) The pharmaceutical composition according to any preceding paragraph wherein the pharmaceutical composition is a semi-solid at room temperature.

(39) The pharmaceutical composition according to paragraph (38) wherein the pharmaceutical composition has a melting point between about 35° C. and about 80° C.

(40) The pharmaceutical composition according to any preceding paragraph wherein the active substance is stable in the pharmaceutical composition for at least about 2 weeks, about 1 month, about 2 months, about 3 months, about 6 months, about 12 months, or about 24 months.

(41) The pharmaceutical composition according to paragraph (40) wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

(42) The pharmaceutical composition according to paragraph (41) wherein the chromatographic method is a HPLC method.

(43) The pharmaceutical composition according to paragraph (42) wherein the HPLC method is a reverse phase HPLC method.

(44) The pharmaceutical composition according to any preceding paragraph wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of about 50 rpm.

(45) The pharmaceutical composition according to paragraph (44) wherein at least about 75% of the total amount of the active substance contained in the pharmaceutical composition is released within about the first 30 minutes when the pharmaceutical composition is subjected to the in vitro dissolution test.

(46) The pharmaceutical composition according to paragraphs (44) or (45) wherein at least about 85% of the total amount of the active substance contained in the pharmaceutical composition is released within about the first 15 minutes when the pharmaceutical composition is subjected to the in vitro dissolution test.

(47) The pharmaceutical composition according to any preceding paragraph wherein the active substance is homogenously distributed throughout the non-aqueous solvent.

(48) The pharmaceutical composition according to paragraph (47) wherein the active substance is homogenously distributed throughout the non-aqueous solvent for at least about 2 weeks, about 1 month, about 2 months, about 3 months, about 6 months, about 12 months, or about 24 months.

(49) The pharmaceutical composition according to paragraphs (47) or (48) wherein the active substance is homogenously distributed throughout the non-aqueous solvent for at least about 2 weeks, about 1 month, about 2 months, about 3 months, about 6 months, about 12 months, or about 24 months upon storage of the pharmaceutical composition at room temperature.

(50) The pharmaceutical composition according to paragraphs (47) to (49) wherein the homogeneous distribution of the active substance in the non-aqueous solvent is determined by an analytical method and wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

(51) A pharmaceutical composition comprising as an active substance Compound I, or a pharmaceutically acceptable salt thereof, wherein the pharmaceutical composition is a semi-solid at room temperature.

(52) The pharmaceutical composition according to paragraph (51) wherein the pharmaceutical composition has a melting point between about 35° C. and about 80° C.

(53) The pharmaceutical composition according to paragraphs (51) or (52) wherein the pharmaceutical composition comprises a non-aqueous solvent for the active substance.

(54) The pharmaceutical composition according to paragraph (53) wherein the non-aqueous solvent for the active substance is a semi-solid at room temperature.

(55) The pharmaceutical composition according to paragraph (54) wherein the non-aqueous solvent has a melting point between about 35° C. and about 80° C.

(56) The pharmaceutical composition according to paragraphs (53) to (55) wherein the active substance has a solubility in the non-aqueous solvent of at least about 0.1% w/w.

(57) The pharmaceutical composition according to paragraphs (53) to (56) wherein the active substance is dissolved in the non-aqueous solvent.

(58) The pharmaceutical composition according to paragraphs (53) to (57) wherein the non-aqueous solvent is water soluble.

(59) The pharmaceutical composition according to paragraphs (53) to (58) wherein the pharmaceutical composition comprises at least about 20% w/w of the non-aqueous solvent by weight of the total pharmaceutical composition.

(60) The pharmaceutical composition according to paragraphs (53) to (59) wherein the pharmaceutical composition comprises at least two non-aqueous solvents for the active substance.

(61) The pharmaceutical composition according to paragraphs (53) to (60) wherein the non-aqueous solvent comprises polyethylene glycol, propylene glycol, ethanol, glycerol, stearoyl polyoxylglyceride, polyoxyethylene stearate, long chain triglyceride, medium chain triglyceride, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, a poloxamer, or vitamin E TPGS or combinations thereof.

(62) The pharmaceutical composition according to paragraphs (53) to (61) wherein the non-aqueous solvent comprises polyethylene glycol, ethanol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, oleoyl polyoxylglyceride, propylene glycol mono fatty ester, propylene glycol di fatty acid ester, diethylene glycol monoethyl ether, poloxamer, or vitamin E TPGS or combinations thereof.

(63) The pharmaceutical composition according to paragraphs (53) to (62) wherein the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, poloxamer, vitamin E TPGS or combinations thereof.

(64) The pharmaceutical composition according to paragraphs (53) to (63) wherein the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

(65) The pharmaceutical composition according to paragraphs (53) to (64) wherein the non-aqueous solvent comprises polyethylene glycol, stearoyl polyoxylglyceride, or polyoxyethylene stearate or combinations thereof.

(66) The pharmaceutical composition according to paragraphs (53) to (65) wherein the non-aqueous solvent comprises polyethylene glycol.

(67) The pharmaceutical composition according to paragraphs (53) to (66) wherein the non-aqueous solvent consists essentially of polyethylene glycol.

(68) The pharmaceutical composition according to paragraphs (53) to (67) wherein the non-aqueous solvent consists of polyethylene glycol.

(69) The pharmaceutical composition according to paragraphs (61) to (68) wherein the polyethylene glycol has an average molecular weight between about 200 and about 25000 g/mol, between about 300 and about 10000 g/mol, between about 400 and about 6000 g/mol, or about 1000 and about 6000 g/mol.

(70) The pharmaceutical composition according to paragraphs (61) to (69) wherein the polyethylene glycol has an average molecular weight of about 400, about 1000, about 1500, about 1540, about 2000, about 3000, about 4000, about 6000, about 8000, or about 20000 g/mol.

(71) The pharmaceutical composition according to paragraphs (61) to (70) wherein the polyethylene glycol has an average molecular weight of about 400, about 1500, about 4000, or about 6000 g/mol.

(72) The pharmaceutical composition according to paragraphs (61) to (71) wherein the polyethylene glycol has an average molecular weight of about 1500 g/mol.

(73) The pharmaceutical composition according to paragraphs (51) to (72) further comprising vitamin E TPGS or lauroyl polyoxyl-32 glyceride.

(74) The pharmaceutical composition according to paragraphs (51) to (73) wherein the pharmaceutical composition comprises about 0.001 to about 0.8% w/w of the active substance by weight of the total pharmaceutical composition.

(75) The pharmaceutical composition according to paragraphs (51) to (74) wherein the pharmaceutical composition further comprises a viscosity modifier, colouring, opacifier, sweetening flavouring, and/or a preservatives agent such as an antioxidant.

(76) The pharmaceutical composition according to paragraphs (51) to (75) wherein the active substance is stable in the pharmaceutical composition for at least about 2 weeks, about 1 month, about 2 months, about 3 months, about 6 months, about 12 months, or about 24 months.

(77) The pharmaceutical composition according to paragraph (76) wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

(78) The pharmaceutical composition according to paragraph (77) wherein the chromatographic method is a HPLC method.

(79) The pharmaceutical composition according to paragraph (78) wherein the HPLC method is a reverse phase HPLC method.

(80) The pharmaceutical composition according to paragraphs (51) to (79) wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

(81) The pharmaceutical composition according to paragraph (80) wherein at least about 75% of the total amount of the active substance contained in the pharmaceutical composition is released within about the first 30 minutes when the pharmaceutical composition is subjected to the in vitro dissolution test.

(82) The pharmaceutical composition according to paragraphs (80) to (81) wherein at least about 85% of the total amount of the active substance contained in the pharmaceutical composition is released within about the first 15 minutes when the pharmaceutical composition is subjected to the in vitro dissolution test.

(83) The pharmaceutical composition according to paragraphs (51) to (82) wherein the active substance is homogenously distributed throughout the non-aqueous solvent.

(84) The pharmaceutical composition according to paragraph (83) wherein the active substance is homogenously distributed throughout the non-aqueous solvent for at least about 2 weeks, about 1 month, about 2 months, about 3 months, about 6 months, about 12 months, or about 24 months.

(85) The pharmaceutical composition according to paragraphs (83) or (84) wherein the active substance is homogenously distributed throughout the non-aqueous solvent for at least about 2 weeks, about 1 month, about 2 months, about 3 months, about 6 months, about 12 months, or about 24 months.

(86) The pharmaceutical composition according to paragraphs (83) to (85) wherein the homogeneous distribution of the active substance in the non-aqueous solvent is determined by an analytical method and wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

(87) A pharmaceutical composition comprising as an active substance Compound I, or a pharmaceutically acceptable salt thereof, wherein the active substance is stable in the pharmaceutical composition for at least about 2 weeks, about 1 month, about 2 months, about 3 months, about 6 months, about 12 months, or about 24 months.

(88) The pharmaceutical composition according to paragraph (87) wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

(89) The pharmaceutical composition according to paragraph (88) wherein the chromatographic method is a HPLC method.

(90) The pharmaceutical composition according to paragraph (89) wherein the HPLC method is a reverse phase HPLC method.

(91) The pharmaceutical composition according to paragraphs (87) to (90) wherein the pharmaceutical composition is a semi-solid at room temperature.

(92) The pharmaceutical composition according to paragraph (91) wherein the pharmaceutical composition has a melting point between about 35° C. and about 80° C.

(93) The pharmaceutical composition according to paragraphs (87) to (92) wherein the pharmaceutical composition comprises a non-aqueous solvent for the active substance.

(94) The pharmaceutical composition according to paragraph (93) wherein the active substance has a solubility in the non-aqueous solvent of at least about 0.1% w/w.

(95) The pharmaceutical composition according to paragraphs (93) to (94) wherein the active substance is dissolved in the non-aqueous solvent.

(96) The pharmaceutical composition according to paragraphs (93) to (95) wherein the non-aqueous solvent is water soluble.

(97) The pharmaceutical composition according to paragraphs (93) to (96) wherein the pharmaceutical composition comprises at least about 20% w/w of the non-aqueous solvent by weight of the total pharmaceutical composition.

(98) The pharmaceutical composition according to paragraphs (93) to (97) wherein the pharmaceutical composition comprises at least one non-aqueous solvents for the active substance.

(99) The pharmaceutical composition according to paragraphs (93) to (98) wherein the non-aqueous solvent is a semi-solid at room temperature.

(100) The pharmaceutical composition according to paragraph (99) wherein the non-aqueous solvent has a melting point between 35° C. and 80° C.

(101) The pharmaceutical composition according to paragraphs (93) to (100) wherein the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, a poloxamer, or vitamin E TPGS or combinations thereof.

(102) The pharmaceutical composition according to paragraphs (93) to (101), wherein the non-aqueous solvent comprises polyethylene glycol, stearoyl polyoxylglyceride, long chain fatty acid, medium chain fatty acid, medium chain monoglyceride, medium chain diglyceride, polyoxyethylene castor oil derivative, polyoxyethylene sorbitan fatty acid ester, polyoxyethylated 12-hydroxystearic acid, propylene glycol di fatty acid ester, diethylene glycol monoethyl ether, or poloxamer or combinations thereof. Suitably, the polyoxyethylene castor oil derivative comprises polyoxyl 40 hydrogenated castor oil. Suitably, the polyoxyethylene castor oil derivative is polyoxyl 40 hydrogenated castor oil (103) The pharmaceutical composition according to paragraphs (93) to (102), wherein the non-aqueous solvent comprises polyethylene glycol, stearoyl polyoxylglyceride, polyoxyethylene stearate, medium chain monoglyceride, medium chain diglyceride, polyoxyethylene sorbitan fatty acid ester, propylene glycol di fatty acid ester, or combinations thereof.

(104) The pharmaceutical composition according to paragraphs (93) to (103) wherein the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

(105) The pharmaceutical composition according to paragraphs (93) to (104)) wherein the non-aqueous solvent comprises polyethylene glycol, stearoyl polyoxylglyceride, or polyoxyethylene stearate or combinations thereof.

(106) The pharmaceutical composition according to paragraphs (101) to (105) wherein the non-aqueous solvent comprises polyethylene glycol.

(107) The pharmaceutical composition according to paragraphs (101) to (106) wherein the non-aqueous solvent consists essentially of polyethylene glycol.

(108) The pharmaceutical composition according to paragraphs (101) to (107) wherein the non-aqueous solvent consists of polyethylene glycol.

(109) The pharmaceutical composition according to paragraphs (101) to (108) wherein the polyethylene glycol has an average molecular weight between about 200 and about 25000 g/mol, between about 300 and about 10000 g/mol, between about 400 and about 6000 g/mol, or between about 1000 and about 6000 g/mol.

(110) The pharmaceutical composition according to paragraphs (101) to (109) wherein the polyethylene glycol has an average molecular weight of about 400, about 1000, about 1500, about 1540, about 2000, about 3000, about 4000, about 6000, about 8000, or about 20000 g/mol.

(111) The pharmaceutical composition according to paragraphs (101) to (110) wherein the polyethylene glycol has an average molecular weight of about 400, about 1500, about 4000, or about 6000 g/mol.

(112) The pharmaceutical composition according to paragraphs (101) to (111) wherein the polyethylene glycol has an average molecular weight of about 1500 g/mol.

(113) The pharmaceutical composition according to paragraphs (87) to (112) further comprising vitamin E TPGS or lauroyl polyoxyl-32 glyceride.

(114) The pharmaceutical composition according to paragraphs (87) to (113) wherein the pharmaceutical composition further comprises a viscosity modifier, colouring, opacifier, sweetening flavouring, and/or a preservatives agent such as an antioxidant.

(115) The pharmaceutical composition according to paragraphs (87) to (114) wherein the pharmaceutical composition comprises about 0.001 to about 0.8% w/w of the active substance by weight of the total pharmaceutical composition.

(116) The pharmaceutical composition according to paragraphs (87) to (115) wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

(117) The pharmaceutical composition according to paragraph (116) wherein at least about 75% of the total amount of the active substance contained in the pharmaceutical composition is released within about the first 30 minutes when the pharmaceutical composition is subjected to the in vitro dissolution test.

(118) The pharmaceutical composition according to paragraphs (116) or (117) wherein at least about 85% of the total amount of the active substance contained in the pharmaceutical composition is released within about the first 15 minutes when the pharmaceutical composition is subjected to the in vitro dissolution test.

(119) The pharmaceutical composition according to paragraphs (93) to (118) wherein the active substance is homogenously distributed throughout the non-aqueous solvent.

(120) The pharmaceutical composition according to paragraph (119) wherein the active substance is homogenously distributed throughout the non-aqueous solvent for at least about 2 weeks, about 1 month, about 2 months, about 3 months, about 6 months, about 12 months, or about 24 months.

(121) The pharmaceutical composition according to paragraphs (119) or (120) wherein the active substance is homogenously distributed throughout the non-aqueous solvent for at least about 2 weeks, about 1 month, about 2 months, about 3 months, about 6 months, about 12 months, or about 24 months upon storage of the pharmaceutical composition at room temperature.

(122) The pharmaceutical composition according to paragraphs (119) to (121) wherein the homogeneous distribution of the active substance in the non-aqueous solvent is determined by an analytical method and wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

(123) A pharmaceutical composition comprising as an active substance Compound I, or a pharmaceutically acceptable salt thereof, wherein:

1) at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm; and
2) the pharmaceutical composition is a semi-solid at room temperature.

(124) The pharmaceutical composition of paragraph (123) wherein at least about 75% of the total amount of the active substance contained in the pharmaceutical composition is released within about the first 30 minutes when the pharmaceutical composition is subjected to the in vitro dissolution test.

(125) The pharmaceutical composition of paragraphs (123) or (124) wherein at least about 85% of the total amount of the active substance contained in the pharmaceutical composition is released within about the first 15 minutes when the pharmaceutical composition is subjected to the in vitro dissolution test.

(126) The pharmaceutical composition according to paragraphs (123) to (125) wherein the active substance is stable in the pharmaceutical for at least about 2 weeks, about 1 month, about 2 months, about 3 months, about 6 months, about 12 months, or about 24 months.

(127) The pharmaceutical composition according to paragraph (126) wherein:

a. the total amount of degradation products of the active substance is less than or equal to about 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or
b. the assay of the active substance is about 90 to about 110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

(128) The pharmaceutical composition according to paragraph (127) wherein the chromatographic method is a HPLC method.

(129) The pharmaceutical composition according to paragraph (128) wherein the HPLC method is a reverse phase HPLC method.

(130) The pharmaceutical composition according to paragraphs (123) to (129) wherein the pharmaceutical composition has a melting point between about 35° C. and about 80° C.

(131) The pharmaceutical composition according to paragraphs (123) to (130) wherein the pharmaceutical composition comprises a non-aqueous solvent for the active substance.

(132) The pharmaceutical composition according to paragraph (131) wherein the active substance has a solubility in the non-aqueous solvent of at least about 0.1% w/w.

(133) The pharmaceutical composition according to paragraphs (131) or (132) wherein the active substance is dissolved in the non-aqueous solvent.

(134) The pharmaceutical composition according to paragraphs (131) to (133) wherein the non-aqueous solvent for the active substance is a semi-solid at room temperature.

(135) The pharmaceutical composition according to paragraph (134) wherein the non-aqueous solvent has a melting point between about 35° C. and about 80° C.

(136) The pharmaceutical composition according to paragraphs (131) to (135) wherein the non-aqueous solvent is water soluble.

(137) The pharmaceutical composition according to paragraphs (131) to (136) wherein the pharmaceutical composition comprises at least about 20% w/w of the non-aqueous solvent by weight of the total pharmaceutical composition.

(138) The pharmaceutical composition according to paragraphs (131) to (137) wherein the pharmaceutical composition comprises at least two non-aqueous solvents for the active substance.

(139) The pharmaceutical composition according to paragraphs (131) to (138) wherein the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, a poloxamer, or vitamin E TPGS or combinations thereof.

(140) The pharmaceutical composition according to paragraphs (131) to (139) wherein the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, or poloxamer or combinations thereof.

(141) The pharmaceutical composition according to paragraphs (131) to (140) wherein the non-aqueous solvent comprises polyethylene glycol, stearoyl polyoxylglyceride, medium chain fatty acid, long chain monoglyceride, long chain diglyceride, medium chain monoglyceride, medium chain diglyceride, polyoxyethylene sorbitan fatty acid ester, caprylocaproyl polyoxylglyceride, propylene glycol mono fatty ester, propylene glycol di fatty acid ester, diethylene glycol monoethyl ether, or poloxamer or combinations thereof.

(142) The pharmaceutical composition according to paragraphs (131) to (141) wherein the non-aqueous solvent comprises polyethylene glycol, polyoxyethylene stearate, polyoxyethylene castor oil derivative, polyoxyethylated 12-hydroxystearic acid, diethylene glycol monoethyl ether, or poloxamer, vitamin E TPGS, or combinations thereof.

(143) The pharmaceutical composition according to paragraphs (131) to (142) wherein the non-aqueous solvent comprises polyethylene glycol, polyoxyethylene castor oil derivative, polyoxyethylated 12-hydroxystearic acid, diethylene glycol monoethyl ether, or poloxamer, or combinations thereof.

(144) The pharmaceutical composition according to paragraphs (131) to (143) wherein the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

(145) The pharmaceutical composition according to paragraphs (131) to (144) wherein the non-aqueous solvent comprises polyethylene glycol, stearoyl polyoxylglyceride, or polyoxyethylene stearate or combinations thereof.

(146) The pharmaceutical composition according to paragraphs (131) to (145) wherein the non-aqueous solvent comprises polyethylene glycol.

(147) The pharmaceutical composition according to paragraphs (131) to (146) wherein the non-aqueous solvent consists essentially of polyethylene glycol.

(148) The pharmaceutical composition according to paragraphs (131) to (147) wherein the non-aqueous solvent consists of polyethylene glycol.

(149) The pharmaceutical composition according to paragraphs (139) to (148) wherein the polyethylene glycol has an average molecular weight between about 200 and about 25000 g/mol, between about 300 and about 10000 g/mol, between about 400 and about 6000 g/mol, or about 1000 and about 6000 g/mol.

(150) The pharmaceutical composition according to paragraphs (139) to (149) wherein the polyethylene glycol has an average molecular weight of about 400, about 1000, about 1500, about 1540, about 2000, about 3000, about 4000, about 6000, about 8000, or about 20000 g/mol.

(151) The pharmaceutical composition according to paragraphs (139) to (150) wherein the polyethylene glycol has an average molecular weight of about 400, about 1500, about 4000, or about 6000 g/mol.

(152) The pharmaceutical composition according to paragraphs (139) to (151) wherein the polyethylene glycol has an average molecular weight of about 1500 g/mol.

(153) The pharmaceutical composition according to paragraphs (123) to (152) wherein the pharmaceutical composition comprises about 0.001 to about 0.8% w/w of the active substance by weight of the total pharmaceutical composition.

(154) The pharmaceutical composition according to paragraphs (123) to (153) further comprising vitamin E TPGS or lauroyl polyoxyl-32 glyceride.

(155) The pharmaceutical composition according to paragraphs (123) to (154) wherein the pharmaceutical composition further comprises a viscosity modifier, colouring, opacifier, sweetening flavouring, and/or a preservatives agent such as an antioxidant.

(156) The pharmaceutical composition according to paragraphs (131) to (155) wherein the active substance is homogenously distributed throughout the non-aqueous solvent.

(157) The pharmaceutical composition according to paragraph (156) wherein the active substance is homogenously distributed throughout the non-aqueous solvent for at least about 2 weeks, about 1 month, about 2 months, about 3 months, about 6 months, about 12 months, or about 24 months.

(158) The pharmaceutical composition according to paragraphs (156) or (157) wherein the active substance is homogenously distributed throughout the non-aqueous solvent for at least about 2 weeks, about 1 month, about 2 months, about 3 months, about 6 months, about 12 months, or about 24 months upon storage of the pharmaceutical composition at room temperature.

(159) The pharmaceutical composition according to paragraphs (156) to (158) wherein the homogeneous distribution of the active substance in the non-aqueous solvent is determined by an analytical method and wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

(160) A pharmaceutical composition for oral use comprising as an active substance Compound I, or a pharmaceutically acceptable salt thereof, and a non-aqueous solvent for the active substance wherein the active substance is homogenously distributed throughout the non-aqueous solvent.

(161) The pharmaceutical composition according to paragraph (160) wherein the active substance is homogenously distributed throughout the non-aqueous solvent for at least about 2 weeks, about 1 month, about 2 months, about 3 months, about 6 months, about 12 months, or about 24 months.

(162) The pharmaceutical composition according to paragraphs (160) or (161) wherein the active substance is homogenously distributed throughout the non-aqueous solvent for at least about 2 weeks, about 1 month, about 2 months, about 3 months, about 6 months, about 12 months, or about 24 months upon storage of the pharmaceutical composition at room temperature.

(163) The pharmaceutical composition according to paragraphs (160) to (162) wherein the homogeneous distribution of the active substance in the non-aqueous solvent is determined by an analytical method.

(164) The pharmaceutical composition according to paragraph (163) wherein the analytical method comprises determining the weight percentage of the active substance within a portion of the pharmaceutical composition.

(165) The pharmaceutical composition according to paragraphs (163) to (164) wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

(166) The pharmaceutical composition according to paragraphs (163) to (165) wherein the analytical method comprises determining the weight percentage of the active substance within a portion of the pharmaceutical composition and wherein the weight percentage of the active substance within the portion of the pharmaceutical composition is ±2% of the expected value based on the total amount of the active substance added to the total amount of the pharmaceutical composition.

(167) The pharmaceutical composition according to paragraphs (163) to (166) wherein the analytical method comprises determining the weight percentage of the active substance within a portion of the pharmaceutical composition and wherein the weight percentage of the active substance within the portion of the pharmaceutical composition is ±1% of the expected value based on the total amount of the active substance added to the total amount of the pharmaceutical composition.

(168) The pharmaceutical composition according to paragraphs (163) to (167) wherein the analytical method comprises a chromatographic method or a spectroscopic method.

(169) The pharmaceutical composition according to paragraph (168) wherein the chromatographic method is HPLC.

(170) The pharmaceutical composition according to paragraphs (160) to (169) wherein the pharmaceutical composition is a semi-solid at room temperature.

(171) The pharmaceutical composition according to paragraph (170) wherein the pharmaceutical composition has a melting point between about 35° C. and about 80° C.

(172) The pharmaceutical composition according to paragraphs (160) to (171) wherein the non-aqueous solvent for the active substance is a semi-solid at room temperature.

(173) The pharmaceutical composition according to paragraph (172) wherein the non-aqueous solvent has a melting point between about 35° C. and about 80° C.

(174) The pharmaceutical composition according to paragraph (160) to (173) wherein the active substance has a solubility in the non-aqueous solvent of at least about 0.1% w/w.

(175) The pharmaceutical composition according to paragraphs (160) to (174) wherein the active substance is dissolved in the non-aqueous solvent.

(176) The pharmaceutical composition according to paragraphs (160) to (175) wherein the non-aqueous solvent is water soluble.

(177) The pharmaceutical composition according to paragraphs (160) to (176) wherein the pharmaceutical composition comprises at least about 20% w/w of the non-aqueous solvent by weight of the total pharmaceutical composition.

(178) The pharmaceutical composition according to paragraphs (160) to (177) wherein the pharmaceutical composition comprises at least two non-aqueous solvents for the active substance.

(179) The pharmaceutical composition according to paragraphs (160) to (178) wherein the non-aqueous solvent comprises polyethylene glycol, propylene glycol, ethanol, glycerol, stearoyl polyoxylglyceride, polyoxyethylene stearate, long chain triglyceride, medium chain triglyceride, long chain fatty acid, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, propylene glycol mono fatty ester, propylene glycol di fatty acid ester, soybean oil, glyceryl palmitostearate, diethylene glycol monoethyl ether, sorbitan ester, a poloxamer, or vitamin E TPGS or combinations thereof.

(180) The pharmaceutical composition according to paragraphs (160) to (179) wherein the non-aqueous solvent comprises polyethylene glycol, ethanol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, oleoyl polyoxylglyceride, propylene glycol mono fatty ester, propylene glycol di fatty acid ester, diethylene glycol monoethyl ether, poloxamer, or vitamin E TPGS or combinations thereof.

(181) The pharmaceutical composition according to paragraphs (160) to (180) wherein the non-aqueous solvent comprises polyethylene glycol, stearoyl polyoxylglyceride, polyoxyethylene stearate, medium chain fatty acid, long chain monoglyceride, long chain diglyceride, medium chain monoglyceride, medium chain diglyceride, polyoxyethylene castor oil derivative, polyoxyethylene sorbitan fatty acid ester, polyoxyethylated 12-hydroxystearic acid, caprylocaproyl polyoxylglyceride, propylene glycol mono fatty ester, propylene glycol di fatty acid ester, diethylene glycol monoethyl ether, poloxamer, vitamin E TPGS or combinations thereof.

(182) The pharmaceutical composition according to paragraphs (160) to (181) wherein the non-aqueous solvent comprises polyethylene glycol, propylene glycol, glycerol, stearoyl polyoxylglyceride, polyoxyethylene stearate, polyoxyethylene castor oil derivatives, polyoxyethylene sorbitan fatty acid ester, polyoxyethylated 12-hydroxystearic acid, caprylocaproyl polyoxylglyceride, linoleoyl polyoxylglyceride, oleoyl polyoxylglyceride, or sorbitan ester or combinations thereof.

(183) The pharmaceutical composition according to paragraphs (160) to (182) wherein the non-aqueous solvent comprises polyethylene glycol, stearoyl polyoxylglyceride, or polyoxyethylene stearate or combinations thereof.

(184) The pharmaceutical composition according to paragraphs (160) to (183) wherein the non-aqueous solvent comprises polyethylene glycol.

(185) The pharmaceutical composition according to paragraphs (160) to (184) wherein the non-aqueous solvent consists essentially of polyethylene glycol.

(186) The pharmaceutical composition according to paragraphs (160) to (185) wherein the non-aqueous solvent consists of polyethylene glycol.

(187) The pharmaceutical composition according to paragraphs (179) to (186) wherein the polyethylene glycol has an average molecular weight between about 200 and about 25000 g/mol, between about 300 and about 10000 g/mol, between about 400 and about 6000 g/mol, or between about 1000 and about 6000 g/mol.

(188) The pharmaceutical composition according to paragraphs (179) to (187) wherein the polyethylene glycol has an average molecular weight of about 400, about 1000, about 1500, about 1540, about 2000, about 3000, about 4000, about 6000, about 8000, or about 20000 g/mol.

(189) The pharmaceutical composition according to paragraphs (179) to (188) wherein the polyethylene glycol has an average molecular weight of about 400, about 1500, about 4000, or about 6000 g/mol.

(190) The pharmaceutical composition according to paragraphs (179) to (189) wherein the polyethylene glycol has an average molecular weight of about 1500 g/mol.

(191) The pharmaceutical composition according to paragraphs (160) to (190) further comprising vitamin E TPGS or lauroyl polyoxyl-32 glyceride.

(192) The pharmaceutical composition according to paragraphs (160) to (191) wherein the pharmaceutical composition comprises about 0.001 to about 0.8% w/w of the active substance by weight of the total pharmaceutical composition.

(193) The pharmaceutical composition according to paragraphs (160) to (192) wherein the pharmaceutical composition further comprises a viscosity modifier, colouring, opacifier, sweetening flavouring, and/or a preservative agent such as an antioxidant.

(194) The pharmaceutical composition according to paragraphs (160) to (193) wherein the active substance is stable in the pharmaceutical composition for at least about 2 weeks, about 1 month, about 2 months, about 3 months, about 6 months, about 12 months, or about 24 months.

(195) The pharmaceutical composition according to paragraph (194) wherein:

a. the total amount of degradation products of the active substance is less than or equal to 4 area % as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months; and/or b. the assay of the active substance is 90-110% of nominal as determined by a chromatographic method when the pharmaceutical composition is stored at 25° C./60% RH and/or 40° C./75% RH for at least about 2 weeks, about 1 month, about 2 months, about 3 months, about 6 months, about 12 months, or about 24 months.

(196) The pharmaceutical composition according to paragraph (195) wherein the chromatographic method is a HPLC method.

(197) The pharmaceutical composition according to paragraph (196) wherein the HPLC method is a reverse phase HPLC method.

(198) The pharmaceutical composition according to paragraphs (160) to (197) wherein at least about 75% of the total amount of the active substance contained in the pharmaceutical composition is released within about the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

(199) The pharmaceutical composition according to paragraph (198) wherein at least about 75% of the total amount of the active substance contained in the pharmaceutical composition is released within about the first 30 minutes when the pharmaceutical composition is subjected to the in vitro dissolution test.

(200) The pharmaceutical composition according to paragraphs (198) or (199) wherein at least about 85% of the total amount of the active substance contained in the pharmaceutical composition is released within about the first 15 minutes when the pharmaceutical composition is subjected to the in vitro dissolution test.

(201) The pharmaceutical composition according to paragraphs (1) to (200) comprising two non-aqueous solvents for the active substance.

(202) The pharmaceutical composition according to paragraph (201) wherein the first non-aqueous solvent comprises polyethylene glycol or vitamin E TPGS.

(203) The pharmaceutical composition according to paragraphs (202) wherein the first non-aqueous solvent comprises polyethylene glycol having an average molecular weight of less than 1000 g/mol.

(204) The pharmaceutical composition according to paragraphs (201) to (203) wherein the first non-aqueous solvent comprises polyethylene glycol having an average molecular weight of about 400 g/mol.

(205) The pharmaceutical composition according to paragraph (201) to (204) wherein the second non-aqueous solvent comprises polyethylene glycol having an average molecular weight of at least about 1000 g/mol.

(206) The pharmaceutical composition according to paragraphs (201) to (205) wherein the weight ratio of the first non-aqueous solvent to the second non-aqueous solvent is between about 1:20 and about 20:1, such as between about 1:10 and about 10:1, such as between about 1:9 and about 9:1.

(207) The pharmaceutical composition according to paragraphs (61)-(65), (73)-(86), (101)-(105), (113)-(122), (139)-(142), (144)-(145), (153)-(159), (179)-(183), (191)-(204) and (206) wherein the polyoxyethylene stearate is PEG-32 stearate or polyethylene glycol monostearate or a mixture thereof.

(208) The pharmaceutical composition according to paragraphs (207) wherein the polyoxyethylene stearate is polyethylene glycol monostearate.

(209) The pharmaceutical composition according to paragraphs (61)-(63), (73)-(86), (101)-(102), (113)-(122), (139)-(141), (153)-(159), (179)-(181), (191-204) and (206) wherein the medium chain fatty acid is caprylic acid, capric acid or lauric acid.

(210) The pharmaceutical composition according to paragraphs (61)-(63), (73)-(86), (101), (113)-(122), (139)-(141), (153)-(159), (179)-(181), (191-204) and (206) wherein the long chain monoglyceride is glyceryl monooleate.

(211) The pharmaceutical composition according to paragraphs (61)-(63), (73)-(86), (101)-(103), (113)-(122), (139)-(141), (153)-(159), (179)-(181), (191-204) and (206) wherein the medium chain monoglyceride is glyceryl monocaprylate.

(212) The pharmaceutical composition according to paragraphs (61)-(64), (73)-(86), (101)-(104), (113)-(122), (139)-(144), (153)-(159), (179)-(182), (191-204) and (206) wherein the polyoxyethylene castor oil derivative is polyoxyl 40 hydrogenated castor oil, polyoxyl-35 castor oil, or a mixture thereof.

(213) The pharmaceutical composition according to paragraph (212) wherein the polyoxyethylene castor oil derivative is polyoxyl 40 hydrogenated castor oil.

(214) The pharmaceutical composition according to paragraphs (61)-(64), (73)-(86), (101)-(104), (113)-(122), (139)-(141), (153)-(159), (179)-(182), (191-204) and (206) wherein the polyoxyethylene sorbitan fatty acid ester is polysorbate 20, polysorbate 80, or a mixture thereof.

(215) The pharmaceutical composition according to paragraph (214) wherein the polyoxyethylene sorbitan fatty acid ester is polysorbate 20.

(216) The pharmaceutical composition according to paragraphs (61)-(63), (73)-(86), (101), (113)-(122), (139)-(141), (153)-(159), (179)-(181), (191-204) and (206) wherein the propylene glycol mono fatty ester is propylene glycol monocaprylate.

(217) The pharmaceutical composition according to paragraphs (61)-(63), (73)-(86), (101)-(103), (113)-(122), (139)-(141), (153)-(159), (179)-(181), (191-204) and (206) wherein the propylene glycol di fatty acid ester is propylene glycol dilaurate.

(218) The pharmaceutical composition according to any preceding paragraph further comprising vitamin E TPGS or lauroyl polyoxylglyceride.

(219) An immediate release pharmaceutical formulation for oral use comprising the pharmaceutical composition according to paragraphs (1) to (218).

(220) The immediate release pharmaceutical formulation according to paragraph (219) wherein when the immediate release pharmaceutical formulation is subjected to a content uniformity test as described in the European Pharmacopeia the acceptance value is less than 15.

(221) The immediate release pharmaceutical formulation according to paragraph (220) wherein the acceptance value is less than 10.

(222) The immediate release pharmaceutical formulation according to paragraphs (220) or (221) wherein the content uniformity test comprises a chromatographic assay of the immediate release pharmaceutical formulation.

(223) The immediate release pharmaceutical formulation according to paragraphs (219) to (222) wherein the immediate release pharmaceutical formulation is an immediate release capsule formulation.

(224) The immediate release pharmaceutical formulation according to paragraph (223) comprising a capsule shell wherein the capsule shell comprises gelatin or HPMC.

(225) The immediate release pharmaceutical formulation according to paragraphs (224) wherein the capsule shell comprises gelatin.

(226) The immediate release pharmaceutical formulation according to paragraph (219) wherein the immediate release pharmaceutical formulation is a spray.

(227) The immediate release pharmaceutical formulation according to paragraphs (219) to (226) wherein the immediate release formulation comprises between about 10 and about 1000 μg, between about 10 and about 650 μg, or between about 100 and about 650 μg of the active substance.

(228) The immediate release pharmaceutical formulation according to paragraphs (219) to (227) wherein the immediate release formulation comprises about 50 μg of the active substance.

(229) The immediate release pharmaceutical formulation according to paragraphs (219) to (227) wherein the immediate release formulation comprises about 200 μg of the active substance.

(230) The pharmaceutical composition according to paragraphs (1) to (218) or the immediate release pharmaceutical formulation according to paragraphs (219) to (229) for use as medicament.

(231) The pharmaceutical composition according to paragraphs (1) to (218) or the immediate release pharmaceutical formulation according to paragraphs (219) to (229) for use in a disease state or disorder in which dysfunction of $CB_1$ and/or $CB_2$ receptors are present or implicated.

(232) The pharmaceutical composition according to paragraphs (1) to (218) or the immediate release pharmaceutical formulation according to paragraphs (219) to (229) for use in the treatment of an anorexia associated condition; a cachexia associated conditions; anorexia nervosa; a pain condition; anxiety disorders; cancer; multiple sclerosis; Parkinson's disease; Huntington's chorea; Alzheimer's disease; AIDS; amyotrophic lateral sclerosis; gastrointestinal disorders; cardiovascular disorders; insomnia; autoimmune diseases such as arthritis, collagen diseases, or allergies; diarrhoea; depression; anxiety and stress-related disorders such as post-traumatic stress disorders, panic disorder, generalized anxiety disorder, social phobia, and obsessive compulsive disorder; urinary incontinence; premature ejaculation; various mental illnesses; cough; lung oedema; various gastro-intestinal disorders, e.g. constipation, functional gastrointestinal disorders such as Irritable Bowel Syndrome and Functional Dyspepsia; Parkinson's disease and other motor disorders; traumatic brain injury; stroke; cardioprotection following miocardial infarction; spinal injury and drug addiction including the treatment of alcohol, nicotine, opioid and other drug abuse; and for disorders of the sympathetic nervous system, such as hypertension.

(233) The pharmaceutical composition or the immediate release pharmaceutical formulation according to paragraph (232) for use in the treatment of an anorexia associated condition; a cachexia associated condition; or anorexia nervosa.

(234) The pharmaceutical composition or the immediate release pharmaceutical formulation according to paragraphs (232) or (233) wherein the anorexia associated condition is anorexia associated with cancer, anorexia associated with HIV, anorexia associated with Chronic Kidney Disease, anorexia associated with dementia, or anorexia associated with chronic congestive heart failure.

(235) The pharmaceutical composition or the immediate release pharmaceutical formulation according to paragraphs (232) to (234) wherein the anorexia associated condition is anorexia associated with cancer.

(236) The pharmaceutical composition or the immediate release pharmaceutical formulation according to paragraphs (232) or (233) wherein the cachexia associated condition is cachexia associated with cancer, cachexia associated with HIV, cachexia associated with Chronic Kidney Disease, cachexia associated with dementia, or cachexia associated with chronic congestive heart failure.

(237) The pharmaceutical composition or the immediate release pharmaceutical formulation according to paragraph (232) wherein the pain condition is a pain condition in cancer, acute pain, chronic pain, neuropathic pain, back pain, cancer pain, visceral pain, pain caused by rheumatoid arthritis, migraine.

(238) The pharmaceutical composition or the immediate release pharmaceutical formulation according to paragraph (237) wherein the pain condition in cancer is a pain condition in cancer associated with the reduction of opiate use, associated with the reduction in nausea and/or vomiting in cancer patients.

(239) The pharmaceutical composition according to paragraphs (1) to (218) or the immediate release pharmaceutical formulation according to paragraphs (219) to (229) for use during general anaesthesia and monitored anaesthesia.

(240) The pharmaceutical composition according to paragraphs (1) to (218) or the immediate release pharmaceutical formulation according to paragraphs (219) to (229) for use as an analgesic agent.

EXAMPLES

The following abbreviations have been used in the Examples:

API active pharmaceutical ingredient, which in the present case is N-(2-(tert-butyl)-1-((4,4-difluorocyclohexyl)methyl)-1H-benzimidazol-5-yl)ethanesulfonamide (Compound I)

AV acceptance value

HPMC hydroxypropyl methylcellulose n/a not applicable

NMT not more than

PEG polyethylene glycol

Vitamin E TPGS D-α-Tocopherol polyethylene glycol succinate

Example 1—Forced Degradation Study of N-(2-(tert-butyl)-1-((4,4-difluorocyclohexyl)methyl)-1H-benzimidazol-5-yl)ethanesulfonamide A forced degradation of N-(2-(tert-butyl)-1-((4,4-difluorocyclohexyl)methyl)-1H-benzimidazol-5-yl)ethanesulfonamide study (active substance) was performed under a number of stressed conditions for up to 13 days. The active substance was shown to be stable to degradation as a solution at room temperature, at 100° C. as a solid, under 1M acidic conditions at room temperature and at 60° C., under 0.5M basic conditions at room temperature and at 60° C., as a solution heated to 60° C., and under photostability conditions as a solid. The active substance showed slight degradation under peroxide conditions, under 1M acidic conditions and 0.5M basic conditions when these tests were extended to 80° C., and as a solution when heated to 80° C. Major degradation of the active substance as a solution under photostability conditions occurred.

Materials

| | | |
|---|---|---|
| Active substance | N-(2-(tert-butyl)-1-((4,4-difluorocyclohexyl)methyl)-1H-benzimidazol-5-yl)ethanesulfonamide | |
| | ex- Onyx Scientific Ltd | Batch no: CB988E |
| LCMS Water | ex- Onyx Scientific Ltd | N/A |
| Acetonitrile | ex- Sigma-Aldrich | Lot no: - STBJ1963 |
| Ammonium acetate | ex- Fluka | Lot no: - H2010 |
| 6.0M Hydrochloric Acid | ex- Fluka | Lot no: - H1370 |
| 1M Sodium Hydroxide | ex- Fisher | Lot no: - 1871868 |
| 30% Hydrogen peroxide | ex- Sigma-Aldrich | Lot no: - MKBS2987V |

Analysis

HPLC Conditions

Instrument: Agilent 1100/1200

Column: YMC Triart Phenyl, 4.6×150 mm. 3 μm particle size (ex-YMC P.N.TPH12S03-1546PTH)

Mobile Phase: A—10 mM Ammonium acetate pH 6.0

B—Acetonitrile

Flow Rate: 1.0 ml·min-1

Injection Volume: 5 μl

Detection: UV @ 220 nm

Column Temp: 30° C.

Post Run: 4 minutes

| | Time (mins) | % A | % B |
|---|---|---|---|
| Gradient: | 0 | 80 | 20 |
| | 20 | 35 | 65 |
| | 26 | 5 | 95 |
| | 30.5 | 5 | 95 |
| | 31 | 80 | 20 |

Diluent: Acetonitrile:deionised water (1:1)

Standard Solution: Make up a solution of 0.2 mg/ml. This is to be made up fresh prior to use at T=3 and T=7 days.

Stock Solution Preparation

Accurately weigh 80 mg of the active substance into a 100 mL volumetric flask and dissolve in 50 mL of diluent. Dilute the resulting solution to volume with diluent and mix well.

Procedure

Table 1 below details the different study tests performed. All solution samples are prepared and stored in sealed vials and heated samples are cooled to ambient prior to sampling to prevent evaporation. Analysis took place on days 3 and 7 after stressing initiation for solutions described for Tests 1-6 and once exposure was complete for samples described in Tests 7-10. Due to the low levels of degradation observed at 7 days, Tests 3, 4 and 5 were heated to 80° C. for a further 4 days and analysed, and Test 6 was analysed after a further 6 days.

The photostability samples were exposed to a total of 1.92 million lux hours and an integrated near-UV energy of 374.6 $Whm^{-2}$.

TABLE 1 forced degradation study tests

| Test | Description | Sample preparation for analysis after study |
|---|---|---|
| Test 1 - Control | Accurately pipette 5 ml of stock solution and 5 ml of diluent into a suitable container and leave at ambient temperature. | Pipette 1 ml of Control Solution into a 2 ml volumetric flask, make up to volume with diluent and mix well. |

TABLE 1-continued forced degradation study tests

| Test | Description | Sample preparation for analysis after study |
|---|---|---|
| Test 2 - Solid state | Store 150 mg of sample at 100° C. | Dissolve in diluent to a concentration of 0.2 mg · $ml^{-1}$. |
| Test 3 - Acid (1M) | Accurately pipette 5 ml of Stock Solution and 5 ml of 2M HCl solution into a suitable container and leave at ambient temperature. | Pipette 1 ml of Acid Sample Solution into a 2 ml volumetric flask, make up to volume with diluent and mix well. |
| Test 3- Acid Blank (1M) | Accurately pipette 5 ml of diluent and 5 ml of 2M HCl solution into a suitable container and leave at ambient temperature. | Pipette 1 ml of Acid Blank Solution into a 2 ml volumetric flask, make up to volume with diluent and mix well. |
| Test 3 - Acid (1M heated) | Accurately pipette 5 ml of Stock Solution and 5 ml of 2M HCl solution into a suitable container and heat at 60° C. | Pipette 1 ml of Acid Sample Solution into a 2 ml volumetric flask, make up to volume with diluent and mix well. |
| Test 3 -Acid Blank (1M heated) | Accurately pipette 5 ml of diluent and 5 ml of 2M HCl solution into a suitable container and heat at 60° C. | Pipette 1 ml of Acid Blank Solution into a 2 ml volumetric flask, make up to volume with diluent and mix well. |
| Test 4 - Base (0.5M) | Accurately pipette 5 ml of Stock Solution and 5 ml of 1M NaOH solution into a suitable container and leave at ambient temperature. | Pipette 1 ml of Base Sample Solution into a 2 ml volumetric flask, make up to volume with diluent and mix well. |
| Test 4 - Base Blank (0.5M) | Accurately pipette 5 ml of diluent and 5 ml of 1M NaOH solution into a suitable container and leave at ambient temperature. | Blank - Pipette 1 ml of Base Blank Solution into a 2 ml volumetric flask, make up to volume with diluent and mix well. |
| Test 4-Base (0.5M heated) | Accurately pipette 5 ml of Stock Solution and 5 ml of 1M NaOH solution into a suitable container and heat at 60° C. | Pipette 1 ml of Base Sample Solution into a 2 ml volumetric flask, make up to volume with diluent and mix well. |
| Test 4 - Base Blank (0.5M heated) | Accurately pipette 5 ml of diluent and 5 ml of 1M NaOH solution into a suitable container and heat at 60° C. | Blank - Pipette 1 ml of Base Blank Solution into a 2 ml volumetric flask, make up to volume with diluent and mix well. |
| Test 5 - Heat (60° C.) | Accurately pipette 5 ml of Stock Solution and 5 ml of diluent into a suitable container and heat at 60° C. | Pipette 1.0 ml of heated sample solution into a 2 ml volumetric flask, make up to volume with diluent and mix well. |
| Test 6 - Peroxide (1.5%) | Accurately pipette 5 ml of Stock Solution and 5 ml of 3% Hydrogen peroxide solution into a suitable container and leave at ambient temperature. | Pipette 1.0 ml of Peroxide Sample solution into a 2 ml volumetric flask, make up to volume with diluent and mix well. |
| Test 6 - Peroxide Blank (1.5%) | Accurately pipette 5 ml of diluent and 5 ml of 3% Hydrogen peroxide solution into a suitable container and leave at ambient temperature. | Pipette 1 ml of Peroxide Blank Solution into a 2 ml volumetric flask, make up to volume with diluent and mix well. |
| Test 7 - Photostability (Solution Control) | Accurately pipette 5 ml of Stock Solution and 5 ml of diluent into a suitable container, wrapped in aluminium foil. Expose to an overall illumination of no less than 1.2 million lux hours and integrated near-UV energy of no less than 200 watt hours per square meter. | Once exposure is complete, pipette 1.0 ml of sample solution into a 2 ml volumetric flask, make up to volume with diluent and mix well. |
| Test 8 - Photostability (Solution Treated) | Accurately pipette 5 ml of Stock Solution and 5 ml of diluent into a suitable container. Expose to an overall illumination of no less than 1.2 million lux hours and integrated near-UV energy of no less than 200 watt hours per square meter. | Once exposure is complete, pipette 1.0 ml of sample solution into a 2 ml volumetric flask, make up to volume with diluent and mix well. |
| Test 9 - Photostability (Solid Control) | Place a thin layer of the solid sample in a glass dish and wrap in aluminium foil. Expose to an overall illumination of no less than 1.2 million lux hours and an integrated near-UV energy of no less than 200 watt hours per square meter. | Once exposure is complete, the sample is to be dissolved in diluent to a concentration of 0.2 mg · $ml^{-1}$. |

TABLE 1-continued forced degradation study tests

| Test | Description | Sample preparation for analysis after study |
|---|---|---|
| Test 10 - Photostability (Solid Treated) | Place a thin layer of the solid sample in a glass dish. Expose to an overall illumination of no less than 1.2 million lux hours and an integrated near-UV energy of no less than 200 watt hours per square meter. | Once exposure is complete, the sample is to be dissolved in diluent to a concentration of 0.2 mg · $ml^{-1}$. |

Results

Observations

TABLE 2

Forced degradation - observations

| Test | Condition | Sample observations |
|---|---|---|
| 1 | Control | Clear colourless solution. No change over study period. |
| 2 | Solid state 100° C. | Off-white solid turning to very faint orange solid over study period. |
| 3 | Acid | Clear colourless solution. No change over study period. |
| 3 | Acid 60° C. | Clear colourless solution. No change over study period. |
| 4 | Base | Clear colourless solution. No change over study period. |
| 4 | Base 40° C. | Clear colourless solution. No change over study period. |
| 5 | Heat 60° C. | Clear colourless solution. No change over study period |
| 6 | Peroxide | Clear colourless solution. No change over study period |
| 7 | Photostability (Solution Control) | Clear colourless solution. No change over study period. |
| 8 | Photostability (Solution Treated) | Clear colourless solution turning to a clear yellow solution over study period. |
| 9 | Photostability (Solid Control) | Off white solid. No change over study period. |
| 10 | Photostability (Solid Treated) | Off-white solid turning to very faint orange solid over study period. |

Analysis

TABLE 3 forced degradation results for Tests 1-6

| Test | Assay of active substance (area %) Timepoint 0 days | 3 days | 7 days | 11 days | 13 days |
|---|---|---|---|---|---|
| 1 - solution control | 99.40 | 99.42 | 99.30 | 99.39 | |
| 2 - solid state at 100° C. | | 99.43 | 99.40 | | |
| 3 - acid (1M) ambient temperature | | 99.40 | 99.41 | | |
| 3 - acid (1M) at 60° C. until day 7, 80° C. until day 11 | | 99.37 | 99.35 | 98.87 | |
| 4 - base (0.5M) ambient temperature | | 99.40 | 99.37 | | |
| 4 - base (0.5M) at 60° C. until day 7, 80° C. until day 11 | | 99.34 | 99.32 | 99.16 | |
| 5 - solution at 60° C. until day 7, 80° C. until day 11 | | 99.13 | 99.34 | 98.00 | |
| 6 - peroxide (1.5%) | | 98.50 | 97.75 | | 96.58 |

TABLE 4 forced degradation results for Tests 7-10

| Test | Assay of active substance (area %) |
|---|---|
| 7 - photocontrol solution | 99.40 |
| 8 - photo treated solution | 74.53 |
| 9 - photocontrol solid | 99.40 |
| 10 - phototreated solid | 99.31 |

Example 2—Preformulation Studies—Compatibility of Active Ingredient with Capsule Shells and Semi-Solid Excipients A preformulation study was performed in order to select excipients for the development of an immediate release capsule containing a low dose of N-(2-(tert-butyl)-1-((4,4-difluorocyclohexyl)methyl)-1H-benzimidazol-5-yl)ethanesulfonamide in a semi-solid carrier. The chemical stability of N-(2-(tert-butyl)-1-((4,4-difluorocyclohexyl)methyl)-1H-benzimidazol-5-yl)ethanesulfonamide in the semi-solid carrier was evaluated for up to 28 days at 40° C. and 50° C.

Both types of capsule shells evaluated (HPMC and PEG-softened hard gelatin shells) were compatible with the active ingredient. Of the three semi-solids tested the solubility of the active ingredient was sufficiently high (>0.1% w/w) so that a low dose capsule could be prepared. The active ingredient showed good chemical stability in PEG and Vitamin E TPGS over 28 days, however there was significant degradation of the active ingredient observed in Gelucire 44/14 at 40° C. incubation.

Methodology

While suspension formulations were not excluded per se, solution-based formulations were preferable in order to maximise the chances of achieving content uniformity. In order for a 200 μg dose strength to be delivered in a size 4 capsule a target solubility of >0.1% w/w of the active ingredient in the excipient was set (max fill weight of Size 4 capsule is ~200 mg, 0.2 mg/200 mg*100=0.1% w/w) and also to minimise the dose of excipient administered. This solubility would allow higher dose strengths to be manufactured in larger capsules should they be required as development progresses—for instance approximately 650 μg in a size 0 capsule.

The chemical compatibility of the active ingredient with excipients was assessed.

Materials

Active Ingredient: (N-(2-(tert-butyl)-1-((4,4-difluorocyclohexyl)methyl)-1H-benzimidazol-5-yl)ethanesulfonamide)

ex IPCA Supplier Lot ID JCM1019B

HMPC capsule White Capsugel VCaps Plus size 4

Hard Gelatin capsule Green/grey Qualicaps Quali-G PEG size 4)

TPGS Vitamin E TPGS from Isochem

Polyethylene glycol PEG 1500, Merck

Polyoxylglycerides Gelucire 44/14

Analytical Methodology

UPLC Conditions

Column: Waters Acquity BEH Shield 100×2.1 mm, 1.7 μm

Column Temp. 40° C.

Sample manager wash (UPLC) Acetonitrile

Sample manager purge (UPLC) HPLC Water:ACN 50:50% v/v

Mobile Phase A (for Semi-solids) pH 9.2 Sodium Hydroxide

Mobile Phase A (for capsule shells) 25% ammonia solution

Mobile Phase B Acetonitrile

Mobile Phase C 2-propanol

Flow Rate 0.3 mL/min

Injection volume 10 μL (for 0.01 mg/mL nominal concentration)

5 μL (for 0.02 mg/mL nominal concentration)

Wavelength 215 nm

Gradient Program

| | Samples containing semi-solid excipient | | | All other samples | | |
|---|---|---|---|---|---|---|
| Time (min) | MP* A (%) | MP* B (%) | MP* C (%) | MP* A (%) | MP* B (%) | MP* C (%) |
| 0 | 95 | 5 | 0 | 95 | 5 | Not used |
| 10 | 5 | 95 | 0 | 5 | 95 | |
| 10.1 | 5 | 45 | 50 | 95 | 5 | |
| 15 | 5 | 45 | 50 | 95 | 5 | |
| 15.1 | 95 | 5 | 0 | | | |
| 20 | 95 | 5 | 0 | | | |

*MP = Mobile Phase

Part 1—Active Ingredient Compatibility with Capsule Shells

Prior to Day 0

Preparation of a 3 mg/mL Doping Solution

A 3 mg/mL active ingredient Doping Solution in ethanol was prepared by dispensing 89.5 to 90.5 mg of the active ingredient (avoid dispensing any agglomerates as these will slow dissolution) directly into a 30 mL amber bottle. A total of 30 mL of ethanol absolute was added to the bottle in a solvent fume cupboard. The contents of the bottle were stirred using a magnetic flea and stirrer plate until all solids had dissolved (a back light outside of the darkroom was briefly used and fibrous material in the bottle was ignored). The bottle was placed in a freezer until required for use.

Day 0

The following stability vials were prepared and stored according to Table 5.

Binary “Dry Excipient” and active ingredient: The dry excipient (HPMC capsule or hard gelatin capsule) is dispensed into a vial and 100 μL of the Doping Solution is applied. It was ensured that the doping solution fully contacted the dry excipient when added to the vial. The solvent was evaporated until a white film was formed.

Placebo Control Samples: The dry excipient (HPMC capsule or hard gelatin capsule) is added to a vial, but no stock solution is applied to it. These served as controls to assist HPLC peak identification.

Active Ingredient Only Control: 100 μL of the Doping Solution is added to an empty vial and the solvent evaporated. These showed the chemical stability of the active ingredient as a control.

For the above vials where solvent evaporation was required, the vials were left open overnight. Once the solvent had evaporated the vials were closed and placed in opaque plastic storage boxes.

TABLE 5

Preformulation stability study vials prepared

| Dry Excipient | Doping Solution added | Storage Conditions (number of vials prepared) | | | | |
|---|---|---|---|---|---|---|
| One HPMC capsule | Yes | Store at 20° C. throughout (2) | 25° C. for 14 days (2) | 25° C. for 28 days (2) | 50° C. for 14 days (2) | 50° C. for 28 days (2) |
| One Hard gelatin capsule | Yes | Store at 20° C. throughout (2) | 25° C. for 14 days (2) | 25° C. for 28 days (2) | 50° C. for 14 days (2) | 50° C. for 28 days (2) |
| None | Yes | Store at 20° C. throughout (2) | 25° C. for 14 days (2) | 25° C. for 28 days (2) | 50° C. for 14 days (2) | 50° C. for 28 days (2) |
| One HPMC capsule | No | Store at 20° C. throughout (1) | | 25° C. for 28 days (1) | | 50° C. for 14 days (1) |
| One Hard gelatin capsule | No | Store at 20° C. throughout (1) | | 25° C. for 28 days (1) | | 50° C. for 14 days (1) |

At the timepoint specified in Table 5, the vials were removed in placed in a freezer until HPLC analysis was performed.

Results

Table 6 shows the assay results of the active ingredient in HPMC and gelatin capsules.

TABLE 6

Assay results of active ingredient in HPMC and gelatin capsules

| Incubation temperature | days | vial | HPMC Assay (%) | Gelatin Assay (%) |
|---|---|---|---|---|
| n/a | initial | 1 | 96.5 | 99.0 |
| | | 2 | 99.0 | 100.2 |
| | | mean | 97.8 | 99.6 |
| 25° C. | 14 | 3 | N/A* | 97.4 |
| | | 4 | 98.9 | 98.9 |
| | | mean | 95.8 | 98.1 |
| | 28 | 5 | 99.3 | 98.8 |
| | | 6 | 99.0 | 99.4 |
| | | mean | 99.1 | 99.1 |
| 50° C. | 14 | 7 | 98.9 | 99.3 |
| | | 8 | 98.7 | 99.4 |
| | | mean | 98.8 | 99.3 |
| | 28 | 9 | 98.8 | 99.4 |
| | | 10 | 98.9 | N/A* |
| | | mean | 98.9 | 89.3 |

*Samples were spilt during preparation and so results are discounted.

Overall, the % assay for both sample sets appear consistent across all conditions and timepoints, indicating there is no degradation of the active ingredient for either HPMC or gelatin capsules.

The only two exceptions are low results for one of the replicates of HPMC at 25° C. after 14 days and one of the Gelatin replicates at 50° C. after 28 days. These results are not matched by the other replicate in either case, and so are considered to be outlier results.

The peak areas of potential active ingredient related substances are shown in Table 7. There is no evidence of active ingredient degradation in both capsule types since the total impurities remained below 1% with no increase with incubation time or temperature for any impurity.

TABLE 7

Summary of related substances in HPMC and gelatin capsules

| | | | | RRT | | | | | | | |
|---|---|---|---|---|---|---|---|---|---|---|---|
| Sample | Condition | Days | Vial | 0.92 | 0.97 | 0.98 | 1.04 | 1.10 | 1.35 | 1.36 | total |
| HPMC | n/a | initial | 1 | 0.08 | ND | 0.3 | 0.07 | 0.09 | 0.13 | 0.13 | 0.81 |
| | | | 2 | 0.07 | ND | 0.31 | 0.07 | 0.10 | 0.13 | 0.13 | 0.82 |
| | 25° C. | 14 | 3 | 0.08 | ND | 0.31 | 0.08 | 0.09 | 0.13 | 0.13 | 0.82 |
| | | | 4 | 0.07 | ND | 0.32 | 0.08 | 0.09 | 0.12 | 0.12 | 0.80 |
| | | 28 | 5 | 0.08 | ND | 0.3 | 0.07 | 0.09 | 0.12 | 0.12 | 0.79 |
| | | | 6 | 0.08 | ND | 0.31 | 0.07 | 0.08 | 0.13 | 0.13 | 0.79 |
| | 50° C. | 14 | 7 | 0.07 | ND | 0.30 | 0.07 | 0.09 | 0.13 | 0.12 | 0.79 |
| | | | 8 | <0.05 | 0.67* | 0.29 | 0.07 | 0.09 | 0.12 | 0.12 | 1.37 |
| | | 28 | 9 | 0.07 | ND | 0.31 | 0.07 | 0.09 | 0.12 | 0.12 | 0.79 |
| | | | 10 | 0.07 | ND | 0.32 | 0.09 | 0.10 | 0.12 | 0.13 | 0.83 |
| Hard Gelatin | n/a | initial | 1 | 0.06 | ND | 0.26 | 0.05 | 0.10 | 0.08 | 0.08 | 0.62 |
| | | | 2 | 0.05 | ND | 0.24 | 0.05 | 0.10 | 0.07 | 0.08 | 0.58 |
| | 25° C. | 14 | 3 | 0.05 | ND | 0.22 | 0.05 | 0.10 | 0.07 | 0.07 | 0.56 |
| | | | 4 | <0.05 | ND | 0.18 | <0.05 | 0.09 | 0.07 | 0.08 | 0.42 |
| | | 28 | 5 | 0.05 | ND | 0.18 | <0.05 | 0.08 | 0.07 | 0.08 | 0.47 |
| | | | 6 | <0.05 | ND | 0.14 | <0.05 | 0.09 | 0.06 | 0.07 | 0.36 |
| | 40° C. | 14 | 7 | <0.05 | ND | 0.14 | <0.05 | 0.09 | 0.06 | 0.07 | 0.37 |
| | | | 8 | <0.05 | ND | 0.12 | <0.05 | 0.09 | 0.06 | 0.07 | 0.34 |
| | | 28 | 9 | <0.05 | ND | 0.11 | <0.05 | 0.09 | 0.06 | 0.07 | 0.33 |
| | | | 10 | <0.05 | ND | 0.09 | <0.05 | 0.11 | 0.06 | 0.07 | 0.33 |

*Appears to be a contamination peak since this high area at RRT 0.97 is not seen in the other replicate at this condition or at the later timepoint at the same (40° C.) storage condition.

Part 2—Solubility and Stability Assessment of Active Ingredient in the Semi-Solid Excipient The solubility of up to three aliquots of the active ingredient in each semi solid solution was evaluated with samples taken for stability evaluation, as follows:

1. While the semi-solid is molten at ~70° C., active ingredient aliquot 1 was added to the molten semi-solid, then homogenised using the Silverson mixer at 2000 RPM.
2. Following the dissolution of the first active ingredient aliquot, 10 stability and 10 'method development' samples were removed (200 µL per vial, not weighed) and placed on stability at 25 and 40° C. for up to 28 days
3. Because the active ingredient was apparently fully soluble in this experiment, active ingredient aliquots 2 and 3 were added then homogenised until dissolved into the remaining solution.
4. The appearance of the solution was recorded after adding each active ingredient aliquot In order to ascertain the mass of semi-solid that had been volumetrically dispensed into the 20 vials in Step 2. the following procedure was employed:

1. The group mass of 5 "method development" vials was measured (mass G).
2. The vials were twice cleaned with ethanol (sonicating for 10 minutes each time) and allowed to dry for 1 hour—the vials were completely clean and dry.
3. The group mass of the 5 clean vials was measured (mass T).
4. The mean net weight of semi solid in the original vial was calculated=(G−T)/5 where G and T.

Table 8 shows the level of active ingredient added to the three different semi-solids.

TABLE 8

| Semi-solid batch compositions (~80 mL batch size) | | | |
|---|---|---|---|
| Semi-Solid Batch ID | N | P | Q |
| | Qty of ingredient: mass per vial and total % w/w of API (homogenisation times and temperatures in brackets) | | |
| Vitamin E TPGS | 84.97 g | | |
| PEG 1500 | | 96.1 g | |
| Gelucire 44/14 | | | 85.0 g |
| Active Ingredient Aliquot #1 | 21.2 mg, 0.025% (60 min @ 67.9-70.5° C.) | 23.0 mg, 0.024% (18 min @ 73.6-71.1° C.) | 20.7 mg, 0.024% (19 min @ 63.5-73.1) |
| Active Ingredient Aliquot #2 | 19.5 mg, 0.049% (30 min @ 62.7-71.4° C.) | 16.1 mg, 0.041 (22 min @ 73.1-71.4° C.) | 16.3 mg, 0.044% (20 min @ 65.7-68.6° C.) |
| Active Ingredient Aliquot #3 | 57.8 mg, 0.121% (18 min @ 70.2-72.1° C.) | 54.9 mg, 0.100% (1 hr @ 64.5-71.3° C.) | 57.0 mg, 0.115% (21 min @ 69.6-68.4° C.) |

Results

All three active ingredient aliquots fully dissolved in each of the three molten semi-solids—Vitamin E TPGS, PEG 1500 and Gelucire 44/14. Clear solutions free from particles and opacity were achieved—only Vitamin E TPGS was slightly yellow while PEG 1500 and Gelucire 44/14 were colourless. The final concentration of API in each semi-solid was 0.10 to 0.12% w/w, consistent with being able to fill the highest dose (200 μg) into the preferred sized capsule (Size 4).

Table 9 summarises the assay of the active ingredient in the semi-solids, sampled after the first aliquot addition only (i.e. active ingredient at 0.024-5% w/w which is the highest risk for stability) following a 28-day stability study at 25 and 40° C.

TABLE 9

Summary of the active ingredient assay in three different Semi-solids

| condition | days | vial | Vitamin E TPGS assay % | PEG 1500 assay % | Gelucire 44/14 assay % |
|---|---|---|---|---|---|
| n/a | initial | 1 | 94.4 | 101.6 | 95.5 |
| | | 2 | 94.2 | 102.2 | 97.9 |
| | | mean | 94.3 | 101.9 | 96.7 |
| 25° C. | 14 | 3 | 94.5 | 102.7 | 98.6 |
| | | 4 | 94.7 | 103.0 | 98.5 |
| | | mean | 94.6 | 102.9 | 98.6 |
| | 28 | 5 | 95.3 | 103.2 | 99.5 |
| | | 6 | 94.9 | 102.0 | 99.6 |
| | | mean | 95.1 | 102.6 | 99.6 |
| 40° C. | 14 | 7 | 93.2 | 124.2* | 89.5 |
| | | 8 | 94.2 | 107.6 | 91.0 |
| | | mean | 93.7 | 115.9 | 90.3 |
| | 28 | 9 | 95.0 | 106.8 | 77.3 |
| | | 10 | 96.2 | 104.2 | 72.4 |
| | | mean | 95.6 | 105.5 | 74.8 |

*The high active ingredient peak area in this sample is believed to be associated with a high sample aliquot weight since the area of the main excipient peak was also 24% higher than for another representative replicate for PEG 1500 (#1 i.e. Initial).

The related substances for the three types of semi-solid excipients is presented in Table 10, Table 11 and Table 12.

Both Vitamin E TPGS and PEG 1500 appear to be stable with no significant effect of incubation time and temperature on assay. However, there is evidence for gross degradation in Gelucire 44/14 under accelerated stability conditions (40° C.).

TABLE 10

Peak Areas (as % of Total) of API Related substances for Vitamin E TPGS Vitamin E TPGS

| condition | days | vial | RRT 0.8 | total |
|---|---|---|---|---|
| n/a | initial | 1 | 0.01 | 0.01 |
| | | 2 | 0.02 | 0.02 |
| 25° C. | 14 | 3 | 0.02 | 0.02 |
| | | 4 | 0.02 | 0.02 |
| | 28 | 5 | 0.02 | 0.02 |
| | | 6 | 0.02 | 0.02 |
| 40° C. | 14 | 7 | 0.02 | 0.02 |
| | | 8 | 0.02 | 0.02 |
| | 28 | 9 | 0.03 | 0.03 |
| | | 10 | 0.03 | 0.03 |

TABLE 11

Peak Areas (as % of Total) of API Related substances for PEG1500 PEG1500

| condition | days | vial | RRT 0.56 | RRT 1.20 | total |
|---|---|---|---|---|---|
| n/a | initial | 1 | 0 | ND | 0 |
| | | 2 | 0 | ND | 0 |
| 25° C. | 14 | 3 | 0 | ND | 0 |
| | | 4 | 0 | ND | 0 |
| | 28 | 5 | 0 | ND | 0 |
| | | 6 | 0 | ND | 0 |
| 40° C. | 14 | 7 | 0.01 | 0.04 | 0.04 |
| | | 8 | 0.02 | 0.03 | 0.05 |
| | 28 | 9 | 0.02 | 0.04 | 0.06 |
| | | 10 | 0.01 | 0.04 | 0.05 |

TABLE 12

Peak Areas (as % of Total) of API Related substances for Gelucire Gelucire 44/14

| Condition | days | vial | RRT 0.20 | RRT 0.82 | RRT 0.85 | total |
|---|---|---|---|---|---|---|
| n/a | initial | 1 | 0.03 | 0.26 | ND | 0.29 |
| | | 2 | 0.03 | 0.26 | ND | 0.29 |
| 25° C. | 14 | 3 | 0.03 | 0.26 | ND | 0.29 |
| | | 4 | 0.03 | 0.28 | ND | 0.31 |
| | 28 | 5 | 0.03 | 0.29 | ND | 0.31 |
| | | 6 | 0.03 | 0.29 | ND | 0.32 |
| 40° C. | 14 | 7 | 0.34 | 1.35 | ND | 1.70 |
| | | 8 | 0.30 | 1.31 | ND | 1.61 |
| | 28 | 9 | 1.38 | 4.72 | 0.53 | 6.62 |
| | | 10 | 1.89 | 7.00 | 0.88 | 9.77 |

Example 3—Preparation, Stability, and Dissolution Analysis of PEG1500 and Vitamin E TPGS Based Immediate Release Formulations Semi-solid capsules containing the active ingredient in either Vitamin E TPGS or PEG were prepared at different doses (50 and 200 μg) and in different sized hard gelatin capsules (size 3 and 4). The prepared capsules were put on a 4-week stability study at 25° C. and 40° C. Both types of semi-solid capsules (Vitamin E TPGS and PEG) were stable under the conditions tested. The PEG1500 formulations met the European Pharmacopoeia specification for a conventional immediate release dosage form (80% of the active ingredient releases within 45 minutes or less), however the Vitamin E TPGS formulations surprisingly did not in some instances.

Methodology

Semi-solid capsule batches containing the active ingredient were prepared according to Table 13 and Table 14.

A suffix code is used in both tables to refer to the two concentrations of the active ingredient used in the PEG or Vitamin E TPGS solution:

L denotes a low concentration (0.1%) of the active ingredient in the L-PEG and L-Vitamin E TPGS solutions H denotes a low concentration (0.4%) of the active ingredient in the H-PEG and H-Vitamin E TPGS solutions The batches listed in Table 13 and Table 14 and were made at a batch size of approximately 80 g by performing the following processes in a darkroom without any environmental control of oxygen or RH levels:

1. Dissolve the active ingredient in molten Vitamin E TPGS or PEG 1500 using a Silverson homogeniser until a clear solution is formed.
2. Using a manual pipette (Gilson Repetman) to fill into the capsules (target fill weight specified in Table 13).

While the filling process worked well at a target temperature of 55° C. for the Vitamin E TPGS throughout, the operators noted that the PEG 1500 tended to solidify at this target temperature (high weight variability).

While weight uniformity was sub-optimal for the H-PEG and H-Vitamin E TPGS in the capsules that were analysed, it was able to improve this in later attempts under more controlled process conditions.

In addition to preparing the capsules, the active ingredient solutions were held for 24 hours at 55° C. to mimic a plausible process hold step.

Due to the some of the dissolution profiles of the Vitamin E TPGS capsules not meeting the European Pharmacopoeia specification for a conventional immediate release dosage form only the PEG1500 capsules were placed on a 4-week stability study at 25° C. and 40° C. and −20° C. (all analysed together and −20 data used as initial).

TABLE 13

Semi-solid PEG and Vitamin E TPGS formulations

| | H-PEG | L-PEG | | H- Vitamin E TPGS | L- Vitamin E TPGS | |
|---|---|---|---|---|---|---|
| Dose (μg) | 200 | 200 | 50 | 200 | 200 | 50 |
| | Composition of Capsule Fill (% w/w) | | | | | |
| Active ingredient | 0.40% | 0.10% | | 0.40% | 0.10% | |
| PEG 1500 (Emprove ™) | 99.60% | 99.90% | | 99.60% | — | |
| Vitamin E TPGS (Isochem) | — | — | | — | 99.90% | |
| Total | 100.00% | 100.00% | | 100.00% | 0.10% | |
| Intended Weight of semi-solid per capsule (mg) | 50 | 200 | 50 | 50 | 200 | 50 |

TABLE 14

Process Variants assessed in semi-solid formulations

| | H-PEG | | L-PEG | | H- Vitamin E TPGS | | L-Vitamin E TPGS | |
|---|---|---|---|---|---|---|---|---|
| API Solution Held at 55 C. for 24-28 hr prior to encapsulation? | No | No | No | Yes | No | No | No | Yes |
| Dose (μg) | 200 | 200 | 50 | 50 | 200 | 200 | 50 | 50 |
| Capsule Type | Size 3 white Quali-G PEG | | Size 4 green/grey Quali-G PEG | | Size 3 white Quali-G PEG | | Size 4 green/grey Quali-G PEG | |

Analytical Methods

Dissolution

Apparatus Paddles (USP apparatus II)

Paddle Speed 50 rpm 200 rpm infinity speed

Dissolution Media 0.1 M Hydrochloric acid/Phosphate pH 6.8 Buffer

Media Volume Dose 50 μg: 500 mL (nominal concentration 0.1 μg/mL)

Dose 200 μg: 500 mL (nominal concentration 0.4 μg/mL)

Temperature 37±0.5° C.

Sinkers Band sinker with O-ring internal diameter suitable for capsule size tested Sampling filters 13 mm, 0.2 μm PVDF syringe filters Cannula filters 10 μm cannula filters (P/N FIL010-CA-a)

Sampling time points 10, 20, 30 and 45 minutes at 50 rpm 60 minutes (infinity speed at 200 rpm after the 45 minutes time point)

Detection HPLC/UPLC

Preparation of 0.1 M HCl Dissolution Medium

Transfer 4000 mL of deionised water or HPLC water to a dissolution aspirator. Transfer 41 mL concentrated HCl to the aspirator using a measuring cylinder. Transfer a further 959 mL of deionised water or HPLC water to the same aspirator. Mix.

Preparation of the pH 6.8 Phosphate Buffer Dissolution Medium

Dissolve 81.6±0.5 g of anhydrous potassium phosphate monobasic ($KH_2PO_4$) in 3000 mL deionised water (Preparation 1). Dissolve 214.8±0.5 g of disodium hydrogen phosphate dodecahydrate ($Na_2HPO_4.12H_2O$) in 3000 mL of deionised water (Preparation 2). Combine 2550 mL of Preparation 1 with 2450 mL of Preparation 2. Measure the pH of the solution. The pH should be pH 6.8±0.05. Adjust to pH 6.8 if necessary using either Preparation 1 or 2 (Preparation 1 to reduce pH or Preparation 2 to increase pH).

Dissolution HPLC/UPLC

Column Halo C18 2.7 μm 3.0×50 mm

Column Temperature 40° C.

Sample manager wash (UPLC) HPLC Water:ACN 50:50% v/v

Needle Wash (HPLC) HPLC Water:ACN 50:50% v/v

Sample manager purge (UPLC) HPLC Water+0.1% phosphoric acid

Mobile Phase A HPLC Water+0.1% phosphoric acid
Mobile Phase B 100% acetonitrile

| | Time | Mobile Phase A (%) | Mobile Phase B (%) |
|---|---|---|---|
| Gradient | 0.00 | 80 | 20 |
| | 0.50 | 80 | 20 |
| | 3.00 | 20 | 80 |
| | 3.01 | 2 | 98 |
| | 6.00 | 2 | 98 |
| | 6.01 | 80 | 20 |
| | 9.50 | 80 | 20 |

Flow Rate 0.5 mL/min
Injection Volume 10 μL (Dose 200 μg)
25 μL (Dose 50 μg)
Wavelength 217 nm Standard Preparation for HPLC/UPLC The active ingredient is light sensitive and requires protection from light.

High Dose Calibration Standard: 0.1 M HCl

Prepare a 0.4 μg/mL active ingredient standard in 90:10 v/v 0.1M HCl:acetonitrile Low Dose Calibration Standard: 0.1 M HCl Prepare a 0.1 μg/mL active ingredient standard in 90:10 v/v 0.1M HCl:acetonitrile High Dose Calibration Standard: pH 6.8 Phosphate Buffer Prepare a 0.4 μg/mL active ingredient standard in 90:10 v/v pH 6.8 phosphate buffer:acetonitrile Low Dose Calibration Standard: pH 6.8 Phosphate Buffer Prepare a 0.1 μg/mL active ingredient standard in 90:10 v/v pH 6.8 phosphate buffer:acetonitrile Content Uniformity Weigh and record the mass of each capsule. Drop each capsule into separate 500 mL amber volumetric flask. Add approximately 200 mL of 90:10 v/v 0.1 M HCl:acetonitrile. Place on an orbital shaker set to approximately 200 rpm to allow sufficient agitation for 2 hours. Ensure the capsule has disintegrated. Allowed to equilibrate to room temperature and make to volume with 90:10 v/v 0.1 M HCl:acetonitrile. Seal flask and invert 15 times to ensure compete mixing. Take a portion of the sample out and place into an amber 8 mL vial. Centrifuge each sample at 4200 rpm for 30 minutes or until a clear supernatant is formed. Transfer 1.5 mL of the clear supernatant into an amber HPLC vial for analysis (see "Dissolution HPLC/UPLC" in Example 3 above. Calculate the acceptance value (AV) as per the Ph. Eur. 2.9.40 using the following formula:

$$AV = |M - X| + ks$$

Wherein

X=Mean of individual contents ($x_1$, $x_2$ . . . $x_3$) expressed as a percentage of the label claim.

k=acceptability constant. If n=10 then k=2.4, if n=30 then 2.0 where n=sample size.

s=Sample standard deviation

M=Reference Value.

For case 1 when T≤101.5:

If 98.5%≤X≤101.5% then M=X (therefore AV=ks)

If X<98.5% then M=98.5% (therefore AV=98.5−X+ks)

If X>101.5%, then M=101.5% (therefore AV=X−101.5+ks)

For case 2 when T>101.5:

If 98.5%≤X≤T then M=X (therefore AV=ks)

If X<98.5% then M=98.5% (therefore AV=98.5−X+ks)

If X>T, then M=T % (therefore AV=X−T+ks)

T=target test sample amount at time of manufacture

Results

Dissolution

Dissolution results were obtained from the various capsules in the 0.1M HCl (pH~1) and in pH 6.8 phosphate buffer media, see FIGS. 1 to 12. PEG 1500 based formulations gave faster dissolution profiles for each dose in both media. Additionally, fill weight appeared to affect the rate of release of the active ingredient from TPGS containing capsules in 0.1M HCl. Release from some of the Vitamin E TPGS formulations in certain media did not meet the European Pharmacopoeia specification for a conventional immediate release dosage form (80% of active ingredient release within typically 45 min or less).

Stability

Due to only some of the Vitamin E TPGS formulations meeting the European Pharmacopoeia specification for a conventional immediate release dosage form in certain dissolution media, only the PEG formulations were put down on stability and analysed.

The assay results for the PEG formulations are shown in Table 15. The assay results from the PEG-based capsules were all below nominal (~90% of target) across the stability study, possibly due to the method used where the semi-solid plugs were scraped out of the shells for analysis. However, there was no clear trend of assay or of the area of any of the impurity peaks with storage temperature (~20, 25 vs. 40° C. over 28 days) or change from the 24-28 hour hold of the API. Based on these results, there are no stability concerns.

TABLE 15

Initial (−20) and stability assay results for PEG immediate release capsules

| Capsule Dose (μg)/ Fill weight (mg) | Storage Condition −20° C./ 'Initial' | 4 week @ 25° C. % Assay (RSD) | 4 weeks @ 40° C. |
|---|---|---|---|
| 200/50 | 87.3 (1.3) | 88.1 (0.6) | 88.9 (1.5) |
| 200/200 | 89.8 (2.4) | 90.2 (1.0) | 87.0 (0.1) |
| 50/50 | 89.9 (2.6) | 92.0 (0.5) | 85.8 (4.9) |
| 50/50 plus 24 hours hold at 55° C. | 86.1 (3.1) | 88.5 (2.3) | 81.4 (0.9) |

Content Uniformity

The content uniformity results for all capsules tested had an acceptance value (AV)<15, see Table 16.

TABLE 16

Content uniformity data for immediate release capsules

| Rep | Dose (μg) | | | | | | | |
|---|---|---|---|---|---|---|---|---|
| | 200 | 200 | 200 | 200 | 50 | 50 | 200 | 200 |
| | Solution Code | | | | | | | |
| | H-Vitamin E TPGS | H-PEG | L-Vitamin E TPGS | L-PEG | L-Vitamin E TPGS | L-PEG | H-Vitamin E TPGS | H-PEG |
| | Fill weight (mg) | | | | | | | |
| | 50 | 50 | 200 | 200 | 50 | 50 | 50 | 50 |
| Rep | Assay (% nominal) | | | | | | Fill Weight (% target) | |
| 1 | 99.6 | 99 | 95.6 | 100 | 99.9 | 101.7 | 95.20% | 100.60% |
| 2 | 104.6 | 98.8 | 94.8 | 100.1 | 99.8 | 99 | 104.60% | 95.20% |
| 3 | 98.5 | 97.7 | 96.1 | 99.8 | 99.6 | 100.2 | 96.30 | 95.40 |
| 4 | 111.4 | 97.1 | 96.1 | 100.9 | 98.7 | 100.6 | 109.60 | 94.10 |
| 5 | 103.1 | 99.5 | 95.7 | 99.7 | 98.6 | 96.5 | 100.60 | 98.80 |
| 6 | 99.9 | 99.2 | 95.3 | 100.5 | 97.9 | 100.9 | 98.70 | 101.90 |
| 7 | 102.9 | 96.8 | 95.5 | 100.5 | 99.2 | 95.5 | 106.10 | 97.80 |
| 8 | 100 | 92.8 | 96.9 | 100 | 99.4 | 99.4 | 103.60 | 93.50 |
| 9 | 99.7 | 108.9 | 99.1 | 99.4 | 99 | 99.5 | 97.20 | 107.90 |
| 10 | 100.9 | 98 | 94.7 | 100.3 | 98.2 | 100.1 | 102.40 | 100.70 |
| MEAN | 102.1 | 98.8 | 96 | 100.1 | 99 | 99.4 | 101.40 | 98.60 |
| RSD % | 3.7 | 4.1 | 1.3 | 0.4 | 0.7 | 1.9 | 4.6 | 4.5 |
| AV | 9.7 | 9.7 | 5.6 | 1.1 | 1.6 | 4.6 | — | — |

Example 4—Preparation and Analysis of Stability Batches of PEG1500 Immediate Release Capsules Semi-solid capsules containing the active ingredient in PEG1500 were prepared at different doses (50 and 200 μg) and in different sized hard gelatin capsules (size 2 and 4). The prepared capsules were put on a stability study at 25° C. and 40° C. and for the timepoints analysed to date stability has been demonstrated. The formulations met the European Pharmacopoeia specification for a conventional immediate release dosage form (80% of the active ingredient releases within 45 minutes or less) and show good content uniformity.

Methodology

Materials

Active substance: (N-(2-(tert-butyl)-1-((4,4-difluorocyclohexyl)methyl)-1H-benzimidazol-5-yl)ethanesulfonamide)

Onyx (lot: JCM1019B)

| | | |
|---|---|---|
| Polyethylene glycol | PEG 1500 Merck, Lot: K51120505 950 | |
| Gelatin capsule | Green/Grey Size 4 Quali G capsules | Qualicaps (ARE) |
| Gelatin capsule | White Size 2 Quali G capsules | Qualicaps (ARE) |
| HPMC capsule | Red Size 4 Quali V Capsules | Qualicaps (ARE) |
| HPMC capsule | White Size 2 Quali V Capsules | Qualicaps (ARE) |

Formulation Compositions

The compositions prepared are summarised in Table 17.

TABLE 17

Formulation compositions prepared

| Material | Active | | | | Placebo | |
|---|---|---|---|---|---|---|
| | % w/w | | g/batch | | | |
| | *Uncorrected concentration | *Corrected concentration | *Uncorrected concentration | *Corrected concentration | % w/w | g/batch |
| | High dose (200 μg) | | | | Matching high dose | |
| Active substance | 0.4 | 0.4 | 0.84 | 0.85 | | |
| PEG | 99.6 | 99.6 | 209.16 | 209.16 | 100 | 130 |
| Total | 100 | | 210 | | 100 | 130 |
| Capsules used | White Size 2 Quali-G PEG ¥ | | | | | |

TABLE 17-continued

| Formulation compositions prepared | | | | | | |
|---|---|---|---|---|---|---|
| | Low dose (50 μg) | | | | Matching low dose | |
| Active substance | 0.1 | 0.1 | 0.2 | 0.2 | | |
| PEG | 99.9 | 99.9 | 198.8 | 199.8 | 100 | 130 |
| Total | 100 | | 200 | | 100 | 130 |
| Capsules used | Green/grey Size 4 Quali-G PEG ¥ | | | | | |

*'Uncorrected' values assume hypothetically pure API, 'corrected' values correct for the 98.92% potency of the API used
¥ The placebo batches were also filled into White Size 2 and Red Size 4 Quali-V (HPMC) Capsules (TRI002/89PC-2H and -4H, respectively). 50 μg of active substance was also filled into Red Size 4 Quali-V capsules (TRI002/89P50-2H). QC testing was not performed on any of these HPMC capsules and they were not put on stability.

Two doses were prepared (50 μg and 200 μg) by melting the PEG 1500. All manufacture was performed in a dark room under Nitrogen (≤2% Oxygen) as follows:

A glycerol bath on a hot plate was used to melt the PEG 1500 and maintain a temperature of 60-66° C. throughout dispensing and encapsulation.

The placebo formulation was made by melting PEG 1500 alone, and dispensing into capsules For the active formulations, once target temperature of the PEG 1500 was reached, the active substance was gradually added.

The active substance was mixed until fully dissolved using a magnetic flea. A spatula was required to break apart the active substance agglomerates.

A Repetman pipette was set to dose 50 mg of the filling fluid. Each formulation was filled into the capsule shells listed in Table 17.

Quali-V capsules were eliminated from further studies (due to challenges with interference in the assay and related substance due to HPMC). Only the Quali-G PEG QC capsules were tested at T=0 and placed on stability.

Analytical Methodology

Dissolution

As per dissolution method described in Example 3. The HPLC/UPLC dissolution methodology used is as described in Example 3.

Content Uniformity

As per content uniformity method described in Example 3.

UPLC/HPLC Parameters Used for Assay and Related Substances Testing

Column Halo C18 2.7 μm 3.0×50 mm

Column Temperature 40° C.

Sample manager wash (UPLC) HPLC Water:ACN 50:50% v/v

Sample manager purge (UPLC) HPLC Water:ACN 50:50% v/v

Mobile Phase A 10 mM ammonium acetate pH 7.0

Mobile Phase B 100% acetonitrile

| Gradient | Time | Mobile Phase A (%) | Mobile Phase B (%) |
|---|---|---|---|
| | 0.00 | 95 | 5 |
| | 2.0 | 55 | 45 |
| | 7.1 | 50 | 50 |
| | 9.7 | 18 | 82 |
| | 10.3 | 2 | 98 |

-continued

| Gradient | Time | Mobile Phase A (%) | Mobile Phase B (%) |
|---|---|---|---|
| | 21.0 | 2 | 98 |
| | 21.1 | 95 | 5 |
| | 26.0 | 95 | 5 |

Flow Rate 0.3 mL/min

Injection Volume 12 or 38 μL

Wavelength 256 nm

Diluent Acetonitrile

Sample preparation: Assay analysis: nominal concentration of 0.01 g/mL

Related Substances: nominal concentration of 0.025 mg/mL

Long Term Stability Study

The PEG1500 active and placebo batches were placed on stability as shown in Table 18.

TABLE 18

| Stability Study Summary for Capsules | | |
|---|---|---|
| Strength (micrograms) | Storage Conditions | Stability Timepoints* (Months)[Optional] |
| 50 and matching placebo | 5° C. | [0[a], 1, 2, 3, 6, 12, 18, 24] |
| | 25° C./60% RH | 0[a], 1, 2, 3, 6, 12[a], 18, 24[a] |
| | 40° C./75% RH | 0[a], 1, 2, 3, 6[a] |
| 200 and matching placebo | 5° C. | [0[a], 1, 2, 3, 6, 12, 18, 24] |
| | 25° C./60% RH | 0[a], 1, 2, 3, 6, 12[a], 18, 24[a] |
| | 40° C./75% RH | 0[a], 1, 2, 3, 6[a] |

[a]Micro testing

Results

Manufacturing Process Evaluation

The four batches in Table 17 were successfully produced, two active formulations at 200 μg and 50 μg, and two matching placebos. During the manufacture, the following challenges were noted:

I. Agglomeration of the active substance when added to the molten PEG, even when gradually added. The agglomeration was more apparent when more active substance was added (i.e. at the high dose). To aid dispersion of the active substance and therefore enhance active substance solubility, a spatula was used to breakdown agglomerates. The total time that took the API to fully dissolve was 1 hour 17 minutes and 1 hr 40 minutes for the low dose and the high dose, respectively.

II. Rapid solidification of the molten formulation in the pipette tip or outer surface of the pipette tip was noted. Therefore, dispensing had to be carried out rapidly.

The process parameters for blend preparation and capsule filling are summarised in Table 19.

TABLE 19

The process parameters during fluid preparation and capsule filling

| Parameters | Placebo Matching low dose | Placebo Matching high dose | Active Low dose (50 μg) | Active High dose (200 μg) |
|---|---|---|---|---|
| Blend Preparation: | | | | |
| Time to melt PEG and reach target temperature (60-65° C.) (hr:min) | 01:10 | 01:15 | 01:40 | 01:40 |
| Time to dissolve active substance (hr:min) | | | 00:33 | 00:55 |
| Mixing speed (RPM) | | | 700 | 600-700 |
| Capsule filling: | | | | |
| Pipette Set volume (μL) | 46.5 | | | |
| Total capsule filling Time (hr:min) | 05:18 | 03:00 | 09:45 | 05:56 |
| Temperature range during capsule filling (° C.) | 61.1-63.1 | 61.1-63.2 | 62.6-63.1 | 62.0-60.4 |
| Oxygen range (%) (throughout blend preparation and capsules filling) | | | 0.2-1.8 | 0.3-1.8 |

Content Uniformity

The results for the 50 μg and 200 μg gelatin capsules (Green/grey size 4 Quali-G PEG and white size 2 Quali-G PEG respectively) are shown in Table 20 and Table 21. The acceptance value determined for both sets of capsules demonstrate good content uniformity.

TABLE 20

Content uniformity for the 50 μg dose capsules

| Sample Replicate | Assay weight (μg) | % Label Claim | Capsule Weight (mg) |
|---|---|---|---|
| 1 | 49.9 | 99.9 | 92.07 |
| 2 | 50.2 | 100.4 | 91.04 |
| 3 | 48.9 | 97.8 | 91.07 |
| 4 | 49.5 | 99.1 | 90.57 |
| 5 | 49.7 | 99.4 | 89.55 |
| 6 | 49.4 | 98.8 | 89.47 |
| 7 | 49.7 | 99.4 | 89.52 |
| 8 | 52.3 | 104.7 | 94.00 |
| 9 | 49.7 | 99.4 | 91.63 |
| 10 | 49.8 | 99.7 | 91.78 |
| Mean | 49.9 | 99.8 | |
| Standard deviation | 0.9 | 1.8 | |

AV = 4.3

TABLE 21

Content uniformity for the 200 μg dose capsules

| Sample Replicate | Assay weight (μg) | % Label Claim | Capsule Weight (mg) |
|---|---|---|---|
| 1 | 203.3 | 101.6 | 114.38 |
| 2 | 206.1 | 103.1 | 114.68 |
| 3 | 203.8 | 101.9 | 113.57 |
| 4 | 204.2 | 102.1 | 112.59 |
| 5 | 203.5 | 101.7 | 112.69 |
| 6 | 206.9 | 103.5 | 114.30 |
| 7 | 205.8 | 102.9 | 110.15 |
| 8 | 203.9 | 102.0 | 110.30 |
| 9 | 205.8 | 102.9 | 111.82 |
| 10 | 204.0 | 102.0 | 111.07 |
| Mean | 0.6 | 102.4 | |
| Standard deviation | 1.3 | 0.6 | |

AV = 2.3

Related Substances Analysis 10 of the Red Size 4 Quali-V (HPMC) capsules containing 50 μg of the active substance and 10 of the green/grey size 4 Quali-G (PEG) capsules containing 50 μg of the active substance were analysed by HPLC/UPLC according to the methodology above. It was observed that the HPMC capsule shells (Quali-V) caused a peak in the chromatogram which had a same relative retention time as a potential peroxide degradation peak. It was observed that strong peaks from the HPMC capsule (including placebo capsules) elute between ~1 and ~4 min, and hence could interfere with detection of this potential degradant. It is notable that gelatin capsules do not give any interference around 3.5 min (or indeed at any elution time).

In addition, a new peak was detected at a retention time of ~12 min in the active HPMC capsules, not seen in the placebo capsules. The concern is that this peak may grow further with storage. As such, the HPMC capsules were not progressed further (i.e., not tested at the initial time point or put down on stability).

It was discovered that upon incubation of the capsules incubated at 60° C. a new peak in the chromatogram was observed at RRT 1.35. This peak was not seen during development or in the forced degradation study and appears to grow when the capsule is incubated at 60° C. when under an air or a nitrogen atmosphere. This peak is not present in the capsules or the vial samples that had not been incubated at 60° C. The growth of this peak is demonstrated in FIG. 13—the area increases with increasing time of incubation, more so under air than under nitrogen (<1% $O_2$). This implies that processing the batch under nitrogen may help reduce chemical degradation of the batch.

Stability Study Results

The stability study results are shown in Table 22, Table 23, Table 24 and Table 25. Dissolution profiles at the initial timepoint are shown in FIGS. 14 and 15; all capsules released 85% of the active substance by 15 minutes as determined by dissolution in 0.1 M HCl and pH 6.8 phosphate buffer.

TABLE 22

Stability data for 50 micrograms capsules (25° C./60% RH)

| Test | Shelf-life Acceptance Criteria | Initial | 1 month |
|---|---|---|---|
| Appearance | Opaque grey body/green cap capsule size 4 with no physical defects | Complies | Complies |
| Assay | 90.0%-110.0% of nominal | 99.1 | 102.8 |
| Related substances | | | |
| Unspecified impurity/ degradation product* | NMT 1.0% | RRT0.94: 0.19 RRT1.05: 0.22 | RRT0.94: 0.22 RRT1.04: 0.18 |
| Total impurities/ degradation products | NMT 4.0% | Total: 0.41 | Total: 0.40 |
| Dissolution | Report result | 105.1 | 99.5 |
| Microbial enumeration | | | |
| TAMC | NMT $10^3$ cfu/g | Complies | NA |
| TYMC | NMT $10^2$ cfu/g | Complies | NA |
| *Escherichia coli* | Absent in 1 g | Complies | NA |

*Only peaks ≥0.10% are reported

TABLE 23

Stability data for 50 micrograms capsules (40° C./75% RH)

| Test | Shelf-life Acceptance Criteria | Initial | 1 month |
|---|---|---|---|
| Appearance | Opaque grey body/ green cap capsule size 4 with no physical defects | Complies | Complies |
| Assay | 90.0%-110.0% of nominal | 99.1 | 95.6 |
| Related substances | | | |
| Unspecified impurity/ degradation product* | NMT 1.0% | RRT0.94: 0.19 RRT1.05: 0.22 | RRT0.94: 0.20 RRT1.06: 0.26 |
| Total impurities/ degradation products | NMT 4.0% | Total: 0.41 | Total: 1.21 |
| Dissolution | Report result | 105.1 | 100.2 |
| Microbial enumeration | | | |
| TAMC | NMT $10^3$ cfu/g | Complies | NA |
| TYMC | NMT $10^2$ cfu/g | Complies | NA |
| *Escherichia coli* | Absent in 1 g | Complies | NA |

*Only peaks ≥0.10% are reported

TABLE 24

Stability data for 200 micrograms capsules (25° C./60% RH)

| Test | Shelf-life Acceptance Criteria | Initial | 1 month |
|---|---|---|---|
| Appearance | White, opaque capsule size 2 with no physical defects | Complies | Complies |
| Assay | 90.0%-110.0% of nominal | 100.4 | 100.3 |
| Related substances | | | |
| Unspecified impurity/ degradation product* | NMT 1.0% | RRT0.94: 0.19 RRT1.05: 0.23 | RRT0.94: 0.22 RRT1.05: 0.23 |
| Total impurities/ degradation products | NMT 4.0% | Total: 0.41 | Total: 0.45 |
| Dissolution | Report result | 103.2 | 104.0 |
| Microbial enumeration | | | |
| TAMC | NMT $10^3$ cfu/g | Complies | NA |
| TYMC | NMT $10^2$ cfu/g | Complies | NA |
| *Escherichia coli* | Absent in 1 g | Complies | NA |

*Only peaks ≥0.10% are reported

TABLE 25

Stability data for 200 micrograms capsules (40° C./75% RH)

| Test | Shelf-life Acceptance Criteria | Initial | 1 month |
|---|---|---|---|
| Appearance | White, opaque capsule size 2 with no physical defects | Complies | Complies |
| Assay | 90.0%-110.0% of nominal | 100.4 | 100.1 |
| Related substances | | | |
| Unspecified impurity/ degradation product* | NMT 1.0% | RRT0.94: 0.19 RRT1.05: 0.23 | RRT0.94: 0.22 RRT1.05: 0.25 RRT1.45: 0.15 |
| Total impurities/ degradation products | NMT 4.0% | Total: 0.41 | Total: 0.61 |
| Dissolution | Report result | 103.2 | 100.9 |
| Microbial enumeration | | | |
| TAMC | NMT $10^3$ cfu/g | Complies | NA |
| TYMC | NMT $10^2$ cfu/g | Complies | NA |
| *Escherichia coli* | Absent in 1 g | Complies | NA |

*Only peaks ≥0.10% are reported

Example 5—Solubility Study

The aim of this study was to assess the solubility of the N-(2-(tert-butyl)-1-((4,4-difluorocyclohexyl)methyl)-1H-benzimidazol-5-yl)ethanesulfonamide in a number of different excipients. Excipients which solubilised the active ingredient at ≥0.0125% w/w were assessed for their compatibility with the active ingredient (see Example 6) and dissolution performance (see Example 7).

Materials

The materials used in this study are summarised in Table 26.

TABLE 26

Materials used in Solubility Study.

| Material | Function | Manufacturer |
|---|---|---|
| Compound I | API | Onyx |
| PEG400 (Kollisolv) | Solvent | BASF |
| 1,2 Propanediol (propylene glycol) | | MERCK |
| Glycerol | | MERCK |
| Corn oil | | Sigma |
| Kolliphor EL (cremophor EL) | | BASF |
| Polysorbate 20 | | Sigma |
| Polysorbate 80 | | Sigma |
| Labrasol ALF | | Gattefosse |
| Labrafil M 2125 CS | | Gattefosse |
| Miglyol 812 (medium-chain triglycerides) | | IOI Oleo GmbH |
| Octanoic acid (Caprylic Acid) | | Sigma |
| Propylene glycol monocaprylate (Capmul MCM C-8) | | Abitec |
| Propylene glycol dilaurate (Capmul PG-2L) | | Abitec |
| Diethylene glycol monoethyl ether | | Sigma |
| Soybean oil | | Sigma |
| Oleic acid | | Sigma |
| Kolliphor ELP (cremophor ELP) | | BASF |
| PEG 4000 | | Merck |
| PEG 6000 | | Merck |
| Cremophor RH40 | | BASF |
| Kolliphor HS15 | | BASF |
| Gelucire 50/13 | | Gattefosse |
| Gelucire 48/16 | | Gattefosse |
| Capmul 808G | | Abitec |
| Sorbitan palmitate | | Sigma |
| Glyceryl palmitostearate | | Gattefosse |
| Glyceryl monooleate (Capmul GMO-50) | | Abitec |
| Vitamin E TPGS 1000 | | Isochem |

Methodology

Preparation of Binary Semi-Solid Compositions

The binary semi-solid compositions are summarised in Table 27.

The binary semi-solid composition mixtures were manufactured as follows:

I. The semi solids were dispensed then molten overnight at ~60° C. (PEG 1500 and Vitamin E TPGS) or at ~80° C. (PEG 6000)

II. PEG 400 was added the next day, as required, (when all the semi-solids were molten)

III. Binary solvent mixture containing PEG 6000 were mixed at ~80° C. and the remaining binaries were mixed at ~70° C., until homogenous

TABLE 27

Binary excipient composition

| Batch details | % w: w/g | PEG 400 | PEG 1500 | PEG 6000 | Vitamin E TPGS | Total |
|---|---|---|---|---|---|---|
| PEG400:PEG 1500 (9:1) | % w/w | 90.1 | 9.9 | | | 100.0 |
| | g | 180.92 | 19.78 | | | 200.69 |
| PEG400:PEG 1500 (1:1) | % w/w | 49.9 | 50.1 | | | 100.0 |
| | g | 99.80 | 100.06 | | | 199.86 |
| PEG400:PEG 1500 (1:9) | % w/w | 9.9 | 90.1 | | | 100.0 |
| | g | 19.83 | 180.06 | | | 199.89 |
| PEG1500:PEG6000 (9:1) | % w/w | | 90.0 | 10.0 | | 100.0 |
| | g | | 180.02 | 19.91 | | 199.94 |
| PEG1500:PEG6000 (1:1) | % w/w | | 50.0 | 50.0 | | 100.0 |
| | g | | 100.04 | 100.00 | | 200.04 |
| PEG1500:PEG6000 (1:9) | % w/w | | 10.0 | 90.0 | | 100.0 |
| | g | | 20.03 | 180.09 | | 200.12 |
| PEG1500:TPGS (9:1) | % w/w | | 89.7 | | 10.3 | 100.0 |
| | g | | 180.01 | | 20.69 | 200.70 |
| PEG1500:TPGS (1:1) | % w/w | | 49.8 | | 50.2 | 100.0 |
| | g | | 100.04 | | 100.86 | 200.90 |
| PEG1500:TPGS (1:9) | % w/w | | 9.8 | | 90.2 | 100.0 |
| | g | | 19.52 | | 179.77 | 199.30 |

Solubility Assessment Methodology:

The quantities of API and solvents used in the solubility study (Parts 1 and 2) are summarised in Table 28.

TABLE 28

Quantities of API and solvents used in Part 1 and 2 of the solubility study.

| | Part 1 Study | | | Part 2 Study | | | |
|---|---|---|---|---|---|---|---|
| API dispensed (mg) | 11.5-13.5 | | | 15-17 | | | |
| Solvent aliquot | Aliquot 1 | Aliquot 2 | Aliquot 3 | Aliquot 1 | Aliquot 2 | Aliquot 3 | Aliquot 4 |
| Solvent volume to be added (mL) | 25 | 25 | 50 | 2.0 | 2.0 | 2.4 | 9.6 |
| Total Cumulative Solvent volume (mL) | 25 | 50 | 100 | 2.0 | 4.0 | 6.4 | 16 |
| Final concentration (% w/v) | 0.05 | 0.025 | 0.0125 | 0.8 | 0.4 | 0.25 | 0.1 |

Where required, the semi solids were melted prior to use (overnight). The solubility of the API in the selected solvents was assessed in two parts (Part 1 and Part 2 Studies) as follows:

i. Solvent aliquots were added to pre-dispensed API while mixing using a magnetic flea and stirrer.
ii. The temperature of the solvents was maintained as follows:
  a. Single-component liquids: Room temperature (ambient)
  b. TPGS and PEG 1500: ~60° C.
  c. PEG 6000 and binary solvent mixtures containing PEG 6000: ~80° C.
iii. Solvents were mixed for a maximum of 1 hour between each aliquot addition.
iv. The solvents were carefully inspected visually between aliquots.
v. The addition of solvent was stopped when:
  a. After Aliquot 2 addition if API fully dissolve—(even if API dissolve after Aliquot 1, Aliquot 2 was added)
  b. After adding all the solvent aliquots in Table 28
vi. The number of solvent aliquots added and mixing times are summarised in Table 29.

TABLE 29 summary of solubility mixing times for each solvent

| Solvent | Part 1 study: Total mixing Time | Part 1 study: Total # aliquots added | Part 2 study: Total mixing Time | Part 2 study: Total # aliquots added |
|---|---|---|---|---|
| Single-component liquids | | | | |
| Octanoic acid | 2 Hr | 2 | 2 Hr | 2 |
| Propylene glycol monocaprylate | 2 Hr | 2 | 2 Hr | 2 |
| Diethylene glycol monoethyl ether | 2 Hr | 2 | Over night (~15 Hrs) | 2 |
| PEG 400 | 2 Hr | 2 | 4 Hr | 4 |
| Polysorbate 20 | Over night (~15 Hrs)# | 3# | Over night (~15 Hrs) # | 4 |
| Polysorbate 80 | Over night (~15 Hrs)# | 3# | Over night (~15 Hrs) # | 4 |
| Propylene glycol dilaurate | 4 Hr | 3 | Over night (~15 Hrs) | 4 |
| Labrasol ALF | 2 Hr | 2 | Over night (~15 Hrs) | 4 |
| 1,2-propane diol | 3 Hr^ | 3^ | NA | |
| Glycerol | 3 Hr^ | 3^ | | |
| Corn oil | 3 Hr^ | 3^ | | |
| Kolliphor EL | 3 Hr^ | 3^ | | |
| Kolliphor ELP | 3 Hr^ | 3^ | | |
| Labrafil M 2125 CS | 3 Hr^ | 3^ | | |
| Miglyol 812 (Medium-chain Triglycerides) | 3 Hr^ | 3^ | | |
| Soybean oil | 3 Hr^ | 3^ | | |
| Oleic acid | 3 Hr^ | 3^ | | |
| Single component Semi-Solids | | | | |
| PEG 6000 | 2 Hr | 2 | 2 Hr | 2 |
| PEG 4000 | 2 Hr | 1 | 2 Hr | 2 |
| Cremophor RH40 | 2 Hr# | 2 Only after Overnight Hold (~15 Hrs) # | 2 Hr# | 2# |
| Kolliphor HS15 | 2 Hr | 2 | 2 Hr | 2 |
| Glyceryl monooleate | 2 Hr | 2 | 2 Hr | 2 |
| Gelucire 50/13 | 2 Hr | 2 | 4 Hr | 4 |
| Capmul 808G | 2 Hr | 2 | 4 Hr | 4 |
| Gelucire 48/16 | 2 Hr | 2 | 4 Hr | 4 |
| Sorbitan palmitate | 4 Hr^ | 3^ | NA | |
| Glyceryl palmitostearate | 4 Hr^ | 3^ | | |
| Binary solvent mixtures | | | | |
| PEG400:PEG 1500 (9:1) | 2 Hr | 2 | 2 Hr | 2 |
| PEG400:PEG 1500 (1:1) | 2 Hr | 2 | 2 Hr | 2 |
| PEG400:PEG 1500 (1:9) | 2 Hr | 2 | 2 Hr | 2 |
| PEG1500:PEG6000 (1:1) | 2 Hr 40 min | 2 | 1 Hr 10 min | 2 |
| PEG1500:PEG6000 (9:1) | 2 Hr | 2 | 2 Hr | 2 |
| PEG1500:PEG6000 (1:9) | 3 Hr | 3 | 3 Hr | 2 |

TABLE 29-continued summary of solubility mixing times for each solvent

| | Part 1 study | | Part 2 study | |
|---|---|---|---|---|
| Solvent | Total mixing Time | Total # aliquots added | Total mixing Time | Total # aliquots added |
| PEG1500:TPGS (9:1) | 2 Hr | 2 | 2 Hr | 2 |
| PEG1500:TPGS (1:1) | 2 Hr | 2 | 2 Hr | 2 |
| PEG1500:TPGS (1:9) | 3 Hr | 3 | 3 Hr | 2 |

#excipients that only dissolved the API after stirring overnight
^Excipients that failed to dissolve the API Results:

Single-Component Liquids:

The liquid solvents used for the solubility study are shown in Table 30.

From Part 1 of the study the following can be noted:

API had the highest solubility in diethylene glycol monoethyl ether where the API fully dissolved after the addition of the first aliquot PEG 400, octanoic acid, propylene glycol monocaprylate and Labrasol ALF dissolved the API following the addition of second solvent aliquot.

Propylene glycol dilaurate, polysorbate 20 and polysorbate 80 dissolved the API but only after the addition of the third aliquot.

The remaining solvents failed to dissolve the API even after the third aliquot addition.

For Part 2 Solubility the following can be noted:

As per Part 1 of the solubility study, the API had the highest solubility in diethylene glycol monoethyl ether, octanoic acid and propylene glycol monocaprylate, dissolving in just two solvents aliquots.

In order to dissolve the API in PEG 400, polysorbate 20, polysorbate 80, propylene glycol dilaurate and Labrasol ALF four solvent aliquots were required. However:

Propylene glycol dilaurate, polysorbate 80, polysorbate 20 had to be mixed overnight (~15 hours) to dissolve the API For Labrasol ALF, the API dissolved after the third aliquot was added, and the solution remained clear with the addition of the 4th aliquot. However after 5 days standing at ambient it was observed on inspection that the API had precipitate out of solution.

TABLE 30

Summary results for API solubility in Liquid excipients

| | Part 1 Study | | | Part 2 Study | | | Solubility range (% w/v) | |
|---|---|---|---|---|---|---|---|---|
| Solvent | Aliquot where API first fully dissolved | Final # aliquots added | Nominal Dose per vial (µg) | Aliquot where API first fully dissolved | Final # aliquots added | Nominal capsule Dose (ug) | Above | Below |
| Octanoic acid | 2nd | 2 | 68.9 | 2nd | 2 | 229 | 0.40% | 0.80% |
| Propylene glycol monocaprylate | 2nd | 2 | 49.9 | 2nd | 2 | 208 | 0.40% | 0.80% |
| Diethylene glycol monoethyl ether | 1st | 2 | 49.9 | 2nd | 2 | 209 | 0.40% | 0.80% |
| PEG 400 | 2nd | 2 | 48.7 | 4th | 4 | 181 | 0.10% | 0.25% |
| Polysorbate 20 | 3rd# | 3# | 34.5 | 4th Only after Overnight Hold# | 4# | 186 | 0.10% | N/K |
| Polysorbate 80 | 3rd# | 3# | 43.1 | 4th Only after Overnight Hold# | 4# | 201 | 0.10% | N/K |
| Propylene glycol dilaurate | 3rd# | 3# | 22.4 | 4th Only after Overnight Hold# | 4# | 210 | 0.10% | N/K |
| Labrasol ALF | 2nd# | 2# | 74.6 | 3rd | 4# Precipitate 5 days later | 186 | 0.025% | 0.05% |

TABLE 30-continued

Summary results for API solubility in Liquid excipients

| | Part 1 Study | | | Part 2 Study | | | | |
|---|---|---|---|---|---|---|---|---|
| | Aliquot where API first fully | Final # aliquots | Nominal Dose per vial | Aliquot where API first fully | Final # aliquots | Nominal capsule Dose | Solubility range (% w/v) | |
| Solvent | dissolved | added | (μg) | dissolved | added | (ug) | Above | Below |
| 1,2-propane diol | | DND* | | | | NA | | |
| Glycerol | | | | | | | | |
| Corn oil | | | | | | | | |
| Kolliphor EL | | | | | | | | |
| Kolliphor ELP | | | | | | | | |
| Labrafil M 2125 CS | | | | | | | | |
| Miglyol 812 (Medium-chain Triglycerides) | | | | | | | | |
| Soybean oil | | | | | | | | |
| Oleic acid | | | | | | | | |

*DND = Did not dissolve even after the addition of 3 aliquots

¥N/K = Not known: in these cases, the API was found to dissolve after the addition of the $4^{th}$ solvent aliquot (corresponding to 0.1% w/v - see Table 3) only after stirring overnight. Since these samples had not been stirred overnight following the $3^{rd}$ solvent aliquot addition (corresponding to 0.25% w/v), it cannot be assumed that the API solubility is below 0.25% w/v. Hence the upper solubility limit is not known.

#excipients that only dissolved the API after stirring overnight

Single-Component Semi-Solids

The single-component semi-solid solvents used for Parts 1 and 2 of the solubility study are summarised in Table 31.

For Part 1 of the study the following observations can be noted:

- API had the highest solubility in PEG 4000, Kolliphor HS15, Capmul 808G and Gelucire 48/16—The API fully dissolved after the addition of the first aliquot
- PEG 6000, Glyceryl monooleate, Gelucire 50/13 and Cremophor RH40 all dissolved the API following the addition of second solvent aliquot. However:
  - API precipitation was observed next day in Gelucire 50/13
  - Cremophor RH40 had to be mixed overnight (~15 hours) to dissolve the API after the addition of the second aliquot.
- The remaining solvents (sorbitan palmitate and glyceryl palmitostearate) failed to dissolve the API even after third aliquot was added.

For Part 2 of the study the following observations can be noted:

- Notably different from Part 1 of the solubility study, the API had the highest solubility in PEG 6000. In addition, the API showed higher solubility in Gelucire 50/13 in Part 2 compared to Part 1. The higher solubility observed in Part 2 vs Part 1 may have occurred due to the smaller volume of this highly viscous solvent. Using this smaller volume:
  - There is likely to be a more even spread of heat throughout the mixture (less chance of cold spots in the viscous fluid).
  - The mixing energy per volume is higher allowing improved hydrodynamics for API dissolution.
  - Controlled temperature and effective mixing are very critical when working with semi-solid that have high melting temperature and high viscosity, such as PEG 6000 and Gelucire 50/13
- The solvents which required two aliquots to dissolve the API were PEG 4000, Cremophor RH40, Kolliphor HS15 and Glyceryl monooleate.
  - Creophor RH40 had to be mixed overnight to dissolve the API
- To dissolve the API in Gelucire 50/13 and Capmul 808G three aliquots of the solvent had to be added.
- To dissolve the API in Gelucire 48/16 four aliquots of solvent were required.

TABLE 31

Summary results for API solubility in single component semisolid excipients

| | Part 1 Study | | | Part 2 Study | | | | |
|---|---|---|---|---|---|---|---|---|
| | Aliquot where API first fully | Final # aliquots | Nominal Dose per vial | Aliquot where API first fully | Final # aliquots | Nominal capsule Dose | Solubility range (% w/v) | |
| Solvent | dissolved | added | (μg) | dissolved | added | (ug) | Above | Below |
| PEG 6000 | 2nd | 2 | 86.6 | 1st | 2 | 197 | 0.80% | N/K¥ |
| PEG 4000 | 1st | 2 | 53.1 | 2nd | 2 | 188 | 0.40% | 0.80% |
| Cremophor | 2nd Only | 2 | 29.0 | 2nd# | 2# | 202 | 0.40% | 0.80% |

TABLE 31-continued

Summary results for API solubility in single component semisolid excipients

| | Part 1 Study | | | Part 2 Study | | | | |
|---|---|---|---|---|---|---|---|---|
| | Aliquot where API first fully | Final # aliquots | Nominal Dose per vial | Aliquot where API first fully | Final # aliquots | Nominal capsule Dose | Solubility range (% w/v) | |
| Solvent | dissolved | added | (μg) | dissolved | added | (ug) | Above | Below |
| RH40 | after Overnight Hold | | | | | | | |
| Kolliphor HS15 | 1st | 2 | 57.4 | 2nd | 2 | 188 | 0.40% | 0.80% |
| Glyceryl monooleate | 2nd | 2 | 51.0 | 2nd | 2 | 203 | 0.40% | 0.80% |
| Gelucire 50/13 | 2nd | 2 | 91.5 | 3rd | 4 | 211 | 0.25% | 0.40% |
| Capmul 808G | 1st | 2 | 48.4 | 3rd | 4 | 199 | 0.25% | 0.40% |
| Gelucire 48/16 | 1st | 2 | 45.5 | 4th | 4 | 196 | 0.10% | 0.40% |
| Sorbitan palmitate | | DND* | | | | NA | | |
| Glyceryl palmito-stearate | | | | | | | | |

*DND = Did not dissolve

¥N/k = Not known

Binary Solvent Mixtures

The API solubility in the binary solvent mixtures is summarised in Table 32. The API showed high solubility in all the binary solvent mixtures for both Parts 1 and 2. With the exception of PEG1500:TPGS (1:9) and PEG1500:PEG6000 (1:9), the API fully dissolved after the addition of the first solvent aliquot. The API solubility in PEG 1500:TPGS (1:9) was unexpectedly lower than all the binary solvent mixtures. Three solvents aliquots were required to dissolve the API in Part 1 and two solvent aliquots were required to dissolve the API in Part 2. However, the API solubility in PEG 1500:TPGS solvent mixture at 1:9 ratio remained acceptable.

TABLE 32

Summary results for API solubility in binary solvent mixtures.

| | Part 1 Study | | | Part 2 Study | | | | |
|---|---|---|---|---|---|---|---|---|
| | Aliquot where API first fully | Final # aliquots | Nominal Dose per vial | Aliquot where API first fully | Final # aliquots | Nominal capsule Dose | Solubility range (% w/v) | |
| Solvent | dissolved | added | (μg) | dissolved | added | (ug) | Above | Below |
| PEG400:PEG 1500 (9:1) | 1st | 2 | 46.6 | 1st | 2 | 194 | 0.80% | N/K¥ |
| PEG400:PEG 1500 (1:1) | 1st | 2 | 48.6 | 1st | 2 | 187 | 0.80% | N/K¥ |
| PEG400:PEG 1500 (1:9) | 1st | 2 | 51.7 | 1st | 2 | 186 | 0.80% | N/K¥ |
| PEG1500:PEG6000 (1:1) | 1st | 2 | 60.9 | 1st | 2 | 183 | 0.80% | N/K¥ |
| PEG1500:PEG6000 (9:1) | 1st | 2 | 50.0 | 1st | 2 | 178 | 0.80% | N/K¥ |
| PEG1500:PEG6000 (1:9) | 3rd | 3 | 23.8 | 1st | 2 | 166 | 0.80% | N/K¥ |
| PEG1500:TPGS (9:1) | 1st | 2 | 47.1 | 1st | 2 | 192 | 0.80% | N/K¥ |
| PEG1500:TPGS (1:1) | 1st | 2 | 48.5 | 1st | 2 | 186 | 0.80% | N/K¥ |
| PEG1500:TPGS (1:9) | 3rd | 3 | 22.6 | 2nd | 2 | 197 | 0.40% | 0.80% |

*DND = Did Not Dissolve

¥N/K = Not known

CONCLUSIONS

For a semi-solid composition it is desirable that the API has some solubility, ideally fully soluble, in the excipients of the composition. Based on the predicted dose for this pharmaceutical product, excipients in which the API had sufficient solubility are:

Octanoic acid, PEG 400, PEG 4000, PEG 6000, cremophor RH40, kolliphor HS15, Gelucire 50/13, polysorbate 20, Gelucire 48/16, polysorbate 80, capmul 808G, propylene glycol monocaprylate, propylene glycol dilaurate, diethylene glycol monoethyl, glyceryl monooleate, PEG 400:PEG 1500 (9:1), PEG 400:PEG 1500 (1:1), PEG 400:PEG 1500 (1:9), PEG 1500:PEG 6000 (1:1), PEG 1500:PEG 6000 (9:1), PEG 1500:PEG 6000 (1:9), PEG 1500:TPGS (9:1), PEG 1500:TPGS (1:1), and PEG 1500:TPGS (1:9).

These solvent systems were further studied in order to determine their compatibility with the API, see Example 6.

Example 6—Excipient Compatibility

For the excipients tested in Example 5 which solubilised the API, samples of the excipient and API solutions were put down on a stability study in order to determine if the API was compatible with the excipient.

Methodology

Based on the results from Example 5, if the API fully dissolved after addition of Aliquot 2 or 3, samples of the API solution were taken for excipient compatibility.

Duplicate active samples and single reps of their placebo controls (no API) were placed on station (−20° C., 25° C. and 40° C.) for 14 and 28 days. Concentration of API in the excipient was 0.025% w/w. Once the incubation period was completed, samples were pulled and placed into a freezer pending their LC testing.

UPLC Method Conditions:

TABLE 33

| UPLC methodology | | | |
|---|---|---|---|
| Parameter | Value | | |
| Column | Halo C18 2.7 μm, 3.0 × 50 mm (PN: 92813-402) | | |
| Column temperature | 40° C. | | |
| Sample manager wash (UPLC) | HPLC Water:ACN 50:50% v/v | | |
| Sample manager purge (UPLC) | HPLC Water:ACN 50:50% v/v | | |
| Mobile phase A | 10 mM Ammonium Acetate pH 7.0 | | |
| Mobile phase B | Acetonitrile | | |
| Gradient program | Time (minutes) | Mobile Phase A (%) | Mobile Phase B (%) |
| | 0 | 95 | 5 |
| | 5.00 | 72 | 28 |
| | 8.04 | 55 | 45 |
| | 13.14 | 50 | 50 |
| | 15.69 | 18 | 82 |
| | 16.31 | 2 | 98 |
| | 27.0 | 2 | 98 |
| | 27.1 | 95 | 5 |
| | 32.0 | 95 | 5 |
| Flow rate | 0.3 mL/min | | |
| Run time | 32 minutes | | |
| Solution for injection | Solution in ACN | HPLC water Auto-Addition | |
| Injection volume | 12 μL | 38 μL | |

TABLE 33-continued

| UPLC methodology | |
|---|---|
| Wavelength | 256 nm |
| 3D data range | 190 to 400 nm |
| Sampling rate | 10 points/sec |

Results:

Assay:

The assay results are presented in Table 34. Most of the samples had a low assay, generally <85%, but few samples had lower assays (<70%). Those cases where the assay values decrease with incubation time and temperature are suggestive of API-excipient incompatibilities.

Apart from these cases, most assay values were consistently low over the course of the study. This has been attributed to poor extraction during sample preparation. The extraction method is optimised for PEG1500 and not the other excipients studied here.

For propylene glycol monocaprylate the API peak and the peak at RRT 0.93 are joined and as such an accurate assay result could not be determined. However, the UV spectrum, of the API peak in the samples does not match that of the standard UV spectrum. Propylene glycol monocaprylate is not compatible with the API.

The cases where the solvents contains at least 50% of PEG 400 showed evidence of gross degradation (i.e. assay values decreasing significantly (lowest for 28 days at 40° C.) with time and temperature) PEG 400, PEG 400:PEG 1500 (9:1) and (PEG 400:PEG 1500 (1:1).

Related Substances:

The related substances detected for each excipient API system are presented in Tables 35-59 below.

Due to retention time shifts during the sequence, some of the excipient peaks did not always completely align with those in the active samples in the overlaid chromatograms. This is to be expected with excipient compatibility analysis. However, such retention times shifts were generally straightforward to account for.

Related substance peaks at RRT 0.96, 0.97, 1.02 & 1.03/1.04 are also present in the chromatogram of the standards. Each sample set is processed so that the API integration is consistent with the standard API peak for that sequence. In some sample sets, the RRT 1.02 and/or 1.03/1.04 peaks are indistinguishable from the API peak, and in some sets, the RRT 0.96 and/or 0.97 peaks are not well resolved due to e.g. interference from excipient peaks.

While all peaks reported are clearly distinguishable from the baseline, if a sample has a particularly low assay result (<50% of nominal) then the related substances % area reported may not be accurate as it will not be within the validated linearity range. This is acceptable for excipient compatibility analysis as results can still be trended.

For several families, peaks were detected in the samples tested at T=14 days but not at T=28 days. Because it is likely that genuine degradation peaks would increase in area from 14 to 28 days, it is unlikely that these peaks are degradation peaks. The potential reasons for the occurrence of these are:

- Inadvertent contamination of the vials during the LC dilution step (potentially not occurring at 28 days).
- More baseline noise at 28 days than at 14 days
- Use of different sequences and different placebo control samples to determine what is API/excipient related substances peaks at the 14 day vs 28-day timepoints. For example, where (excipient) peaks are seen in the placebo control sample at 28 days but not that (in the frozen control) at 14 days. This may indicate thermal degradation of the excipient at (40° C. for) 28 days.

Related Substances Conclusions

There was no evidence of related substances growth with incubation time and temperature for Polysorbate 20, Gelucire 50/13, Gelucire 48/16, Capmul 808G, propylene glycol monocaprylate, and propylene glycol dilaurate. However, it should be noted that all of these showed at least one peak (without a clear dependence of time or temperature) that were not present in the corresponding placebo control sample at the corresponding timepoint).

Comparing the areas of the related substance across all the PEG grades for the single-component solvents (see Tables 35-37), the following differences can be noted:

- PEG 400 showed several peaks that grew with incubation time and temperature: RRT 0.63, RRT 0.64, RRT 0.77, RRT 0.87, RRT 1.07 and RRT 1.08. The peaks at RRT 0.64 and RRT 0.77 had individual areas>1% after 28 days at 40° C.
- PEG 4000 showed only one peak (RRT 1.18) which grew with incubation time and temperature. However, this remained below 0.5% throughout.
- PEG 6000 showed two peaks which grew with incubation time and temperature: RRT 0.63 and RRT 1.65. However, these remained below 0.2% throughout.

For the binary samples where the ratios of the two solvents were adjusted, the following could be noted:

PEG1500+Vitamin E TPGS:

- Weak peaks (area NMT 0.3%), which grew with incubation time and temperature, were detected at RRT 0.85 and RRT 0.86/0.87, and were seen in all of these samples stored for T=28 days at 25° C. and 40° C. The areas of these peaks increased slightly with Vitamin E TPGS content suggesting they may be associated with the Vitamin E TPGS.
- A pair of peaks were also detected between RRT 1.61 and 1.65 (exact RRT of both peaks changed across the three sample families) whose area increased markedly with Vitamin E TPGS content reaching up to ~3% and 7% for the earlier and later eluting peak, respectively, in the case of 1:9 PEG 1500:TPGS after 28 days at 40° C., suggesting they are associated with the Vitamin E TPGS.
- Samples made at 1:9 PEG1500:TPGS showed additional peaks (RRT0.56, RRT0.69, RRT0.71, RRT0.82, and RRT1.20), which did not increase with time or temperature). Because these peaks are not seen in PEG:TPGS=9:1, they are likely associated with the TPGS and not the PEG 1500.

PEG 400+PEG1500

Numerous peaks were detected (at least after 28 days at 40° C.) which grew with incubation time and temperature, for example see peaks at RRT~0.62, RRT~0.63, RRT 0.77, RRT 0.89, RRT 1.06 and RRT 1.34 were seen. The area % of all of these peaks tended to increase as the ratio of PEG 400 increases in the binary mixture, for example, see RRT 0.63 and 0.77.

The drop in assay seen with sample PEG400:PEG1500 (9:1) and PEG400:PEG1500 (1:1) for the samples stored at 40° C. for 28 day appears to be associated with the growth of the related substance peaks in these samples.

PEG 1500+PEG 6000

Peaks with low area (<0.2% of the total) grew with incubation time and temperature in both families but at different RRTs:

- At 1:9 PEG 1500:PEG 6000, the peaks detected were RRT 0.83 and RRT 0.85
- At 9:1 PEG 1500:PEG 6000, the peaks detected were RRT 0.61, RRT 0.62 and RRT0.77.

Overall Conclusions

- There was no evidence of excipient:API incompatibilities with incubation time and temperature for Polysorbate 20, Gelucire 50/13, Gelucire 48/16, Capmul 808G, and propylene glycol dilaurate.
- Consistent assays were determined with incubation time/temperature for PEG 4000, PEG 6000, Cremophor RH40, Kolliphor HS15, Polysorbate 80, octanoic acid, diethylene glycol monoethyl ether, PEG400:PEG1500 (1:9), PEG1500:PEG6000 (9:1), glyceryl monooleate, PEG1500:PEG6000 (1:9), PEG1500:TPGS (1:1), PEG1500:TPGS (9:1), and PEG1500:TPGS (1:9).
- The grade of PEG 400 used (alone or in combination with PEG1500 in a 9:1 and 1:1 PEG400:PEG1500) was incompatible with the API as assay decreased and related substances peaks increased with incubation time/temperature. It is postulated that the grade of PEG400 used may in part be contributing to the API incompatibility and that a super refined grade of PEG400 may be compatible with the API considering other PEG solvents have been demonstrated to be compatible with the API (see this Example and Example 4). Using a super-refined PEG may be advantageous for other PEGs (e.g. PEG1500, PEG4000, PEG6000), for example, extend the shelf life of the product.

TABLE 34

Assay (as % of nominal) stability data

| | Assay as % of Nominal | | | | | | | | | | | | | | |
|---|---|---|---|---|---|---|---|---|---|---|---|---|---|---|---|
| | 14 days (−20° C.) | | | 14 days (25° C.) | | | 14 days (40° C.) | | | 28 days (25° C.) | | | 28 days (40° C.) | | |
| Excipient | Rep 1 | Rep 2 | Mean | Rep 1 | Rep 2 | Mean | Rep 1 | Rep 2 | Mean | Rep 1 | Rep 2 | Mean | Rep 1 | Rep 2 | Mean |
| PEG 400 | 95.8 | 90.9 | 93.3 | 92.2 | 93.0 | 92.6 | 90.4 | 94.1 | 92.3 | 92.9 | 91.5 | 92.2 | 84.9 | 81.4 | 83.1 |
| PEG 4000 | 82.3 | 84.6 | 83.4 | 89.7 | 89.9 | 89.8 | 90.6 | 90.7 | 90.7 | 85.3 | 90.4 | 87.9 | 91.4 | 95.4 | 93.4 |
| PEG 6000 | 49.5 | 53.3 | 51.4 | 65.6 | 58.2 | 61.9 | 69.2 | 59.9 | 64.5 | 58 | 68.7 | 63.3 | 59.8 | 67.5 | 63.7 |
| Cremophor RH40 | 71 | 75.2 | 73.1 | 70.1 | 71.1 | 70.6 | 69.2 | 74.6 | 71.9 | 71.2 | 73.0 | 72.1 | 74.2 | 78.1 | 76.1 |
| Kolliphor HS15 | 83.9 | 90.6 | 87.2 | 87.9 | 90.2 | 89.1 | 88.8 | 89.3 | 89.1 | 90.2 | 94.1 | 92.1 | 86.3 | 95.4 | 90.9 |
| Gelucire 50/13 | 43.3 | 42.7 | 43.0 | 46.8 | 37.8 | 42.3 | 42.4 | 37.9 | 40.1 | 51.6 | 49.5 | 50.5 | 48.9 | 42.7 | 45.8 |
| Polysorbate 20 | 43.4* | 65.0 | 54.2 | 58.5 | 61.4 | 60.0 | 60.4 | 61.1 | 60.7 | 60.4 | 59.6 | 60.0 | 59.3 | 62.4 | 60.9 |
| Gelucire 48/16 | 72.0 | n/a* | 72.0 | 78.6 | 78.6 | 78.6 | 80.6 | 80.8 | 80.7 | 83.7 | 82.4 | 83.0 | 82.3 | 81.2 | 81.7 |

TABLE 34-continued

Assay (as % of nominal) stability data

| | Assay as % of Nominal | | | | | | | | | | | | | | |
|---|---|---|---|---|---|---|---|---|---|---|---|---|---|---|---|
| | 14 days (−20° C.) | | | 14 days (25° C.) | | | 14 days (40° C.) | | | 28 days (25° C.) | | | 28 days (40° C.) | | |
| Excipient | Rep 1 | Rep 2 | Mean | Rep 1 | Rep 2 | Mean | Rep 1 | Rep 2 | Mean | Rep 1 | Rep 2 | Mean | Rep 1 | Rep 2 | Mean |
| Polysorbate 80 | 54.2 | 58.2 | 56.2 | 59.8 | 53.8 | 56.8 | 66.1 | 65.8 | 66.0 | 57.0 | 59.8 | 58.4 | 61.1 | 72.4 | 66.8 |
| Capmul 808G | 86.7 | 89.5 | 88.1 | 88.1 | 86.6 | 87.3 | 93.7 | 85.1 | 89.4 | 84.1 | 88.2 | 86.1 | 84.4 | 86.0 | 85.2 |
| Octanoic acid | 69.3 | 69.1 | 69.2 | 69.0 | 67.8 | 68.4 | 67.6 | 67.9 | 67.8 | 59.9 | 61.8 | 60.9 | 67.8 | 58.7 | 63.2 |
| Propylene Glycol monocaprylate | 26.9 | 23.7 | 25.3 | 24 | 27.6 | 25.8 | 25.5 | 27.3 | 26.4 | 23.8 | 24.4 | 24.1 | 23.9 | 24.2 | 24.1 |
| Propylene Glycol dilaurate | 87.1 | 88.1 | 87.6 | 85.1 | 82.8 | 83.9 | 86.2 | 83.9 | 85.0 | 86.2 | 77.1 | 81.7 | 46.8# | 80.9 | 63.9 |
| Diethylene glycol monoethyl ether | 87.7 | 88.1 | 87.9 | 87.1 | 84.2 | 85.7 | 86.5 | 47.2# | 66.9 | 8.4# | 88.8 | 48.6 | 83.4 | 83.1 | 83.2 |
| Glyceryl monooleate | 87.2 | 87.9 | 87.5 | 94.0 | 92.6 | 93.3 | 89.5 | 93.4 | 91.5 | 94.2 | 95.8 | 95.0 | 88.7 | 80.8 | 84.8 |
| PEG400:PEG1500 (9:1) | 92.9 | 93.8 | 93.4 | 91.6 | 85.7 | 88.6 | 91.0 | 92.1 | 91.6 | 92.0 | 86.9 | 89.5 | 78.6 | 84.1 | 81.4 |
| PEG400:PEG1500 (1:1) | 90.2 | 72.4* | 81.3 | 94.2 | 93.9 | 94.0 | 92.7 | 93.1 | 92.9 | 94.3 | 94.2 | 94.2 | 85.6 | 80.8 | 83.2 |
| PEG400:PEG1500 (1:9) | 102.0 | 97.3 | 99.7 | 99.9 | 95.9 | 97.9 | 96.5 | 94.9 | 95.7 | 99.7 | 93.8 | 96.7 | 93.8 | 99.0 | 96.4 |
| PEG1500:PEG6000 (9:1) | 93.6 | 93.4 | 93.5 | 89.4 | 91.0 | 90.2 | 88.7 | 90.8 | 89.8 | 91.6 | 90.9 | 91.2 | 89.1 | 92.8 | 91.0 |
| PEG1500:PEG6000 (1:9) | 77.0 | 75.7 | 76.3 | 76.1 | 75.3 | 75.7 | 74.9 | 75.0 | 74.9 | 77.0 | 75.2 | 76.1 | 77.1 | 74.3 | 75.7 |
| PEG1500:TPGS (1:1) | 91.7 | 92.1 | 91.9 | 95.1 | 95.6 | 95.4 | 93.4 | 99.2 | 96.3 | 98.4 | 96.7 | 97.5 | 99.7 | 100.2 | 99.9 |
| PEG1500:TPGS (9:1) | 87.4 | 86.6 | 87.0 | 90.0 | 91.0 | 90.5 | 90.6 | 87.2 | 88.9 | 88.4 | 88.2 | 88.3 | 92.7 | 87.3 | 90.0 |
| PEG1500:TPGS (1:9) | 74.4 | 77.4 | 75.9 | 73.7 | 74.9 | 74.3 | 70.8 | 75.3 | 73.1 | 73.6 | 75.7 | 74.7 | 70.6 | 68.7 | 69.7 |

*Low assay value seen for one of the replicates.

#A low assay result was observed - all peaks for this sample in the chromatogram were reduced which suggests a lower volume of solution was injected into the UPLC.

TABLE 35

Related substances stability data for PEG 400

| | | | Area of Peak (as % of Total peak area) RRT ± 0.01 | | | | | | | | | | |
|---|---|---|---|---|---|---|---|---|---|---|---|---|---|
| Excipient | Storage | Time point | RRT 0.63 | RRT 0.64 | RRT 0.70 | RRT 0.77 | RRT 0.87 | RRT 0.96 | RRT 1.01 | RRT 1.04 | RRT 1.07 | RRT 1.08 | Total |
| PEG 400 | −20° C. | 14 days | ND | ND | <0.10 | ND | 0.12 | 0.20 | 0.79 | 0.53 | | | 1.64 |
| PEG 400 | 25° C. | 14 days | ND | ND | 0.18 | 0.27 | <0.10 | 0.19 | 0.75 | 0.47 | | | 1.86 |
| PEG 400 | 40° C. | 14 days | 0.15 | 0.27 | 0.16 | 0.35 | <0.10 | 0.17 | 0.85 | 0.46 | | | 2.41 |
| PEG 400 | 25° C. | 28 days | ND | ND | | <0.10 | ND | 0.18 | 0.20 | ND | ND | ND | 0.37 |
| PEG 400 | 40° C. | 28 days | 0.61 | 1.29 | | 2.1 | 0.2 | 0.15 | 0.16 | 0.17 | 0.18 | 0.26 | 5.11 |

TABLE 36

Related substances stability data for PEG 4000

| | | | Area of Peak (as % of Total peak area) RRT ± 0.01 | | | | | | | | | | | | |
|---|---|---|---|---|---|---|---|---|---|---|---|---|---|---|---|
| Excipient | Storage | Time point | RRT 0.15 | RRT 0.39 | RRT 0.41 | RRT 0.65 | RRT 0.89 | RRT 0.96 | RRT 0.97 | RRT 1.02 | RRT 1.07 | RRT 1.18 | RRT 1.20 | RRT 1.36 | Total |
| PEG 4000 | −20° C. | 14 days | 0.29 | ND | ND | ND | ND | 0.20 | <0.10 | 0.31 | ND | | 0.37 | ND | 1.18 |
| PEG 4000 | 25° C. | 14 days | 1.84 | 0.24* | 1.21* | 0.12* | 0.20* | 0.17 | 0.10 | 0.28 | 0.17 | | 0.34 | 0.10 | 4.77 |
| PEG 4000 | 40° C. | 14 days | ND | ND | ND | ND | ND | 0.19 | <0.10 | 0.29 | ND | | 0.39 | ND | 0.87 |
| PEG 4000 | 25° C. | 28 days | | | | | | 0.24 | 0.11 | 0.34 | | 0.38 | | | 1.07 |
| PEG 4000 | 40° C. | 28 days | | | | | | 0.24 | 0.11 | 0.34 | | 0.40 | | | 1.09 |

*peaks only seen for one on the two replicates - indicates likely inadvertent contamination for that replicate

TABLE 37

Related substances stability data for PEG 6000

| | | | Area of Peak (as % of Total peak area) RRT ± 0.01 | | | | | | | | |
|---|---|---|---|---|---|---|---|---|---|---|---|
| Excipient | Storage | Time point | RRT 0.57 | RRT 0.63 | RRT 0.81 | RRT 0.89 | RRT 0.96 | RRT 1.01 | RRT 1.21 | RRT 1.65 | Total |
| PEG 6000 | −20° C. | 14 days | ND | | ND | <0.10 | 0.20 | 1.04 | 0.35 | ND | 1.6 |
| PEG 6000 | 25° C. | 14 days | ND | | ND | <0.10 | 0.19 | 0.79 | 0.34 | ND | 1.31 |
| PEG 6000 | 40° C. | 14 days | 0.13 | | 0.32 | 0.16 | 0.20 | 0.72 | 0.37 | 0.13 | 2.03 |
| PEG 6000 | 25° C. | 28 days | 0.12 | ND | | | 0.16 | 0.19 | 0.36 | ND | 0.83 |
| PEG 6000 | 40° C. | 28 days | ND | 0.11 | | | 0.17 | 0.20 | 0.38 | 0.19 | 1.05 |

TABLE 38

Related substances stability data for Cremophor RH40

| | | | Area of Peak (as % of Total peak area) RRT ± 0.01 | | | | | | | | | |
|---|---|---|---|---|---|---|---|---|---|---|---|---|
| Excipient | Storage | Time point | RRT 0.53 | RRT 0.88 | RRT 0.96 | RRT 0.97 | RRT 1.01 | RRT 1.03 | RRT 1.17 | RRT 1.33 | RRT 1.36 | Total |
| Cremophor RH40 | −20° C. | 14 days | ND | ND | 0.13 | <0.10 | | | | | | 0.13 |
| Cremophor RH40 | 25° C. | 14 days | ND | 0.16 | 0.14 | <0.10 | | | | | | 0.31 |
| Cremophor RH40 | 40° C. | 14 days | 0.11 | 0.13 | 0.22 | 0.13 | | | | | | 0.59 |
| Cremophor RH40 | 25° C. | 28 days | | | 0.23 | 0.12 | 0.33 | 0.18 | ND | ND | ND | 0.85 |
| Cremophor RH40 | 40° C. | 28 days | | | 0.23 | 0.17 | 0.47 | ND | 0.25 | 0.56 | 0.17 | 1.85 |

Note:
peak shifting from placebo injection to the active sample occurred, as a result the related substance data for T = 28 days (mainly 40° C.) is not as accurate as for the other samples.

TABLE 39

Related substances stability data for Kolliphor HS15

| | | | Area of Peak (as % of Total peak area) RRT ± 0.01 | | | | | | | | | |
|---|---|---|---|---|---|---|---|---|---|---|---|---|
| Excipient | Storage | Time point | RRT 0.96 | RRT 0.97 | RRT 1.01 | RRT 1.04 | RRT 1.22 | RRT 1.44 | RRT 1.63 | RRT 1.64 | RRT 1.97 | Total |
| Kolliphor HS15 | −20° C. | 14 days | 0.21 | | 0.67 | 0.46 | 0.10 | <0.10 | 0.33 | 0.28 | | 2.05 |
| Kolliphor HS15 | 25° C. | 14 days | 0.21 | | 0.68 | 0.53 | <0.10 | 0.11 | 0.39 | 0.26 | | 2.17 |
| Kolliphor HS15 | 40° C. | 14 days | 0.21 | | 0.56 | 0.45 | <0.10 | 0.10 | 0.38 | 0.28 | | 1.97 |
| Kolliphor HS15 | 25° C. | 28 days | 0.22 | 0.10 | 0.38 | | | | | | ND | 0.70 |
| Kolliphor HS15 | 40° C. | 28 days | 0.22 | <0.10 | 0.37 | | | | | | 0.25 | 0.84 |

Difference in RRT 1.01 and RRT 1.04 peaks between T = initial and T = 14 days compared to T = 28 days is likely due to variation of API peak integration between the two sequences.

TABLE 40

Related substances stability data for Gelucire 50/13

| | | | Area of Peak (as % of Total peak area) RRT ± 0.01 | | | | | | | | | |
|---|---|---|---|---|---|---|---|---|---|---|---|---|
| Excipient | Storage | Time point | RRT 0.55 | RRT 0.87 | RRT 0.96 | RRT 0.97 | RRT 1.01 | RRT 1.10 | RRT 1.32 | RRT 1.54 | RRT 1.71 | Total |
| Gelucire 50/13 | −20° C. | 14 days | <0.10 | 0.14 | 0.23 | 0.11 | 0.29 | 0.12 | 0.46 | | 0.13 | 1.47 |
| Gelucire 50/13 | 25° C. | 14 days | <0.10 | 0.14 | 0.20 | 0.10 | 0.29 | 0.11 | 0.47 | | ND | 1.31 |
| Gelucire 50/13 | 40° C. | 14 days | 0.10 | 0.14 | 0.19 | 0.10 | 0.31 | 0.11 | 0.38 | | ND | 1.31 |
| Gelucire 50/13 | 25° C. | 28 days | | | 0.22 | | 0.19 | | | 0.42 | | 0.83 |
| Gelucire 50/13 | 40° C. | 28 days | | | 0.19 | | 0.20 | | | ND | | 0.40 |

TABLE 41

| Related substances stability data for Polysorbate 20 | | | | | | | | | | | |
|---|---|---|---|---|---|---|---|---|---|---|---|
| | | | Area of Peak (as % of Total peak area) RRT ± 0.01 | | | | | | | | |
| Excipient | Storage | Time point | RRT 0.15 | RRT 0.84 | RRT 0.85 | RRT 0.87 | RRT 0.89 | RRT 0.90 | RRT 0.96 | RRT 1.01 | Total |
| Polysorbate 20 | −20° C. | 14 days | 2.90 | 0.11 | 0.29 | 1.18 | ND | 1.60 | 0.16 | 0.11 | 6.36 |
| Polysorbate 20 | 25° C. | 14 days | 1.96 | <0.10 | 0.21 | 0.74 | ND | 1.31 | 0.18 | <0.10 | 4.42 |
| Polysorbate 20 | 40° C. | 14 days | ND | ND | ND | ND | 0.46 | 0.10 | 0.11 | <0.10 | 0.67 |
| Polysorbate 20 | 25° C. | 28 days | | | | | | | | 0.20 | 0.20 |
| Polysorbate 20 | 40° C. | 28 days | | | | | | | | ND | 0.00 |

TABLE 42

| Related substances stability data for Gelucire 48/16 | | | | | | | | | |
|---|---|---|---|---|---|---|---|---|---|
| | | | Area of Peak (as % of Total peak area) RRT ± 0.01 | | | | | | |
| Excipient | Storage | Time point | RRT 0.40 | RRT 0.96 | RRT 0.97 | RRT 1.02 | RRT 1.11 | RRT 1.53 | Total |
| Gelucire 48/16 | −20° C. | 14 days | | 0.20 | <0.10 | | ND | ND | 0.20 |
| Gelucire 48/16 | 25° C. | 14 days | | 0.20 | 0.10 | | ND | ND | 0.30 |
| Gelucire 48/16 | 40° C. | 14 days | | 0.21 | <0.10 | | 0.15 | 0.85 | 1.21 |
| Gelucire 48/16 | 25° C. | 28 days | 0.1 | 0.22 | 0.11 | 0.36 | | | 0.79 |
| Gelucire 48/16 | 40° C. | 28 days | ND | 0.21 | 0.11 | 0.37 | | | 0.69 |

TABLE 43

| Related substances stability data for Polysorbate 80 | | | | | | | | | | | | | | | | | |
|---|---|---|---|---|---|---|---|---|---|---|---|---|---|---|---|---|---|
| | | | Area of Peak (as % of Total peak area) RRT ± 0.01 | | | | | | | | | | | | | | |
| Excipient | Storage | Time point | RRT 0.41 | RRT 0.43 | RRT 0.53 | RRT 0.55 | RRT 0.56 | RRT 0.58 | RRT 0.62 | RRT 0.66 | RRT 0.71 | RRT 0.72 | RRT 0.74 | RRT 0.81 | RRT 0.82 | RRT 0.83 | RRT 0.84 |
| Polysorbate 80 | −20° C. | 14 days | | | | | | | | | | | | | | | |
| Polysorbate 80 | 25° C. | 14 days | | | | | | | | | | | | | | | |
| Polysorbate 80 | 40° C. | 14 days | 0.67 | 0.52 | 0.49 | 0.38 | 0.37 | 0.49 | | | 0.56 | 0.32 | 0.26 | 0.14 | 0.29 | 0.20 | 0.15 |
| Polysorbate 80 | 25° C. | 28 days | | | | | | | ND | ND | | | | | | | |
| Polysorbate 80 | 40° C. | 28 days | | | | | | | 0.55 | 0.22 | | | | | | | |

The related substances data for both replicates at 40° C. at 14 days were consistent. However, significant placebo degradation is seen at T=28 days 40° C. compared to T=28 days 25° C. and T=initial. The additional peaks at 40° C. 14 days are likely from placebo degradation, but the peaks could not be discounted at the time of the analysis as there was not a representative degraded placebo for T=14 days at 40° C.

TABLE 44

| Related substances stability data for Polysorbate 80 (continued) | | | | | | | | | | | | | | | | | |
|---|---|---|---|---|---|---|---|---|---|---|---|---|---|---|---|---|---|
| | | | Area of Peak (as % of Total peak area) RRT ± 0.01 | | | | | | | | | | | | | | |
| Excipient | Storage | Time point | RRT 0.85 | RRT 0.86 | RRT 0.90 | RRT 1.06 | RRT 1.09 | RRT 1.11 | RRT 1.13 | RRT 1.16 | RRT 1.18 | RRT 1.22 | RRT 1.32 | RRT 1.35 | RRT 1.76 | RRT 1.78 | Total 0.00 |
| Polysorbate 80 | −20° C. | 14 days | | | | | | | | | | | | | | | 0.00 |
| Polysorbate 80 | 25° C. | 14 days | | | | | | | | | | | | | | | 0.00 |
| Polysorbate 80 | 40° C. | 14 days | 0.15 | 0.24 | 3.12 | 2.11 | 1.69 | 1.77 | 1.00 | 0.98 | 0.55 | 0.34 | 2.14 | 1.87 | 3.23 | 16.06 | 40.06 |
| Polysorbate 80 | 25° C. | 28 days | | | | | | | | | | | | | | | 0.00 |
| Polysorbate 80 | 40° C. | 28 days | | | | | | | | | | | | | | | 0.00 |

The related substances data for both replicates at 40° C. at 14 days were consistent. However, significant placebo degradation is seen at T=28 days 40° C. compared to T=28 days 25° C. and T=initial. The additional peaks at 40° C. 14 days are likely from placebo degradation, but the peaks could not be discounted at the time of the analysis as there was not a representative degraded placebo for T=14 days at 40° C.

TABLE 45

Related substances stability data for Capmul 808G

| | | | Area of Peak (as % of Total peak area) RRT ± 0.01 | | | | | | | | | |
|---|---|---|---|---|---|---|---|---|---|---|---|---|
| Excipient | Storage | Time point | RRT 0.30 | RRT 0.31 | RRT 0.73 | RRT 0.79 | RRT 0.82 | RRT 0.86 | RRT 1.02 | RRT 1.10 | RRT 1.51 | Total |
| Capmul 808G | −20° C. | 14 days | ND | ND | 0.82 | 0.14 | 0.23 | 0.33 | 1.08 | | <0.10 | 2.59 |
| Capmul 808G | 25° C. | 14 days | ND | ND | 0.84 | 0.15 | 0.35 | 0.38 | 1.04 | | <0.10 | 2.76 |
| Capmul 808G | 40° C. | 14 days | 0.85 | 0.28 | 0.81 | 0.13 | 0.51 | 0.36 | 0.83 | | 0.11 | 3.86 |
| Capmul 808G | 25° C. | 28 days | | | 0.33 | | | 0.34 | | 0.10 | | 0.77 |
| Capmul 808G | 40° C. | 28 days | | | 0.33 | | | 0.37 | | <0.10 | | 0.69 |

TABLE 46

Related substances stability data for Octanoic Acid

| | | | Area of Peak (as % of Total peak area) RRT ± 0.01 | | | |
|---|---|---|---|---|---|---|
| Excipient | Storage | Time point | RRT 0.34 | RRT 0.55 | RRT 0.96 | Total |
| Octanoic Acid | −20° C. | 14 days | | 0.26 | <0.10 | 0.26 |
| Octanoic Acid | 25° C. | 14 days | | 0.27 | <0.10 | 0.27 |
| Octanoic Acid | 40° C. | 14 days | | 0.28 | <0.10 | 0.28 |
| Octanoic Acid | 25° C. | 28 days | ND | | 0.19 | 0.19 |
| Octanoic Acid | 40° C. | 28 days | 0.19 | | 0.21 | 0.40 |

TABLE 47

Related substances stability data for propylene glycol monocaprylate

| | | | Area of Peak (as % of Total peak area) RRT ± 0.01 | | |
|---|---|---|---|---|---|
| Excipient | Storage | Time point | RRT 0.92 | RRT 0.93 | Total |
| Propylene Glycol monocaprylate | −20° C. | 14 days | | 69.3 | 69.3 |
| Propylene Glycol monocaprylate | 25° C. | 14 days | | 72.2 | 72.2 |
| Propylene Glycol monocaprylate | 40° C. | 14 days | | 70.5 | 70.5 |
| Propylene Glycol monocaprylate | 25° C. | 28 days | 0.34 | 70.9 | 71.3 |
| Propylene Glycol monocaprylate | 40° C. | 28 days | | 67.7 | 67.7 |

TABLE 48

Related substances stability data for propylene glycol dilaurate

| | | | Area of Peak (as % of Total peak area) RRT ± 0.01 | | | |
|---|---|---|---|---|---|---|
| Excipient | Storage | Time point | RRT 0.96 | RRT 1.02 | RRT 1.22 | Total |
| Propylene glycol dilaurate | −20° C. | 14 days | 0.12 | | 0.16 | 0.28 |
| Propylene glycol dilaurate | 25° C. | 14 days | 0.13 | | 0.14 | 0.27 |
| Propylene glycol dilaurate | 40° C. | 14 days | 0.14 | | 0.10 | 0.24 |
| Propylene glycol dilaurate | 25° C. | 28 days | 0.23 | 0.50 | | 0.74 |
| Propylene glycol dilaurate | 40° C. | 28 days | 0.34 | 0.48 | | 0.83 |

TABLE 49

Related substances stability data for diethylene glycol monoethyl ether

| Excipient | Storage | Time point | Area of Peak (as % of Total peak area) RRT ± 0.01 | | | | | | | | | | | | | | |
|---|---|---|---|---|---|---|---|---|---|---|---|---|---|---|---|---|---|
| | | | RRT 0.37 | RRT 0.41 | RRT 0.45 | RRT 0.47 | RRT 0.48 | RRT 0.53 | RRT 0.54 | RRT 0.55 | RRT 0.62 | RRT 0.63 | RRT 0.73 | RRT 0.75 | RRT 0.79 | RRT 0.85 | RRT 0.89 |
| Diethylene glycol monoethyl ether | −20° C. | 14 days | 1.43 | 2.31 | 0.36 | 0.19 | 0.10 | 0.30 | 0.11 | 0.11 | | 0.83 | 0.53 | 1.21 | ND | 0.12 | 0.24 |
| Diethylene glycol monoethyl ether | 25° C. | 14 days | 1.23 | 2.02 | ND | ND | ND | 0.31 | 0.12 | 0.13 | | ND | 0.17 | 0.91 | ND | <0.10 | <0.10 |
| Diethylene glycol monoethyl ether | 40° C. | 14 days | 0.19 | 0.35 | ND | ND | ND | 0.33 | 0.31 | 0.13 | | ND | 0.45 | 0.57 | 0.10 | <0.10 | <0.10 |
| Diethylene glycol monoethyl ether | 25° C. | 28 days | 1.03 | 1.78 | | | | | | | ND | ND | | | ND | | |
| Diethylene glycol monoethyl ether | 40° C. | 28 days | ND | ND | | | | | | | 0.21 | 0.53 | | | 0.43 | | |

TABLE 50

Related substances stability data for diethylene glycol monoethyl ether (continued)

| Excipient | Storage | Time point | Area of Peak (as % of Total peak area) RRT ± 0.01 | | | | | | | | | | |
|---|---|---|---|---|---|---|---|---|---|---|---|---|---|
| | | | RRT 0.91 | RRT 0.94 | RRT 0.96 | RRT 0.97 | RRT 1.02 | RRT 1.06 | RRT 1.37 | RRT 1.50 | RRT 1.53 | RRT 1.94 | Total |
| Diethylene glycol monoethyl ether | −20° C. | 14 days | 0.52 | 0.11 | 0.13 | | | 2.94 | | 0.13 | 0.12 | 0.18 | 11.95 |
| Diethylene glycol monoethyl ether | 25° C. | 14 days | 0.35 | <0.10 | 0.18 | | | 3.12 | ND | <0.10 | <0.10 | ND | 8.54 |
| Diethylene glycol monoethyl ether | 40° C. | 14 days | 0.34 | <0.10 | 0.19 | | | 2.86 | 0.14 | <0.10 | <0.10 | ND | 5.98 |
| Diethylene glycol monoethyl ether | 25° C. | 28 days | | | 0.19 | 0.11 | 0.33 | | ND | | <0.10 | | 3.44 |
| Diethylene glycol monoethyl ether | 40° C. | 28 days | | | 0.16 | <0.10 | 0.30 | | 1.03 | | 0.10 | | 2.76 |

TABLE 51

Related substances stability data for glyceryl monooleate

| Excipient | Storage | Time point | Area of Peak (as % of Total peak area) RRT ± 0.01 | | | |
|---|---|---|---|---|---|---|
| | | | RRT 0.96 | RRT 1.17 | RRT 1.43 | Total |
| Glyceryl monooleate | −20° C. | 14 days | | | 3.77* | 3.77 |
| Glyceryl monooleate | 25° C. | 14 days | | | 4.39* | 4.39 |
| Glyceryl monooleate | 40° C. | 14 days | | | 6.43* | 6.43 |

TABLE 51-continued

Related substances stability data for glyceryl monooleate

| Excipient | Storage | Time point | Area of Peak (as % of Total peak area) RRT ± 0.01 | | | |
|---|---|---|---|---|---|---|
| | | | RRT 0.96 | RRT 1.17 | RRT 1.43 | Total |
| Glyceryl monooleate | 25° C. | 28 days | ND | 0.95 | | 0.95 |
| Glyceryl monooleate | 40° C. | 28 days | 0.48 | 1.31 | | 1.79 |

*likely to be an excipient related peak

TABLE 52

Related substances stability data for PEG400:PEG1500 (9:1)

| Excipient | Storage | Time point | Area of Peak (as % of Total peak area) RRT ± 0.01 | | | | | | | | | | | | | |
|---|---|---|---|---|---|---|---|---|---|---|---|---|---|---|---|---|
| | | | RRT 0.62 | RRT 0.63 | RRT 0.77 | RRT 0.80 | RRT 0.87 | RRT 0.89 | RRT 0.96 | RRT 0.97 | RRT 1.01 | RRT 1.03 | RRT 1.04 | RRT 1.06 | RRT 1.34 | Total |
| PEG 400:PEG 1500 (9:1) | −20° C. | 14 days | ND | ND | <0.10 | | 0.10 | | 0.20 | 0.10 | 0.28 | | | | | 0.67 |
| PEG 400:PEG 1500 (9:1) | 25° C. | 14 days | ND | ND | <0.10 | | 0.13 | | 0.20 | <0.10 | 0.27 | | | | | 0.60 |

TABLE 52-continued

Related substances stability data for PEG400:PEG1500 (9:1)

| Excipient | Storage | Time point | Area of Peak (as % of Total peak area) RRT ± 0.01 RRT 0.62 | RRT 0.63 | RRT 0.77 | RRT 0.80 | RRT 0.87 | RRT 0.89 | RRT 0.96 | RRT 0.97 | RRT 1.01 | RRT 1.03 | RRT 1.04 | RRT 1.06 | RRT 1.34 | Total |
|---|---|---|---|---|---|---|---|---|---|---|---|---|---|---|---|---|
| PEG 400:PEG 1500 (9:1) | 40° C. | 14 days | 0.16 | 0.30 | 0.23 | | 0.10 | | 0.20 | 0.10 | 0.27 | | | | | 1.36 |
| PEG 400:PEG 1500 (9:1) | 25° C. | 28 days | ND | ND | <0.10 | ND | | ND | 0.22 | 0.10 | 0.36 | 0.10 | ND | ND | ND | 0.77 |
| PEG 400:PEG 1500 (9:1) | 40° C. | 28 days | 0.92 | 2.06 | 3.83 | 0.19 | | 0.21 | 0.16 | 0.13 | 0.20 | <0.10 | 0.14 | 0.60 | 0.21 | 8.64 |

TABLE 53

Related substances stability data for PEG400:PEG1500 (1:1)

| Excipient | Storage | Time point | Area of Peak (as % of Total peak area) RRT ± 0.01 RRT 0.53 | RRT 0.54 | RRT 0.61 | RRT 0.63 | RRT 0.77 | RRT 0.87 | RRT 0.89 | RRT 0.96 | RRT 0.97 | RRT 1.01 | RRT 1.03 | RRT 1.06 | RRT 1.34 | Total |
|---|---|---|---|---|---|---|---|---|---|---|---|---|---|---|---|---|
| PEG 400:PEG 1500 (1:1) | −20° C. | 14 days | | | | ND | <0.10 | 0.13 | | 0.21 | 0.1 | 0.35 | | | | 0.79 |
| PEG 400:PEG 1500 (1:1) | 25° C. | 14 days | | | | ND | <0.10 | 0.11 | | 0.20 | <0.10 | 0.33 | | | | 0.64 |
| PEG 400:PEG 1500 (1:1) | 40° C. | 14 days | | | | 0.24 | 0.17 | <0.10 | | 0.19 | <0.10 | 0.33 | | | | 0.94 |
| PEG 400:PEG 1500 (1:1) | 25° C. | 28 days | 0.18 | 0.46 | ND | ND | <0.10 | | ND | 0.23 | 0.11 | 0.34 | 0.10 | 0.22 | ND | 1.63 |
| PEG 400:PEG 1500 (1:1) | 40° C. | 28 days | ND | ND | 0.32 | 1.19 | 1.54 | | 0.18 | 0.20 | 0.12 | 0.22 | <0.10 | 0.57 | 0.13 | 4.45 |

TABLE 54

Related substances stability data for PEG400:PEG1500 (1:9)

| Excipient | Storage | Time point | Area of Peak (as % of Total peak area) RRT ± 0.01 RRT 0.15 | RRT 0.41 | RRT 0.48 | RRT 0.55 | RRT 0.60 | RRT 0.61 | RRT 0.66 | RRT 0.69 | RRT 0.77 | RRT 0.86 | RRT 0.96 | RRT 0.97 | RRT 1.01 |
|---|---|---|---|---|---|---|---|---|---|---|---|---|---|---|---|
| PEG 400:PEG 1500 (1:9) | −20° C. | 14 days | ND | ND | ND | 0.10 | | | ND | ND | ND | ND | 0.20 | <0.10 | 0.36 |
| PEG 400:PEG 1500 (1:9) | 25° C. | 14 days | 0.57* | 0.20* | 0.13* | 0.86 | | | 0.13* | 0.30* | ND | 0.14* | 0.18 | <0.10 | 0.31 |
| PEG 400:PEG 1500 (1:9) | 40° C. | 14 days | ND | ND | ND | 0.17 | | | ND | ND | 0.12 | ND | 0.21 | 0.10 | 0.35 |
| PEG 400:PEG 1500 (1:9) | 25° C. | 28 days | | | | | ND | ND | | | <0.10 | | 0.22 | 0.10 | 0.36 |
| PEG 400:PEG 1500 (1:9) | 40° C. | 28 days | | | | | 0.23 | 0.29 | | | 0.46 | | 0.21 | 0.10 | 0.32 |

TABLE 54-continued

Related substances stability data for PEG400:PEG1500 (1:9)

| Excipient | Storage | Time point | Area of Peak (as % of Total peak area) RRT ± 0.01 RRT 1.06 | RRT 1.34 | RRT 1.58 | Total |
|---|---|---|---|---|---|---|
| PEG 400:PEG 1500 (1:9) | −20° C. | 14 days | | | ND | 0.66 |
| PEG 400:PEG 1500 (1:9) | 25° C. | 14 days | | | 0.12* | 2.94 |
| PEG 400:PEG 1500 (1:9) | 40° C. | 14 days | | | ND | 0.95 |
| PEG 400:PEG 1500 (1:9) | 25° C. | 28 days | <0.10 | ND | | 0.68 |
| PEG 400:PEG 1500 (1:9) | 40° C. | 28 days | 0.29 | 0.13 | | 2.03 |

*peaks only seen for one on the two replicates - indicates likely inadvertent contamination for that replicate

TABLE 55

Related substances stability data for PEG1500:PEG6000 (9:1)

| | | | Area of Peak (as % of Total peak area) RRT ± 0.01 | | | | | | | |
|---|---|---|---|---|---|---|---|---|---|---|
| Excipient | Storage | Time point | RRT 0.55 | RRT 0.61 | RRT 0.62 | RRT 0.77 | RRT 0.96 | RRT 0.97 | RRT 1.01 | Total |
| PEG 1500:PEG 6000 (9:1) | −20° C. | 14 days | 0.12 | | | | 0.21 | 0.10 | 0.36 | 0.80 |
| PEG 1500:PEG 6000 (9:1) | 25° C. | 14 days | 0.14 | | | | 0.20 | <0.10 | 0.37 | 0.71 |
| PEG 1500:PEG 6000 (9:1) | 40° C. | 14 days | 0.18 | | | | 0.20 | <0.10 | 0.36 | 0.74 |
| PEG 1500:PEG 6000 (9:1) | 25° C. | 28 days | | ND | ND | ND | 0.20 | | 0.24 | 0.44 |
| PEG 1500:PEG 6000 (9:1) | 40° C. | 28 days | | 0.12 | 0.14 | 0.15 | 0.19 | | 0.23 | 0.84 |

TABLE 56

Related substances stability data for PEG1500:PEG6000 (1:9)

| | | Time | Area of Peak (as % of Total peak area) RRT ± 0.01 | | | | | |
|---|---|---|---|---|---|---|---|---|
| Excipient | Storage | point | RRT 0.83 | RRT 0.85 | RRT 0.96 | RRT 1.02 | RRT 1.66 | Total |
| PEG1500:PEG6000 (1:9) | −20° C. | 14 days | | | 0.18 | 0.32 | | 0.51 |
| PEG1500:PEG6000 (1:9) | 25° C. | 14 days | | | 0.18 | 0.32 | | 0.49 |
| PEG1500:PEG6000 (1:9) | 40° C. | 14 days | | | 0.17 | 0.31 | | 0.48 |
| PEG1500:PEG6000 (1:9) | 25° C. | 28 days | 0.14 | 0.12 | 0.17 | 0.20 | 0.20 | 0.83 |
| PEG1500:PEG6000 (1:9) | 40° C. | 28 days | 0.17 | 0.15 | 0.14 | 0.20 | ND | 0.66 |

TABLE 57

Related substances stability data for PEG1500:TPGS (1:1)

| | | | Area of Peak (as % of Total peak area) RRT ± 0.01 | | | | | | | | |
|---|---|---|---|---|---|---|---|---|---|---|---|
| Excipient | Storage | Time point | RRT 0.56 | RRT 0.85 | RRT 0.86 | RRT 0.96 | RRT 0.97 | RRT 1.01 | RRT 1.62 | RRT 1.64 | Total |
| PEG1500:TPGS (1:1) | −20° C. | 14 days | 0.30 | | | 0.20 | | 0.29 | 0.79 | 1.84 | 3.40 |
| PEG1500:TPGS (1:1) | 25° C. | 14 days | 0.22 | | | 0.20 | | 0.31 | 0.91 | 1.77 | 3.40 |
| PEG1500:TPGS (1:1) | 40° C. | 14 days | 0.42 | | | 0.20 | | 0.29 | 1.51 | 1.76 | 4.18 |

TABLE 57-continued

| Related substances stability data for PEG1500:TPGS (1:1) | | | | | | | | | | | |
|---|---|---|---|---|---|---|---|---|---|---|---|
| | | | Area of Peak (as % of Total peak area) RRT ± 0.01 | | | | | | | | |
| Excipient | Storage | Time point | RRT 0.56 | RRT 0.85 | RRT 0.86 | RRT 0.96 | RRT 0.97 | RRT 1.01 | RRT 1.62 | RRT 1.64 | Total |
| PEG1500:TPGS (1:1) | 25° C. | 28 days | 0.14 | 0.17 | 0.10 | 0.19 | 0.10 | 0.22 | 1.82 | 1.83 | 4.57 |
| PEG1500:TPGS (1:1) | 40° C. | 28 days | 0.30 | 0.20 | 0.12 | 0.20 | 0.11 | 0.21 | 2.30 | 1.69 | 5.14 |

TABLE 58

| Related substances stability data for PEG1500:TPGS (9:1) | | | | | | | | | | | |
|---|---|---|---|---|---|---|---|---|---|---|---|
| | | | Area of Peak (as % of Total peak area) RRT ± 0.01 | | | | | | | | |
| Excipient | Storage | Time point | RRT 0.40 | RRT 0.54 | RRT 0.85 | RRT 0.86 | RRT 0.96 | RRT 1.01 | RRT 1.61 | RRT 1.63 | Total |
| PEG1500:TPGS (9:1) | −20° C. | 14 days | | ND | | | 0.18 | 0.34 | 0.11 | 0.40 | 1.03 |
| PEG1500:TPGS (9:1) | 25° C. | 14 days | | 3.31 | | | 0.19 | 0.33 | 0.13 | 0.39 | 4.34 |
| PEG1500:TPGS (9:1) | 40° C. | 14 days | | ND | | | 0.18 | 0.33 | 0.19 | 0.37 | 1.06 |
| PEG1500:TPGS (9:1) | 25° C. | 28 days | 0.38* | | 0.17 | 0.14 | 0.20 | 0.22 | 0.17 | 0.36 | 1.64 |
| PEG1500:TPGS (9:1) | 40° C. | 28 days | ND | | 0.15 | 0.12 | 0.23 | 0.20 | 0.28 | 0.32 | 1.30 |

*peak only seen for one on the two replicates - indicates likely inadvertent contamination for that replicate

TABLE 59

| Related substances stability data for PEG1500:TPGS (1:9) | | | | | | | | | | | | | | | |
|---|---|---|---|---|---|---|---|---|---|---|---|---|---|---|---|
| | | | Area of Peak (as % of Total peak area) RRT ± 0.01 | | | | | | | | | | | | |
| Excipient | Storage | Time point | RRT 0.56 | RRT 0.69 | RRT 0.71 | RRT 0.82 | RRT 0.85 | RRT 0.87 | RRT 0.96 | RRT 0.97 | RRT 1.01 | RRT 1.20 | RRT 1.63 | RRT 1.65 | Total |
| PEG1500:TPGS (1:9) | −20° C. | 14 days | 1.33 | 0.23 | 0.15 | 0.33 | | | 0.19 | | 1.51 | 0.39 | 2.26 | | 6.39 |
| PEG1500:TPGS (1:9) | 25° C. | 14 days | 1.04 | 0.20 | 0.17 | 0.31 | | | 0.19 | | 0.39 | 0.45 | 2.97 | | 5.72 |
| PEG1500:TPGS (1:9) | 40° C. | 14 days | 1.32 | 0.23 | 0.13 | 0.29 | | | 0.20 | | 1.96 | 0.56 | 3.36 | | 8.05 |
| PEG1500:TPGS (1:9) | 25° C. | 28 days | 2.62 | 0.20 | | 0.23 | 0.26 | 0.17 | 0.17 | 0.12 | 0.18 | | 1.47 | 7.50 | 12.94 |
| PEG1500:TPGS (1:9) | 40° C. | 28 days | 1.31 | 0.23 | | 0.28 | 0.30 | 0.18 | 0.17 | 0.12 | 0.28 | | 3.37 | 6.81 | 13.05 |

1st replicate of 25° C. 28 days displayed more peaks than 2nd replicate but no more than replicates for 40° C. 28 days

Example 7—Dissolution Testing of Capsules

A number of capsules were prepared using a selection of solvents and dissolution testing was performed.

Part 1:

Methodology:

Materials

The materials used during this study are summarised in Table 60.

TABLE 60

| Materials list | | |
|---|---|---|
| Material | Function | Manufacturer |
| Compound I | API | Onyx |
| PEG 1500 | Solvents | Merck |
| PEG 6000 | | Merck |
| Vitamin E TPGS 1000 | | Isochem |
| Size 2 Quali-G PEG capsules | Capsules | Qualicaps |

Preparation of Blends

The following blends were prepared:

Blend A: 0.4% w/w API in Vitamin E TPGS

Blend B: 0.4% w/w API in PEG1500

Blend C: 0.4% w/w API in PEG6000

Blend Ww: 0.4% w/w API in PEG1500:TPGS (1:1)

Blend Yy: 0.4% w/w API in PEG1500:TPGS (9:1)

Blend Zz: 0.4% w/w API in PEG1500:TPGS (1:9)

The composition and preparation process of the blends are summarised in Table 61.

TABLE 61

| Summary compositions of semisolid blends | | | |
|---|---|---|---|
| Material | Blend A | Blend B | Blend C |
| Blend Composition | | | |
| Compound I | 0.044 | 0.043 | 0.042 |
| Vitamin E TPGS | 9.97 | | |
| PEG1500 | | 9.95 | |
| PEG6000 | | | 9.95 |
| Total | 10.01 | 10.00 | 9.99 |
| Preparation Process | | | |
| Total mixing time (hr:min) | 02:40 | 01:20 | 01:20 |

TABLE 61-continued

| Summary compositions of semisolid blends | | | |
|---|---|---|---|
| Material | Blend A | Blend B | Blend C |
| Mixing temperature (° C.) | 66.1 | 62.4 | 79.2 |

API solutions Yy, VVw and Zz were prepared as described in Example 5.

The API solutions used for encapsulation were manufactured as described below:

I. The semi solids were dispensed as follows:
  a. The required amount of PEG 1500 and PEG 6000 were dispensed and then molten at ~60° C. (PEG 1500) or at ~80° C. (PEG 6000)
  b. Vitamin E TPGS was molten at ~60° C., prior to dispensing the required amount
II. The API was added to the molten semi-solid and mixed until fully dissolved (at ~60° C. for PEG1500 and Vitamin E TPGS or 80° C. for PEG 6000)

Encapsulation

The API solutions prepared as described above or in Example 5 were left to melt for 30-60 minutes at 70-80° C. (for the semi-solids containing PEG 6000) or 60° C.-70° C. (for the remaining semi-solids). Liquid solutions were encapsulated at room temperature. The solution were encapsulated as follows:

1. A Size 2 Profiller was loaded with 10×size 2 Quali-G PEG capsules
2. A pipette (set to dispense 0.49-0.51 g of the blend) was used to systemically fill the capsule with one aliquot of the molten blend
3. The capsules were than locked Analytical Testing The dissolution was carried out in two different dissolution media (n=2 per media), 0.1 M HCl and pH 6.8 phosphate buffer. For both dissolution media the dissolution parameters were as follows:

Paddles (USP apparatus II)
500 mL media volume
50 rpm paddle speed and 200 rpm infinity spin.
Temperature of 37±0.5° C.
Band sinker—O-ring internal diameter between 6 mm to 7 mm Results Blend Preparation and Encapsulation The three API solutions (in Vitamin E TPGS, PEG 6000 and PEG 1500 and the mixtures of Vitamin E TPGS and PEG 1500) containing 0.4% w/w API were successfully produced. The API fully dissolved in the semi-solids in <2 hours for PEG 1500 and PEG 6000 and <3 hours in Vitamin E TPGS. All solutions appeared clear and free from particles.

All six solutions were successfully filled into Size 2 Quali-G-PEG capsules.

Dissolution:

The dissolution data is presented in FIGS. 16 and 17. FIG. 16 shows the dissolution profiles Raw Data (mean API dissolved from the 2 capsules, expressed as % of the nominal dose). This is replotted as Normalised Data in FIG. 17 where the Raw Data result at each sample point is expressed as a % of the mean result at the final (60 min) sample point.

With two exceptions, the dissolution Raw Data result at the final timepoint (60 min) was within ±10% of nominal API content of the capsules:

PEG 1500 capsules in both media were ~12-14% above the nominal API content. The capsule weights were very close of the target weight, so there is no clear explanation for the high % API released.

PEG 6000 in both media were ~30% below the nominal API content. Below are the investigated potential causes of the incomplete API release, followed by the investigation conclusion (in brackets) and the underlying rationale for the status:

Incorrect Drug loading of the blend (discounted)—When the composition was checked the quantities were found to be correct Capsule fill weight (discounted)—Capsule weights were checked and the fill weight deduced to be within ±10% of target API degradation (considered very unlikely)—PEG 1500 (chemically similar to PEG 6000) was known to be compatible with the API (see Example 4).

Incomplete disintegration of the PEG 6000 matrix (only likely explanation)—PEG 6000 is likely to be translucent in the dissolution media which could be difficult to notice any small undissolved residues in an amber dissolution vessel—its high molecular weight plausibly slows the disintegration of the matrix, i.e., reducing the ultimate drug release with the 60 minutes of the test.

All the capsules plateaued to within ±2% ultimate (60 min) value at or before 45 minutes with the exception of PEG1500:TPGS 1:9 in the pH6.8 medium where the API released increased by about 8% from 45 to 60 min, consistent with it being the slowest releasing capsule formulation.

(From the Normalised Data) Capsules made from all the API solutions showed slower dissolution rate in pH 6.8 phosphate buffer than in 0.1 M HCl.

(Excluding the anomaly of PEG 6000, discussed above) PEG1500:TPGS 1:9 capsules, showed the slowest Normalised drug release in pH 6.8 phosphate buffer, followed by TPGS capsules. This implies that (excluding the PEG 6000 anomaly) the API solvent with the slowest erosion in the medium is Vitamin E TPGS.

Part 2:

A number of different solvents were used to prepare capsules, either at 0.1% w/v or 0.4% w/v depending on the solubility of the API in the solvent. These capsules were analysed by dissolution (n=2) in 0.1 M HCl and pH 6.8 phosphate buffer media.

Methodology:

Encapsulate 13 sets of ~200 μg capsules prepared with either 0.1% or 0.4% API (dissolved), one set per solvent. The composition of the blends are summarised in Table 62.

TABLE 62

Summary of blend compositions
Blend Composition (% w/w)

| Blend detail | Blend Code | API | Diethylene glycol monoethyl ether | PEG 400 | PEG 4000 | Capmul PG-2L | PEG 1500 | Cremophor RH40 | Kolliphor HS15 | Gelucire 48/16 | PEG 6000 | TPGS |
|---|---|---|---|---|---|---|---|---|---|---|---|---|
| Diethylene glycol monoethyl ether | O | 0.4 | 99.6 | | | | | | | | | |
| PEG 400 | A | 0.1 | | 99.9 | | | | | | | | |
| PEG 4000 | Aa | 0.4 | | | 99.6 | | | | | | | |
| Cremophor RH40 | Dd | 0.4 | | | | | | 99.6 | | | | |
| Kolliphor HS15 | Ee | 0.4 | | | | | | | 99.9 | | | |
| Gelucire 48/16 | Gg | 0.1 | | | | | | | | 99.6 | | |
| PEG400:PEG1500 @ 9:1 | Mm | 0.4 | | 89.6 | | | 9.96 | | | | | |
| PEG400:PEG1500 @ 1:1 | Nn | 0.4 | | 49.8 | | | 49.8 | | | | | |
| PEG400:PEG1500 @ 1:9 | Qq | 0.4 | | 9.96 | | | 89.6 | | | | | |
| PEG1500:PEG6000 @ 9:1 | Rr | 0.4 | | | | | 89.6 | | | | 9.96 | |
| PEG1500:PEG6000 @ 1:1¥ | Tt | 0.4 | | | | | 49.8 | | | | 49.8 | |
| PEG1500:PEG6000 @ 1:9 | Uu | 0.4 | | | | | 9.96 | | | 89.6 | | |

Materials

Most of the materials needed to make the capsules are already listed in Example 5. The additional materials are listed in Table 63.

TABLE 63

List of Materials to make the capsules

| Compound I | API | Onyx |
|---|---|---|
| Size 2 Quali-G PEG capsules | Capsules | Qualicaps |

Preparation of Blends

API solutions were prepared as described in Example 5 the API solutions used for encapsulation were manufactured as described below:

I. In case of semi-solid excipients, the API was added to the molten semi-solid and mixed until fully dissolved.

II. In case of excipients that were liquid at room temperature, the API was added at room temperature and mixed until fully dissolved Encapsulation The API solutions prepared as described above and in Example 5. Whereas the liquid solutions were encapsulated at room temperature, the semi-solid API solutions were left to melt for 30-60 minutes at 70-80° C. (for the semi-solids containing PEG 6000) or 60° C.-70° C. (for the remaining semi-solids). All the solutions were encapsulated as follows:

a) A Size 2 Profiller was loaded with 10×size 2 Quali-G PEG capsules b) A pipette was used to systemically fill the capsule with one aliquot of the molten blend (set to dispense i) 0.245-0.255 g—For 0.4% drug loading blends ii) 0.98-1.02 g—For 0.1% drug loading blends c) The capsules were then locked Analytical Testing As per Part 1.

Results and Discussion

Blend Preparation and Encapsulation:

All solutions appeared clear and free from particles.

All solutions were successfully filled into Size 2 Quali-G-PEG capsules

Dissolution:

The dissolution profiles are separated into two groups of solvents to make them easy to compare:

Single excipients

Binary mixtures of excipients

The results are plotted as the mean results for the two capsules tested for each solvent studied—there was very good agreement between the results from the two individual capsules in all cases. Two representations of the same data are shown:

The Raw Data where the dissolution is calculated as the API dissolved as % of the nominal dose.

The Normalised Data where the result for each timepoint is expressed as % of the result at the end of the test (60 minutes).

The single excipient dissolution profiles are summarised in FIG. 18 (Raw Data) and FIG. 19 (Normalized), and the binary mixture dissolution profiles in FIG. 20 (Raw Data) and FIG. 21 (Normalized).

The dissolution plots are broadly similar with the following trends and differences:

All capsule batches plateau plateaued to within ±3% of their ultimate (60 min or 45 min) value at or before 20 minutes.

All capsules fully disintegrated within the first 15 minutes of the dissolution test.

Gelucire 48/16 gave the slowest dissolution—it was the only capsule batch to not reach its ultimate release value at 45 min in both medium. Slow disintegration of the capsule was not reported.

All the Capsules batches showed slower dissolution rate in pH 6.8 phosphate buffer than in 0.1 M HCl.

It might have been anticipated that the dissolution rate (and potentially also the disintegration rate) of the API from PEG-based capsules might increase with decreasing molecular weight of the PEG i.e., increase in the order PEG 6000<PEG 4000<PEG 1500<PEG 400. However, across the normalised dissolution data in this study, no clear trend was seen between the dissolution rate and either:

The molecular weight of the PEG in the single-solvent systems.

The proportions of the higher molecular weight PEG in the mixed solvent systems (PEG 400+PEG 1500 or PEG 1500+PEG 6000).

Overall Conclusions

All capsules prepared released at least 75% of API (normalised data) within 45 minutes of the dissolution test.

Example 7: Stability Study of PEG1500 in Gelatine Capsules Comprising 50 μg and 200 μg of N-(2-(tert-butyl)-1-((4,4-difluorocyclohexyl)methyl)-1H-benzimidazol-5-yl)ethanesulfonamide Capsules were prepared containing either 50 μg or 200 μg N-(2-(tert-butyl)-1-((4,4-difluorocyclohexyl)methyl)-1H-benzimidazol-5-yl)ethanesulfonamide in PEG1500. Gelatine capsule shells were used (Compositions of capsules and preparation as per Example 4). The capsules were put down on stability at 25° C./60% RH for 12 months and 45° C./75% RH for 6 months. Capsules were stored in 50 mL HDPE DUMA bottle with PP DUMA twist off cap.

The results show that the capsules comply with the specifications when stored for at least 12 months at 25° C./60% RH.

The results also show that the capsules comply with specification when stored for 3 months at 40° C./75% RH. Some results at 6 months for the 50 μg capsule are outside of specification (assay and dissolution) but this is considered to be due to residue been observed on capsules at this time point.

Results:

Appearance:

50 μg Dose Capsules;

| Storage Condition | Specification | Time Point (Months) | Results |
|---|---|---|---|
| N/A | Opaque green/grey | Initial | Complies with specification |
| 25° C./ | size 4 capsules with | 1 | Complies with specification |
| 60% RH | no physical defects | 3 | Complies with specification |
| | | 6 | Complies with specification |
| | | 9 | Complies with specification |
| | | 12 | Complies with specification |
| 40° C./ | | 1 | Complies with specification |
| 75% RH | | 3 | Complies with specification |
| | | 6 | Complies with specification |

200 μg Dose Capsules;

| Storage Condition | Specification | Time Point (Months) | Results |
|---|---|---|---|
| N/A | Opaque size 2 | Initial | Complies with specification |
| 25° C./ | white capsules | 1 | Complies with specification |
| 60% RH | with no physical | 3 | Complies with specification |
| | defects | 6 | Complies with specification |
| | | 9 | Complies with specification |
| | | 12 | 8/10 capsules complied with the specification. Physical defects for 2/10 capsules; 1 capsule has a small blue line on the surface and 1 capsule has a small red dot on the surface |
| 40° C./ | | 1 | Complies with specification |
| 75% RH | | 3 | Complies with specification |
| | | 6 | Complies with specification |

Assay:

50 μg Dose Capsules;

| Storage Condition | Specification | Time Point (Months) | Result (%) Weight corrected | Result (%) Non-weight corrected |
|---|---|---|---|---|
| N/A | 90.0-110.0% of label claim | Initial | Rep 1 = 96.2%<br>Rep 2 = 100.4%<br>Mean = 98.3% | Rep 1 = 97.5%<br>Rep 2 = 102.0%<br>Mean = 99.8% |
| 25° C./ 60% RH | | 1 | Rep 1 = 99.0%<br>Rep 2 = 100.0%<br>Mean = 99.5% | Rep 1 = 100.8%<br>Rep 2 = 100.7%<br>Mean = 100.8% |
| | | 3 | Rep 1 = 100.8%<br>Rep 2 = 99.2%<br>Mean = 100.0% | Rep 1 = 103.7%<br>Rep 2 = 99.5%<br>Mean = 101.6% |
| | | 6 | Rep 1 = 98.7%<br>Rep 2 = 97.7%<br>Mean = 98.2% | Rep 1 = 100.4%<br>Rep 2 = 100.4%<br>Mean = 100.4% |
| | | 9 | Rep 1 = 96.6%<br>Rep 2 = 97.3%<br>Mean = 96.9% | Rep 1 = 100.0%<br>Rep 2 = 100.0%<br>Mean = 100.0% |
| | | 12 | Rep 1 = 98.7%<br>Rep 2 = 98.7%<br>Mean = 98.7% | Rep 1 = 102.5%<br>Rep 2 = 101.4%<br>Mean = 102.0% |
| 40° C./ 75% RH | | 1 | Rep 1 = 98.0%<br>Rep 2 = 97.9%<br>Mean = 98.0% | Rep 1 = 100.5%<br>Rep 2 = 99.3%<br>Mean = 99.9% |
| | | 3 | Rep 1 = 95.2%<br>Rep 2 = 97.0%<br>Mean = 96.1% | Rep 1 = 98.7%<br>Rep 2 = 100.9%<br>Mean = 99.8% |
| | | 6[1] | Rep 1 = 81.8%<br>Rep 2 = 95.4%<br>Mean = 88.6% | Rep 1 = 85.7%<br>Rep 2 = 100.1%<br>Mean = 92.9% |

[1]Out of specification investigation performed. Result considered valid due to residue seen on capsules during inspection 200 μg Dose Capsules;

| Storage Condition | Specification | Time Point (Months) | Result (%) Weight corrected | Result (%) Non-weight corrected |
|---|---|---|---|---|
| N/A | 90.0-110.0% of label claim | Initial | Rep 1 = 101.1%<br>Rep 2 = 101.2%<br>Mean = 101.1% | Rep 1 = 102.6%<br>Rep 2 = 103.1%<br>Mean = 102.9% |
| 25° C./ 60% RH | | 1 | Rep 1 = 99.9%<br>Rep 2 = 99.3%<br>Mean = 99.6% | Rep 1 = 102.1%<br>Rep 2 = 101.1%<br>Mean = 101.6% |
| | | 3 | Rep 1 = 100.1%<br>Rep 2 = 99.4%<br>Mean = 99.8% | Rep 1 = 101.7%<br>Rep 2 = 101.8%<br>Mean = 101.8% |
| | | 6 | Rep 1 = 100.6%<br>Rep 2 = 102.3%<br>Mean = 101.5% | Rep 1 = 102.3%<br>Rep 2 = 103.2%<br>Mean = 102.7% |
| | | 9 | Rep 1 = 99.5%<br>Rep 2 = 100.0% | Rep 1 = 100.6%<br>Rep 2 = 103.0% |

-continued

| Storage Condition | Specification | Time Point (Months) | Result (%) Weight corrected | Result (%) Non-weight corrected |
|---|---|---|---|---|
| | | | Mean = 99.8% | Mean = 101.8% |
| | | 12 | Rep 1 = 99.7% | Rep 1 = 102.5% |
| | | | Rep 2 = 98.5% | Rep 2 = 100.9% |
| | | | Mean = 99.1% | Mean = 101.7% |
| 40° C./ 75% RH | | 1 | Rep 1 = 98.9% | Rep 1 = 101.1% |
| | | | Rep 2 = 100.5% | Rep 2 = 102.2% |
| | | | Mean = 99.7% | Mean = 101.6% |
| | | 3 | Rep 1 = 96.7% | Rep 1 = 99.7% |
| | | | Rep 2 = 97.5% | Rep 2 = 100.7% |
| | | | Mean = 97.1% | Mean = 100.2% |
| | | 6 | Rep 1 = 94.3% | Rep 1 = 99.4% |
| | | | Rep 2 = 95.6% | Rep 2 = 99.8% |
| | | | Mean = 94.9% | Mean = 99.6% |

Related Substances:
50 µg Dose Capsules;

| Storage Condition | Specification | Time Point (Months) | Result (%) Rep 1 | Result (%) Rep 2 |
|---|---|---|---|---|
| N/A | Individual impurities NMT 1.00%<br>Total Impurities NMT 3.00% | Initial | RRT0.94: 0.12<br>RRT0.96: 0.10<br>RRT1.05-1.06: 0.24<br>RRT1.40: 0.19<br>RRT1.65: 0.12<br>Total: 0.76 | RRT0.94: 0.13<br>RRT0.96: 0.14<br>RRT1.05-1.06: 0.27<br>RRT1.40: 0.21<br>Total: 0.75 |
| 25° C./60% RH | | 1 | RRT0.80: <0.10<br>RRT0.94: 0.14<br>RRT0.96: 0.15<br>RRT1.05: 0.26<br>RRT1.41: 0.22<br>Total: 0.77 | RRT0.94: 0.16<br>RRT0.96: 0.16<br>RRT1.05: 0.20<br>RRT1.41: 0.21<br>Total: 0.72 |
| | | 3 | RRT0.96: 0.10<br>RRT0.97: 0.12<br>RRT1.03: 0.11<br>RRT1.05: 0.11<br>RRT1.06: <0.10<br>RRT1.07: <0.10<br>RRT1.23: 0.27<br>Total: 0.72 | RRT0.96: 0.10<br>RRT0.97: 0.12<br>RRT1.03: <0.10<br>RRT1.04: 0.26<br>RRT1.05: <0.10<br>RRT1.07: <0.10<br>RRT1.23: 0.26<br>Total: 0.74 |
| | | 6 | RRT0.97: 0.14<br>RRT1.01: 0.41<br>RRT1.04: 0.16<br>Total: 0.71 | RRT0.71: <0.10<br>RRT0.97: 0.13<br>RRT1.01: 0.36<br>RRT1.04: 0.11<br>Total: 0.61 |
| | | 9 | RRT0.96: 0.13<br>RRT0.97: 0.16<br>RRT1.04: 0.22<br>Total: 0.51 | RRT0.96: 0.14<br>RRT0.97: 0.16<br>RRT1.04: 0.21<br>Total: 0.51 |
| | | 12 | RRT0.96: <0.10<br>RRT0.97: <0.10<br>RRT1.03: <0.10<br>RRT1.22: 0.18<br>Total: 0.18 | RRT0.96: 0.10<br>RRT0.97: <0.10<br>RRT1.03: 0.13<br>RRT1.23: 0.17<br>Total: 0.40 |
| 40° C./75% RH | | 1 | RRT0.69: <0.10<br>RRT0.94: 0.16<br>RRT0.96: 0.16<br>RRT0.97: <0.10<br>RRT1.06: 0.17<br>RRT1.14: 0.24<br>RRT1.36: <0.10<br>RRT1.41: 0.22<br>Total: 0.94 | RRT0.69: <0.10<br>RRT0.94: 0.18<br>RRT0.96: 0.18<br>RRT0.97: <0.10<br>RRT1.06: 0.18<br>RRT1.14: 0.23<br>RRT1.36: <0.10<br>RRT1.41: 0.32<br>Total: 1.00 |
| | | 3 | RRT0.77: 0.29<br>RRT0.96: 0.10<br>RRT0.97: 0.12<br>RRT1.03: 0.11<br>RRT1.04: 0.25<br>RRT1.05: <0.10<br>RRT1.09: <0.10<br>RRT1.11: 0.19<br>RRT1.12: <0.10<br>Total: 1.05 | RRT0.77: <0.1<br>RRT0.96: 0.10<br>RRT0.97: 0.10<br>RRT1.04: <0.10<br>RRT1.05: 0.21<br>RRT1.06: <0.10<br>RRT1.09: <0.10<br>RRT1.11: 0.16<br>RRT1.49: 0.47<br>Total: 1.04 |
| | | 6 | RRT0.76: 0.17<br>RRT0.97: 0.12<br>RRT1.01: 0.67<br>RRT1.08: <0.10 | RRT0.76: 0.21<br>RRT0.85: 0.49<br>RRT0.97: 0.10<br>RRT1.01: 0.56 |

-continued

| Storage Condition | Specification | Time Point (Months) | Result (%) Rep 1 | Result (%) Rep 2 |
|---|---|---|---|---|
| | | | RRT1.09: 0.14<br>RRT1.12: 0.16<br>RRT1.13: 0.10<br>Total: 1.34 | RRT1.09: 0.16<br>RRT1.12: 0.15<br>RRT1.13: 0.12<br>Total: 1.79 |

200 μg Dose Capsules;

| Storage Condition | Specification | Time Point (Months) | Result (%) Rep 1 | Result (%) Rep 2 |
|---|---|---|---|---|
| N/A | Individual impurities NMT 1.00%<br>Total Impurities NMT 3.00% | Initial | RRT0.66: 0.25<br>RRT0.94: 0.13<br>RRT0.96: 0.12<br>RRT1.05-1.06: 0.23<br>RRT1.26: <0.10<br>RRT1.30: 0.12<br>RRT1.40: 0.20<br>RRT1.92: <0.10<br>Total: 1.06 | RRT0.66: <0.10<br>RRT0.94: 0.13<br>RRT0.96: 0.13<br>RRT1.05-1.06: 0.37<br>RRT1.40: 0.22<br>Total: 0.86 |
| 25° C./60% RH | | 1 | RRT0.66: <0.10<br>RRT0.94: 0.13<br>RRT0.96: 0.14<br>RRT1.06: 0.28<br>RRT1.40: 0.21<br>Total: 0.77 | RRT0.66: <0.10<br>RRT0.94: 0.14<br>RRT0.96: 0.15<br>RRT1.05: 0.34<br>RRT1.41: 0.22<br>Total: 0.86 |
| | | 3 | RRT0.96: 0.10<br>RRT0.97: <0.10<br>RRT1.03: 0.13<br>RRT1.05: 0.11<br>RRT1.06: <0.10<br>Total: 0.34 | RRT0.96: 0.11<br>RRT0.97: 0.13<br>RRT1.04: <0.10<br>RRT1.05: 0.11<br>RRT1.06: <0.10<br>RRT1.09: <0.10<br>Total: 0.35 |
| | | 6 | RRT0.75: <0.10<br>RRT0.96: 0.10<br>RRT0.97: 0.12<br>RRT1.01: 0.37<br>RRT1.04: 0.14<br>Total: 0.73 | RRT0.96: 0.12<br>RRT0.97: 0.13<br>RRT1.01: 0.38<br>RRT1.04: 0.20<br>RRT1.70: <0.10<br>Total: 0.83 |
| | | 9 | RRT0.96: 0.14<br>RRT0.97: 0.15<br>RRT1.04: 0.21<br>Total: 0.49 | RRT0.96: 0.15<br>RRT0.97: 0.16<br>RRT1.04: 0.21<br>Total: 0.52 |
| | | 12 | RRT0.96: 0.15<br>RRT0.97: 0.10<br>RRT1.03: <0.10<br>RRT1.22: 0.12<br>Total: 0.37 | RRT0.96: <0.10<br>RRT0.97: 0.10<br>RRT1.03: <0.10<br>RRT1.22: 0.16<br>Total: 0.26 |
| 40° C./75% RH | | 1 | RRT0.66: <0.10<br>RRT0.93: 0.15<br>RRT0.96: 0.15<br>RRT1.05: 0.31<br>RRT1.40: 0.23<br>Total: 0.84 | RRT0.66: <0.10<br>RRT0.94: 0.14<br>RRT0.96: 0.15<br>RRT1.05: 0.25<br>RRT1.40: 0.23<br>Total: 0.77 |
| | | 3 | RRT0.96: 0.11<br>RRT0.97: 0.13<br>RRT1.04: <0.10<br>RRT1.05: 0.13<br>RRT1.06: <0.10<br>RRT1.09: 0.15<br>RRT1.11: 0.20<br>RRT1.24: 0.30<br>Total: 1.02 | RRT0.77: 0.42<br>RRT0.96: 0.11<br>RRT0.97: 0.13<br>RRT1.04: <0.10<br>RRT1.05: <0.10<br>RRT1.09: 0.16<br>RRT1.11: 0.18<br>RRT1.24: 0.28<br>Total: 1.29 |
| | | 6 | RRT0.75: <0.10<br>RRT0.77: 0.15<br>RRT0.96: 0.14<br>RRT0.97: 0.15<br>RRT1.04: 0.15<br>RRT1.09: 0.15<br>RRT1.12: 0.26<br>Total: 1.00 | RRT0.77: 0.19<br>RRT0.96: 0.13<br>RRT0.97: 0.13<br>RRT1.04: 0.18<br>RRT1.09: 0.14<br>RRT1.11: 0.25<br>Total: 1.02 |

Dissolution:

For dissolution plots for the 50 μg and 200 μg see FIGS. 22-29

Dissolution 0.1M HCl

50 μg Dose Capsules;

| Storage Condition | Specification | Time Point (Months) | Result |
|---|---|---|---|
| N/A | NLT Q + 5 (Q = 75%) release at 45 minutes in HCl medium | Initial | 45 minutes Mean = 102.4% Min = 99.7% Max = 105.2% |
| 25° C./60% RH | | 1 | 45 minutes Mean = 104.3% Min = 102.0% Max = 107.5% |
| | | 3 | 45 minutes Mean = 102.4% Min = 100.6% Max = 104.7% |
| | | 6 | 45 minutes Mean = 100.8% Min = 98.2% Max = 102.6% |
| | | 9 | 45 minutes Mean = 101.4% Min = 99.3% Max = 104.8% |
| | | 12 | 45 minutes Mean = 99.8% Min = 91.9% Max = 103.7% |
| 40° C./75% RH | | 1 | 45 minutes Mean = 101.4% Min = 100.7% Max = 101.7% |
| | | 3 | 45 minutes Mean = 100.2% Min = 96.8% Max = 103.6% |
| | | 6[1] | 45 minutes Mean = 96.2% Min = 77.6% Max = 105.4% |

[1]Low results are seen on the 40° C./75% RH samples for assay.

200 μg Dose Capsules;

| Storage Condition | Specification | Time Point (Months) | Result |
|---|---|---|---|
| N/A | NLT Q + 5 (Q = 75%) release at 45 minutes in HCl medium | Initial | 45 minutes Mean = 99.9% Min = 92.7% Max = 104.5% |
| 25° C./ 60% RH | | 1 | 45 minutes Mean = 103.2% Min = 102.4% Max = 103.8% |
| | | 3 | 45 minutes Mean = 100.8% Min = 97.2% Max = 102.2% |
| | | 6 | 45 minutes Mean = 101.2% Min = 99.9% Max = 102.6% |
| | | 9 | 45 minutes Mean = 102.9% Min = 101.4% Max = 104.9% |
| | | 12 | 45 minutes Mean = 103.0% Min = 101.2% Max = 104.6% |
| 40° C./ 75% RH | | 1 | 45 minutes Mean = 101.4% Min = 96.6% Max = 103.5% |
| | | 3 | 45 minutes Mean = 100.6% Min = 100.4% Max = 100.9% |
| | | 6 | 45 minutes Mean = 98.6% Max = 101.4% Min = 96.9% |

Dissolution Phosphate Buffer pH 6.8

50 μg Dose Capsules;

| Storage Condition | Specification | Time Point (Months) | Result |
|---|---|---|---|
| N/A | NLT Q + 5 (Q = 75%) release at 45 minutes in HCl medium | Initial | 45 minutes Mean = 102.5% Min = 100.8% Max = 105.4% |
| 25° C./60% RH | | 1 | 45 minutes Mean = 100.4% Min = 99.8% Max = 100.9% |
| | | 3 | 45 minutes Mean = 105.8% Min = 103.9% Max = 107.7% |
| | | 6 | 45 minutes Mean = 102.3% Min = 99.3% Max = 107.2% |
| | | 9 | 45 minutes Mean = 106.8% Min = 102.9% Max = 109.5% |
| | | 12 | 45 minutes Mean = 98.5% Min = 97.7% Max = 99.0% |
| 40° C./75% RH | | 1 | 45 minutes Mean = 96.4% Min = 95.5% Max = 97.3% |
| | | 3 | 45 minutes Mean = 98.7% Min = 98.2% Max = 99.4% |
| | | 6[1] | 45 minutes Mean = 69.7% Min = 56.5% Max = 77.3% |

[1]Low results are seen on the 40° C./75% RH samples for assay.

200 μg Dose Capsules;

| Storage Condition | Specification | Time Point (Months) | Result |
|---|---|---|---|
| N/A | NLT Q + 5 (Q = 75%) release at 45 minutes in HCl medium | Initial | 45 minutes Mean = 100.3% Min = 99.6% Max = 101.0% |
| 25° C./60% RH | | 1 | 45 minutes Mean = 102.4% Min = 99.3% Max = 104.0% |
| | | 3 | 45 minutes Mean = 101.4% Min = 96.7% Max = 104.0% |
| | | 6 | 45 minutes Mean = 97.8% Min = 96.0% Max = 99.2% |
| | | 9 | 45 minutes Mean = 102.9% Min = 101.9% Max = 104.9% |
| | | 12 | 45 minutes Mean = 89.9% Min = 88.9% Max = 91.1% |
| 40° C./75% RH | | 1 | 45 minutes Mean = 102.2% Min = 99.2% Max = 104.2% |
| | | 3 | 45 minutes Mean = 95.2% Min = 94.7% Max = 96.1% |
| | | 6 | 45 minutes Mean = 98.1% Min = 96.3% Max = 99.5% |

Uniformity of Dosage Units:

50 μg Dose Capsules;

| Storage Condition | Specification | Time Point (months) | Results |
|---|---|---|---|
| N/A | Complies with Ph. Eur 2.9.40 | Initial | AV = 13.0 |

200 μg Dose Capsules;

| Storage Condition | Specification | Time Point (months) | Results |
|---|---|---|---|
| N/A | Complies with Ph. Eur 2.9.40 | Initial | AV = 3.4 |

Identity:

50 μg and 200 μg Dose Capsules;

| Storage Condition | Specification | Time Point (months) | Results |
|---|---|---|---|
| N/A | RT of samples is ±0.5 mins of the RT of reference standard UV spectra matches that of the reference standard | Initial | RT of samples is ±0.5 mins of the RT of reference standard UV spectra matches that of the reference standard |

Micro:

50 μg Dose Capsules;

| Storage Condition | Specification | Method | Time point (Months) | Result |
|---|---|---|---|---|
| N/A | TAMC NMT $10^3$ CFU/g TYMC NMT $10^2$ CFU/g Absence of | Ph. Eur. 2.6.12 Ph. Eur. 2.6.13 RSSL method reference: P20-08080 | Initial | 135 cfu/g <10 cfu/g Absent in 1 g |
| 25° C./ 60% RH | *E. Coli* | Ph. Eur. 2.6.12 Ph. Eur. 2.6.13 RSSL method reference: P20-08080 | 12 months | 10 cfu/g <10 cfu/g Absent in 1 g |
| 40° C./ 75% RH | | Ph. Eur. 2.6.12 Ph. Eur. 2.6.13 RSSL method reference: P20-08080 | 6 months | <10 cfu/g <10 cfu/g Absent in 1 g |

200 μg Dose Capsules;

| Storage Condition | Specification | Method | Time point (Months) | Result |
|---|---|---|---|---|
| N/A | TAMC NMT $10^3$ CFU/g TYMC NMT $10^2$ CFU/g Absence of | Ph. Eur. 2.6.12 Ph. Eur. 2.6.13 RSSL method reference: P20-08080 | Initial | 45 cfu/g 18 cfu/g Absent in 1 g |
| 25° C./ 60% RH | *E. Coli* | Ph. Eur. 2.6.12 Ph. Eur. 2.6.13 RSSL method reference: P20-08080 | 12 months | 100 cfu/g <100 cfu/g Absent in 1 g |

-continued

| Storage Condition | Specification | Method | Time point (Months) | Result |
|---|---|---|---|---|
| 40° C./ 75% RH | | Ph. Eur. 2.6.12 Ph. Eur. 2.6.13 RSSL method reference: P20-08080 | 6 months | <10 cfu/g <10 cfu/g Absent in 1 g |

Example 8: Clinical Trial Protocol: A Phase ½ Trial of Formulations Comprising (N-(2-(tert-butyl)-1-((4,4-difluorocyclohexyl)methyl)-1H-benzimidazol-5-yl)ethanesulfonamide (50 μg and 200 μg) in Patients with Cancer Anorexia and Weight Loss Objectives:

Stage 1 (Phase 1)

Primary Objectives:

- Determine the safety profile of the product in patients with cancer anorexia at different doses.
- Determine dose-limiting toxicity, if any, within the range of doses used during the 4 weeks after the first dose of the product.
- Determine the most effective, safe dose (recommended Phase 2 dose, or RP2D) to be used in Stage 2.

Secondary Objectives:

- Assess the activity of the product in the patient population in terms of increase in lean body mass, weight gain, and improvement of anorexia.
- Assess quality of life (QoL) of patients.
- Determine the pharmacokinetic profile of the product in the patient population.
- Assess any change in Karnofsky Performance Status (KPS)

Exploratory Objectives:

- Assess the anti-inflammatory and hormonal effects of the product.
- Assess any effect on mood of patients while on the trial.
- Assess the abuse potential of the product.
- Assess the opioid-sparing effects of the product.

Stage 2 (Phase 2)

Primary Objectives:

- Determine point estimates of activity of the product in terms of weight gain, lean body mass, KPS, and improvement of anorexia at the RP2D at 12 weeks.

Secondary Objectives:

- Continue to assess the safety profile of the product in patients with cancer anorexia.
- Assess QoL of patients.

Exploratory Objectives:

- Assess the anti-inflammatory and hormonal effects of the product.
- Assess the mood of patients while on the trial.
- Assess the abuse potential of the product.
- Assess the physical activity of patients while on the trial based on activity reported by a wearable, physical activity monitor.
- Assess the opioid sparing effects of the product.

Study Design:

Phase 1 dose escalation in Stage 1 to determine the dose of a randomized, doubleblind, placebo-controlled, Phase 2 trial in Stage 2

Study Treatments:

In Stage 1, the product alone; in Stage 2, the product and placebo (4:1 randomization)

Dose-Limiting Toxicity:

Dose-limiting toxicities are those that occur during the first 4 weeks of dosing with the product and that cannot be explained by the underlying malignancy, its treatment, comorbidities, or their treatment and are:

- Grade 3 or 4 myelotoxicity that does not reduce to Grade 2 within two weeks of onset despite adequate supportive therapy.
- Grade 3 or 4 non-haematological toxicity lasting for more than 4 days despite adequate supportive therapy or preventing the next scheduled dose from being administered within 4 days of scheduled day; for Grade 3 fatigue to be considered a Dose Limiting Toxicity (DLT), it must be present for more than 7 days.
- Any Grade 2 single adverse event or constellation of adverse events that, in the opinion of the patient, is intolerable.

Stage 1 Dose-Escalation:

Dose levels are 150, 250, and 400 μg/dose/day. If in the 400 μg/dose/day dose group, no dose-limiting toxicities have been observed through 4 weeks and average weight gain of at least 2% body weight has not been achieved, a higher dose group up to 650 μg/dose/day may be explored in another 6 patients.

Stage 2 Dose and Design:

RP2D determined in Stage 1. Stage 2 is randomized, double-blind, placebo-controlled at the most active dose found in Stage 1. If the most active dose is not deemed safe, then the next lowest dose will be used. In the case the initial dose level is above the MTD, the participating Investigators and Medical Monitor with the consent of the Sponsor, may allow a lower dose level to be evaluated. Given that smallest capsule size is limited to 50 μg, the possible dose levels are 50 or 100 μg. Twenty-five patients will be randomized 4:1 (drug to placebo) in Stage 2.

Number of Patients:

Assuming a screen failure rate of 15%, approximately 60 patients will be consented to enter the study, and up to 49 evaluable patients (up to 24 patients in Stage 1 and 25 in Stage 2) will receive study treatment.

Study Population:

Patients with certain cancers who are on no anticancer therapy or stable daily doses of certain treatments and have documented weight loss of >5% body weight in the prior 6 months from signing the informed consent document (enrolment).

Inclusion Criteria:

1. Have cancer (except those excluded by the exclusion criteria) documented by histopathology or cytology.
2. Have anorexia as determined by self-reported decrease or lack of appetite or aversion to food.
3. Have documented, unintentional weight loss of >5% of body weight in the past 6 months dating back from the date of enrolment.
4. Patients are on either:
   a. no anti-cancer therapy for the 2 weeks before enrolment and are not expected to have anti-cancer therapy for the first 12 weeks after the first dose of the product (Stage 1) or if in Stage 2, after the start of the product/placebo; or
   b. stable daily dosing from 2 weeks before enrolment and expected to be on such therapy for another 12 weeks of anti-cancer monotherapy therapy with hormonal therapy for breast, prostate, or uterine cancer or capecitabine for breast or colon cancer.
5. Estimated life expectancy of at least 12 weeks as judged by the Investigator based on clinical impression.
6. Have a KPS of >50.
7. At least 18 years of age at the time of enrolment.
8. Adequate haematological, renal, and hepatic function based on laboratory values obtained within 14 days of randomization:
   - Absolute neutrophil count≥1.0×109/L
   - Platelets≥75×109/L
   - Serum creatinine≤1.5 times upper limit of laboratory normal (ULN)
   - Total serum bilirubin≤1.5 times ULN (≤3.0 times ULN if patient has been diagnosed with Gilbert's syndrome)
   - Aspartate aminotransferase (AST), alanine aminotransferase (ALT), and alkaline phosphatase (AP)≤2.5 times ULN
9. For women of child-bearing potential and for men with partners of child-bearing potential, patient must agree to take contraceptive measures for duration of treatments and for 6 months after last study treatment.
10. Understand and voluntarily sign and date an Informed Consent Document ICD prior to any study related assessments/procedures.
11. Willing and able to adhere to the study visit schedule and other protocol requirements.
12. Willing to avoid sun exposure by using protective measures such as sunscreen, clothing, and sunglasses during therapy because the phototoxicity of the product has not been studied in animals.
13. Agree to not driving or operating heavy machinery for the first 4 weeks of treatment or longer if adverse events warrant as known adverse events of the product include dizziness and somnolence.

Exclusion Criteria:

1. Primary brain tumours or symptomatic brain metastases.
2. Unable to swallow food or medication capsules.
3. Patients with oral mucositis or oral fungal infection causing anorexia or impairing taste.
4. Have a disorder that causes obstruction of the gastro-intestinal tract or limits the absorption of calories such as bowel obstruction or celiac disease.
5. Receiving tube feedings or parenteral nutrition.
6. Be on, been on within 4 weeks prior to enrolment, or expected to be on medications that have the potential to affect anorexia or caloric intake. Examples of such medications include any synthetic or natural cannabinoid (inhaled or administered by any other route) and megestrol.
7. Corticosteroids are allowed if on a stable or tapering dose for 2 weeks prior to enrolment. Patients taking inhaled corticosteroids are permitted.
8. History of any recreational or illicit drug use, alcohol misuse, or other drug misuse. Current illicit drug use or recreational or medicinal use of cannabinoids is also excluded.
9. Known hypersensitivity to API or any of its excipients. A list of ingredients of the product will be provided to sites prior to the start of Stage 1 of the protocol. Prior to the start of Stage 2, the list of ingredients will be provided for placebo.
10. Pregnant or breast feeding.
11. Clinically significant depression requiring current use of antidepressant medications.

12. Condition other than cancer that could cause anorexia and/or weight loss such as AIDS, chronic obstructive pulmonary disease, chronic kidney disease, heart failure, or pathological eating disorder.
13. Uncontrolled, intercurrent illness including, but not limited to, ongoing or active infection requiring intravenous (IV) antibiotics & psychiatric illness/social situations that would limit compliance with study requirements.
14. Major surgery within 2 weeks prior to enrolment.
15. Any comorbid condition that confounds the ability to interpret data from the study as judged by the Investigator or Medical Monitor.
16. Known human immunodeficiency virus infection, acute or chronic hepatitis B, or acute hepatitis C infection.
17. Clinically significant ascites requiring or expected to require paracentesis.
18. Corrected QT intervals (QTc) intervals calculated according to Fridericia's formula (QTcF)>480 ms.
19. Anticipated need for anti-cancer therapy from 2 weeks prior to enrolment and 12 weeks after the first dose of the product or in Stage 2 the product/placebo. (Continued use of current daily-dose anti-cancer therapy is allowed.)
20. Investigational agent within 4 weeks prior to enrolment or expected need for an investigational agent for 12 weeks after the first dose of the product or in Stage 2 placebo.
21. Receiving radiotherapy within 2 weeks dating back from enrolment or anticipated to need radiotherapy within 12 weeks of enrolment. Short term palliative radiation treatment involving a local lesion is allowed.

Formulations: As Per Example 4 for 50 and 200 μg Doses

Overview of Assessments:

Safety will be based on physical examinations, assessments of adverse events, vital signs, and electrocardiograms, and the results of haematology and chemistry tests and urinalysis. Pharmacokinetic parameters will be assessed. Activity will be assessed by changes in lean body mass, weight, body mass index, and degree of anorexia. In Stage 2, physical activity will be monitored by a wearable, physical activity monitor. The potential for drug abuse and opioid sparing effects will also be assessed.

Statistical Analyses:

Descriptive statistics will be used to describe the multiple dose groups and in Stage 2 placebo for demographics and measures of safety and efficacy. Non-compartmental models will be used to describe pharmacokinetics. Any comparative analytical tests conducted after the trial data has been collected and unblinded will be considered hypothesis generating.

Study Endpoints:

Primary Endpoints

Safety:

- Analysis of the type of, frequency, and severity of adverse drug effects as determined by reported AEs and evaluation of routine chemistry and hematologic values, urinalyses, vital signs, and electrocardiograms.
- Assessment of type and incidence of dose-limiting toxicity (DLT).
- Most effective, safe dose (RP2D) to be used in Stage 2. Effectiveness is based primarily on the endpoint of lean body mass and weight gain at 4 weeks.

Secondary Endpoints:

Activity:

- Change in lean body mass as determined by weight and DEXA scans.
- Change in anorexia as determined by a visual analog scale (VAS).
- Assess QoL using the Functional Assessment of Anorexia Cachexia Therapy (FAACT), the patient-generated subjective global assessment (PG-SGA), the European Organization for Research and Treatment of Cancer (EORTC) QLQ-C15-PAL, and revised Edmonton Symptom Assessment Scale (ESAS-r) questionnaires.
- Change in KPS.

Pharmacokinetics:

- Determine the pharmacokinetics of API in patients with cancer anorexia by analysing the blood concentrations of API and metabolites over time.

Exploratory Endpoints:

Anti-Inflammatory:

- Change in sedimentation rate, C-reactive protein, and IL-6 levels.

Hormonal:

- Change in thyroid stimulating hormone (TSH), thyroxine (T4), luteinizing hormone (LH), and testosterone levels.

Mood:

- Change in mood as measured by the Beck's Depression Inventory-II (BDI-II).

Abuse Potential:

- Assess the abuse potential by the assessment of AEs that might suggest abuse and 4 VAS for drug liking, high, take drug again, and overall drug liking.

Opioid-Sparing Effect

- Decrease in opioid use for patients taking opioids medications as determined from patient diaries.

Stage 2

Primary Endpoints

Activity:

- Change in lean body mass as determined by weight and DEXA scans at 12 weeks.
- Change in anorexia as determined by a visual analog scale (VAS) and (FAACT) questionnaire.
- Change in KPS.

Secondary Endpoints

Safety:

- Assessment of the safety profile of the product by analysing the type of, frequency, and severity of adverse drug effects as determined by reporting AEs and evaluation of routine chemistry and hematologic values, urinalyses, vital signs, and electrocardiograms.

Quality of Life:

- Assess QoL using the Functional Assessment of Anorexia Cachexia Therapy (FAACT), the patient-generated subjective global assessment (PG-SGA), the EORTC QLQ-C15-PAL, and revised Edmonton Symptom Assessment Scale (ESAS-r) questionnaires Exploratory Endpoints Anti-Inflammatory:

- Change in sedimentation rate, C-reactive protein, and IL-6 levels.

Hormonal:

- Change in TSH, T4, LH, and testosterone levels.

Mood:

- Change in mood as measured by the BDI-II.

Abuse Potential

Assess the abuse potential by the assessment of AEs that might suggest abuse and 4 VAS for drug liking, high, take drug again, and overall drug liking.

Physical Activity

Change in physical activity as determined by a wearable, physical activity monitor.

Opioid-Sparing Effect

Decrease in opioid use for patients taking opioids medications as determined from patient diaries.

Duration of Study Participation

The expected duration of patient participation is 18 weeks, which includes 2 weeks of screening, 12 weeks of treatment, and 4 weeks for follow-up. Participation may be shorter if the patient is prematurely withdrawn. During Stage 2, participation may be up to 34 weeks if patients are randomized to receive placebo and go on to receive the product (see below).

The study duration will be divided into pre-treatment, treatment, and follow-up periods. Cycle length is 28 days.

The invention claimed is:

1. A pharmaceutical composition for oral use comprising as an active substance N-(2-(tert-butyl)-1-((4,4-difluorocyclohexyl)methyl)-1H-benzimidazol-5-yl)ethanesulfonamide, or a pharmaceutically acceptable salt thereof, and a non-aqueous solvent for the active substance, wherein:

(i) the pharmaceutical composition comprises 0.001% (+/−10%) to 0.8% (+/−10%) w/w of the active substance by weight of the total pharmaceutical composition; and (ii) the pharmaceutical composition comprises at least 20% w/w of the non-aqueous solvent by weight of the total pharmaceutical composition and the non-aqueous solvent comprises polyethylene glycol having an average molecular weight of between 400 and 10000 g/mol.

2. The pharmaceutical composition according to claim 1 wherein the active substance has a solubility in the non-aqueous solvent of at least 0.1% w/w at room temperature.

3. The pharmaceutical composition according to claim 1 wherein the active substance is dissolved in the non-aqueous solvent.

4. The pharmaceutical composition according to claim 1 wherein the non-aqueous solvent is water soluble.

5. The pharmaceutical composition according to claim 1 wherein the pharmaceutical composition comprises at least two non-aqueous solvents for the active substance.

6. The pharmaceutical composition according to claim 1 wherein the polyethylene glycol has an average molecular weight between 400 and 6000 g/mol, between 1000 and 6000 g/mol, between 1200 and 1800 g/mol, or between 1400 and 1600 g/mol.

7. The pharmaceutical composition according to claim 1 wherein the non-aqueous solvent is a semi-solid at room temperature.

8. The pharmaceutical composition according to claim 1 wherein the pharmaceutical composition comprises 0.1 to 0.4% w/w of the active substance by weight of the total pharmaceutical composition.

9. The pharmaceutical composition according to claim 1 wherein the pharmaceutical composition is a semi-solid at room temperature.

10. The pharmaceutical composition according to claim 1 wherein the active substance is stable in the pharmaceutical composition for at least 2 weeks, 1, 2, 3, 6, 12, or 24 months.

11. The pharmaceutical composition according to claim 1 wherein at least 75% of the total amount of the active substance contained in the pharmaceutical composition is released within the first 45 minutes when the pharmaceutical composition is subjected to an in vitro dissolution test employing 0.1 M HCl or pH 6.8 phosphate buffer as the dissolution medium and the dissolution profile is determined as described in the United States Pharmacopoeia at 37° C. using a rotation speed of 50 rpm.

12. The pharmaceutical composition according to claim 1 wherein the active substance is homogenously distributed throughout the non-aqueous solvent.

13. The pharmaceutical composition according to claim 12 wherein the active substance is homogenously distributed throughout the non-aqueous solvent for at least 2 weeks, 1, 2, 3, 6, 12, or 24 months.

14. The pharmaceutical composition according to claim 12 wherein the homogeneous distribution of the active substance in the non-aqueous solvent is determined by an analytical method and wherein the analytical method comprises determining the weight percentage of the active substance within a portion of the pharmaceutical composition and wherein the weight percentage of the active substance within the portion of the pharmaceutical composition is ±5% of the expected value based on the total amount of the active substance added to the total amount of the pharmaceutical composition.

15. An immediate release pharmaceutical formulation for oral use comprising the pharmaceutical composition according to claim 1.

16. The immediate release pharmaceutical formulation according to claim 15 wherein when the immediate release pharmaceutical formulation is subjected to a content uniformity test as described in the European Pharmacopeia the acceptance value is less than 15.

17. The immediate release pharmaceutical formulation according to claim 15 wherein the immediate release pharmaceutical formulation is an immediate release capsule formulation.

18. A method of treating a disease state or disorder in which dysfunction of $CB_1$ and/or $CB_2$ receptors are present or implicated, the method comprising administering to a patient in need of such therapy a pharmaceutical composition according to claim 1.

19. A method of treating a disease state or disorder in which dysfunction of $CB_1$ and/or $CB_2$ receptors are present or implicated, the method comprising administering to a patient in need of such therapy an immediate release formulation according to claim 15.

20. A method of treating anorexia or cachexia, the method comprising administering to a patient in need of such therapy a pharmaceutical composition according to claim 1.

21. A method of treating anorexia or cachexia, the method comprising administering to a patient in need of such therapy an immediate release formulation according to claim 15.

* * * * *